United States Patent
Ge et al.

(10) Patent No.: US 10,723,767 B2
(45) Date of Patent: Jul. 28, 2020

(54) TRUNCATED ROTAVIRUS VP4 PROTEIN AND APPLICATION THEREOF

(71) Applicants: XIAMEN UNIVERSITY, Xiamen, Fujian Province (CN); Xiamen Innovax Biotech Co., Ltd., Xiamen, Fujian (CN)

(72) Inventors: Shengxiang Ge, Fujian (CN); Tingdong Li, Fujian (CN); Lianzhi Jia, Fujian (CN); Yijian Li, Fujian (CN); Miaoge Xue, Fujian (CN); Yuanjun Zeng, Fujian (CN); Huirong Pan, Fujian (CN); Jun Zhang, Fujian (CN); Ningshao Xia, Fujian (CN)

(73) Assignees: Xiamen University, Xiamen, Fujian (CN); Xiamen Innovax Biotech Co., Ltd., Xiamen, Fujian (CN)

( * ) Notice: Subject to any disclaimer, the term of this patent is extended or adjusted under 35 U.S.C. 154(b) by 0 days.

(21) Appl. No.: 15/575,140

(22) PCT Filed: May 20, 2016

(86) PCT No.: PCT/CN2016/082780
§ 371 (c)(1),
(2) Date: Nov. 17, 2017

(87) PCT Pub. No.: WO2016/184425
PCT Pub. Date: Nov. 24, 2016

(65) Prior Publication Data
US 2018/0141978 A1 May 24, 2018

(30) Foreign Application Priority Data
May 21, 2015 (CN) .......................... 2015 1 0260020

(51) Int. Cl.
| C07K 14/005 | (2006.01) |
| C12N 7/00 | (2006.01) |
| A61K 39/12 | (2006.01) |
| A61K 39/15 | (2006.01) |
| A61P 31/14 | (2006.01) |
| A61P 1/12 | (2006.01) |
| A61P 1/00 | (2006.01) |
| A61P 29/00 | (2006.01) |
| A61K 39/00 | (2006.01) |

(52) U.S. Cl.
CPC ............ *C07K 14/005* (2013.01); *A61K 39/12* (2013.01); *A61K 39/15* (2013.01); *A61P 1/00* (2018.01); *A61P 1/12* (2018.01); *A61P 29/00* (2018.01); *A61P 31/14* (2018.01); *C12N 7/00* (2013.01); *A61K 2039/552* (2013.01); *A61K 2039/55505* (2013.01); *A61K 2039/575* (2013.01); *C12N 2720/12322* (2013.01); *C12N 2720/12334* (2013.01); *C12N 2720/12351* (2013.01)

(58) Field of Classification Search
None
See application file for complete search history.

(56) References Cited

FOREIGN PATENT DOCUMENTS

| CN | 102618506 A | 8/2012 |
| CN | 102695522 A | 9/2012 |
| CN | 103304642 A | 9/2013 |
| CN | 103319604 A | 9/2013 |
| CN | 104284978 A | 1/2015 |
| WO | 2010132561 A2 | 11/2010 |
| WO | 2013166609 A1 | 11/2013 |

OTHER PUBLICATIONS

Changhan et al. "Expression of human group A rotavirus outer capsid protein VP4 in *Escherichia coli*", Chinese J Exp Clin Virol. 996; 10(2):114-117.*
Shi Changxin, et al; Expression of Human Grup A Rotavirus Outer Capsid Protein VP4 in *Escherichia Coli*; Chinese J Exp Clin Virol, Jun. 1996, vol. 10, No. 2.
Wang Ming-zhong, et al; Prokaryotic Expression of Grup A Human Rotavirus VP4 She II Protein; Biotechnology; vol. 14, No. 1:6; Feb. 2004; China Academic Journal Electronic Publishing House.
Wang Ming-zhong, et al; Expression of Rotavirus Structural Protein Gene in Potato; Immunological Journal; vol. 20, No. 3; May 2004; China Academic Journal Electronic Publishing House.
Xiaobo Wen, et al; Construction and Characterization of Human Rotavirus Recombinant VP8* Subunit Parenteral Vaccine Candidates; Vaccine; JVAC 134371-6; 2012; Elsevier.
PCT/CN2016/082780 International Search Report dated Aug. 4, 2016.
Bergeron-Sandoval, Louis-Phillippe, et al., Production of Human Rotavirus and Salmonella Antigens in Plants and Elicitation of ftjB-Specific Humoral Responses in Mice, Mol. Biotechnol. (2011) 47:157-168, published online Aug. 20, 2010, Springer Science+Business Media, LLC, Humana Press.
Komoto, Satoshi, et al., Geneation of Recombinant Rotavirus with an Antigenic Mosaic of Cross-Reactive Neutralization Epitopes on VP4, J of Virology, vol. 82, No. 13, Jul. 2008, pp. 6753-6757, Am Society for Microbiology.

(Continued)

*Primary Examiner* — Stacy B Chen
(74) *Attorney, Agent, or Firm* — Honigman LLP; Thomas A. Wootton, Esq.; Jonathan P. O'Brien

(57) ABSTRACT

The invention relates to a truncated rotavirus VP4 protein, a sequence encoding the same, a method for preparing the same, and a pharmaceutical composition and a vaccine comprising the protein, wherein the protein, the pharmaceutical composition and the vaccine are useful for preventing, alleviating or treating rotavirus infection and a disease caused by rotavirus infection, such as rotavirus gastroenteritis and diarrhea. The invention further relates to use of the protein in the manufacture of a pharmaceutical composition or a vaccine for preventing, alleviating or treating rotavirus infection and a disease caused by rotavirus infection, such as rotavirus gastroenteritis and diarrhea.

16 Claims, 14 Drawing Sheets
Specification includes a Sequence Listing.

(56) References Cited

OTHER PUBLICATIONS

Li, Yijian et al., Expression and Characterization of a Novel Truncated Rotavirus VP4 for the Development of a Recombinant Rotavirus Vaccine, Vaccine 36 (2018) 2086-2092, Elsevier.

Mackow, Erich R., et al., DNA Amplification-Restricted Transcription-Translation: Rapid Analysis of Rhesus Rotavirus Neutralization Sites, Biochemistry, Proc. Natl. Acad. Sci. USA 87 (1990), 518-522; Proceedings of the Natl Acad of Sci of the USA, 87 Jan. 1990, No. 2, Washington, DC, US.

Wen, Xiaobo, et al; Construction and Characterization of Human Rotavirus Recombinant VP8* Subunit Parenteral Vaccine Candidates, Vaccine 30 (2012) 6121-6126, Elsevier.

Xue, Miaoge, et al., Characterization and Protective Efficacy in an Animal Model of a Novel Truncated Rotavirus VP8 Subunit Parenteral Vaccine Candidate, Vaccine 33 (2015) 2606-2613, Elsevier Ltd.

Luis Padilla-Noriega, et al.,"Humoral Immune Responses to VP4 and Its Cleavage Products VP5* and VP8* in Infants Vaccinated with Rhesus Rotavirus," Journal of Clinical Microbiology, Jun. 1992, pp. 1392-1397, vol. 30, No. 6.

* cited by examiner

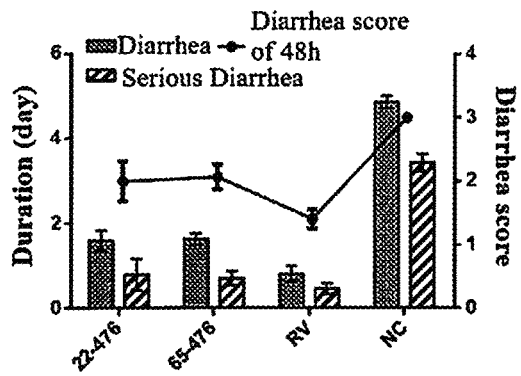
Fig. 14A
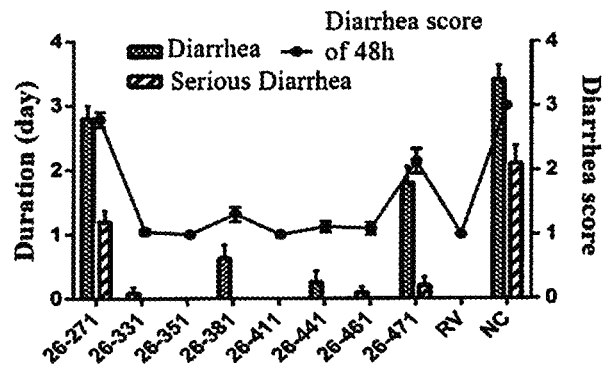
Fig. 14B
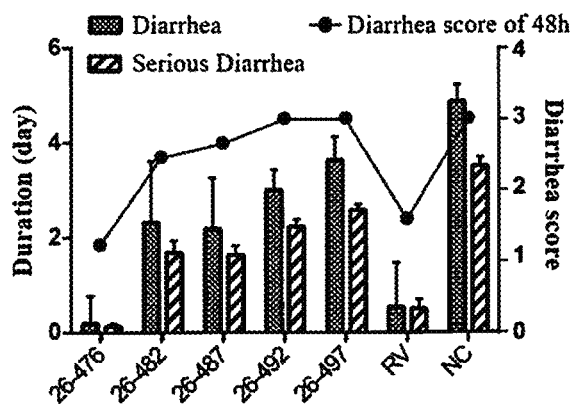
Fig. 14C
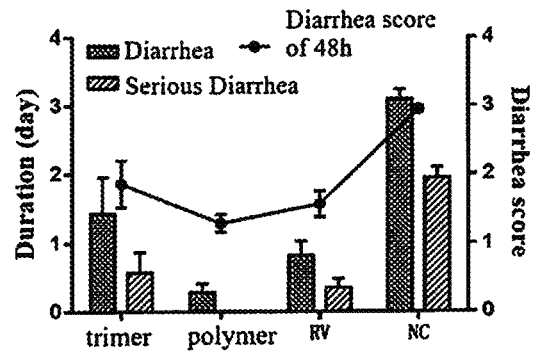
Fig. 14D
LLR SA11 EDIM P[8] P[6] P[4] Marker
Fig. 15

SEQUENCE LISTING

<160> NUMBER OF SEQ ID NOS: 91

<210> SEQ ID NO 1
<211> LENGTH: 456
<212> TYPE: PRT
<213> ORGANISM: Artificial Sequence
<220> FEATURE:
<223> OTHER INFORMATION: Artificial protein

<400> SEQUENCE: 1

Met Ile Gln Leu Ile Gly Ser Glu Lys Thr Gln Arg Thr Thr Val Asn
1               5                   10                  15

Pro Gly Pro Phe Ala Gln Thr Gly Tyr Ala Pro Val Asn Trp Gly Pro
            20                  25                  30

Gly Glu Thr Ser Asp Ser Thr Thr Val Glu Pro Val Leu Asn Gly Pro
        35                  40                  45

Tyr Gln Pro Thr Thr Phe Asn Pro Pro Val Glu Tyr Trp Met Leu Leu
    50                  55                  60

Ala Pro Thr Ser Glu Gly Val Val Glu Gly Thr Asn Gly Thr Asp
65                  70                  75                  80

Arg Trp Leu Ala Thr Ile Leu Ile Glu Pro Asn Val Pro Glu Thr Thr
                85                  90                  95

Arg Asn Tyr Thr Leu Phe Gly Glu Thr Ala Ser Ile Ser Val Ala Asn
            100                 105                 110

Pro Ser Gln Ser Lys Trp Arg Phe Val Asp Val Ala Lys Thr Thr Ala
        115                 120                 125

Asn Gly Thr Tyr Ser Gln Tyr Gly Pro Leu Leu Ser Asp Thr Lys Leu
    130                 135                 140

Tyr Gly Val Met Lys Tyr Asn Gly Lys Leu Tyr Thr Tyr Asn Gly Glu
145                 150                 155                 160

Thr Pro Asn Ala Thr Thr Asn Tyr Tyr Ser Thr Thr Asn Tyr Asp Ser
                165                 170                 175

Val Asn Met Thr Ser Tyr Cys Asp Phe Tyr Ile Ile Pro Arg Ala Gln
            180                 185                 190

Glu Ser Lys Cys Thr Glu Tyr Val Asn Asn Gly Leu Pro Pro Ile Gln
        195                 200                 205

Asn Thr Arg Asn Val Val Pro Leu Ala Leu Ser Ser Arg Ser Ile Val
    210                 215                 220

Ala Arg Arg Ala Ala Val Asn Glu Asp Ile Val Ile Ser Lys Thr Ser
225                 230                 235                 240

Leu Trp Lys Glu Met Gln Tyr Asn Arg Asp Ile Ile Ile Arg Phe Lys
                245                 250                 255

Phe Ala Asn Ser Ile Ile Lys Ser Gly Gly Leu Gly Tyr Lys Trp Ser
            260                 265                 270

Glu Ile Ser Phe Lys Pro Ala Asn Tyr Gln Tyr Thr Tyr Ile Arg Asp
        275                 280                 285

Gly Glu Glu Val Thr Ala His Thr Thr Cys Ser Val Asn Gly Val Asn
    290                 295                 300

Asp Phe Asn Tyr Asn Gly Gly Ser Leu Pro Thr Asp Phe Val Ile Ser
305                 310                 315                 320

Arg Tyr Glu Val Ile Lys Glu Asn Ser Tyr Val Tyr Ile Asp Tyr Trp
                325                 330                 335

Asp Asp Ser Gln Ala Phe Arg Asn Met Val Tyr Val Arg Ser Leu Ala
            340                 345                 350

Ala Asp Leu Asn Glu Val Thr Cys Ala Gly Gly Thr Tyr Asn Phe Gln

```
                355                 360                 365
Leu Pro Val Gly Gln Trp Pro Val Met Ser Gly Gly Ser Val Ser Leu
    370                 375                 380

Arg Ser Ala Gly Val Thr Leu Ser Thr Gln Phe Thr Asp Phe Val Ser
385                 390                 395                 400

Leu Asn Ser Leu Arg Phe Arg Phe Ser Leu Ala Val Glu Glu Pro Pro
                405                 410                 415

Phe Ser Ile Ser Arg Thr Arg Ile Ser Gly Leu Tyr Gly Leu Pro Ala
                420                 425                 430

Ala Asn Pro Asn Asn Gly Arg Asp Phe Tyr Glu Ile Ala Gly Arg Phe
                435                 440                 445

Ser Leu Ile Leu Leu Val Pro Ser
                450                 455

<210> SEQ ID NO 2
<211> LENGTH: 476
<212> TYPE: PRT
<213> ORGANISM: Artificial Sequence
<220> FEATURE:
<223> OTHER INFORMATION: Artificial protein

<400> SEQUENCE: 2

Met Ala Ser Leu Ile Tyr Arg Gln Leu Leu Thr Asn Ser Tyr Thr Val
1               5                   10                  15

Asn Leu Ser Asp Glu Ile Gln Leu Ile Gly Ser Glu Lys Thr Gln Arg
                20                  25                  30

Thr Thr Val Asn Pro Gly Pro Phe Ala Gln Thr Gly Tyr Ala Pro Val
                35                  40                  45

Asn Trp Gly Pro Gly Glu Thr Ser Asp Ser Thr Thr Val Glu Pro Val
                50                  55                  60

Leu Asn Gly Pro Tyr Gln Pro Thr Thr Phe Asn Pro Pro Val Glu Tyr
65                  70                  75                  80

Trp Met Leu Leu Ala Pro Thr Ser Glu Gly Val Val Val Glu Gly Thr
                85                  90                  95

Asn Gly Thr Asp Arg Trp Leu Ala Thr Ile Leu Ile Glu Pro Asn Val
                100                 105                 110

Pro Glu Thr Thr Arg Asn Tyr Thr Leu Phe Gly Glu Thr Ala Ser Ile
                115                 120                 125

Ser Val Ala Asn Pro Ser Gln Ser Lys Trp Arg Phe Val Asp Val Ala
                130                 135                 140

Lys Thr Thr Ala Asn Gly Thr Tyr Ser Gln Tyr Gly Pro Leu Leu Ser
145                 150                 155                 160

Asp Thr Lys Leu Tyr Gly Val Met Lys Tyr Asn Gly Lys Leu Tyr Thr
                165                 170                 175

Tyr Asn Gly Glu Thr Pro Asn Ala Thr Thr Asn Tyr Tyr Ser Thr Thr
                180                 185                 190

Asn Tyr Asp Ser Val Asn Met Thr Ser Tyr Cys Asp Phe Tyr Ile Ile
                195                 200                 205

Pro Arg Ala Gln Glu Ser Lys Cys Thr Glu Tyr Val Asn Asn Gly Leu
                210                 215                 220

Pro Pro Ile Gln Asn Thr Arg Asn Val Val Pro Leu Ala Leu Ser Ser
225                 230                 235                 240

Arg Ser Ile Val Ala Arg Arg Ala Ala Val Asn Glu Asp Ile Val Ile
                245                 250                 255

Ser Lys Thr Ser Leu Trp Lys Glu Met Gln Tyr Asn Arg Asp Ile Ile
```

```
                    260                 265                 270
Ile Arg Phe Lys Phe Ala Asn Ser Ile Ile Lys Ser Gly Gly Leu Gly
            275                 280                 285

Tyr Lys Trp Ser Glu Ile Ser Phe Lys Pro Ala Asn Tyr Gln Tyr Thr
        290                 295                 300

Tyr Ile Arg Asp Gly Glu Val Thr Ala His Thr Thr Cys Ser Val
305                 310                 315                 320

Asn Gly Val Asn Asp Phe Asn Tyr Asn Gly Gly Ser Leu Pro Thr Asp
                325                 330                 335

Phe Val Ile Ser Arg Tyr Glu Val Ile Lys Glu Asn Ser Tyr Val Tyr
            340                 345                 350

Ile Asp Tyr Trp Asp Asp Ser Gln Ala Phe Arg Asn Met Val Tyr Val
        355                 360                 365

Arg Ser Leu Ala Ala Asp Leu Asn Glu Val Thr Cys Ala Gly Gly Thr
    370                 375                 380

Tyr Asn Phe Gln Leu Pro Val Gly Gln Trp Pro Val Met Ser Gly Gly
385                 390                 395                 400

Ser Val Ser Leu Arg Ser Ala Gly Val Thr Leu Ser Thr Gln Phe Thr
                405                 410                 415

Asp Phe Val Ser Leu Asn Ser Leu Arg Phe Arg Phe Ser Leu Ala Val
            420                 425                 430

Glu Glu Pro Pro Phe Ser Ile Ser Arg Thr Arg Ile Ser Gly Leu Tyr
        435                 440                 445

Gly Leu Pro Ala Ala Asn Pro Asn Asn Gly Arg Asp Phe Tyr Glu Ile
    450                 455                 460

Ala Gly Arg Phe Ser Leu Ile Leu Leu Val Pro Ser
465                 470                 475

<210> SEQ ID NO 3
<211> LENGTH: 472
<212> TYPE: PRT
<213> ORGANISM: Artificial Sequence
<220> FEATURE:
<223> OTHER INFORMATION: Artificial protein

<400> SEQUENCE: 3

Met Tyr Arg Gln Leu Leu Thr Asn Ser Tyr Thr Val Asn Leu Ser Asp
1               5                   10                  15

Glu Ile Gln Leu Ile Gly Ser Glu Lys Thr Gln Arg Thr Thr Val Asn
            20                  25                  30

Pro Gly Pro Phe Ala Gln Thr Gly Tyr Ala Pro Val Asn Trp Gly Pro
        35                  40                  45

Gly Glu Thr Ser Asp Ser Thr Thr Val Glu Pro Val Leu Asn Gly Pro
    50                  55                  60

Tyr Gln Pro Thr Thr Phe Asn Pro Pro Val Glu Tyr Trp Met Leu Leu
65                  70                  75                  80

Ala Pro Thr Ser Glu Gly Val Val Val Glu Gly Thr Asn Gly Thr Asp
                85                  90                  95

Arg Trp Leu Ala Thr Ile Leu Ile Glu Pro Asn Val Pro Glu Thr Thr
            100                 105                 110

Arg Asn Tyr Thr Leu Phe Gly Glu Thr Ala Ser Ile Ser Val Ala Asn
        115                 120                 125

Pro Ser Gln Ser Lys Trp Arg Phe Val Asp Val Ala Lys Thr Thr Ala
    130                 135                 140

Asn Gly Thr Tyr Ser Gln Tyr Gly Pro Leu Leu Ser Asp Thr Lys Leu
```

```
            145                 150                 155                 160
        Tyr Gly Val Met Lys Tyr Asn Gly Lys Leu Tyr Thr Tyr Asn Gly Glu
                        165                 170                 175
        Thr Pro Asn Ala Thr Thr Asn Tyr Tyr Ser Thr Thr Asn Tyr Asp Ser
                    180                 185                 190
        Val Asn Met Thr Ser Tyr Cys Asp Phe Tyr Ile Ile Pro Arg Ala Gln
                195                 200                 205
        Glu Ser Lys Cys Thr Glu Tyr Val Asn Asn Gly Leu Pro Pro Ile Gln
            210                 215                 220
        Asn Thr Arg Asn Val Val Pro Leu Ala Leu Ser Ser Arg Ser Ile Val
        225                 230                 235                 240
        Ala Arg Arg Ala Ala Val Asn Glu Asp Ile Val Ile Ser Lys Thr Ser
                        245                 250                 255
        Leu Trp Lys Glu Met Gln Tyr Asn Arg Asp Ile Ile Arg Phe Lys
                    260                 265                 270
        Phe Ala Asn Ser Ile Ile Lys Ser Gly Gly Leu Gly Tyr Lys Trp Ser
                275                 280                 285
        Glu Ile Ser Phe Lys Pro Ala Asn Tyr Gln Tyr Thr Tyr Ile Arg Asp
            290                 295                 300
        Gly Glu Glu Val Thr Ala His Thr Thr Cys Ser Val Asn Gly Val Asn
        305                 310                 315                 320
        Asp Phe Asn Tyr Asn Gly Gly Ser Leu Pro Thr Asp Phe Val Ile Ser
                        325                 330                 335
        Arg Tyr Glu Val Ile Lys Glu Asn Ser Tyr Val Tyr Ile Asp Tyr Trp
                    340                 345                 350
        Asp Asp Ser Gln Ala Phe Arg Asn Met Val Tyr Val Arg Ser Leu Ala
                355                 360                 365
        Ala Asp Leu Asn Glu Val Thr Cys Ala Gly Gly Thr Tyr Asn Phe Gln
            370                 375                 380
        Leu Pro Val Gly Gln Trp Pro Val Met Ser Gly Gly Ser Val Ser Leu
        385                 390                 395                 400
        Arg Ser Ala Gly Val Thr Leu Ser Thr Gln Phe Thr Asp Phe Val Ser
                        405                 410                 415
        Leu Asn Ser Leu Arg Phe Arg Phe Ser Leu Ala Val Glu Glu Pro Pro
                    420                 425                 430
        Phe Ser Ile Ser Arg Thr Arg Ile Ser Gly Leu Tyr Gly Leu Pro Ala
                435                 440                 445
        Ala Asn Pro Asn Asn Gly Arg Asp Phe Tyr Glu Ile Ala Gly Arg Phe
            450                 455                 460
        Ser Leu Ile Leu Leu Val Pro Ser
        465                 470

<210> SEQ ID NO 4
<211> LENGTH: 456
<212> TYPE: PRT
<213> ORGANISM: Artificial Sequence
<220> FEATURE:
<223> OTHER INFORMATION: Artificial protein

<400> SEQUENCE: 4

Met Ile Gln Leu Ile Gly Ser Glu Lys Thr Gln Arg Thr Thr Val Asn
1               5                   10                  15
Pro Gly Pro Phe Ala Gln Thr Gly Tyr Ala Pro Val Asn Trp Gly Pro
                20                  25                  30
Gly Glu Thr Ser Asp Ser Thr Thr Val Glu Pro Val Leu Asn Gly Pro
```

```
            35                  40                  45
Tyr Gln Pro Thr Thr Phe Asn Pro Pro Val Glu Tyr Trp Met Leu Leu
 50                  55                  60
Ala Pro Thr Ser Glu Gly Val Val Glu Gly Thr Asn Gly Thr Asp
 65              70                  75                  80
Arg Trp Leu Ala Thr Ile Leu Ile Glu Pro Asn Val Pro Glu Thr Thr
                     85                  90                  95
Arg Asn Tyr Thr Leu Phe Gly Glu Thr Ala Ser Ile Ser Val Ala Asn
                100                 105                 110
Pro Ser Gln Ser Lys Trp Arg Phe Val Asp Val Ala Lys Thr Thr Ala
            115                 120                 125
Asn Gly Thr Tyr Ser Gln Tyr Gly Pro Leu Leu Ser Asp Thr Lys Leu
        130                 135                 140
Tyr Gly Val Met Lys Tyr Asn Gly Lys Leu Tyr Thr Tyr Asn Gly Glu
145                 150                 155                 160
Thr Pro Asn Ala Thr Thr Asn Tyr Tyr Ser Thr Thr Asn Tyr Asp Ser
                165                 170                 175
Val Asn Met Thr Ser Tyr Cys Asp Phe Tyr Ile Ile Pro Arg Ala Gln
                180                 185                 190
Glu Ser Lys Cys Thr Glu Tyr Val Asn Asn Gly Leu Pro Pro Ile Gln
            195                 200                 205
Asn Thr Arg Asn Val Val Pro Leu Ala Leu Ser Ser Arg Ser Ile Val
        210                 215                 220
Ala Arg Arg Ala Ala Val Asn Glu Asp Ile Val Ile Ser Lys Thr Ser
225                 230                 235                 240
Leu Trp Lys Glu Met Gln Tyr Asn Arg Asp Ile Ile Arg Phe Lys
                245                 250                 255
Phe Ala Asn Ser Ile Ile Lys Ser Gly Gly Leu Gly Tyr Lys Trp Ser
                260                 265                 270
Glu Ile Ser Phe Lys Pro Ala Asn Tyr Gln Tyr Thr Tyr Ile Arg Asp
            275                 280                 285
Gly Glu Glu Val Thr Ala His Thr Thr Cys Ser Val Asn Gly Val Asn
        290                 295                 300
Asp Phe Asn Tyr Asn Gly Gly Ser Leu Pro Thr Asp Phe Val Ile Ser
305                 310                 315                 320
Arg Tyr Glu Val Ile Lys Glu Asn Ser Tyr Val Tyr Ile Asp Tyr Trp
                325                 330                 335
Asp Asp Ser Gln Ala Phe Arg Asn Met Val Tyr Val Arg Ser Leu Ala
                340                 345                 350
Ala Asp Leu Asn Glu Val Thr Cys Ala Gly Gly Thr Tyr Asn Phe Gln
            355                 360                 365
Leu Pro Val Gly Gln Trp Pro Val Met Ser Gly Ser Val Ser Leu
        370                 375                 380
Arg Ser Ala Gly Val Thr Leu Ser Thr Gln Phe Thr Asp Phe Val Ser
385                 390                 395                 400
Leu Asn Ser Leu Arg Phe Arg Phe Ser Leu Ala Val Glu Glu Pro Pro
                405                 410                 415
Phe Ser Ile Ser Arg Thr Arg Ile Ser Gly Leu Tyr Gly Leu Pro Ala
                420                 425                 430
Ala Asn Pro Asn Asn Gly Arg Asp Phe Tyr Glu Ile Ala Gly Arg Phe
            435                 440                 445
Ser Leu Ile Leu Leu Val Pro Ser
        450                 455
```

<210> SEQ ID NO 5
<211> LENGTH: 413
<212> TYPE: PRT
<213> ORGANISM: Artificial Sequence
<220> FEATURE:
<223> OTHER INFORMATION: Artificial protein

<400> SEQUENCE: 5

```
Met Leu Asn Gly Pro Tyr Gln Pro Thr Thr Phe Asn Pro Pro Val Glu
1               5                  10                  15

Tyr Trp Met Leu Leu Ala Pro Thr Ser Glu Gly Val Val Glu Gly
            20                  25                  30

Thr Asn Gly Thr Asp Arg Trp Leu Ala Thr Ile Leu Ile Glu Pro Asn
            35                  40                  45

Val Pro Glu Thr Thr Arg Asn Tyr Thr Leu Phe Gly Glu Thr Ala Ser
    50                  55                  60

Ile Ser Val Ala Asn Pro Ser Gln Ser Lys Trp Arg Phe Val Asp Val
65                  70                  75                  80

Ala Lys Thr Thr Ala Asn Gly Thr Tyr Ser Gln Tyr Gly Pro Leu Leu
                85                  90                  95

Ser Asp Thr Lys Leu Tyr Gly Val Met Lys Tyr Asn Gly Lys Leu Tyr
            100                 105                 110

Thr Tyr Asn Gly Glu Thr Pro Asn Ala Thr Thr Asn Tyr Tyr Ser Thr
            115                 120                 125

Thr Asn Tyr Asp Ser Val Asn Met Thr Ser Tyr Cys Asp Phe Tyr Ile
    130                 135                 140

Ile Pro Arg Ala Gln Glu Ser Lys Cys Thr Glu Tyr Val Asn Asn Gly
145                 150                 155                 160

Leu Pro Pro Ile Gln Asn Thr Arg Asn Val Pro Leu Ala Leu Ser
                165                 170                 175

Ser Arg Ser Ile Val Ala Arg Arg Ala Ala Val Asn Glu Asp Ile Val
            180                 185                 190

Ile Ser Lys Thr Ser Leu Trp Lys Glu Met Gln Tyr Asn Arg Asp Ile
            195                 200                 205

Ile Ile Arg Phe Lys Phe Ala Asn Ser Ile Ile Lys Ser Gly Gly Leu
210                 215                 220

Gly Tyr Lys Trp Ser Glu Ile Ser Phe Lys Pro Ala Asn Tyr Gln Tyr
225                 230                 235                 240

Thr Tyr Ile Arg Asp Gly Glu Glu Val Thr Ala His Thr Thr Cys Ser
            245                 250                 255

Val Asn Gly Val Asn Asp Phe Asn Tyr Asn Gly Gly Ser Leu Pro Thr
            260                 265                 270

Asp Phe Val Ile Ser Arg Tyr Glu Val Ile Lys Glu Asn Ser Tyr Val
    275                 280                 285

Tyr Ile Asp Tyr Trp Asp Ser Gln Ala Phe Arg Asn Met Val Tyr
            290                 295                 300

Val Arg Ser Leu Ala Ala Asp Leu Asn Glu Val Thr Cys Ala Gly Gly
305                 310                 315                 320

Thr Tyr Asn Phe Gln Leu Pro Val Gly Gln Trp Pro Val Met Ser Gly
            325                 330                 335

Gly Ser Val Ser Leu Arg Ser Ala Gly Val Thr Leu Ser Thr Gln Phe
            340                 345                 350

Thr Asp Phe Val Ser Leu Asn Ser Leu Arg Phe Arg Phe Ser Leu Ala
    355                 360                 365
```

Val Glu Glu Pro Pro Phe Ser Ile Ser Arg Thr Arg Ile Ser Gly Leu
    370                 375                 380

Tyr Gly Leu Pro Ala Ala Asn Pro Asn Asn Gly Arg Asp Phe Tyr Glu
385                 390                 395                 400

Ile Ala Gly Arg Phe Ser Leu Ile Leu Leu Val Pro Ser
                405                 410

<210> SEQ ID NO 6
<211> LENGTH: 223
<212> TYPE: PRT
<213> ORGANISM: Artificial Sequence
<220> FEATURE:
<223> OTHER INFORMATION: Artificial protein

<400> SEQUENCE: 6

Met Gly Ser Glu Lys Thr Gln Arg Thr Thr Val Asn Pro Gly Pro Phe
1               5                   10                  15

Ala Gln Thr Gly Tyr Ala Pro Val Asn Trp Gly Pro Gly Glu Thr Ser
            20                  25                  30

Asp Ser Thr Thr Val Glu Pro Val Leu Asn Gly Pro Tyr Gln Pro Thr
        35                  40                  45

Thr Phe Asn Pro Pro Val Glu Tyr Trp Met Leu Leu Ala Pro Thr Ser
    50                  55                  60

Glu Gly Val Val Val Glu Gly Thr Asn Gly Thr Asp Arg Trp Leu Ala
65                  70                  75                  80

Thr Ile Leu Ile Glu Pro Asn Val Pro Glu Thr Thr Arg Asn Tyr Thr
                85                  90                  95

Leu Phe Gly Glu Thr Ala Ser Ile Ser Val Ala Asn Pro Ser Gln Ser
            100                 105                 110

Lys Trp Arg Phe Val Asp Val Ala Lys Thr Thr Ala Asn Gly Thr Tyr
        115                 120                 125

Ser Gln Tyr Gly Pro Leu Leu Ser Asp Thr Lys Leu Tyr Gly Val Met
    130                 135                 140

Lys Tyr Asn Gly Lys Leu Tyr Thr Tyr Asn Gly Glu Thr Pro Asn Ala
145                 150                 155                 160

Thr Thr Asn Tyr Tyr Ser Thr Thr Asn Tyr Asp Ser Val Asn Met Thr
                165                 170                 175

Ser Tyr Cys Asp Phe Tyr Ile Ile Pro Arg Ala Gln Glu Ser Lys Cys
            180                 185                 190

Thr Glu Tyr Val Asn Asn Gly Leu Pro Pro Ile Gln Asn Thr Arg Asn
        195                 200                 205

Val Val Pro Leu Ala Leu Ser Ser Arg Ser Ile Val Ala Arg Arg
    210                 215                 220

<210> SEQ ID NO 7
<211> LENGTH: 227
<212> TYPE: PRT
<213> ORGANISM: Artificial Sequence
<220> FEATURE:
<223> OTHER INFORMATION: Artificial protein

<400> SEQUENCE: 7

Met Gly Ser Glu Lys Thr Gln Arg Thr Thr Val Asn Pro Gly Pro Phe
1               5                   10                  15

Ala Gln Thr Gly Tyr Ala Pro Val Asn Trp Gly Pro Gly Glu Thr Ser
            20                  25                  30

Asp Ser Thr Thr Val Glu Pro Val Leu Asn Gly Pro Tyr Gln Pro Thr

```
                35                  40                  45
Thr Phe Asn Pro Pro Val Glu Tyr Trp Met Leu Leu Ala Pro Thr Ser
 50                  55                  60

Glu Gly Val Val Val Glu Gly Thr Asn Gly Thr Asp Arg Trp Leu Ala
 65                  70                  75                  80

Thr Ile Leu Ile Glu Pro Asn Val Pro Glu Thr Thr Arg Asn Tyr Thr
                 85                  90                  95

Leu Phe Gly Glu Thr Ala Ser Ile Ser Val Ala Asn Pro Ser Gln Ser
                100                 105                 110

Lys Trp Arg Phe Val Asp Val Ala Lys Thr Thr Ala Asn Gly Thr Tyr
                115                 120                 125

Ser Gln Tyr Gly Pro Leu Leu Ser Asp Thr Lys Leu Tyr Gly Val Met
130                 135                 140

Lys Tyr Asn Gly Lys Leu Tyr Thr Tyr Asn Gly Glu Thr Pro Asn Ala
145                 150                 155                 160

Thr Thr Asn Tyr Tyr Ser Thr Thr Asn Tyr Asp Ser Val Asn Met Thr
                165                 170                 175

Ser Tyr Cys Asp Phe Tyr Ile Ile Pro Arg Ala Gln Glu Ser Lys Cys
                180                 185                 190

Thr Glu Tyr Val Asn Asn Gly Leu Pro Pro Ile Gln Asn Thr Arg Asn
                195                 200                 205

Val Val Pro Leu Ala Leu Ser Ser Arg Ser Ile Val Ala Arg Arg Ala
    210                 215                 220

Ala Val Asn
225

<210> SEQ ID NO 8
<211> LENGTH: 237
<212> TYPE: PRT
<213> ORGANISM: Artificial Sequence
<220> FEATURE:
<223> OTHER INFORMATION: Artificial protein

<400> SEQUENCE: 8

Met Gly Ser Glu Lys Thr Gln Arg Thr Thr Val Asn Pro Gly Pro Phe
 1               5                  10                  15

Ala Gln Thr Gly Tyr Ala Pro Val Asn Trp Gly Pro Gly Glu Thr Ser
                20                  25                  30

Asp Ser Thr Thr Val Glu Pro Val Leu Asn Gly Pro Tyr Gln Pro Thr
                35                  40                  45

Thr Phe Asn Pro Pro Val Glu Tyr Trp Met Leu Leu Ala Pro Thr Ser
 50                  55                  60

Glu Gly Val Val Val Glu Gly Thr Asn Gly Thr Asp Arg Trp Leu Ala
 65                  70                  75                  80

Thr Ile Leu Ile Glu Pro Asn Val Pro Glu Thr Thr Arg Asn Tyr Thr
                 85                  90                  95

Leu Phe Gly Glu Thr Ala Ser Ile Ser Val Ala Asn Pro Ser Gln Ser
                100                 105                 110

Lys Trp Arg Phe Val Asp Val Ala Lys Thr Thr Ala Asn Gly Thr Tyr
                115                 120                 125

Ser Gln Tyr Gly Pro Leu Leu Ser Asp Thr Lys Leu Tyr Gly Val Met
130                 135                 140

Lys Tyr Asn Gly Lys Leu Tyr Thr Tyr Asn Gly Glu Thr Pro Asn Ala
145                 150                 155                 160

Thr Thr Asn Tyr Tyr Ser Thr Thr Asn Tyr Asp Ser Val Asn Met Thr
```

```
                        165                 170                 175
Ser Tyr Cys Asp Phe Tyr Ile Ile Pro Arg Ala Gln Glu Ser Lys Cys
            180                 185                 190

Thr Glu Tyr Val Asn Asn Gly Leu Pro Pro Ile Gln Asn Thr Arg Asn
        195                 200                 205

Val Val Pro Leu Ala Leu Ser Ser Arg Ser Ile Val Ala Arg Arg Ala
    210                 215                 220

Ala Val Asn Glu Asp Ile Val Ile Ser Lys Thr Ser Leu
225                 230                 235
```

<210> SEQ ID NO 9
<211> LENGTH: 247
<212> TYPE: PRT
<213> ORGANISM: Artificial Sequence
<220> FEATURE:
<223> OTHER INFORMATION: Artificial protein

<400> SEQUENCE: 9

```
Met Gly Ser Glu Lys Thr Gln Arg Thr Thr Val Asn Pro Gly Pro Phe
1               5                   10                  15

Ala Gln Thr Gly Tyr Ala Pro Val Asn Trp Gly Pro Gly Glu Thr Ser
            20                  25                  30

Asp Ser Thr Thr Val Glu Pro Val Leu Asn Gly Pro Tyr Gln Pro Thr
        35                  40                  45

Thr Phe Asn Pro Pro Val Glu Tyr Trp Met Leu Leu Ala Pro Thr Ser
    50                  55                  60

Glu Gly Val Val Val Glu Gly Thr Asn Gly Thr Asp Arg Trp Leu Ala
65                  70                  75                  80

Thr Ile Leu Ile Glu Pro Asn Val Pro Glu Thr Thr Arg Asn Tyr Thr
                85                  90                  95

Leu Phe Gly Glu Thr Ala Ser Ile Ser Val Ala Asn Pro Ser Gln Ser
            100                 105                 110

Lys Trp Arg Phe Val Asp Val Ala Lys Thr Thr Ala Asn Gly Thr Tyr
        115                 120                 125

Ser Gln Tyr Gly Pro Leu Leu Ser Asp Thr Lys Leu Tyr Gly Val Met
    130                 135                 140

Lys Tyr Asn Gly Lys Leu Tyr Thr Tyr Asn Gly Glu Thr Pro Asn Ala
145                 150                 155                 160

Thr Thr Asn Tyr Tyr Ser Thr Thr Asn Tyr Asp Ser Val Asn Met Thr
                165                 170                 175

Ser Tyr Cys Asp Phe Tyr Ile Ile Pro Arg Ala Gln Glu Ser Lys Cys
            180                 185                 190

Thr Glu Tyr Val Asn Asn Gly Leu Pro Pro Ile Gln Asn Thr Arg Asn
        195                 200                 205

Val Val Pro Leu Ala Leu Ser Ser Arg Ser Ile Val Ala Arg Arg Ala
    210                 215                 220

Ala Val Asn Glu Asp Ile Val Ile Ser Lys Thr Ser Leu Trp Lys Glu
225                 230                 235                 240

Met Gln Tyr Asn Arg Asp Ile
                245
```

<210> SEQ ID NO 10
<211> LENGTH: 257
<212> TYPE: PRT
<213> ORGANISM: Artificial Sequence
<220> FEATURE:
<223> OTHER INFORMATION: Artificial protein

<400> SEQUENCE: 10

```
Met Gly Ser Glu Lys Thr Gln Arg Thr Thr Val Asn Pro Gly Pro Phe
1               5                   10                  15

Ala Gln Thr Gly Tyr Ala Pro Val Asn Trp Gly Pro Gly Glu Thr Ser
            20                  25                  30

Asp Ser Thr Thr Val Glu Pro Val Leu Asn Gly Pro Tyr Gln Pro Thr
        35                  40                  45

Thr Phe Asn Pro Pro Val Glu Tyr Trp Met Leu Leu Ala Pro Thr Ser
    50                  55                  60

Glu Gly Val Val Val Glu Gly Thr Asn Gly Thr Asp Arg Trp Leu Ala
65                  70                  75                  80

Thr Ile Leu Ile Glu Pro Asn Val Pro Glu Thr Thr Arg Asn Tyr Thr
                85                  90                  95

Leu Phe Gly Glu Thr Ala Ser Ile Ser Val Ala Asn Pro Ser Gln Ser
            100                 105                 110

Lys Trp Arg Phe Val Asp Val Ala Lys Thr Thr Ala Asn Gly Thr Tyr
        115                 120                 125

Ser Gln Tyr Gly Pro Leu Leu Ser Asp Thr Lys Leu Tyr Gly Val Met
    130                 135                 140

Lys Tyr Asn Gly Lys Leu Tyr Thr Tyr Asn Gly Glu Thr Pro Asn Ala
145                 150                 155                 160

Thr Thr Asn Tyr Tyr Ser Thr Thr Asn Tyr Asp Ser Val Asn Met Thr
                165                 170                 175

Ser Tyr Cys Asp Phe Tyr Ile Ile Pro Arg Ala Gln Glu Ser Lys Cys
            180                 185                 190

Thr Glu Tyr Val Asn Asn Gly Leu Pro Pro Ile Gln Asn Thr Arg Asn
        195                 200                 205

Val Val Pro Leu Ala Leu Ser Ser Arg Ser Ile Val Ala Arg Arg Ala
    210                 215                 220

Ala Val Asn Glu Asp Ile Val Ile Ser Lys Thr Ser Leu Trp Lys Glu
225                 230                 235                 240

Met Gln Tyr Asn Arg Asp Ile Ile Ile Arg Phe Lys Phe Ala Asn Ser
                245                 250                 255

Ile
```

<210> SEQ ID NO 11
<211> LENGTH: 267
<212> TYPE: PRT
<213> ORGANISM: Artificial Sequence
<220> FEATURE:
<223> OTHER INFORMATION: Artificial protein

<400> SEQUENCE: 11

```
Met Gly Ser Glu Lys Thr Gln Arg Thr Thr Val Asn Pro Gly Pro Phe
1               5                   10                  15

Ala Gln Thr Gly Tyr Ala Pro Val Asn Trp Gly Pro Gly Glu Thr Ser
            20                  25                  30

Asp Ser Thr Thr Val Glu Pro Val Leu Asn Gly Pro Tyr Gln Pro Thr
        35                  40                  45

Thr Phe Asn Pro Pro Val Glu Tyr Trp Met Leu Leu Ala Pro Thr Ser
    50                  55                  60

Glu Gly Val Val Val Glu Gly Thr Asn Gly Thr Asp Arg Trp Leu Ala
65                  70                  75                  80

Thr Ile Leu Ile Glu Pro Asn Val Pro Glu Thr Thr Arg Asn Tyr Thr
```

```
            85                  90                  95
Leu Phe Gly Glu Thr Ala Ser Ile Ser Val Ala Asn Pro Ser Gln Ser
            100                 105                 110

Lys Trp Arg Phe Val Asp Val Ala Lys Thr Thr Ala Asn Gly Thr Tyr
            115                 120                 125

Ser Gln Tyr Gly Pro Leu Leu Ser Asp Thr Lys Leu Tyr Gly Val Met
            130                 135                 140

Lys Tyr Asn Gly Lys Leu Tyr Thr Tyr Asn Gly Glu Thr Pro Asn Ala
145                 150                 155                 160

Thr Thr Asn Tyr Tyr Ser Thr Thr Asn Tyr Asp Ser Val Asn Met Thr
                    165                 170                 175

Ser Tyr Cys Asp Phe Tyr Ile Ile Pro Arg Ala Gln Glu Ser Lys Cys
                180                 185                 190

Thr Glu Tyr Val Asn Asn Gly Leu Pro Pro Ile Gln Asn Thr Arg Asn
            195                 200                 205

Val Val Pro Leu Ala Leu Ser Ser Arg Ser Ile Val Ala Arg Arg Ala
210                 215                 220

Ala Val Asn Glu Asp Ile Val Ile Ser Lys Thr Ser Leu Trp Lys Glu
225                 230                 235                 240

Met Gln Tyr Asn Arg Asp Ile Ile Ile Arg Phe Lys Phe Ala Asn Ser
                245                 250                 255

Ile Ile Lys Ser Gly Gly Leu Gly Tyr Lys Trp
                260                 265
```

<210> SEQ ID NO 12
<211> LENGTH: 277
<212> TYPE: PRT
<213> ORGANISM: Artificial Sequence
<220> FEATURE:
<223> OTHER INFORMATION: Artificial protein

<400> SEQUENCE: 12

```
Met Gly Ser Glu Lys Thr Gln Arg Thr Thr Val Asn Pro Gly Pro Phe
1               5                   10                  15

Ala Gln Thr Gly Tyr Ala Pro Val Asn Trp Gly Pro Gly Glu Thr Ser
            20                  25                  30

Asp Ser Thr Thr Val Glu Pro Val Leu Asn Gly Pro Tyr Gln Pro Thr
            35                  40                  45

Thr Phe Asn Pro Pro Val Glu Tyr Trp Met Leu Leu Ala Pro Thr Ser
            50                  55                  60

Glu Gly Val Val Val Glu Gly Thr Asn Gly Thr Asp Arg Trp Leu Ala
65                  70                  75                  80

Thr Ile Leu Ile Glu Pro Asn Val Pro Glu Thr Thr Arg Asn Tyr Thr
                    85                  90                  95

Leu Phe Gly Glu Thr Ala Ser Ile Ser Val Ala Asn Pro Ser Gln Ser
            100                 105                 110

Lys Trp Arg Phe Val Asp Val Ala Lys Thr Thr Ala Asn Gly Thr Tyr
            115                 120                 125

Ser Gln Tyr Gly Pro Leu Leu Ser Asp Thr Lys Leu Tyr Gly Val Met
            130                 135                 140

Lys Tyr Asn Gly Lys Leu Tyr Thr Tyr Asn Gly Glu Thr Pro Asn Ala
145                 150                 155                 160

Thr Thr Asn Tyr Tyr Ser Thr Thr Asn Tyr Asp Ser Val Asn Met Thr
                    165                 170                 175

Ser Tyr Cys Asp Phe Tyr Ile Ile Pro Arg Ala Gln Glu Ser Lys Cys
```

```
            180                 185                 190
Thr Glu Tyr Val Asn Asn Gly Leu Pro Pro Ile Gln Asn Thr Arg Asn
            195                 200                 205

Val Val Pro Leu Ala Leu Ser Ser Arg Ser Ile Val Ala Arg Arg Ala
            210                 215                 220

Ala Val Asn Glu Asp Ile Val Ile Ser Lys Thr Ser Leu Trp Lys Glu
225                 230                 235                 240

Met Gln Tyr Asn Arg Asp Ile Ile Ile Arg Phe Lys Phe Ala Asn Ser
                245                 250                 255

Ile Ile Lys Ser Gly Gly Leu Gly Tyr Lys Trp Ser Glu Ile Ser Phe
            260                 265                 270

Lys Pro Ala Asn Tyr
            275

<210> SEQ ID NO 13
<211> LENGTH: 287
<212> TYPE: PRT
<213> ORGANISM: Artificial Sequence
<220> FEATURE:
<223> OTHER INFORMATION: Artificial protein

<400> SEQUENCE: 13

Met Gly Ser Glu Lys Thr Gln Arg Thr Thr Val Asn Pro Gly Pro Phe
1               5                   10                  15

Ala Gln Thr Gly Tyr Ala Pro Val Asn Trp Gly Pro Gly Glu Thr Ser
            20                  25                  30

Asp Ser Thr Thr Val Glu Pro Val Leu Asn Gly Pro Tyr Gln Pro Thr
            35                  40                  45

Thr Phe Asn Pro Pro Val Glu Tyr Trp Met Leu Leu Ala Pro Thr Ser
        50                  55                  60

Glu Gly Val Val Glu Gly Thr Asn Gly Thr Asp Arg Trp Leu Ala
65              70                  75                  80

Thr Ile Leu Ile Glu Pro Asn Val Pro Glu Thr Thr Arg Asn Tyr Thr
                85                  90                  95

Leu Phe Gly Glu Thr Ala Ser Ile Ser Val Ala Asn Pro Ser Gln Ser
            100                 105                 110

Lys Trp Arg Phe Val Asp Val Ala Lys Thr Thr Ala Asn Gly Thr Tyr
            115                 120                 125

Ser Gln Tyr Gly Pro Leu Leu Ser Asp Thr Lys Leu Tyr Gly Val Met
            130                 135                 140

Lys Tyr Asn Gly Lys Leu Tyr Thr Tyr Asn Gly Glu Thr Pro Asn Ala
145                 150                 155                 160

Thr Thr Asn Tyr Tyr Ser Thr Thr Asn Tyr Asp Ser Val Asn Met Thr
                165                 170                 175

Ser Tyr Cys Asp Phe Tyr Ile Ile Pro Arg Ala Gln Glu Ser Lys Cys
            180                 185                 190

Thr Glu Tyr Val Asn Asn Gly Leu Pro Pro Ile Gln Asn Thr Arg Asn
            195                 200                 205

Val Val Pro Leu Ala Leu Ser Ser Arg Ser Ile Val Ala Arg Arg Ala
            210                 215                 220

Ala Val Asn Glu Asp Ile Val Ile Ser Lys Thr Ser Leu Trp Lys Glu
225                 230                 235                 240

Met Gln Tyr Asn Arg Asp Ile Ile Ile Arg Phe Lys Phe Ala Asn Ser
                245                 250                 255

Ile Ile Lys Ser Gly Gly Leu Gly Tyr Lys Trp Ser Glu Ile Ser Phe
```

```
                260                 265                 270
Lys Pro Ala Asn Tyr Gln Tyr Thr Tyr Ile Arg Asp Gly Glu Glu
            275                 280                 285

<210> SEQ ID NO 14
<211> LENGTH: 297
<212> TYPE: PRT
<213> ORGANISM: Artificial Sequence
<220> FEATURE:
<223> OTHER INFORMATION: Artificial protein

<400> SEQUENCE: 14

Met Gly Ser Glu Lys Thr Gln Arg Thr Thr Val Asn Pro Gly Pro Phe
1               5                   10                  15

Ala Gln Thr Gly Tyr Ala Pro Val Asn Trp Gly Pro Gly Glu Thr Ser
            20                  25                  30

Asp Ser Thr Thr Val Glu Pro Val Leu Asn Gly Pro Tyr Gln Pro Thr
        35                  40                  45

Thr Phe Asn Pro Pro Val Glu Tyr Trp Met Leu Leu Ala Pro Thr Ser
    50                  55                  60

Glu Gly Val Val Glu Gly Thr Asn Gly Thr Asp Arg Trp Leu Ala
65                  70                  75                  80

Thr Ile Leu Ile Glu Pro Asn Val Pro Glu Thr Thr Arg Asn Tyr Thr
                85                  90                  95

Leu Phe Gly Glu Thr Ala Ser Ile Ser Val Ala Asn Pro Ser Gln Ser
            100                 105                 110

Lys Trp Arg Phe Val Asp Val Ala Lys Thr Thr Ala Asn Gly Thr Tyr
        115                 120                 125

Ser Gln Tyr Gly Pro Leu Leu Ser Asp Thr Lys Leu Tyr Gly Val Met
    130                 135                 140

Lys Tyr Asn Gly Lys Leu Tyr Thr Tyr Asn Gly Glu Thr Pro Asn Ala
145                 150                 155                 160

Thr Thr Asn Tyr Tyr Ser Thr Thr Asn Tyr Asp Ser Val Asn Met Thr
                165                 170                 175

Ser Tyr Cys Asp Phe Tyr Ile Ile Pro Arg Ala Gln Glu Ser Lys Cys
            180                 185                 190

Thr Glu Tyr Val Asn Asn Gly Leu Pro Pro Ile Gln Asn Thr Arg Asn
        195                 200                 205

Val Val Pro Leu Ala Leu Ser Ser Arg Ser Ile Val Ala Arg Arg Ala
    210                 215                 220

Ala Val Asn Glu Asp Ile Val Ile Ser Lys Thr Ser Leu Trp Lys Glu
225                 230                 235                 240

Met Gln Tyr Asn Arg Asp Ile Ile Ile Arg Phe Lys Phe Ala Asn Ser
                245                 250                 255

Ile Ile Lys Ser Gly Gly Leu Gly Tyr Lys Trp Ser Glu Ile Ser Phe
            260                 265                 270

Lys Pro Ala Asn Tyr Gln Tyr Thr Tyr Ile Arg Asp Gly Glu Glu Val
        275                 280                 285

Thr Ala His Thr Thr Cys Ser Val Asn
    290                 295

<210> SEQ ID NO 15
<211> LENGTH: 307
<212> TYPE: PRT
<213> ORGANISM: Artificial Sequence
<220> FEATURE:
<223> OTHER INFORMATION: Artificial protein
```

<400> SEQUENCE: 15

Met Gly Ser Glu Lys Thr Gln Arg Thr Thr Val Asn Pro Gly Pro Phe
1               5                   10                  15

Ala Gln Thr Gly Tyr Ala Pro Val Asn Trp Gly Pro Gly Glu Thr Ser
            20                  25                  30

Asp Ser Thr Thr Val Glu Pro Val Leu Asn Gly Pro Tyr Gln Pro Thr
        35                  40                  45

Thr Phe Asn Pro Pro Val Glu Tyr Trp Met Leu Leu Ala Pro Thr Ser
    50                  55                  60

Glu Gly Val Val Glu Gly Thr Asn Gly Thr Asp Arg Trp Leu Ala
65                  70                  75                  80

Thr Ile Leu Ile Glu Pro Asn Val Pro Glu Thr Thr Arg Asn Tyr Thr
                85                  90                  95

Leu Phe Gly Glu Thr Ala Ser Ile Ser Val Ala Asn Pro Ser Gln Ser
            100                 105                 110

Lys Trp Arg Phe Val Asp Val Ala Lys Thr Thr Ala Asn Gly Thr Tyr
        115                 120                 125

Ser Gln Tyr Gly Pro Leu Leu Ser Asp Thr Lys Leu Tyr Gly Val Met
    130                 135                 140

Lys Tyr Asn Gly Lys Leu Tyr Thr Tyr Asn Gly Glu Thr Pro Asn Ala
145                 150                 155                 160

Thr Thr Asn Tyr Tyr Ser Thr Thr Asn Tyr Asp Ser Val Asn Met Thr
                165                 170                 175

Ser Tyr Cys Asp Phe Tyr Ile Ile Pro Arg Ala Gln Glu Ser Lys Cys
            180                 185                 190

Thr Glu Tyr Val Asn Asn Gly Leu Pro Pro Ile Gln Asn Thr Arg Asn
        195                 200                 205

Val Val Pro Leu Ala Leu Ser Ser Arg Ser Ile Val Ala Arg Arg Ala
    210                 215                 220

Ala Val Asn Glu Asp Ile Val Ile Ser Lys Thr Ser Leu Trp Lys Glu
225                 230                 235                 240

Met Gln Tyr Asn Arg Asp Ile Ile Ile Arg Phe Lys Phe Ala Asn Ser
                245                 250                 255

Ile Ile Lys Ser Gly Gly Leu Gly Tyr Lys Trp Ser Glu Ile Ser Phe
            260                 265                 270

Lys Pro Ala Asn Tyr Gln Tyr Thr Tyr Ile Arg Asp Gly Glu Glu Val
        275                 280                 285

Thr Ala His Thr Thr Cys Ser Val Asn Gly Val Asn Asp Phe Asn Tyr
    290                 295                 300

Asn Gly Gly
305

<210> SEQ ID NO 16
<211> LENGTH: 317
<212> TYPE: PRT
<213> ORGANISM: Artificial Sequence
<220> FEATURE:
<223> OTHER INFORMATION: Artificial protein

<400> SEQUENCE: 16

Met Gly Ser Glu Lys Thr Gln Arg Thr Thr Val Asn Pro Gly Pro Phe
1               5                   10                  15

Ala Gln Thr Gly Tyr Ala Pro Val Asn Trp Gly Pro Gly Glu Thr Ser
            20                  25                  30

```
Asp Ser Thr Thr Val Glu Pro Val Leu Asn Gly Pro Tyr Gln Pro Thr
            35                  40                  45

Thr Phe Asn Pro Pro Val Glu Tyr Trp Met Leu Leu Ala Pro Thr Ser
        50                  55                  60

Glu Gly Val Val Val Glu Gly Thr Asn Gly Thr Asp Arg Trp Leu Ala
 65                  70                  75                  80

Thr Ile Leu Ile Glu Pro Asn Val Pro Glu Thr Thr Arg Asn Tyr Thr
                85                  90                  95

Leu Phe Gly Glu Thr Ala Ser Ile Ser Val Ala Asn Pro Ser Gln Ser
            100                 105                 110

Lys Trp Arg Phe Val Asp Val Ala Lys Thr Thr Ala Asn Gly Thr Tyr
        115                 120                 125

Ser Gln Tyr Gly Pro Leu Leu Ser Asp Thr Lys Leu Tyr Gly Val Met
130                 135                 140

Lys Tyr Asn Gly Lys Leu Tyr Thr Tyr Asn Gly Glu Thr Pro Asn Ala
145                 150                 155                 160

Thr Thr Asn Tyr Tyr Ser Thr Thr Asn Tyr Asp Ser Val Asn Met Thr
                165                 170                 175

Ser Tyr Cys Asp Phe Tyr Ile Ile Pro Arg Ala Gln Glu Ser Lys Cys
            180                 185                 190

Thr Glu Tyr Val Asn Asn Gly Leu Pro Pro Ile Gln Asn Thr Arg Asn
        195                 200                 205

Val Val Pro Leu Ala Leu Ser Ser Arg Ser Ile Val Ala Arg Arg Ala
210                 215                 220

Ala Val Asn Glu Asp Ile Val Ile Ser Lys Thr Ser Leu Trp Lys Glu
225                 230                 235                 240

Met Gln Tyr Asn Arg Asp Ile Ile Ile Arg Phe Lys Phe Ala Asn Ser
                245                 250                 255

Ile Ile Lys Ser Gly Gly Leu Gly Tyr Lys Trp Ser Glu Ile Ser Phe
            260                 265                 270

Lys Pro Ala Asn Tyr Gln Tyr Thr Tyr Ile Arg Asp Gly Glu Glu Val
        275                 280                 285

Thr Ala His Thr Thr Cys Ser Val Asn Gly Val Asn Asp Phe Asn Tyr
290                 295                 300

Asn Gly Gly Ser Leu Pro Thr Asp Phe Val Ile Ser Arg
305                 310                 315

<210> SEQ ID NO 17
<211> LENGTH: 327
<212> TYPE: PRT
<213> ORGANISM: Artificial Sequence
<220> FEATURE:
<223> OTHER INFORMATION: Artificial protein

<400> SEQUENCE: 17

Met Gly Ser Glu Lys Thr Gln Arg Thr Thr Val Asn Pro Gly Pro Phe
1               5                   10                  15

Ala Gln Thr Gly Tyr Ala Pro Val Asn Trp Gly Pro Gly Glu Thr Ser
            20                  25                  30

Asp Ser Thr Thr Val Glu Pro Val Leu Asn Gly Pro Tyr Gln Pro Thr
            35                  40                  45

Thr Phe Asn Pro Pro Val Glu Tyr Trp Met Leu Leu Ala Pro Thr Ser
        50                  55                  60

Glu Gly Val Val Val Glu Gly Thr Asn Gly Thr Asp Arg Trp Leu Ala
 65                  70                  75                  80
```

```
Thr Ile Leu Ile Glu Pro Asn Val Pro Glu Thr Thr Arg Asn Tyr Thr
                85                  90                  95

Leu Phe Gly Glu Thr Ala Ser Ile Ser Val Ala Asn Pro Ser Gln Ser
            100                 105                 110

Lys Trp Arg Phe Val Asp Val Ala Lys Thr Thr Ala Asn Gly Thr Tyr
        115                 120                 125

Ser Gln Tyr Gly Pro Leu Leu Ser Asp Thr Lys Leu Tyr Gly Val Met
    130                 135                 140

Lys Tyr Asn Gly Lys Leu Tyr Thr Tyr Asn Gly Glu Thr Pro Asn Ala
145                 150                 155                 160

Thr Thr Asn Tyr Tyr Ser Thr Thr Asn Tyr Asp Ser Val Asn Met Thr
                165                 170                 175

Ser Tyr Cys Asp Phe Tyr Ile Ile Pro Arg Ala Gln Glu Ser Lys Cys
            180                 185                 190

Thr Glu Tyr Val Asn Asn Gly Leu Pro Pro Ile Gln Asn Thr Arg Asn
        195                 200                 205

Val Val Pro Leu Ala Leu Ser Ser Arg Ser Ile Val Ala Arg Arg Ala
    210                 215                 220

Ala Val Asn Glu Asp Ile Val Ile Ser Lys Thr Ser Leu Trp Lys Glu
225                 230                 235                 240

Met Gln Tyr Asn Arg Asp Ile Ile Ile Arg Phe Lys Phe Ala Asn Ser
                245                 250                 255

Ile Ile Lys Ser Gly Gly Leu Gly Tyr Lys Trp Ser Glu Ile Ser Phe
            260                 265                 270

Lys Pro Ala Asn Tyr Gln Tyr Thr Tyr Ile Arg Asp Gly Glu Glu Val
        275                 280                 285

Thr Ala His Thr Thr Cys Ser Val Asn Gly Val Asn Asp Phe Asn Tyr
    290                 295                 300

Asn Gly Gly Ser Leu Pro Thr Asp Phe Val Ile Ser Arg Tyr Glu Val
305                 310                 315                 320

Ile Lys Glu Asn Ser Tyr Val
                325

<210> SEQ ID NO 18
<211> LENGTH: 337
<212> TYPE: PRT
<213> ORGANISM: Artificial Sequence
<220> FEATURE:
<223> OTHER INFORMATION: Artificial protein

<400> SEQUENCE: 18

Met Gly Ser Glu Lys Thr Gln Arg Thr Thr Val Asn Pro Gly Pro Phe
1               5                   10                  15

Ala Gln Thr Gly Tyr Ala Pro Val Asn Trp Gly Pro Gly Glu Thr Ser
            20                  25                  30

Asp Ser Thr Thr Val Glu Pro Val Leu Asn Gly Pro Tyr Gln Pro Thr
        35                  40                  45

Thr Phe Asn Pro Pro Val Glu Tyr Trp Met Leu Leu Ala Pro Thr Ser
    50                  55                  60

Glu Gly Val Val Val Glu Gly Thr Asn Gly Thr Asp Arg Trp Leu Ala
65                  70                  75                  80

Thr Ile Leu Ile Glu Pro Asn Val Pro Glu Thr Thr Arg Asn Tyr Thr
                85                  90                  95

Leu Phe Gly Glu Thr Ala Ser Ile Ser Val Ala Asn Pro Ser Gln Ser
            100                 105                 110
```

```
Lys Trp Arg Phe Val Asp Val Ala Lys Thr Thr Ala Asn Gly Thr Tyr
            115                 120                 125

Ser Gln Tyr Gly Pro Leu Leu Ser Asp Thr Lys Leu Tyr Gly Val Met
130                 135                 140

Lys Tyr Asn Gly Lys Leu Tyr Thr Tyr Asn Gly Glu Thr Pro Asn Ala
145                 150                 155                 160

Thr Thr Asn Tyr Tyr Ser Thr Asn Tyr Asp Ser Val Asn Met Thr
                165                 170                 175

Ser Tyr Cys Asp Phe Tyr Ile Ile Pro Arg Ala Gln Glu Ser Lys Cys
            180                 185                 190

Thr Glu Tyr Val Asn Asn Gly Leu Pro Pro Ile Gln Asn Thr Arg Asn
            195                 200                 205

Val Val Pro Leu Ala Leu Ser Ser Arg Ser Ile Val Ala Arg Arg Ala
210                 215                 220

Ala Val Asn Glu Asp Ile Val Ile Ser Lys Thr Ser Leu Trp Lys Glu
225                 230                 235                 240

Met Gln Tyr Asn Arg Asp Ile Ile Ile Arg Phe Lys Phe Ala Asn Ser
            245                 250                 255

Ile Ile Lys Ser Gly Gly Leu Gly Tyr Lys Trp Ser Glu Ile Ser Phe
            260                 265                 270

Lys Pro Ala Asn Tyr Gln Tyr Thr Tyr Ile Arg Asp Gly Glu Glu Val
            275                 280                 285

Thr Ala His Thr Thr Cys Ser Val Asn Gly Val Asn Asp Phe Asn Tyr
            290                 295                 300

Asn Gly Gly Ser Leu Pro Thr Asp Phe Val Ile Ser Arg Tyr Glu Val
305                 310                 315                 320

Ile Lys Glu Asn Ser Tyr Val Tyr Ile Asp Tyr Trp Asp Asp Ser Gln
                325                 330                 335

Ala

<210> SEQ ID NO 19
<211> LENGTH: 347
<212> TYPE: PRT
<213> ORGANISM: Artificial Sequence
<220> FEATURE:
<223> OTHER INFORMATION: Artificial protein

<400> SEQUENCE: 19

Met Gly Ser Glu Lys Thr Gln Arg Thr Thr Val Asn Pro Gly Pro Phe
1               5                   10                  15

Ala Gln Thr Gly Tyr Ala Pro Val Asn Trp Gly Pro Gly Glu Thr Ser
                20                  25                  30

Asp Ser Thr Thr Val Glu Pro Val Leu Asn Gly Pro Tyr Gln Pro Thr
            35                  40                  45

Thr Phe Asn Pro Pro Val Glu Tyr Trp Met Leu Leu Ala Pro Thr Ser
50                  55                  60

Glu Gly Val Val Val Glu Gly Thr Asn Gly Thr Asp Arg Trp Leu Ala
65                  70                  75                  80

Thr Ile Leu Ile Glu Pro Asn Val Pro Glu Thr Thr Arg Asn Tyr Thr
                85                  90                  95

Leu Phe Gly Glu Thr Ala Ser Ile Ser Val Ala Asn Pro Ser Gln Ser
            100                 105                 110

Lys Trp Arg Phe Val Asp Val Ala Lys Thr Thr Ala Asn Gly Thr Tyr
            115                 120                 125

Ser Gln Tyr Gly Pro Leu Leu Ser Asp Thr Lys Leu Tyr Gly Val Met
```

```
            130                 135                 140
Lys Tyr Asn Gly Lys Leu Tyr Thr Tyr Asn Gly Glu Thr Pro Asn Ala
145                 150                 155                 160

Thr Thr Asn Tyr Tyr Ser Thr Thr Asn Tyr Asp Ser Val Asn Met Thr
                165                 170                 175

Ser Tyr Cys Asp Phe Tyr Ile Ile Pro Arg Ala Gln Glu Ser Lys Cys
            180                 185                 190

Thr Glu Tyr Val Asn Asn Gly Leu Pro Pro Ile Gln Asn Thr Arg Asn
        195                 200                 205

Val Val Pro Leu Ala Leu Ser Ser Arg Ser Ile Val Ala Arg Arg Ala
    210                 215                 220

Ala Val Asn Glu Asp Ile Val Ile Ser Lys Thr Ser Leu Trp Lys Glu
225                 230                 235                 240

Met Gln Tyr Asn Arg Asp Ile Ile Ile Arg Phe Lys Phe Ala Asn Ser
                245                 250                 255

Ile Ile Lys Ser Gly Gly Leu Gly Tyr Lys Trp Ser Glu Ile Ser Phe
            260                 265                 270

Lys Pro Ala Asn Tyr Gln Tyr Thr Tyr Ile Arg Asp Gly Glu Glu Val
        275                 280                 285

Thr Ala His Thr Thr Cys Ser Val Asn Gly Val Asn Asp Phe Asn Tyr
    290                 295                 300

Asn Gly Gly Ser Leu Pro Thr Asp Phe Val Ile Ser Arg Tyr Glu Val
305                 310                 315                 320

Ile Lys Glu Asn Ser Tyr Val Tyr Ile Asp Tyr Trp Asp Asp Ser Gln
                325                 330                 335

Ala Phe Arg Asn Met Val Tyr Val Arg Ser Leu
            340                 345
```

<210> SEQ ID NO 20
<211> LENGTH: 357
<212> TYPE: PRT
<213> ORGANISM: Artificial Sequence
<220> FEATURE:
<223> OTHER INFORMATION: Artificial protein

<400> SEQUENCE: 20

```
Met Gly Ser Glu Lys Thr Gln Arg Thr Thr Val Asn Pro Gly Pro Phe
1               5                   10                  15

Ala Gln Thr Gly Tyr Ala Pro Val Asn Trp Gly Pro Gly Glu Thr Ser
            20                  25                  30

Asp Ser Thr Thr Val Glu Pro Val Leu Asn Gly Pro Tyr Gln Pro Thr
        35                  40                  45

Thr Phe Asn Pro Pro Val Glu Tyr Trp Met Leu Leu Ala Pro Thr Ser
    50                  55                  60

Glu Gly Val Val Val Glu Gly Thr Asn Gly Thr Asp Arg Trp Leu Ala
65                  70                  75                  80

Thr Ile Leu Ile Glu Pro Asn Val Pro Glu Thr Thr Arg Asn Tyr Thr
                85                  90                  95

Leu Phe Gly Glu Thr Ala Ser Ile Ser Val Ala Asn Pro Ser Gln Ser
            100                 105                 110

Lys Trp Arg Phe Val Asp Val Ala Lys Thr Thr Ala Asn Gly Thr Tyr
        115                 120                 125

Ser Gln Tyr Gly Pro Leu Leu Ser Asp Thr Lys Leu Tyr Gly Val Met
    130                 135                 140

Lys Tyr Asn Gly Lys Leu Tyr Thr Tyr Asn Gly Glu Thr Pro Asn Ala
```

145                 150                 155                 160

Thr Thr Asn Tyr Tyr Ser Thr Thr Asn Tyr Asp Ser Val Asn Met Thr
                    165                 170                 175

Ser Tyr Cys Asp Phe Tyr Ile Ile Pro Arg Ala Gln Glu Ser Lys Cys
                    180                 185                 190

Thr Glu Tyr Val Asn Asn Gly Leu Pro Pro Ile Gln Asn Thr Arg Asn
                    195                 200                 205

Val Val Pro Leu Ala Leu Ser Ser Arg Ser Ile Val Ala Arg Arg Ala
        210                 215                 220

Ala Val Asn Glu Asp Ile Val Ile Ser Lys Thr Ser Leu Trp Lys Glu
225                 230                 235                 240

Met Gln Tyr Asn Arg Asp Ile Ile Ile Arg Phe Lys Phe Ala Asn Ser
                    245                 250                 255

Ile Ile Lys Ser Gly Gly Leu Gly Tyr Lys Trp Ser Glu Ile Ser Phe
                    260                 265                 270

Lys Pro Ala Asn Tyr Gln Tyr Thr Tyr Ile Arg Asp Gly Glu Glu Val
                    275                 280                 285

Thr Ala His Thr Thr Cys Ser Val Asn Gly Val Asn Asp Phe Asn Tyr
        290                 295                 300

Asn Gly Gly Ser Leu Pro Thr Asp Phe Val Ile Ser Arg Tyr Glu Val
305                 310                 315                 320

Ile Lys Glu Asn Ser Tyr Val Tyr Ile Asp Tyr Trp Asp Asp Ser Gln
                    325                 330                 335

Ala Phe Arg Asn Met Val Tyr Val Arg Ser Leu Ala Ala Asp Leu Asn
                    340                 345                 350

Glu Val Thr Cys Ala
        355

<210> SEQ ID NO 21
<211> LENGTH: 367
<212> TYPE: PRT
<213> ORGANISM: Artificial Sequence
<220> FEATURE:
<223> OTHER INFORMATION: Artificial protein

<400> SEQUENCE: 21

Met Gly Ser Glu Lys Thr Gln Arg Thr Thr Val Asn Pro Gly Pro Phe
1               5                   10                  15

Ala Gln Thr Gly Tyr Ala Pro Val Asn Trp Gly Pro Gly Glu Thr Ser
                20                  25                  30

Asp Ser Thr Thr Val Glu Pro Val Leu Asn Gly Pro Tyr Gln Pro Thr
            35                  40                  45

Thr Phe Asn Pro Pro Val Glu Tyr Trp Met Leu Leu Ala Pro Thr Ser
        50                  55                  60

Glu Gly Val Val Glu Gly Thr Asn Gly Thr Asp Arg Trp Leu Ala Thr
65                  70                  75                  80

Thr Ile Leu Ile Glu Pro Asn Val Pro Glu Thr Thr Arg Asn Tyr Thr
                85                  90                  95

Leu Phe Gly Glu Thr Ala Ser Ile Ser Val Ala Asn Pro Ser Gln Ser
                100                 105                 110

Lys Trp Arg Phe Val Asp Val Ala Lys Thr Thr Ala Asn Gly Thr Tyr
            115                 120                 125

Ser Gln Tyr Gly Pro Leu Leu Ser Asp Thr Lys Leu Tyr Gly Val Met
        130                 135                 140

Lys Tyr Asn Gly Lys Leu Tyr Thr Tyr Asn Gly Glu Thr Pro Asn Ala

```
                145                 150                 155                 160
Thr Thr Asn Tyr Tyr Ser Thr Thr Asn Tyr Asp Ser Val Asn Met Thr
                    165                 170                 175

Ser Tyr Cys Asp Phe Tyr Ile Ile Pro Arg Ala Gln Glu Ser Lys Cys
                    180                 185                 190

Thr Glu Tyr Val Asn Asn Gly Leu Pro Pro Ile Gln Asn Thr Arg Asn
                    195                 200                 205

Val Val Pro Leu Ala Leu Ser Ser Arg Ser Ile Val Ala Arg Arg Ala
            210                 215                 220

Ala Val Asn Glu Asp Ile Val Ile Ser Lys Thr Ser Leu Trp Lys Glu
225                 230                 235                 240

Met Gln Tyr Asn Arg Asp Ile Ile Ile Arg Phe Lys Phe Ala Asn Ser
                    245                 250                 255

Ile Ile Lys Ser Gly Gly Leu Gly Tyr Lys Trp Ser Glu Ile Ser Phe
                    260                 265                 270

Lys Pro Ala Asn Tyr Gln Tyr Thr Tyr Ile Arg Asp Gly Glu Glu Val
                    275                 280                 285

Thr Ala His Thr Thr Cys Ser Val Asn Gly Val Asn Asp Phe Asn Tyr
            290                 295                 300

Asn Gly Gly Ser Leu Pro Thr Asp Phe Val Ile Ser Arg Tyr Glu Val
305                 310                 315                 320

Ile Lys Glu Asn Ser Tyr Val Tyr Ile Asp Tyr Trp Asp Asp Ser Gln
                    325                 330                 335

Ala Phe Arg Asn Met Val Tyr Val Arg Ser Leu Ala Ala Asp Leu Asn
                    340                 345                 350

Glu Val Thr Cys Ala Gly Gly Thr Tyr Asn Phe Gln Leu Pro Val
            355                 360                 365

<210> SEQ ID NO 22
<211> LENGTH: 377
<212> TYPE: PRT
<213> ORGANISM: Artificial Sequence
<220> FEATURE:
<223> OTHER INFORMATION: Artificial protein

<400> SEQUENCE: 22

Met Gly Ser Glu Lys Thr Gln Arg Thr Thr Val Asn Pro Gly Pro Phe
1               5                   10                  15

Ala Gln Thr Gly Tyr Ala Pro Val Asn Trp Gly Pro Gly Glu Thr Ser
                20                  25                  30

Asp Ser Thr Thr Val Glu Pro Val Leu Asn Gly Pro Tyr Gln Pro Thr
            35                  40                  45

Thr Phe Asn Pro Pro Val Glu Tyr Trp Met Leu Leu Ala Pro Thr Ser
        50                  55                  60

Glu Gly Val Val Glu Gly Thr Asn Gly Thr Asp Arg Trp Leu Ala
65                  70                  75                  80

Thr Ile Leu Ile Glu Pro Asn Val Pro Glu Thr Thr Arg Asn Tyr Thr
                85                  90                  95

Leu Phe Gly Glu Thr Ala Ser Ile Ser Val Ala Asn Pro Ser Gln Ser
                100                 105                 110

Lys Trp Arg Phe Val Asp Val Ala Lys Thr Thr Ala Asn Gly Thr Tyr
            115                 120                 125

Ser Gln Tyr Gly Pro Leu Leu Ser Asp Thr Lys Leu Tyr Gly Val Met
        130                 135                 140

Lys Tyr Asn Gly Lys Leu Tyr Thr Tyr Asn Gly Glu Thr Pro Asn Ala
```

```
             145                 150                 155                 160
        Thr Thr Asn Tyr Tyr Ser Thr Thr Asn Tyr Asp Ser Val Asn Met Thr
                         165                 170                 175

Ser Tyr Cys Asp Phe Tyr Ile Ile Pro Arg Ala Gln Glu Ser Lys Cys
                         180                 185                 190

Thr Glu Tyr Val Asn Asn Gly Leu Pro Pro Ile Gln Asn Thr Arg Asn
                         195                 200                 205

Val Val Pro Leu Ala Leu Ser Ser Arg Ser Ile Val Ala Arg Arg Ala
                 210                 215                 220

Ala Val Asn Glu Asp Ile Val Ile Ser Lys Thr Ser Leu Trp Lys Glu
        225                 230                 235                 240

Met Gln Tyr Asn Arg Asp Ile Ile Arg Phe Lys Phe Ala Asn Ser
                         245                 250                 255

Ile Ile Lys Ser Gly Gly Leu Gly Tyr Lys Trp Ser Glu Ile Ser Phe
                         260                 265                 270

Lys Pro Ala Asn Tyr Gln Tyr Thr Tyr Ile Arg Asp Gly Glu Glu Val
                         275                 280                 285

Thr Ala His Thr Thr Cys Ser Val Asn Gly Val Asn Asp Phe Asn Tyr
                 290                 295                 300

Asn Gly Gly Ser Leu Pro Thr Asp Phe Val Ile Ser Arg Tyr Glu Val
        305                 310                 315                 320

Ile Lys Glu Asn Ser Tyr Val Tyr Ile Asp Tyr Trp Asp Asp Ser Gln
                         325                 330                 335

Ala Phe Arg Asn Met Val Tyr Val Arg Ser Leu Ala Ala Asp Leu Asn
                         340                 345                 350

Glu Val Thr Cys Ala Gly Gly Thr Tyr Asn Phe Gln Leu Pro Val Gly
                     355                 360                 365

Gln Trp Pro Val Met Ser Gly Gly Ser
                370                 375

<210> SEQ ID NO 23
<211> LENGTH: 387
<212> TYPE: PRT
<213> ORGANISM: Artificial Sequence
<220> FEATURE:
<223> OTHER INFORMATION: Artificial protein

<400> SEQUENCE: 23

Met Gly Ser Glu Lys Thr Gln Arg Thr Thr Val Asn Pro Gly Pro Phe
1               5                   10                  15

Ala Gln Thr Gly Tyr Ala Pro Val Asn Trp Gly Pro Gly Glu Thr Ser
                20                  25                  30

Asp Ser Thr Thr Val Glu Pro Val Leu Asn Gly Pro Tyr Gln Pro Thr
            35                  40                  45

Thr Phe Asn Pro Pro Val Glu Tyr Trp Met Leu Leu Ala Pro Thr Ser
        50                  55                  60

Glu Gly Val Val Val Glu Gly Thr Asn Gly Thr Asp Arg Trp Leu Ala
65                  70                  75                  80

Thr Ile Leu Ile Glu Pro Asn Val Pro Glu Thr Thr Arg Asn Tyr Thr
                85                  90                  95

Leu Phe Gly Glu Thr Ala Ser Ile Ser Val Ala Asn Pro Ser Gln Ser
                100                 105                 110

Lys Trp Arg Phe Val Asp Val Ala Lys Thr Thr Ala Asn Gly Thr Tyr
            115                 120                 125

Ser Gln Tyr Gly Pro Leu Leu Ser Asp Thr Lys Leu Tyr Gly Val Met
```

```
                130                 135                 140
Lys Tyr Asn Gly Lys Leu Tyr Thr Tyr Asn Gly Glu Thr Pro Asn Ala
145                 150                 155                 160

Thr Thr Asn Tyr Tyr Ser Thr Thr Asn Tyr Asp Ser Val Asn Met Thr
                165                 170                 175

Ser Tyr Cys Asp Phe Tyr Ile Ile Pro Arg Ala Gln Glu Ser Lys Cys
            180                 185                 190

Thr Glu Tyr Val Asn Asn Gly Leu Pro Pro Ile Gln Asn Thr Arg Asn
        195                 200                 205

Val Val Pro Leu Ala Leu Ser Ser Arg Ser Ile Val Ala Arg Arg Ala
    210                 215                 220

Ala Val Asn Glu Asp Ile Val Ile Ser Lys Thr Ser Leu Trp Lys Glu
225                 230                 235                 240

Met Gln Tyr Asn Arg Asp Ile Ile Ile Arg Phe Lys Phe Ala Asn Ser
                245                 250                 255

Ile Ile Lys Ser Gly Gly Leu Gly Tyr Lys Trp Ser Glu Ile Ser Phe
            260                 265                 270

Lys Pro Ala Asn Tyr Gln Tyr Thr Tyr Ile Arg Asp Gly Glu Glu Val
        275                 280                 285

Thr Ala His Thr Thr Cys Ser Val Asn Gly Val Asn Asp Phe Asn Tyr
    290                 295                 300

Asn Gly Gly Ser Leu Pro Thr Asp Phe Val Ile Ser Arg Tyr Glu Val
305                 310                 315                 320

Ile Lys Glu Asn Ser Tyr Val Tyr Ile Asp Tyr Trp Asp Asp Ser Gln
                325                 330                 335

Ala Phe Arg Asn Met Val Tyr Val Arg Ser Leu Ala Ala Asp Leu Asn
            340                 345                 350

Glu Val Thr Cys Ala Gly Gly Thr Tyr Asn Phe Gln Leu Pro Val Gly
        355                 360                 365

Gln Trp Pro Val Met Ser Gly Ser Val Ser Leu Arg Ser Ala Gly
370                 375                 380

Val Thr Leu
385

<210> SEQ ID NO 24
<211> LENGTH: 397
<212> TYPE: PRT
<213> ORGANISM: Artificial Sequence
<220> FEATURE:
<223> OTHER INFORMATION: Artificial protein

<400> SEQUENCE: 24

Met Gly Ser Glu Lys Thr Gln Arg Thr Thr Val Asn Pro Gly Pro Phe
1               5                   10                  15

Ala Gln Thr Gly Tyr Ala Pro Val Asn Trp Gly Pro Gly Glu Thr Ser
            20                  25                  30

Asp Ser Thr Thr Val Glu Pro Val Leu Asn Gly Pro Tyr Gln Pro Thr
        35                  40                  45

Thr Phe Asn Pro Pro Val Glu Tyr Trp Met Leu Leu Ala Pro Thr Ser
    50                  55                  60

Glu Gly Val Val Val Glu Gly Thr Asn Gly Thr Asp Arg Trp Leu Ala
65                  70                  75                  80

Thr Ile Leu Ile Glu Pro Asn Val Pro Glu Thr Thr Arg Asn Tyr Thr
                85                  90                  95

Leu Phe Gly Glu Thr Ala Ser Ile Ser Val Ala Asn Pro Ser Gln Ser
```

```
                100             105             110
Lys Trp Arg Phe Val Asp Val Ala Lys Thr Thr Ala Asn Gly Thr Tyr
            115                 120                 125

Ser Gln Tyr Gly Pro Leu Leu Ser Asp Thr Lys Leu Tyr Gly Val Met
            130                 135                 140

Lys Tyr Asn Gly Lys Leu Tyr Thr Tyr Asn Gly Glu Thr Pro Asn Ala
145                 150                 155                 160

Thr Thr Asn Tyr Tyr Ser Thr Thr Asn Tyr Asp Ser Val Asn Met Thr
                165                 170                 175

Ser Tyr Cys Asp Phe Tyr Ile Ile Pro Arg Ala Gln Glu Ser Lys Cys
            180                 185                 190

Thr Glu Tyr Val Asn Asn Gly Leu Pro Pro Ile Gln Asn Thr Arg Asn
            195                 200                 205

Val Val Pro Leu Ala Leu Ser Ser Arg Ser Ile Val Ala Arg Arg Ala
210                 215                 220

Ala Val Asn Glu Asp Ile Val Ile Ser Lys Thr Ser Leu Trp Lys Glu
225                 230                 235                 240

Met Gln Tyr Asn Arg Asp Ile Ile Ile Arg Phe Lys Phe Ala Asn Ser
                245                 250                 255

Ile Ile Lys Ser Gly Gly Leu Gly Tyr Lys Trp Ser Glu Ile Ser Phe
            260                 265                 270

Lys Pro Ala Asn Tyr Gln Tyr Thr Tyr Ile Arg Asp Gly Glu Glu Val
            275                 280                 285

Thr Ala His Thr Thr Cys Ser Val Asn Gly Val Asn Asp Phe Asn Tyr
            290                 295                 300

Asn Gly Gly Ser Leu Pro Thr Asp Phe Val Ile Ser Arg Tyr Glu Val
305                 310                 315                 320

Ile Lys Glu Asn Ser Tyr Val Tyr Ile Asp Tyr Trp Asp Asp Ser Gln
                325                 330                 335

Ala Phe Arg Asn Met Val Tyr Val Arg Ser Leu Ala Ala Asp Leu Asn
            340                 345                 350

Glu Val Thr Cys Ala Gly Gly Thr Tyr Asn Phe Gln Leu Pro Val Gly
            355                 360                 365

Gln Trp Pro Val Met Ser Gly Gly Ser Val Ser Leu Arg Ser Ala Gly
            370                 375                 380

Val Thr Leu Ser Thr Gln Phe Thr Asp Phe Val Ser Leu
385                 390                 395

<210> SEQ ID NO 25
<211> LENGTH: 407
<212> TYPE: PRT
<213> ORGANISM: Artificial Sequence
<220> FEATURE:
<223> OTHER INFORMATION: Artificial protein

<400> SEQUENCE: 25

Met Gly Ser Glu Lys Thr Gln Arg Thr Thr Val Asn Pro Gly Pro Phe
1               5                   10                  15

Ala Gln Thr Gly Tyr Ala Pro Val Asn Trp Gly Pro Gly Glu Thr Ser
            20                  25                  30

Asp Ser Thr Thr Val Glu Pro Val Leu Asn Gly Pro Tyr Gln Pro Thr
            35                  40                  45

Thr Phe Asn Pro Pro Val Glu Tyr Trp Met Leu Leu Ala Pro Thr Ser
        50                  55                  60

Glu Gly Val Val Val Glu Gly Thr Asn Gly Thr Asp Arg Trp Leu Ala
```

```
            65                  70                  75                  80
Thr Ile Leu Ile Glu Pro Asn Val Pro Glu Thr Thr Arg Asn Tyr Thr
                85                  90                  95

Leu Phe Gly Glu Thr Ala Ser Ile Ser Val Ala Asn Pro Ser Gln Ser
            100                 105                 110

Lys Trp Arg Phe Val Asp Val Ala Lys Thr Thr Ala Asn Gly Thr Tyr
            115                 120                 125

Ser Gln Tyr Gly Pro Leu Leu Ser Asp Thr Lys Leu Tyr Gly Val Met
            130                 135                 140

Lys Tyr Asn Gly Lys Leu Tyr Thr Tyr Asn Gly Glu Thr Pro Asn Ala
145                 150                 155                 160

Thr Thr Asn Tyr Tyr Ser Thr Thr Asn Tyr Asp Ser Val Asn Met Thr
                165                 170                 175

Ser Tyr Cys Asp Phe Tyr Ile Ile Pro Arg Ala Gln Glu Ser Lys Cys
            180                 185                 190

Thr Glu Tyr Val Asn Asn Gly Leu Pro Pro Ile Gln Asn Thr Arg Asn
            195                 200                 205

Val Val Pro Leu Ala Leu Ser Ser Arg Ser Ile Val Ala Arg Arg Ala
            210                 215                 220

Ala Val Asn Glu Asp Ile Val Ile Ser Lys Thr Ser Leu Trp Lys Glu
225                 230                 235                 240

Met Gln Tyr Asn Arg Asp Ile Ile Arg Phe Lys Phe Ala Asn Ser
                245                 250                 255

Ile Ile Lys Ser Gly Gly Leu Gly Tyr Lys Trp Ser Glu Ile Ser Phe
            260                 265                 270

Lys Pro Ala Asn Tyr Gln Tyr Thr Tyr Ile Arg Asp Gly Glu Glu Val
            275                 280                 285

Thr Ala His Thr Thr Cys Ser Val Asn Gly Val Asn Asp Phe Asn Tyr
            290                 295                 300

Asn Gly Gly Ser Leu Pro Thr Asp Phe Val Ile Ser Arg Tyr Glu Val
305                 310                 315                 320

Ile Lys Glu Asn Ser Tyr Val Tyr Ile Asp Tyr Trp Asp Asp Ser Gln
                325                 330                 335

Ala Phe Arg Asn Met Val Tyr Val Arg Ser Leu Ala Ala Asp Leu Asn
            340                 345                 350

Glu Val Thr Cys Ala Gly Gly Tyr Asn Phe Gln Leu Pro Val Gly
            355                 360                 365

Gln Trp Pro Val Met Ser Gly Ser Val Ser Leu Arg Ser Ala Gly
370                 375                 380

Val Thr Leu Ser Thr Gln Phe Thr Asp Phe Val Ser Leu Asn Ser Leu
385                 390                 395                 400

Arg Phe Arg Phe Ser Leu Ala
                405

<210> SEQ ID NO 26
<211> LENGTH: 417
<212> TYPE: PRT
<213> ORGANISM: Artificial Sequence
<220> FEATURE:
<223> OTHER INFORMATION: Artificial protein

<400> SEQUENCE: 26

Met Gly Ser Glu Lys Thr Gln Arg Thr Thr Val Asn Pro Gly Pro Phe
1               5                   10                  15

Ala Gln Thr Gly Tyr Ala Pro Val Asn Trp Gly Pro Gly Glu Thr Ser
```

-continued

```
                20                  25                  30
Asp Ser Thr Thr Val Glu Pro Val Leu Asn Gly Pro Tyr Gln Pro Thr
                35                  40                  45
Thr Phe Asn Pro Pro Val Glu Tyr Trp Met Leu Leu Ala Pro Thr Ser
     50                  55                  60
Glu Gly Val Val Val Glu Gly Thr Asn Gly Thr Asp Arg Trp Leu Ala
 65                  70                  75                  80
Thr Ile Leu Ile Glu Pro Asn Val Pro Glu Thr Thr Arg Asn Tyr Thr
                 85                  90                  95
Leu Phe Gly Glu Thr Ala Ser Ile Ser Val Ala Asn Pro Ser Gln Ser
                100                 105                 110
Lys Trp Arg Phe Val Asp Val Ala Lys Thr Thr Ala Asn Gly Thr Tyr
                115                 120                 125
Ser Gln Tyr Gly Pro Leu Leu Ser Asp Thr Lys Leu Tyr Gly Val Met
                130                 135                 140
Lys Tyr Asn Gly Lys Leu Tyr Thr Tyr Asn Gly Glu Thr Pro Asn Ala
145                 150                 155                 160
Thr Thr Asn Tyr Tyr Ser Thr Thr Asn Tyr Asp Ser Val Asn Met Thr
                    165                 170                 175
Ser Tyr Cys Asp Phe Tyr Ile Ile Pro Arg Ala Gln Glu Ser Lys Cys
                180                 185                 190
Thr Glu Tyr Val Asn Asn Gly Leu Pro Pro Ile Gln Asn Thr Arg Asn
                195                 200                 205
Val Val Pro Leu Ala Leu Ser Ser Arg Ser Ile Val Ala Arg Arg Ala
                210                 215                 220
Ala Val Asn Glu Asp Ile Val Ile Ser Lys Thr Ser Leu Trp Lys Glu
225                 230                 235                 240
Met Gln Tyr Asn Arg Asp Ile Ile Ile Arg Phe Lys Phe Ala Asn Ser
                    245                 250                 255
Ile Ile Lys Ser Gly Gly Leu Gly Tyr Lys Trp Ser Glu Ile Ser Phe
                260                 265                 270
Lys Pro Ala Asn Tyr Gln Tyr Thr Tyr Ile Arg Asp Gly Glu Glu Val
                275                 280                 285
Thr Ala His Thr Thr Cys Ser Val Asn Gly Val Asn Asp Phe Asn Tyr
                290                 295                 300
Asn Gly Gly Ser Leu Pro Thr Asp Phe Val Ile Ser Arg Tyr Glu Val
305                 310                 315                 320
Ile Lys Glu Asn Ser Tyr Val Tyr Ile Asp Tyr Trp Asp Asp Ser Gln
                    325                 330                 335
Ala Phe Arg Asn Met Val Tyr Val Arg Ser Leu Ala Ala Asp Leu Asn
                340                 345                 350
Glu Val Thr Cys Ala Gly Gly Thr Tyr Asn Phe Gln Leu Pro Val Gly
                355                 360                 365
Gln Trp Pro Val Met Ser Gly Gly Ser Val Ser Leu Arg Ser Ala Gly
                370                 375                 380
Val Thr Leu Ser Thr Gln Phe Thr Asp Phe Val Ser Leu Asn Ser Leu
385                 390                 395                 400
Arg Phe Arg Phe Ser Leu Ala Val Glu Glu Pro Pro Phe Ser Ile Ser
                    405                 410                 415
Arg
```

<210> SEQ ID NO 27
<211> LENGTH: 427

```
<212> TYPE: PRT
<213> ORGANISM: Artificial Sequence
<220> FEATURE:
<223> OTHER INFORMATION: Artificial protein

<400> SEQUENCE: 27
```

| | | | | | | | | | | | | | | |
|---|---|---|---|---|---|---|---|---|---|---|---|---|---|---|
| Met | Gly | Ser | Glu | Lys | Thr | Gln | Arg | Thr | Thr | Val | Asn | Pro | Gly | Pro | Phe |
| 1 | | | | 5 | | | | | 10 | | | | | 15 | |
| Ala | Gln | Thr | Gly | Tyr | Ala | Pro | Val | Asn | Trp | Gly | Pro | Gly | Glu | Thr | Ser |
| | | | 20 | | | | | 25 | | | | | 30 | | |
| Asp | Ser | Thr | Thr | Val | Glu | Pro | Val | Leu | Asn | Gly | Pro | Tyr | Gln | Pro | Thr |
| | | | 35 | | | | | 40 | | | | | 45 | | |
| Thr | Phe | Asn | Pro | Pro | Val | Glu | Tyr | Trp | Met | Leu | Leu | Ala | Pro | Thr | Ser |
| | 50 | | | | | 55 | | | | | 60 | | | | |
| Glu | Gly | Val | Val | Val | Glu | Gly | Thr | Asn | Gly | Thr | Asp | Arg | Trp | Leu | Ala |
| 65 | | | | | 70 | | | | | 75 | | | | | 80 |
| Thr | Ile | Leu | Ile | Glu | Pro | Asn | Val | Pro | Glu | Thr | Thr | Arg | Asn | Tyr | Thr |
| | | | | 85 | | | | | 90 | | | | | 95 | |
| Leu | Phe | Gly | Glu | Thr | Ala | Ser | Ile | Ser | Val | Ala | Asn | Pro | Ser | Gln | Ser |
| | | | 100 | | | | | 105 | | | | | 110 | | |
| Lys | Trp | Arg | Phe | Val | Asp | Val | Ala | Lys | Thr | Thr | Ala | Asn | Gly | Thr | Tyr |
| | | | 115 | | | | | 120 | | | | | 125 | | |
| Ser | Gln | Tyr | Gly | Pro | Leu | Leu | Ser | Asp | Thr | Lys | Leu | Tyr | Gly | Val | Met |
| | 130 | | | | | 135 | | | | | 140 | | | | |
| Lys | Tyr | Asn | Gly | Lys | Leu | Tyr | Thr | Tyr | Asn | Gly | Glu | Thr | Pro | Asn | Ala |
| 145 | | | | | 150 | | | | | 155 | | | | | 160 |
| Thr | Thr | Asn | Tyr | Tyr | Ser | Thr | Thr | Asn | Tyr | Asp | Ser | Val | Asn | Met | Thr |
| | | | | 165 | | | | | 170 | | | | | 175 | |
| Ser | Tyr | Cys | Asp | Phe | Tyr | Ile | Ile | Pro | Arg | Ala | Gln | Glu | Ser | Lys | Cys |
| | | | 180 | | | | | 185 | | | | | 190 | | |
| Thr | Glu | Tyr | Val | Asn | Asn | Gly | Leu | Pro | Pro | Ile | Gln | Asn | Thr | Arg | Asn |
| | | | 195 | | | | | 200 | | | | | 205 | | |
| Val | Val | Pro | Leu | Ala | Leu | Ser | Ser | Arg | Ser | Ile | Val | Ala | Arg | Arg | Ala |
| | 210 | | | | | 215 | | | | | 220 | | | | |
| Ala | Val | Asn | Glu | Asp | Ile | Val | Ile | Ser | Lys | Thr | Ser | Leu | Trp | Lys | Glu |
| 225 | | | | | 230 | | | | | 235 | | | | | 240 |
| Met | Gln | Tyr | Asn | Arg | Asp | Ile | Ile | Ile | Arg | Phe | Lys | Phe | Ala | Asn | Ser |
| | | | | 245 | | | | | 250 | | | | | 255 | |
| Ile | Ile | Lys | Ser | Gly | Gly | Leu | Gly | Tyr | Lys | Trp | Ser | Glu | Ile | Ser | Phe |
| | | | 260 | | | | | 265 | | | | | 270 | | |
| Lys | Pro | Ala | Asn | Tyr | Gln | Tyr | Thr | Tyr | Ile | Arg | Asp | Gly | Glu | Glu | Val |
| | | | 275 | | | | | 280 | | | | | 285 | | |
| Thr | Ala | His | Thr | Thr | Cys | Ser | Val | Asn | Gly | Val | Asn | Asp | Phe | Asn | Tyr |
| | 290 | | | | | 295 | | | | | 300 | | | | |
| Asn | Gly | Gly | Ser | Leu | Pro | Thr | Asp | Phe | Val | Ile | Ser | Arg | Tyr | Glu | Val |
| 305 | | | | | 310 | | | | | 315 | | | | | 320 |
| Ile | Lys | Glu | Asn | Ser | Tyr | Val | Tyr | Ile | Asp | Tyr | Trp | Asp | Asp | Ser | Gln |
| | | | | 325 | | | | | 330 | | | | | 335 | |
| Ala | Phe | Arg | Asn | Met | Val | Tyr | Val | Arg | Ser | Leu | Ala | Ala | Asp | Leu | Asn |
| | | | 340 | | | | | 345 | | | | | 350 | | |
| Glu | Val | Thr | Cys | Ala | Gly | Gly | Thr | Tyr | Asn | Phe | Gln | Leu | Pro | Val | Gly |
| | | | 355 | | | | | 360 | | | | | 365 | | |
| Gln | Trp | Pro | Val | Met | Ser | Gly | Gly | Ser | Val | Ser | Leu | Arg | Ser | Ala | Gly |
| | 370 | | | | | 375 | | | | | 380 | | | | |

```
Val Thr Leu Ser Thr Gln Phe Thr Asp Phe Val Ser Leu Asn Ser Leu
385                 390                 395                 400

Arg Phe Arg Phe Ser Leu Ala Val Glu Glu Pro Pro Phe Ser Ile Ser
            405                 410                 415

Arg Thr Arg Ile Ser Gly Leu Tyr Gly Leu Pro
            420                 425

<210> SEQ ID NO 28
<211> LENGTH: 437
<212> TYPE: PRT
<213> ORGANISM: Artificial Sequence
<220> FEATURE:
<223> OTHER INFORMATION: Artificial protein

<400> SEQUENCE: 28

Met Gly Ser Glu Lys Thr Gln Arg Thr Thr Val Asn Pro Gly Pro Phe
1               5                   10                  15

Ala Gln Thr Gly Tyr Ala Pro Val Asn Trp Gly Pro Gly Glu Thr Ser
                20                  25                  30

Asp Ser Thr Thr Val Glu Pro Val Leu Asn Gly Pro Tyr Gln Pro Thr
            35                  40                  45

Thr Phe Asn Pro Pro Val Glu Tyr Trp Met Leu Leu Ala Pro Thr Ser
    50                  55                  60

Glu Gly Val Val Glu Gly Thr Asn Gly Thr Asp Arg Trp Leu Ala
65                  70                  75                  80

Thr Ile Leu Ile Glu Pro Asn Val Pro Glu Thr Thr Arg Asn Tyr Thr
                85                  90                  95

Leu Phe Gly Glu Thr Ala Ser Ile Ser Val Ala Asn Pro Ser Gln Ser
            100                 105                 110

Lys Trp Arg Phe Val Asp Val Ala Lys Thr Thr Ala Asn Gly Thr Tyr
        115                 120                 125

Ser Gln Tyr Gly Pro Leu Leu Ser Asp Thr Lys Leu Tyr Gly Val Met
130                 135                 140

Lys Tyr Asn Gly Lys Leu Tyr Thr Tyr Asn Gly Glu Thr Pro Asn Ala
145                 150                 155                 160

Thr Thr Asn Tyr Tyr Ser Thr Thr Asn Tyr Asp Ser Val Asn Met Thr
                165                 170                 175

Ser Tyr Cys Asp Phe Tyr Ile Ile Pro Arg Ala Gln Glu Ser Lys Cys
            180                 185                 190

Thr Glu Tyr Val Asn Asn Gly Leu Pro Pro Ile Gln Asn Thr Arg Asn
        195                 200                 205

Val Val Pro Leu Ala Leu Ser Ser Arg Ser Ile Val Ala Arg Arg Ala
    210                 215                 220

Ala Val Asn Glu Asp Ile Val Ile Ser Lys Thr Ser Leu Trp Lys Glu
225                 230                 235                 240

Met Gln Tyr Asn Arg Asp Ile Ile Arg Phe Lys Phe Ala Asn Ser
                245                 250                 255

Ile Ile Lys Ser Gly Gly Leu Gly Tyr Lys Trp Ser Glu Ile Ser Phe
            260                 265                 270

Lys Pro Ala Asn Tyr Gln Tyr Thr Tyr Ile Arg Asp Gly Glu Glu Val
        275                 280                 285

Thr Ala His Thr Thr Cys Ser Val Asn Gly Val Asn Asp Phe Asn Tyr
    290                 295                 300

Asn Gly Gly Ser Leu Pro Thr Asp Phe Val Ile Ser Arg Tyr Glu Val
305                 310                 315                 320
```

```
Ile Lys Glu Asn Ser Tyr Val Tyr Ile Asp Tyr Trp Asp Asp Ser Gln
            325                 330                 335

Ala Phe Arg Asn Met Val Tyr Val Arg Ser Leu Ala Ala Asp Leu Asn
            340                 345                 350

Glu Val Thr Cys Ala Gly Gly Thr Tyr Asn Phe Gln Leu Pro Val Gly
            355                 360                 365

Gln Trp Pro Val Met Ser Gly Ser Val Ser Leu Arg Ser Ala Gly
        370                 375                 380

Val Thr Leu Ser Thr Gln Phe Thr Asp Phe Val Ser Leu Asn Ser Leu
385                 390                 395                 400

Arg Phe Arg Phe Ser Leu Ala Val Glu Glu Pro Pro Phe Ser Ile Ser
                405                 410                 415

Arg Thr Arg Ile Ser Gly Leu Tyr Gly Leu Pro Ala Ala Asn Pro Asn
            420                 425                 430

Asn Gly Arg Asp Phe
        435

<210> SEQ ID NO 29
<211> LENGTH: 447
<212> TYPE: PRT
<213> ORGANISM: Artificial Sequence
<220> FEATURE:
<223> OTHER INFORMATION: Artificial protein

<400> SEQUENCE: 29

Met Gly Ser Glu Lys Thr Gln Arg Thr Thr Val Asn Pro Gly Pro Phe
1               5                   10                  15

Ala Gln Thr Gly Tyr Ala Pro Val Asn Trp Gly Pro Gly Glu Thr Ser
            20                  25                  30

Asp Ser Thr Thr Val Glu Pro Val Leu Asn Gly Pro Tyr Gln Pro Thr
        35                  40                  45

Thr Phe Asn Pro Pro Val Glu Tyr Trp Met Leu Leu Ala Pro Thr Ser
    50                  55                  60

Glu Gly Val Val Val Glu Gly Thr Asn Gly Thr Asp Arg Trp Leu Ala
65                  70                  75                  80

Thr Ile Leu Ile Glu Pro Asn Val Pro Glu Thr Thr Arg Asn Tyr Thr
                85                  90                  95

Leu Phe Gly Glu Thr Ala Ser Ile Ser Val Ala Asn Pro Ser Gln Ser
            100                 105                 110

Lys Trp Arg Phe Val Asp Val Ala Lys Thr Thr Ala Asn Gly Thr Tyr
        115                 120                 125

Ser Gln Tyr Gly Pro Leu Leu Ser Asp Thr Lys Leu Tyr Gly Val Met
    130                 135                 140

Lys Tyr Asn Gly Lys Leu Tyr Thr Tyr Asn Gly Glu Thr Pro Asn Ala
145                 150                 155                 160

Thr Thr Asn Tyr Tyr Ser Thr Thr Asn Tyr Asp Ser Val Asn Met Thr
                165                 170                 175

Ser Tyr Cys Asp Phe Tyr Ile Ile Pro Arg Ala Gln Glu Ser Lys Cys
            180                 185                 190

Thr Glu Tyr Val Asn Asn Gly Leu Pro Pro Ile Gln Asn Thr Arg Asn
        195                 200                 205

Val Val Pro Leu Ala Leu Ser Ser Arg Ser Ile Val Ala Arg Arg Ala
    210                 215                 220

Ala Val Asn Glu Asp Ile Val Ile Ser Lys Thr Ser Leu Trp Lys Glu
225                 230                 235                 240
```

-continued

```
Met Gln Tyr Asn Arg Asp Ile Ile Arg Phe Lys Phe Ala Asn Ser
            245                 250                 255

Ile Ile Lys Ser Gly Gly Leu Gly Tyr Lys Trp Ser Glu Ile Ser Phe
        260                 265                 270

Lys Pro Ala Asn Tyr Gln Tyr Thr Tyr Ile Arg Asp Gly Glu Glu Val
            275                 280                 285

Thr Ala His Thr Thr Cys Ser Val Asn Gly Val Asn Asp Phe Asn Tyr
        290                 295                 300

Asn Gly Gly Ser Leu Pro Thr Asp Phe Val Ile Ser Arg Tyr Glu Val
305                 310                 315                 320

Ile Lys Glu Asn Ser Tyr Val Tyr Ile Asp Tyr Trp Asp Asp Ser Gln
            325                 330                 335

Ala Phe Arg Asn Met Val Tyr Val Arg Ser Leu Ala Ala Asp Leu Asn
            340                 345                 350

Glu Val Thr Cys Ala Gly Gly Thr Tyr Asn Phe Gln Leu Pro Val Gly
            355                 360                 365

Gln Trp Pro Val Met Ser Gly Ser Val Ser Leu Arg Ser Ala Gly
            370                 375                 380

Val Thr Leu Ser Thr Gln Phe Thr Asp Phe Val Ser Leu Asn Ser Leu
385                 390                 395                 400

Arg Phe Arg Phe Ser Leu Ala Val Glu Glu Pro Pro Phe Ser Ile Ser
            405                 410                 415

Arg Thr Arg Ile Ser Gly Leu Tyr Gly Leu Pro Ala Ala Asn Pro Asn
            420                 425                 430

Asn Gly Arg Asp Phe Tyr Glu Ile Ala Gly Arg Phe Ser Leu Ile
            435                 440                 445
```

<210> SEQ ID NO 30
<211> LENGTH: 452
<212> TYPE: PRT
<213> ORGANISM: Artificial Sequence
<220> FEATURE:
<223> OTHER INFORMATION: Artificial protein

<400> SEQUENCE: 30

```
Met Gly Ser Glu Lys Thr Gln Arg Thr Thr Val Asn Pro Gly Pro Phe
1               5                   10                  15

Ala Gln Thr Gly Tyr Ala Pro Val Asn Trp Gly Pro Gly Glu Thr Ser
            20                  25                  30

Asp Ser Thr Thr Val Glu Pro Val Leu Asn Gly Pro Tyr Gln Pro Thr
        35                  40                  45

Thr Phe Asn Pro Pro Val Glu Tyr Trp Met Leu Leu Ala Pro Thr Ser
    50                  55                  60

Glu Gly Val Val Val Glu Gly Thr Asn Gly Thr Asp Arg Trp Leu Ala
65                  70                  75                  80

Thr Ile Leu Ile Glu Pro Asn Val Pro Glu Thr Thr Arg Asn Tyr Thr
                85                  90                  95

Leu Phe Gly Glu Thr Ala Ser Ile Ser Val Ala Asn Pro Ser Gln Ser
            100                 105                 110

Lys Trp Arg Phe Val Asp Val Ala Lys Thr Thr Ala Asn Gly Thr Tyr
        115                 120                 125

Ser Gln Tyr Gly Pro Leu Leu Ser Asp Thr Lys Leu Tyr Gly Val Met
    130                 135                 140

Lys Tyr Asn Gly Lys Leu Tyr Thr Tyr Asn Gly Glu Thr Pro Asn Ala
145                 150                 155                 160
```

Thr Thr Asn Tyr Tyr Ser Thr Thr Asn Tyr Asp Ser Val Asn Met Thr
            165                 170                 175

Ser Tyr Cys Asp Phe Tyr Ile Ile Pro Arg Ala Gln Glu Ser Lys Cys
        180                 185                 190

Thr Glu Tyr Val Asn Asn Gly Leu Pro Pro Ile Gln Asn Thr Arg Asn
            195                 200                 205

Val Val Pro Leu Ala Leu Ser Ser Arg Ser Ile Val Ala Arg Arg Ala
210                 215                 220

Ala Val Asn Glu Asp Ile Val Ile Ser Lys Thr Ser Leu Trp Lys Glu
225                 230                 235                 240

Met Gln Tyr Asn Arg Asp Ile Ile Arg Phe Lys Phe Ala Asn Ser
            245                 250                 255

Ile Ile Lys Ser Gly Gly Leu Gly Tyr Lys Trp Ser Glu Ile Ser Phe
            260                 265                 270

Lys Pro Ala Asn Tyr Gln Tyr Thr Tyr Ile Arg Asp Gly Glu Glu Val
            275                 280                 285

Thr Ala His Thr Thr Cys Ser Val Asn Gly Val Asn Asp Phe Asn Tyr
            290                 295                 300

Asn Gly Gly Ser Leu Pro Thr Asp Phe Val Ile Ser Arg Tyr Glu Val
305                 310                 315                 320

Ile Lys Glu Asn Ser Tyr Val Tyr Ile Asp Tyr Trp Asp Ser Gln
            325                 330                 335

Ala Phe Arg Asn Met Val Tyr Val Arg Ser Leu Ala Ala Asp Leu Asn
            340                 345                 350

Glu Val Thr Cys Ala Gly Gly Thr Tyr Asn Phe Gln Leu Pro Val Gly
            355                 360                 365

Gln Trp Pro Val Met Ser Gly Gly Ser Val Ser Leu Arg Ser Ala Gly
            370                 375                 380

Val Thr Leu Ser Thr Gln Phe Thr Asp Phe Val Ser Leu Asn Ser Leu
385                 390                 395                 400

Arg Phe Arg Phe Ser Leu Ala Val Glu Glu Pro Pro Phe Ser Ile Ser
            405                 410                 415

Arg Thr Arg Ile Ser Gly Leu Tyr Gly Leu Pro Ala Ala Asn Pro Asn
            420                 425                 430

Asn Gly Arg Asp Phe Tyr Glu Ile Ala Gly Arg Phe Ser Leu Ile Leu
            435                 440                 445

Leu Val Pro Ser
    450

<210> SEQ ID NO 31
<211> LENGTH: 458
<212> TYPE: PRT
<213> ORGANISM: Artificial Sequence
<220> FEATURE:
<223> OTHER INFORMATION: Artificial protein

<400> SEQUENCE: 31

Met Gly Ser Glu Lys Thr Gln Arg Thr Thr Val Asn Pro Gly Pro Phe
1               5                   10                  15

Ala Gln Thr Gly Tyr Ala Pro Val Asn Trp Gly Pro Gly Glu Thr Ser
            20                  25                  30

Asp Ser Thr Thr Val Glu Pro Val Leu Asn Gly Pro Tyr Gln Pro Thr
        35                  40                  45

Thr Phe Asn Pro Pro Val Glu Tyr Trp Met Leu Leu Ala Pro Thr Ser
    50                  55                  60

-continued

```
Glu Gly Val Val Val Glu Gly Thr Asn Gly Thr Asp Arg Trp Leu Ala
 65                  70                  75                  80

Thr Ile Leu Ile Glu Pro Asn Val Pro Glu Thr Thr Arg Asn Tyr Thr
                 85                  90                  95

Leu Phe Gly Glu Thr Ala Ser Ile Ser Val Ala Asn Pro Ser Gln Ser
            100                 105                 110

Lys Trp Arg Phe Val Asp Val Ala Lys Thr Thr Ala Asn Gly Thr Tyr
        115                 120                 125

Ser Gln Tyr Gly Pro Leu Leu Ser Asp Thr Lys Leu Tyr Gly Val Met
    130                 135                 140

Lys Tyr Asn Gly Lys Leu Tyr Thr Tyr Asn Gly Glu Thr Pro Asn Ala
145                 150                 155                 160

Thr Thr Asn Tyr Tyr Ser Thr Thr Asn Tyr Asp Ser Val Asn Met Thr
                165                 170                 175

Ser Tyr Cys Asp Phe Tyr Ile Ile Pro Arg Ala Gln Glu Ser Lys Cys
            180                 185                 190

Thr Glu Tyr Val Asn Asn Gly Leu Pro Pro Ile Gln Asn Thr Arg Asn
        195                 200                 205

Val Val Pro Leu Ala Leu Ser Ser Arg Ser Ile Val Ala Arg Arg Ala
210                 215                 220

Ala Val Asn Glu Asp Ile Val Ile Ser Lys Thr Ser Leu Trp Lys Glu
225                 230                 235                 240

Met Gln Tyr Asn Arg Asp Ile Ile Ile Arg Phe Lys Phe Ala Asn Ser
                245                 250                 255

Ile Ile Lys Ser Gly Gly Leu Gly Tyr Lys Trp Ser Glu Ile Ser Phe
            260                 265                 270

Lys Pro Ala Asn Tyr Gln Tyr Thr Tyr Ile Arg Asp Gly Glu Glu Val
        275                 280                 285

Thr Ala His Thr Thr Cys Ser Val Asn Gly Val Asn Asp Phe Asn Tyr
    290                 295                 300

Asn Gly Gly Ser Leu Pro Thr Asp Phe Val Ile Ser Arg Tyr Glu Val
305                 310                 315                 320

Ile Lys Glu Asn Ser Tyr Val Tyr Ile Asp Tyr Trp Asp Asp Ser Gln
                325                 330                 335

Ala Phe Arg Asn Met Val Tyr Val Arg Ser Leu Ala Ala Asp Leu Asn
            340                 345                 350

Glu Val Thr Cys Ala Gly Gly Thr Tyr Asn Phe Gln Leu Pro Val Gly
        355                 360                 365

Gln Trp Pro Val Met Ser Gly Ser Val Ser Leu Arg Ser Ala Gly
    370                 375                 380

Val Thr Leu Ser Thr Gln Phe Thr Asp Phe Val Ser Leu Asn Ser Leu
385                 390                 395                 400

Arg Phe Arg Phe Ser Leu Ala Val Glu Glu Pro Phe Ser Ile Ser
                405                 410                 415

Arg Thr Arg Ile Ser Gly Leu Tyr Gly Leu Pro Ala Ala Asn Pro Asn
            420                 425                 430

Asn Gly Arg Asp Phe Tyr Glu Ile Ala Gly Arg Phe Ser Leu Ile Leu
        435                 440                 445

Leu Val Pro Ser Asn Asp Asp Tyr Gln Thr
    450                 455
```

<210> SEQ ID NO 32
<211> LENGTH: 463
<212> TYPE: PRT

<213> ORGANISM: Artificial Sequence
<220> FEATURE:
<223> OTHER INFORMATION: Artificial protein

<400> SEQUENCE: 32

```
Met Gly Ser Glu Lys Thr Gln Arg Thr Thr Val Asn Pro Gly Pro Phe
1               5                   10                  15

Ala Gln Thr Gly Tyr Ala Pro Val Asn Trp Gly Pro Gly Glu Thr Ser
            20                  25                  30

Asp Ser Thr Thr Val Glu Pro Val Leu Asn Gly Pro Tyr Gln Pro Thr
        35                  40                  45

Thr Phe Asn Pro Pro Val Glu Tyr Trp Met Leu Leu Ala Pro Thr Ser
    50                  55                  60

Glu Gly Val Val Val Glu Gly Thr Asn Gly Thr Asp Arg Trp Leu Ala
65                  70                  75                  80

Thr Ile Leu Ile Glu Pro Asn Val Pro Glu Thr Thr Arg Asn Tyr Thr
                85                  90                  95

Leu Phe Gly Glu Thr Ala Ser Ile Ser Val Ala Asn Pro Ser Gln Ser
            100                 105                 110

Lys Trp Arg Phe Val Asp Val Ala Lys Thr Thr Ala Asn Gly Thr Tyr
        115                 120                 125

Ser Gln Tyr Gly Pro Leu Leu Ser Asp Thr Lys Leu Tyr Gly Val Met
    130                 135                 140

Lys Tyr Asn Gly Lys Leu Tyr Thr Tyr Asn Gly Glu Thr Pro Asn Ala
145                 150                 155                 160

Thr Thr Asn Tyr Tyr Ser Thr Thr Asn Tyr Asp Ser Val Asn Met Thr
                165                 170                 175

Ser Tyr Cys Asp Phe Tyr Ile Ile Pro Arg Ala Gln Glu Ser Lys Cys
            180                 185                 190

Thr Glu Tyr Val Asn Asn Gly Leu Pro Pro Ile Gln Asn Thr Arg Asn
        195                 200                 205

Val Val Pro Leu Ala Leu Ser Ser Arg Ser Ile Val Ala Arg Arg Ala
    210                 215                 220

Ala Val Asn Glu Asp Ile Val Ile Ser Lys Thr Ser Leu Trp Lys Glu
225                 230                 235                 240

Met Gln Tyr Asn Arg Asp Ile Ile Arg Phe Lys Phe Ala Asn Ser
                245                 250                 255

Ile Ile Lys Ser Gly Gly Leu Gly Tyr Lys Trp Ser Glu Ile Ser Phe
            260                 265                 270

Lys Pro Ala Asn Tyr Gln Tyr Thr Tyr Ile Arg Asp Gly Glu Glu Val
        275                 280                 285

Thr Ala His Thr Thr Cys Ser Val Asn Gly Val Asn Asp Phe Asn Tyr
    290                 295                 300

Asn Gly Gly Ser Leu Pro Thr Asp Phe Val Ile Ser Arg Tyr Glu Val
305                 310                 315                 320

Ile Lys Glu Asn Ser Tyr Val Tyr Ile Asp Tyr Trp Asp Asp Ser Gln
                325                 330                 335

Ala Phe Arg Asn Met Val Tyr Val Arg Ser Leu Ala Ala Asp Leu Asn
            340                 345                 350

Glu Val Thr Cys Ala Gly Gly Thr Tyr Asn Phe Gln Leu Pro Val Gly
        355                 360                 365

Gln Trp Pro Val Met Ser Gly Gly Ser Val Ser Leu Arg Ser Ala Gly
    370                 375                 380

Val Thr Leu Ser Thr Gln Phe Thr Asp Phe Val Ser Leu Asn Ser Leu
```

```
                385                 390                 395                 400
Arg Phe Arg Phe Ser Leu Ala Val Glu Glu Pro Pro Phe Ser Ile Ser
                    405                 410                 415

Arg Thr Arg Ile Ser Gly Leu Tyr Gly Leu Pro Ala Ala Asn Pro Asn
                    420                 425                 430

Asn Gly Arg Asp Phe Tyr Glu Ile Ala Gly Arg Phe Ser Leu Ile Leu
                    435                 440                 445

Leu Val Pro Ser Asn Asp Tyr Gln Thr Pro Ile Met Asn Ser
                    450                 455                 460

<210> SEQ ID NO 33
<211> LENGTH: 468
<212> TYPE: PRT
<213> ORGANISM: Artificial Sequence
<220> FEATURE:
<223> OTHER INFORMATION: Artificial protein

<400> SEQUENCE: 33

Met Gly Ser Glu Lys Thr Gln Arg Thr Thr Val Asn Pro Gly Pro Phe
1               5                   10                  15

Ala Gln Thr Gly Tyr Ala Pro Val Asn Trp Gly Pro Gly Glu Thr Ser
                20                  25                  30

Asp Ser Thr Thr Val Glu Pro Val Leu Asn Gly Pro Tyr Gln Pro Thr
            35                  40                  45

Thr Phe Asn Pro Pro Val Glu Tyr Trp Met Leu Leu Ala Pro Thr Ser
        50                  55                  60

Glu Gly Val Val Val Glu Gly Thr Asn Gly Thr Asp Arg Trp Leu Ala
65                  70                  75                  80

Thr Ile Leu Ile Glu Pro Asn Val Pro Glu Thr Thr Arg Asn Tyr Thr
                85                  90                  95

Leu Phe Gly Glu Thr Ala Ser Ile Ser Val Ala Asn Pro Ser Gln Ser
                100                 105                 110

Lys Trp Arg Phe Val Asp Val Ala Lys Thr Thr Ala Asn Gly Thr Tyr
                115                 120                 125

Ser Gln Tyr Gly Pro Leu Leu Ser Asp Thr Lys Leu Tyr Gly Val Met
            130                 135                 140

Lys Tyr Asn Gly Lys Leu Tyr Thr Tyr Asn Gly Glu Thr Pro Asn Ala
145                 150                 155                 160

Thr Thr Asn Tyr Tyr Ser Thr Thr Asn Tyr Asp Ser Val Asn Met Thr
                165                 170                 175

Ser Tyr Cys Asp Phe Tyr Ile Ile Pro Arg Ala Gln Glu Ser Lys Cys
                180                 185                 190

Thr Glu Tyr Val Asn Asn Gly Leu Pro Pro Ile Gln Asn Thr Arg Asn
                195                 200                 205

Val Val Pro Leu Ala Leu Ser Ser Arg Ser Ile Val Ala Arg Arg Ala
            210                 215                 220

Ala Val Asn Glu Asp Ile Val Ile Ser Lys Thr Ser Leu Trp Lys Glu
225                 230                 235                 240

Met Gln Tyr Asn Arg Asp Ile Ile Ile Arg Phe Lys Phe Ala Asn Ser
                245                 250                 255

Ile Ile Lys Ser Gly Gly Leu Gly Tyr Lys Trp Ser Glu Ile Ser Phe
                260                 265                 270

Lys Pro Ala Asn Tyr Gln Tyr Thr Tyr Ile Arg Asp Gly Glu Glu Val
                275                 280                 285

Thr Ala His Thr Thr Cys Ser Val Asn Gly Val Asn Asp Phe Asn Tyr
```

```
                290                 295                 300
Asn Gly Gly Ser Leu Pro Thr Asp Phe Val Ile Ser Arg Tyr Glu Val
305                 310                 315                 320

Ile Lys Glu Asn Ser Tyr Val Tyr Ile Asp Tyr Trp Asp Ser Gln
                325                 330                 335

Ala Phe Arg Asn Met Val Tyr Val Arg Ser Leu Ala Ala Asp Leu Asn
                340                 345                 350

Glu Val Thr Cys Ala Gly Gly Thr Tyr Asn Phe Gln Leu Pro Val Gly
                355                 360                 365

Gln Trp Pro Val Met Ser Gly Gly Ser Val Ser Leu Arg Ser Ala Gly
                370                 375                 380

Val Thr Leu Ser Thr Gln Phe Thr Asp Phe Val Ser Leu Asn Ser Leu
385                 390                 395                 400

Arg Phe Arg Phe Ser Leu Ala Val Glu Glu Pro Pro Phe Ser Ile Ser
                405                 410                 415

Arg Thr Arg Ile Ser Gly Leu Tyr Gly Leu Pro Ala Ala Asn Pro Asn
                420                 425                 430

Asn Gly Arg Asp Phe Tyr Glu Ile Ala Gly Arg Phe Ser Leu Ile Leu
                435                 440                 445

Leu Val Pro Ser Asn Asp Asp Tyr Gln Thr Pro Ile Met Asn Ser Val
                450                 455                 460

Thr Val Arg Gln
465

<210> SEQ ID NO 34
<211> LENGTH: 473
<212> TYPE: PRT
<213> ORGANISM: Artificial Sequence
<220> FEATURE:
<223> OTHER INFORMATION: Artificial protein

<400> SEQUENCE: 34

Met Gly Ser Glu Lys Thr Gln Arg Thr Thr Val Asn Pro Gly Pro Phe
1               5                   10                  15

Ala Gln Thr Gly Tyr Ala Pro Val Asn Trp Gly Pro Gly Glu Thr Ser
                20                  25                  30

Asp Ser Thr Thr Val Glu Pro Val Leu Asn Gly Pro Tyr Gln Pro Thr
                35                  40                  45

Thr Phe Asn Pro Pro Val Glu Tyr Trp Met Leu Leu Ala Pro Thr Ser
            50                  55                  60

Glu Gly Val Val Val Glu Gly Thr Asn Gly Thr Asp Arg Trp Leu Ala
65                  70                  75                  80

Thr Ile Leu Ile Glu Pro Asn Val Pro Glu Thr Thr Arg Asn Tyr Thr
                85                  90                  95

Leu Phe Gly Glu Thr Ala Ser Ile Ser Val Ala Asn Pro Ser Gln Ser
                100                 105                 110

Lys Trp Arg Phe Val Asp Val Ala Lys Thr Thr Ala Asn Gly Thr Tyr
                115                 120                 125

Ser Gln Tyr Gly Pro Leu Leu Ser Asp Thr Lys Leu Tyr Gly Val Met
                130                 135                 140

Lys Tyr Asn Gly Lys Leu Tyr Thr Tyr Asn Gly Glu Thr Pro Asn Ala
145                 150                 155                 160

Thr Thr Asn Tyr Tyr Ser Thr Thr Asn Tyr Asp Ser Val Asn Met Thr
                165                 170                 175

Ser Tyr Cys Asp Phe Tyr Ile Ile Pro Arg Ala Gln Glu Ser Lys Cys
```

```
                180             185             190
Thr Glu Tyr Val Asn Asn Gly Leu Pro Pro Ile Gln Asn Thr Arg Asn
            195                 200                 205
Val Val Pro Leu Ala Leu Ser Ser Arg Ser Ile Val Ala Arg Arg Ala
            210                 215                 220
Ala Val Asn Glu Asp Ile Val Ile Ser Lys Thr Ser Leu Trp Lys Glu
225                 230                 235                 240
Met Gln Tyr Asn Arg Asp Ile Ile Arg Phe Lys Phe Ala Asn Ser
            245                 250                 255
Ile Ile Lys Ser Gly Gly Leu Gly Tyr Lys Trp Ser Glu Ile Ser Phe
            260                 265                 270
Lys Pro Ala Asn Tyr Gln Tyr Thr Tyr Ile Arg Asp Gly Glu Glu Val
            275                 280                 285
Thr Ala His Thr Thr Cys Ser Val Asn Gly Val Asn Asp Phe Asn Tyr
            290                 295                 300
Asn Gly Gly Ser Leu Pro Thr Asp Phe Val Ile Ser Arg Tyr Glu Val
305                 310                 315                 320
Ile Lys Glu Asn Ser Tyr Val Tyr Ile Asp Tyr Trp Asp Asp Ser Gln
            325                 330                 335
Ala Phe Arg Asn Met Val Tyr Val Arg Ser Leu Ala Ala Asp Leu Asn
            340                 345                 350
Glu Val Thr Cys Ala Gly Gly Thr Tyr Asn Phe Gln Leu Pro Val Gly
            355                 360                 365
Gln Trp Pro Val Met Ser Gly Gly Ser Val Ser Leu Arg Ser Ala Gly
            370                 375                 380
Val Thr Leu Ser Thr Gln Phe Thr Asp Phe Val Ser Leu Asn Ser Leu
385                 390                 395                 400
Arg Phe Arg Phe Ser Leu Ala Val Glu Glu Pro Pro Phe Ser Ile Ser
            405                 410                 415
Arg Thr Arg Ile Ser Gly Leu Tyr Gly Leu Pro Ala Ala Asn Pro Asn
            420                 425                 430
Asn Gly Arg Asp Phe Tyr Glu Ile Ala Gly Arg Phe Ser Leu Ile Leu
            435                 440                 445
Leu Val Pro Ser Asn Asp Asp Tyr Gln Thr Pro Ile Met Asn Ser Val
            450                 455                 460
Thr Val Arg Gln Asp Leu Glu Arg Gln
465                 470

<210> SEQ ID NO 35
<211> LENGTH: 452
<212> TYPE: PRT
<213> ORGANISM: Artificial Sequence
<220> FEATURE:
<223> OTHER INFORMATION: Artificial protein

<400> SEQUENCE: 35

Met Gly Ser Glu Lys Thr Gln Asn Val Thr Val Asn Pro Gly Pro Phe
1               5                   10                  15
Ala Gln Thr Arg Tyr Ala Pro Val Asn Trp Gly His Gly Glu Ile Asn
            20                  25                  30
Asp Ser Thr Thr Val Glu Pro Val Leu Asp Gly Pro Tyr Gln Pro Thr
            35                  40                  45
Thr Phe Lys Pro Pro Asn Asp Tyr Trp Leu Leu Ile Ser Ser Asn Thr
            50                  55                  60
Asp Gly Val Val Tyr Glu Ser Thr Asn Asn Ser Asp Phe Trp Thr Ala
```

```
             65                  70                  75                  80
Val Ile Ala Val Glu Pro His Val Ser Gln Thr Asn Arg Gln Tyr Val
                 85                  90                  95

Leu Phe Gly Glu Asn Lys Gln Phe Asn Ile Glu Asn Ser Ser Asp Lys
            100                 105                 110

Trp Lys Phe Leu Glu Met Phe Arg Gly Ser Gly Gln Ser Asp Phe Ser
            115                 120                 125

Asn Arg Arg Thr Leu Thr Ser Asn Asn Arg Leu Val Gly Met Leu Lys
        130                 135                 140

Tyr Gly Gly Arg Val Trp Thr Phe His Gly Glu Thr Pro Arg Ala Thr
145                 150                 155                 160

Thr Asp Ser Ser Asn Thr Ala Asp Leu Asn Asn Ile Ser Ile Ile Ile
                165                 170                 175

His Ser Glu Phe Tyr Ile Ile Pro Arg Ser Gln Glu Ser Lys Cys Asn
            180                 185                 190

Glu Tyr Ile Asn Asn Gly Leu Pro Pro Ile Gln Asn Thr Arg Asn Val
            195                 200                 205

Val Pro Leu Ser Leu Ser Ser Arg Ser Ile Gln Tyr Arg Arg Ala Gln
        210                 215                 220

Val Asn Glu Asp Ile Thr Ile Ser Lys Thr Ser Leu Trp Lys Glu Met
225                 230                 235                 240

Gln Tyr Asn Arg Asp Ile Ile Ile Arg Phe Lys Phe Gly Asn Ser Val
                245                 250                 255

Ile Lys Leu Gly Gly Leu Gly Tyr Lys Trp Ser Glu Ile Ser Tyr Lys
            260                 265                 270

Ala Ala Asn Tyr Gln Tyr Ser Tyr Ser Arg Asp Gly Glu Gln Val Thr
            275                 280                 285

Ala His Thr Thr Cys Ser Val Asn Gly Val Asn Asn Phe Ser Tyr Asn
        290                 295                 300

Gly Gly Ser Leu Pro Thr Asp Phe Ser Ile Ser Arg Tyr Glu Val Ile
305                 310                 315                 320

Lys Glu Asn Ser Tyr Val Tyr Ile Asp Tyr Trp Asp Ser Lys Ala
                325                 330                 335

Phe Arg Asn Met Val Tyr Val Arg Ser Leu Ala Ala Asn Leu Asn Ser
            340                 345                 350

Val Lys Cys Val Gly Gly Ser Tyr Asp Phe Arg Leu Pro Val Gly Glu
            355                 360                 365

Trp Pro Ile Met Asn Gly Gly Ala Val Ser Leu His Phe Ala Gly Val
        370                 375                 380

Thr Leu Ser Thr Gln Phe Thr Asp Phe Val Ser Leu Asn Ser Leu Arg
385                 390                 395                 400

Phe Arg Phe Ser Leu Thr Val Asp Glu Pro Ser Phe Ser Ile Ile Arg
                405                 410                 415

Thr Arg Thr Met Asn Leu Tyr Gly Leu Pro Ala Ala Asn Pro Asn Asn
            420                 425                 430

Gly Asn Glu Tyr Tyr Glu Val Ser Gly Arg Phe Ser Leu Ile Ser Leu
            435                 440                 445

Val Pro Thr Asn
        450

<210> SEQ ID NO 36
<211> LENGTH: 452
<212> TYPE: PRT
<213> ORGANISM: Artificial Sequence
```

<220> FEATURE:
<223> OTHER INFORMATION: Artificial protein

<400> SEQUENCE: 36

```
Met Gly Ser Glu Lys Ser Gln Asn Val Thr Ile Asn Pro Gly Pro Phe
1               5                   10                  15

Ala Gln Thr Asn Tyr Ala Pro Val Thr Trp Ser His Gly Glu Val Asn
            20                  25                  30

Asp Ser Thr Thr Ile Glu Pro Val Leu Asp Gly Pro Tyr Gln Pro Thr
        35                  40                  45

Asn Phe Lys Pro Pro Asn Asp Tyr Trp Ile Leu Leu Asn Pro Thr Asn
    50                  55                  60

Gln Gln Val Val Leu Glu Gly Thr Asn Lys Thr Asp Ile Trp Val Ala
65                  70                  75                  80

Leu Leu Leu Val Glu Pro Asn Val Thr Asn Gln Ser Arg Gln Tyr Thr
                85                  90                  95

Leu Phe Gly Glu Thr Lys Gln Ile Thr Val Glu Asn Asn Thr Asn Lys
            100                 105                 110

Trp Lys Phe Phe Glu Met Phe Arg Ser Asn Val Ser Ala Glu Phe Gln
        115                 120                 125

His Lys Arg Thr Leu Thr Ser Asp Thr Lys Leu Ala Gly Phe Met Lys
    130                 135                 140

Phe Tyr Asn Ser Val Trp Thr Phe His Gly Glu Thr Pro His Ala Thr
145                 150                 155                 160

Thr Asp Tyr Ser Ser Thr Ser Asn Leu Ser Glu Val Glu Thr Val Ile
                165                 170                 175

His Val Glu Phe Tyr Ile Ile Pro Arg Ser Gln Glu Ser Lys Cys Ser
            180                 185                 190

Glu Tyr Ile Asn Thr Gly Leu Pro Pro Met Gln Asn Thr Arg Asn Ile
        195                 200                 205

Val Pro Val Ala Leu Ser Ser Arg Ser Val Thr Tyr Gln Arg Ala Gln
210                 215                 220

Val Asn Glu Asp Ile Ile Ile Ser Lys Thr Ser Leu Trp Lys Glu Met
225                 230                 235                 240

Gln Tyr Asn Arg Asp Ile Ile Ile Arg Phe Lys Phe Asn Asn Ser Ile
                245                 250                 255

Val Lys Leu Gly Gly Leu Gly Tyr Lys Trp Ser Glu Ile Ser Phe Lys
            260                 265                 270

Ala Ala Asn Tyr Gln Tyr Ser Tyr Leu Arg Asp Gly Glu Gln Val Thr
        275                 280                 285

Ala His Thr Thr Cys Ser Val Asn Gly Val Asn Asn Phe Ser Tyr Asn
    290                 295                 300

Gly Gly Ser Leu Pro Thr Asp Phe Ser Val Ser Arg Tyr Glu Val Ile
305                 310                 315                 320

Lys Glu Asn Ser Tyr Val Tyr Val Asp Tyr Trp Asp Asp Ser Gln Ala
                325                 330                 335

Phe Arg Asn Met Val Tyr Val Arg Ser Leu Ala Ala Asn Leu Asn Ser
            340                 345                 350

Val Lys Cys Ser Gly Gly Asn Tyr Asn Phe Gln Ile Pro Val Gly Ala
        355                 360                 365

Trp Pro Val Met Ser Gly Gly Ala Val Ser Leu His Phe Ala Gly Val
    370                 375                 380

Thr Leu Ser Thr Gln Phe Thr Asp Phe Val Ser Leu Asn Ser Leu Arg
385                 390                 395                 400
```

```
Phe Arg Phe Ser Leu Thr Val Glu Glu Pro Pro Phe Ser Ile Leu Arg
                405                 410                 415

Thr Arg Val Ser Gly Leu Tyr Gly Leu Pro Ala Phe Asn Pro Asn Asn
            420                 425                 430

Gly His Glu Tyr Tyr Glu Ile Ala Gly Arg Phe Ser Leu Ile Ser Leu
        435                 440                 445

Val Pro Ser Asn
    450

<210> SEQ ID NO 37
<211> LENGTH: 452
<212> TYPE: PRT
<213> ORGANISM: Artificial Sequence
<220> FEATURE:
<223> OTHER INFORMATION: Artificial protein

<400> SEQUENCE: 37

Met Gly Ser Glu Lys Thr Gln Asn Val Thr Ile Asn Pro Ser Pro Phe
1               5                   10                  15

Ala Gln Thr Arg Tyr Ala Pro Val Asn Trp Gly His Gly Glu Ile Asn
            20                  25                  30

Asp Ser Thr Thr Val Glu Pro Met Leu Asp Gly Pro Tyr Gln Pro Thr
        35                  40                  45

Thr Phe Thr Pro Pro Asn Asp Tyr Trp Ile Leu Ile Asn Ser Asn Thr
    50                  55                  60

Asn Gly Val Val Tyr Glu Ser Thr Asn Ser Asp Phe Trp Thr Ala
65                  70                  75                  80

Val Val Ala Ile Glu Pro His Val Asn Pro Val Asp Arg Gln Tyr Thr
                85                  90                  95

Ile Phe Gly Glu Ser Lys Gln Phe Asn Val Ser Asn Asp Ser Asn Lys
            100                 105                 110

Trp Lys Phe Leu Glu Met Phe Arg Ser Ser Gln Asn Glu Phe Tyr
        115                 120                 125

Asn Arg Arg Thr Leu Thr Ser Asp Thr Arg Phe Val Gly Ile Leu Lys
    130                 135                 140

Tyr Gly Gly Arg Val Trp Thr Phe His Gly Glu Thr Pro Arg Ala Thr
145                 150                 155                 160

Thr Asp Ser Ser Ser Thr Ala Asn Leu Asn Asn Ile Ser Ile Thr Ile
                165                 170                 175

His Ser Glu Phe Tyr Ile Ile Pro Arg Ser Gln Glu Ser Lys Cys Asn
            180                 185                 190

Glu Tyr Ile Asn Asn Gly Leu Pro Pro Ile Gln Asn Thr Arg Asn Val
        195                 200                 205

Val Pro Leu Pro Leu Ser Ser Arg Ser Ile Gln Tyr Lys Arg Ala Gln
    210                 215                 220

Val Asn Glu Asp Ile Ile Val Ser Lys Thr Ser Leu Trp Lys Glu Met
225                 230                 235                 240

Gln Tyr Asn Arg Asp Ile Ile Ile Arg Phe Lys Phe Gly Asn Ser Ile
                245                 250                 255

Val Lys Met Gly Gly Leu Gly Tyr Lys Trp Ser Glu Ile Ser Tyr Lys
            260                 265                 270

Ala Ala Asn Tyr Gln Tyr Asn Tyr Leu Arg Asp Gly Glu Gln Val Thr
        275                 280                 285

Ala His Thr Thr Cys Ser Val Asn Gly Val Asn Asn Phe Ser Tyr Asn
    290                 295                 300
```

```
Gly Gly Phe Leu Pro Thr Asp Phe Gly Ile Ser Arg Tyr Glu Val Ile
305                 310                 315                 320

Lys Glu Asn Ser Tyr Val Tyr Val Asp Tyr Trp Asp Ser Lys Ala
            325                 330                 335

Phe Arg Asn Met Val Tyr Val Arg Ser Leu Ala Ala Asn Leu Asn Ser
                340                 345                 350

Val Lys Cys Thr Gly Gly Ser Tyr Asn Phe Ser Ile Pro Val Gly Ala
            355                 360                 365

Trp Pro Val Met Asn Gly Gly Ala Val Ser Leu His Phe Ala Gly Val
        370                 375                 380

Thr Leu Ser Thr Gln Phe Thr Asp Phe Val Ser Leu Asn Ser Leu Arg
385                 390                 395                 400

Phe Arg Phe Ser Leu Thr Val Asp Glu Pro Pro Phe Ser Ile Leu Arg
                405                 410                 415

Thr Arg Thr Val Asn Leu Tyr Gly Leu Pro Ala Ala Asn Pro Asn Asn
                420                 425                 430

Gly Asn Glu Tyr Tyr Glu Ile Ser Gly Arg Phe Ser Leu Ile Tyr Leu
            435                 440                 445

Val Pro Thr Asn
        450

<210> SEQ ID NO 38
<211> LENGTH: 452
<212> TYPE: PRT
<213> ORGANISM: Artificial Sequence
<220> FEATURE:
<223> OTHER INFORMATION: Artificial protein

<400> SEQUENCE: 38

Met Gly Ala Glu Lys Thr Gln Asn Val Thr Val Asn Pro Gly Pro Phe
1               5                   10                  15

Ala Gln Thr Gly Tyr Ala Pro Ala Asn Trp Gly Pro Gly Glu Thr Asn
            20                  25                  30

Asp Ser Thr Thr Val Glu Pro Val Leu Asp Gly Pro Tyr Gln Pro Ile
        35                  40                  45

Ala Phe Ser Pro Pro Glu Tyr Tyr Ile Leu Leu Ser Pro Thr Ala
    50                  55                  60

Pro Gly Val Ile Ala Glu Cys Thr Asn Thr Val Asn Arg Trp Ile Ala
65                  70                  75                  80

Ile Ile Ala Ile Glu Pro Asn Val Ser Pro Thr Asn Arg Thr Tyr Thr
                85                  90                  95

Leu Phe Gly Ile Thr Glu Gln Leu Thr Val Glu Asn Ser Ser Val Asp
                100                 105                 110

Lys Trp Lys Phe Ile Asp Phe Met Lys Thr Pro Thr Thr Gly Ser Tyr
            115                 120                 125

Val Arg Tyr Asn Ile Leu Leu Ser Ser Thr Lys Leu Cys Ala Val Ala
            130                 135                 140

Lys His Thr Asp Asn Leu Tyr Ser Tyr Val Gly Glu Thr Pro Thr Ala
145                 150                 155                 160

Gly Gln Ala Tyr Tyr Ser Ser Phe Asn Ile Phe Asn Leu Thr Ala His
                165                 170                 175

Cys Asp Phe Tyr Ile Ile Pro Trp Ser Gln Gln Ser Leu Cys Thr Gln
                180                 185                 190

Tyr Val Asn Asn Gly Leu Pro Pro Ile Gln Asn Thr Arg Asn Val Val
            195                 200                 205
```

```
Pro Arg His Leu Ser Ala Arg Ser Ile Ile Thr Gln Arg Ala Gln Ala
    210                 215                 220

Asn Glu Asp Ile Val Val Ser Lys Thr Ser Leu Trp Lys Glu Met Gln
225                 230                 235                 240

Phe Asn Arg Asp Ile Thr Ile Arg Phe Lys Phe Ala Asn Ala Ile Ile
                245                 250                 255

Lys Ser Gly Gly Leu Gly Tyr Lys Trp Ser Glu Ile Ser Phe Lys Pro
                260                 265                 270

Ala Asn Tyr Gln Tyr Thr Tyr Thr Arg Asp Gly Glu Glu Val Thr Ala
                275                 280                 285

His Thr Thr Cys Ser Val Asn Gly Val Asn Asn Phe Asp Phe Phe Gly
                290                 295                 300

Gly Ser Leu Pro Thr Asp Phe Gly Ile Ser Arg Tyr Glu Val Ile Lys
305                 310                 315                 320

Glu Asn Ser Phe Val Tyr Ile Asp Tyr Trp Asp Asp Ser Gln Ala Phe
                325                 330                 335

Arg Asn Met Val Tyr Val Arg Ser Leu Ala Ala Asp Leu Asn Thr Val
                340                 345                 350

Glu Cys Thr Gly Gly Ala Tyr Ser Phe Ser Leu Pro Val Gly Gln Trp
                355                 360                 365

Pro Val Met Thr Gly Gly Ala Val Ser Leu Arg Ala Ala Gly Val Thr
370                 375                 380

Leu Ser Thr Gln Phe Thr Asp Phe Val Ser Leu Asn Ser Leu Arg Phe
385                 390                 395                 400

Arg Phe Arg Leu Ser Val Glu Glu Pro Ser Phe Ser Ile Thr Arg Thr
                405                 410                 415

Arg Val Ser Gly Leu Tyr Gly Leu Pro Ala Ala Asp Pro Asn Asn Gly
                420                 425                 430

Arg Glu Tyr Tyr Glu Ile Ala Gly Arg Phe Ser Leu Ile Ser Leu Val
                435                 440                 445

Pro Ser Asn Asp
    450

<210> SEQ ID NO 39
<211> LENGTH: 452
<212> TYPE: PRT
<213> ORGANISM: Artificial Sequence
<220> FEATURE:
<223> OTHER INFORMATION: Artificial protein

<400> SEQUENCE: 39

Met Gly Ser Thr Lys Ser Gln Asn Val Thr Ile Asn Pro Gly Pro Phe
1               5                   10                  15

Ala Gln Thr Gly Tyr Ala Pro Val Asn Trp Gly Pro Gly Glu Ile Asn
                20                  25                  30

Asp Ser Thr Thr Val Glu Pro Leu Leu Asp Gly Pro Tyr Gln Pro Thr
                35                  40                  45

Thr Phe Asn Pro Pro Val Asp Tyr Trp Met Leu Leu Ala Pro Thr Thr
            50                  55                  60

Pro Gly Val Ile Val Glu Gly Thr Asn Asn Thr Asp Arg Trp Leu Ala
65                  70                  75                  80

Thr Ile Leu Ile Glu Pro Asn Val Gln Ser Glu Asn Arg Thr Tyr Thr
                85                  90                  95

Ile Phe Gly Ile Gln Glu Gln Leu Thr Val Ser Asn Thr Ser Gln Asp
                100                 105                 110
```

```
Gln Trp Lys Phe Ile Asp Val Val Lys Thr Thr Ala Asn Gly Ser Ile
        115                 120                 125

Gly Gln Tyr Gly Ser Leu Leu Ser Ser Pro Lys Leu Tyr Ala Val Met
    130                 135                 140

Lys His Asn Glu Lys Leu Tyr Thr Tyr Glu Gly Gln Thr Pro Asn Ala
145                 150                 155                 160

Arg Thr Gly His Tyr Ser Thr Thr Asn Tyr Asp Ser Val Asn Met Thr
                165                 170                 175

Ala Phe Cys Asp Phe Tyr Ile Ile Pro Arg Ser Glu Glu Ser Lys Cys
            180                 185                 190

Thr Glu Tyr Ile Asn Asn Gly Leu Pro Pro Ile Gln Asn Thr Arg Asn
        195                 200                 205

Val Val Pro Leu Ser Leu Thr Ala Arg Asp Val Ile His Tyr Arg Ala
    210                 215                 220

Gln Ala Asn Glu Asp Ile Val Ile Ser Lys Thr Ser Leu Trp Lys Glu
225                 230                 235                 240

Met Gln Tyr Asn Arg Asp Ile Thr Ile Arg Phe Lys Phe Ala Asn Thr
                245                 250                 255

Ile Ile Lys Ser Gly Gly Leu Gly Tyr Lys Trp Ser Glu Ile Ser Phe
            260                 265                 270

Lys Pro Ala Asn Tyr Gln Tyr Thr Tyr Thr Arg Asp Gly Glu Glu Val
        275                 280                 285

Thr Ala His Thr Thr Cys Ser Val Asn Gly Val Asn Asp Phe Ser Phe
    290                 295                 300

Asn Gly Gly Ser Leu Pro Thr Asp Phe Val Val Ser Lys Phe Glu Val
305                 310                 315                 320

Ile Lys Glu Asn Ser Tyr Val Tyr Ile Asp Tyr Trp Asp Asp Ser Gln
                325                 330                 335

Ala Phe Arg Asn Val Val Tyr Val Arg Ser Leu Ala Ala Asn Leu Asn
            340                 345                 350

Ser Val Met Cys Thr Gly Gly Ser Tyr Asn Phe Ser Leu Pro Val Gly
        355                 360                 365

Gln Trp Pro Val Leu Thr Gly Gly Ala Val Ser Leu His Ser Ala Gly
    370                 375                 380

Val Thr Leu Ser Thr Gln Phe Thr Asp Phe Val Ser Leu Asn Ser Leu
385                 390                 395                 400

Arg Phe Arg Phe Arg Leu Ala Val Glu Glu Pro His Phe Lys Leu Thr
                405                 410                 415

Arg Thr Arg Leu Asp Arg Leu Tyr Gly Leu Pro Ala Ala Asp Pro Asn
            420                 425                 430

Asn Gly Lys Glu Tyr Tyr Glu Ile Ala Gly Arg Phe Ser Leu Ile Ser
        435                 440                 445

Leu Val Pro Ser
    450

<210> SEQ ID NO 40
<211> LENGTH: 776
<212> TYPE: PRT
<213> ORGANISM: Rotovirus strain LLR

<400> SEQUENCE: 40

Met Ala Ser Leu Ile Tyr Arg Gln Leu Leu Thr Asn Ser Tyr Thr Val
1               5                   10                  15

Asn Leu Ser Asp Glu Ile Gln Leu Ile Gly Ser Glu Lys Thr Gln Arg
```

```
            20                  25                  30
Thr Thr Val Asn Pro Gly Pro Phe Ala Gln Thr Gly Tyr Ala Pro Val
            35                  40                  45
Asn Trp Gly Pro Gly Glu Thr Ser Asp Ser Thr Thr Val Glu Pro Val
50                  55                  60
Leu Asn Gly Pro Tyr Gln Pro Thr Thr Phe Asn Pro Pro Val Glu Tyr
65                  70                  75                  80
Trp Met Leu Leu Ala Pro Thr Ser Glu Gly Val Val Glu Gly Thr
                85                  90                  95
Asn Gly Thr Asp Arg Trp Leu Ala Thr Ile Leu Ile Glu Pro Asn Val
                100                 105                 110
Pro Glu Thr Thr Arg Asn Tyr Thr Leu Phe Gly Glu Thr Ala Ser Ile
                115                 120                 125
Ser Val Ala Asn Pro Ser Gln Ser Lys Trp Arg Phe Val Asp Val Ala
                130                 135                 140
Lys Thr Thr Ala Asn Gly Thr Tyr Ser Gln Tyr Gly Pro Leu Leu Ser
145                 150                 155                 160
Asp Thr Lys Leu Tyr Gly Val Met Lys Tyr Asn Gly Lys Leu Tyr Thr
                165                 170                 175
Tyr Asn Gly Glu Thr Pro Asn Ala Thr Thr Asn Tyr Tyr Ser Thr Thr
                180                 185                 190
Asn Tyr Asp Ser Val Asn Met Thr Ser Tyr Cys Asp Phe Tyr Ile Ile
                195                 200                 205
Pro Arg Ala Gln Glu Ser Lys Cys Thr Glu Tyr Val Asn Asn Gly Leu
                210                 215                 220
Pro Pro Ile Gln Asn Thr Arg Asn Val Val Pro Leu Ala Leu Ser Ser
225                 230                 235                 240
Arg Ser Ile Val Ala Arg Arg Ala Ala Val Asn Glu Asp Ile Val Ile
                245                 250                 255
Ser Lys Thr Ser Leu Trp Lys Glu Met Gln Tyr Asn Arg Asp Ile Ile
                260                 265                 270
Ile Arg Phe Lys Phe Ala Asn Ser Ile Ile Lys Ser Gly Gly Leu Gly
                275                 280                 285
Tyr Lys Trp Ser Glu Ile Ser Phe Lys Pro Ala Asn Tyr Gln Tyr Thr
                290                 295                 300
Tyr Ile Arg Asp Gly Glu Glu Val Thr Ala His Thr Thr Cys Ser Val
305                 310                 315                 320
Asn Gly Val Asn Asp Phe Asn Tyr Asn Gly Gly Ser Leu Pro Thr Asp
                325                 330                 335
Phe Val Ile Ser Arg Tyr Glu Val Ile Lys Glu Asn Ser Tyr Val Tyr
                340                 345                 350
Ile Asp Tyr Trp Asp Asp Ser Gln Ala Phe Arg Asn Met Val Tyr Val
                355                 360                 365
Arg Ser Leu Ala Ala Asp Leu Asn Glu Val Thr Cys Ala Gly Gly Thr
                370                 375                 380
Tyr Asn Phe Gln Leu Pro Val Gly Gln Trp Pro Val Met Ser Gly Gly
385                 390                 395                 400
Ser Val Ser Leu Arg Ser Ala Gly Val Thr Leu Ser Thr Gln Phe Thr
                405                 410                 415
Asp Phe Val Ser Leu Asn Ser Leu Arg Phe Arg Phe Ser Leu Ala Val
                420                 425                 430
Glu Glu Pro Pro Phe Ser Ile Ser Arg Thr Arg Ile Ser Gly Leu Tyr
                435                 440                 445
```

```
Gly Leu Pro Ala Ala Asn Pro Asn Asn Gly Arg Asp Phe Tyr Glu Ile
    450                 455                 460

Ala Gly Arg Phe Ser Leu Ile Leu Leu Val Pro Ser Asn Asp Asp Tyr
465                 470                 475                 480

Gln Thr Pro Ile Met Asn Ser Val Thr Val Arg Gln Asp Leu Glu Arg
                485                 490                 495

Gln Leu Gly Glu Leu Arg Glu Glu Phe Asn Ala Leu Ser Gln Glu Ile
            500                 505                 510

Ala Met Ser Gln Leu Ile Asp Leu Ala Leu Leu Pro Leu Asp Met Phe
        515                 520                 525

Ser Met Phe Ser Gly Ile Lys Thr Thr Ile Asp Ala Ala Lys Ser Met
    530                 535                 540

Ala Thr Asn Val Met Lys Lys Phe Lys Ser Ser Gly Leu Ala Thr Ser
545                 550                 555                 560

Val Ser Thr Leu Thr Asp Ser Leu Ser Asp Ala Ala Ser Ala Val Ser
                565                 570                 575

Arg Asn Ser Ser Ile Arg Ser Ile Gly Ser Thr Ala Ser Ala Trp Thr
            580                 585                 590

Asp Ile Ser Ser Gln Ile Val Asp Thr Gln Ala Ser Val Asn Thr Leu
        595                 600                 605

Ala Thr Gln Thr Ser Thr Ile Ser Lys Arg Leu Arg Leu Lys Glu Ile
    610                 615                 620

Ala Thr Gln Thr Glu Gly Met Asn Phe Asp Asp Ile Ser Ala Ala Val
625                 630                 635                 640

Leu Lys Thr Lys Ile Asp Lys Ser Ser Gln Ile Gly Pro Ser Thr Leu
                645                 650                 655

Pro Asp Ile Val Thr Glu Ala Ser Glu Lys Phe Ile Pro Asn Arg Thr
            660                 665                 670

Tyr Arg Val Ile Asp Asp Asp Thr Val Phe Glu Ala Gly Thr Asp Gly
        675                 680                 685

Arg Phe Tyr Ala Tyr Arg Val Glu Thr Phe Glu Glu Val Pro Phe Asp
    690                 695                 700

Val Gln Lys Phe Ala Asp Leu Val Thr Asp Ser Pro Val Ile Ser Ala
705                 710                 715                 720

Ile Ile Asp Phe Lys Thr Leu Lys Asn Leu Asn Asp Asn Tyr Gly Ile
                725                 730                 735

Thr Arg Ser Gln Ala Leu Asn Leu Ile Arg Ser Asp Pro Arg Val Leu
            740                 745                 750

Arg Glu Phe Ile Asn Gln Asp Asn Pro Ile Ile Arg Asn Arg Ile Glu
        755                 760                 765

Gln Leu Ile Leu Gln Cys Arg Leu
    770                 775
```

<210> SEQ ID NO 41
<211> LENGTH: 2331
<212> TYPE: DNA
<213> ORGANISM: Rotovirus strain LLR

<400> SEQUENCE: 41

```
atggcttcgc tcatttacag acaattactt acgaattcat atacagtgaa tctttcagat      60
gaaatacagt taattggatc agaaaaaacg cagagaacta cagtaaatcc aggtccattt     120
gcacaaactg gttatgcacc agtgaattgg gggcctgggg aaacgagtga ttccactact     180
gttgagccag tgttgaatgg accatatcag ccgacgactt tcaatccacc agtagaatat     240
```

```
tggatgcttc tagcaccaac atcagaaggg gtagttgttg aaggtactaa tggtacggat    300
agatggctag ctacaatact tatagaacca aatgtgcctg agacgactag aaattacaca    360
ttatttgggg aaacagcgag tatatcagta gcaaacccat cacaaagtaa atggcgtttt    420
gttgacgtag ctaagaccac tgcaaatgga acatattcac aatatggacc attactatca    480
gatacaaaac tgtatggagt aatgaaatac aacgggaagt tgtatacgta taatggtgaa    540
actccgaatg ctacaacaaa ttattattca actacaaatt atgactcagt gaatatgaca    600
tcttattgcg atttttacat tataccaaga gcacaagaat caaagtgcac agaatacgta    660
aataatggat taccaccaat acaaaacacc agaaatgtcg taccattagc tttatcttca    720
cgatcaatag ttgctagaag agctgcagtg aacgaagaca tagttatatc gaaaacgtca    780
ttgtggaaag aaatgcaata taatcgagat atcataataa gatttaagtt tgcaaactca    840
attattaaat caggtggact agggtataaa tggtcagaga tttcattcaa accagcaaac    900
tatcaatata catatatacg tgatggagag gaagtaactg cacatacaac atgttcagtg    960
aatggagtga acgacttcaa ctataacgga ggatcattac caactgactt tgtaatatca   1020
cgttatgaag ttataaaaga gaactcttat gtatatatag attattggga tgattccacaa  1080 gcattcagaa acatggtata tgtgagatca ttagctgcgg acttaaatga agtgacatgt   1140 gcaggggta cttataattt ccaactacca gttggacaat ggcctgtgat gagtggtggc    1200
tcagtatcat tgcgttcagc tggagtaacg ttatcaactc aatttacaga ctttgtgtca   1260
ttaaattcgt taagatttag gttcagttta gcagtagaag aaccgccatt ctctatttca   1320
aggacacgga tatcagggtt atatgggtta ccggcagcca atccaaataa tggaagagac   1380
ttctatgaaa ttgcgggtag atttttcatta attttattag taccatcaaa tgatgattat   1440
caaactccta taatgaactc agtgacggtg agacaggact tagagaggca gttaggagaa   1500
ttgagagaag aatttaacgc attatcacaa gagatagcta tgtcacaatt gatagatcta   1560
gctttactac cattggacat gttctcaatg ttttcaggaa ttaaaacaac gatagatgca   1620
gctaaatcaa tggccactaa tgtaatgaag aagtttaaaa gctcaggctt ggccacgtct   1680
gtatccacgt tgacagactc attatctgac gccgcatcag cggtatcaag gaacagctca   1740
ataagatcaa ttggatcaac agcatcagct tggacagaca tttcttcaca aatagtggat   1800
acgcaagcat cagtcaatac gttggcaact caaacgtcaa ctatcagcaa gagattaagg   1860
ttaaaagaaa ttgcgactca aacagaggga atgaatttcg acgacatatc agcagctgtg   1920
ttaaaaacta aaattgacaa atcatcacaa ataggaccaa gtactttacc agatattgtt   1980
actgaagcgt cggagaagtt tataccaaat agaacgtata gagtaattga cgatgatact   2040
gtgtttgaag caggaacaga tgggagattt tacgcatata gagtcgagac gtttgaggaa   2100
gttccatttg atgtgcaaaa attcgcagat ttagtaactg actctccagt aatctcggcc   2160
attatagact ttaaaacgct taaaaacttg aatgataact atggaattac tcgttcgcaa   2220
gcattaaatc taattagatc agatccaagg gttctgcgag aatttatcaa tcaagataat   2280
ccaataataa gaaacaggat agagcagtta attctgcaat gtagattgta a             2331
```

<210> SEQ ID NO 42
<211> LENGTH: 30
<212> TYPE: DNA
<213> ORGANISM: Artificial Sequence
<220> FEATURE:
<223> OTHER INFORMATION: primer

```
<400> SEQUENCE: 42
ggatcccata tgatggcttc gctcatttac                                30

<210> SEQ ID NO 43
<211> LENGTH: 35
<212> TYPE: DNA
<213> ORGANISM: Artificial Sequence
<220> FEATURE:
<223> OTHER INFORMATION: primer

<400> SEQUENCE: 43
ggatcccata tgtacagaca attacttacg aattc                          35

<210> SEQ ID NO 44
<211> LENGTH: 35
<212> TYPE: DNA
<213> ORGANISM: Artificial Sequence
<220> FEATURE:
<223> OTHER INFORMATION: primer

<400> SEQUENCE: 44
ggatcccata tgatacagtt aattggatca gaaaa                          35

<210> SEQ ID NO 45
<211> LENGTH: 30
<212> TYPE: DNA
<213> ORGANISM: Artificial Sequence
<220> FEATURE:
<223> OTHER INFORMATION: primer

<400> SEQUENCE: 45
ggatcccata tgggatcaga aaaaacgcag                                30

<210> SEQ ID NO 46
<211> LENGTH: 24
<212> TYPE: DNA
<213> ORGANISM: Artificial Sequence
<220> FEATURE:
<223> OTHER INFORMATION: primer

<400> SEQUENCE: 46
ggatcccata tgttgaatgg acca                                      24

<210> SEQ ID NO 47
<211> LENGTH: 25
<212> TYPE: DNA
<213> ORGANISM: Artificial Sequence
<220> FEATURE:
<223> OTHER INFORMATION: primer

<400> SEQUENCE: 47
aagcttaggt gttttgtatt ggtgg                                     25

<210> SEQ ID NO 48
<211> LENGTH: 29
<212> TYPE: DNA
<213> ORGANISM: Artificial Sequence
<220> FEATURE:
<223> OTHER INFORMATION: primer

<400> SEQUENCE: 48
aagcttatct tctagcaact attgatcgt                                 29

<210> SEQ ID NO 49
<211> LENGTH: 28
```

```
<212> TYPE: DNA
<213> ORGANISM: Artificial Sequence
<220> FEATURE:
<223> OTHER INFORMATION: primer

<400> SEQUENCE: 49
aagcttagtt cactgcagct cttctagc                                          28

<210> SEQ ID NO 50
<211> LENGTH: 30
<212> TYPE: DNA
<213> ORGANISM: Artificial Sequence
<220> FEATURE:
<223> OTHER INFORMATION: primer

<400> SEQUENCE: 50
aagcttacaa tgacgttttc gatataacta                                        30

<210> SEQ ID NO 51
<211> LENGTH: 31
<212> TYPE: DNA
<213> ORGANISM: Artificial Sequence
<220> FEATURE:
<223> OTHER INFORMATION: primer

<400> SEQUENCE: 51
aagcttagat atctcgatta tattgcattt c                                      31

<210> SEQ ID NO 52
<211> LENGTH: 29
<212> TYPE: DNA
<213> ORGANISM: Artificial Sequence
<220> FEATURE:
<223> OTHER INFORMATION: primer

<400> SEQUENCE: 52
aagcttaaat tgagtttgca aacttaaat                                         29

<210> SEQ ID NO 53
<211> LENGTH: 28
<212> TYPE: DNA
<213> ORGANISM: Artificial Sequence
<220> FEATURE:
<223> OTHER INFORMATION: primer

<400> SEQUENCE: 53
aagcttacca tttataccct agtccacc                                          28

<210> SEQ ID NO 54
<211> LENGTH: 28
<212> TYPE: DNA
<213> ORGANISM: Artificial Sequence
<220> FEATURE:
<223> OTHER INFORMATION: primer

<400> SEQUENCE: 54
aagcttaata gtttgctggt ttgaatga                                          28

<210> SEQ ID NO 55
<211> LENGTH: 30
<212> TYPE: DNA
<213> ORGANISM: Artificial Sequence
<220> FEATURE:
<223> OTHER INFORMATION: primer

<400> SEQUENCE: 55
```

```
aagcttattc ctctccatca cgtatatatg                                      30

<210> SEQ ID NO 56
<211> LENGTH: 30
<212> TYPE: DNA
<213> ORGANISM: Artificial Sequence
<220> FEATURE:
<223> OTHER INFORMATION: primer

<400> SEQUENCE: 56
aagcttaatt cactgaacat gttgtatgtg                                      30

<210> SEQ ID NO 57
<211> LENGTH: 28
<212> TYPE: DNA
<213> ORGANISM: Artificial Sequence
<220> FEATURE:
<223> OTHER INFORMATION: primer

<400> SEQUENCE: 57
aagcttatcc tccgttatag ttgaagtc                                        28

<210> SEQ ID NO 58
<211> LENGTH: 30
<212> TYPE: DNA
<213> ORGANISM: Artificial Sequence
<220> FEATURE:
<223> OTHER INFORMATION: primer

<400> SEQUENCE: 58
aagcttaacg tgatattaca aagtcagttg                                      30

<210> SEQ ID NO 59
<211> LENGTH: 34
<212> TYPE: DNA
<213> ORGANISM: Artificial Sequence
<220> FEATURE:
<223> OTHER INFORMATION: primer

<400> SEQUENCE: 59
aagcttatac ataagagttc tcttttataa cttc                                 34

<210> SEQ ID NO 60
<211> LENGTH: 26
<212> TYPE: DNA
<213> ORGANISM: Artificial Sequence
<220> FEATURE:
<223> OTHER INFORMATION: primer

<400> SEQUENCE: 60
aagcttatgc ttgtgaatca tcccaa                                          26

<210> SEQ ID NO 61
<211> LENGTH: 32
<212> TYPE: DNA
<213> ORGANISM: Artificial Sequence
<220> FEATURE:
<223> OTHER INFORMATION: primer

<400> SEQUENCE: 61
aagcttataa tgatctcaca tataccatgt tt                                   32

<210> SEQ ID NO 62
<211> LENGTH: 29
<212> TYPE: DNA
<213> ORGANISM: Artificial Sequence
```

```
<220> FEATURE:
<223> OTHER INFORMATION: primer

<400> SEQUENCE: 62
aagcttatgc acatgtcact tcatttaag                                          29

<210> SEQ ID NO 63
<211> LENGTH: 32
<212> TYPE: DNA
<213> ORGANISM: Artificial Sequence
<220> FEATURE:
<223> OTHER INFORMATION: primer

<400> SEQUENCE: 63
aagcttaaac tggtagttgg aaattataag ta                                      32

<210> SEQ ID NO 64
<211> LENGTH: 26
<212> TYPE: DNA
<213> ORGANISM: Artificial Sequence
<220> FEATURE:
<223> OTHER INFORMATION: primer

<400> SEQUENCE: 64
aagcttatga gccaccactc atcaca                                             26

<210> SEQ ID NO 65
<211> LENGTH: 27
<212> TYPE: DNA
<213> ORGANISM: Artificial Sequence
<220> FEATURE:
<223> OTHER INFORMATION: primer

<400> SEQUENCE: 65
aagcttataa cgttactcca gctgaac                                            27

<210> SEQ ID NO 66
<211> LENGTH: 31
<212> TYPE: DNA
<213> ORGANISM: Artificial Sequence
<220> FEATURE:
<223> OTHER INFORMATION: primer

<400> SEQUENCE: 66
aagcttataa tgacacaaag tctgtaaatt g                                       31

<210> SEQ ID NO 67
<211> LENGTH: 30
<212> TYPE: DNA
<213> ORGANISM: Artificial Sequence
<220> FEATURE:
<223> OTHER INFORMATION: primer

<400> SEQUENCE: 67
aagcttatgc taaactgaac ctaaatctta                                         30

<210> SEQ ID NO 68
<211> LENGTH: 27
<212> TYPE: DNA
<213> ORGANISM: Artificial Sequence
<220> FEATURE:
<223> OTHER INFORMATION: primer

<400> SEQUENCE: 68
aagcttacct tgaaatagag aatggcg                                            27
```

<210> SEQ ID NO 69
<211> LENGTH: 26
<212> TYPE: DNA
<213> ORGANISM: Artificial Sequence
<220> FEATURE:
<223> OTHER INFORMATION: primer

<400> SEQUENCE: 69
aagcttacgg taacccatat aaccct                                    26

<210> SEQ ID NO 70
<211> LENGTH: 29
<212> TYPE: DNA
<213> ORGANISM: Artificial Sequence
<220> FEATURE:
<223> OTHER INFORMATION: primer

<400> SEQUENCE: 70
aagcttagaa gtctcttcca ttatttgga                                 29

<210> SEQ ID NO 71
<211> LENGTH: 28
<212> TYPE: DNA
<213> ORGANISM: Artificial Sequence
<220> FEATURE:
<223> OTHER INFORMATION: primer

<400> SEQUENCE: 71
aagcttaaat taatgaaaat ctacccgc                                  28

<210> SEQ ID NO 72
<211> LENGTH: 42
<212> TYPE: DNA
<213> ORGANISM: Artificial Sequence
<220> FEATURE:
<223> OTHER INFORMATION: primer

<400> SEQUENCE: 72
agatctaagc ttatgatggt actaataaaa ttaatgaaaa tc                  42

<210> SEQ ID NO 73
<211> LENGTH: 42
<212> TYPE: DNA
<213> ORGANISM: Artificial Sequence
<220> FEATURE:
<223> OTHER INFORMATION: primer

<400> SEQUENCE: 73
agatctaagc ttaagtttga taatcatcat ttgatggtac ta                  42

<210> SEQ ID NO 74
<211> LENGTH: 42
<212> TYPE: DNA
<213> ORGANISM: Artificial Sequence
<220> FEATURE:
<223> OTHER INFORMATION: primer

<400> SEQUENCE: 74
agatctaagc ttatgagttc attataggag tttgataatc at                  42

<210> SEQ ID NO 75
<211> LENGTH: 35
<212> TYPE: DNA
<213> ORGANISM: Artificial Sequence
<220> FEATURE:
<223> OTHER INFORMATION: primer

<400> SEQUENCE: 75
agatctaagc ttatgtctca ccgtcactga gttca                              35

<210> SEQ ID NO 76
<211> LENGTH: 36
<212> TYPE: DNA
<213> ORGANISM: Artificial Sequence
<220> FEATURE:
<223> OTHER INFORMATION: primer

<400> SEQUENCE: 76
agatctaagc ttactgcctc tctaagtcct gtctca                             36

<210> SEQ ID NO 77
<211> LENGTH: 30
<212> TYPE: DNA
<213> ORGANISM: Artificial Sequence
<220> FEATURE:
<223> OTHER INFORMATION: primer

<400> SEQUENCE: 77
ggatcccata tgggatcgga gaaaactcaa                                    30

<210> SEQ ID NO 78
<211> LENGTH: 32
<212> TYPE: DNA
<213> ORGANISM: Artificial Sequence
<220> FEATURE:
<223> OTHER INFORMATION: primer

<400> SEQUENCE: 78
aagcttaatt agttggaact aaagaaataa gt                                 32

<210> SEQ ID NO 79
<211> LENGTH: 33
<212> TYPE: DNA
<213> ORGANISM: Artificial Sequence
<220> FEATURE:
<223> OTHER INFORMATION: primer

<400> SEQUENCE: 79
ggatcccata tgggatcaga gaaaagtcaa aat                                33

<210> SEQ ID NO 80
<211> LENGTH: 27
<212> TYPE: DNA
<213> ORGANISM: Artificial Sequence
<220> FEATURE:
<223> OTHER INFORMATION: primer

<400> SEQUENCE: 80
aagcttaatt agacggtact aatgaaa                                       27

<210> SEQ ID NO 81
<211> LENGTH: 34
<212> TYPE: DNA
<213> ORGANISM: Artificial Sequence
<220> FEATURE:
<223> OTHER INFORMATION: primer

<400> SEQUENCE: 81
ggatcccata tgggatcaga aaaaactcaa aatg                               34

<210> SEQ ID NO 82

```
<211> LENGTH: 27
<212> TYPE: DNA
<213> ORGANISM: Artificial Sequence
<220> FEATURE:
<223> OTHER INFORMATION: primer

<400> SEQUENCE: 82
aagcttagtt ggttggaact aaagaaa                                          27

<210> SEQ ID NO 83
<211> LENGTH: 29
<212> TYPE: DNA
<213> ORGANISM: Artificial Sequence
<220> FEATURE:
<223> OTHER INFORMATION: primer

<400> SEQUENCE: 83
ggatcccata tgggagcaga gaagacaca                                        29

<210> SEQ ID NO 84
<211> LENGTH: 22
<212> TYPE: DNA
<213> ORGANISM: Artificial Sequence
<220> FEATURE:
<223> OTHER INFORMATION: primer

<400> SEQUENCE: 84
aagcttaatc gttggacggc ac                                               22

<210> SEQ ID NO 85
<211> LENGTH: 34
<212> TYPE: DNA
<213> ORGANISM: Artificial Sequence
<220> FEATURE:
<223> OTHER INFORMATION: primer

<400> SEQUENCE: 85
ggatcccata tgggatcaac taaatcacaa aatg                                  34

<210> SEQ ID NO 86
<211> LENGTH: 29
<212> TYPE: DNA
<213> ORGANISM: Artificial Sequence
<220> FEATURE:
<223> OTHER INFORMATION: primer

<400> SEQUENCE: 86
aagcttatga tggcactaat gatataagt                                        29

<210> SEQ ID NO 87
<211> LENGTH: 776
<212> TYPE: PRT
<213> ORGANISM: Rotovirus strain SA11

<400> SEQUENCE: 87

Met Ala Ser Leu Ile Tyr Arg Gln Leu Leu Thr Asn Ser Tyr Thr Val
1               5                   10                  15

Asp Leu Ser Asp Glu Ile Gln Glu Ile Gly Ser Thr Lys Ser Gln Asn
                20                  25                  30

Val Thr Ile Asn Pro Gly Pro Phe Ala Gln Thr Gly Tyr Ala Pro Val
            35                  40                  45

Asn Trp Gly Pro Gly Glu Ile Asn Asp Ser Thr Thr Val Glu Pro Leu
        50                  55                  60

Leu Asp Gly Pro Tyr Gln Pro Met Thr Phe Asn Pro Pro Val Asp Tyr
```

```
                65                  70                  75                  80
        Trp Met Leu Leu Ala Pro Thr Thr Pro Gly Val Ile Val Glu Gly Thr
                            85                  90                  95

Asn Asn Thr Asp Arg Trp Leu Ala Thr Ile Leu Ile Glu Pro Asn Val
                        100                 105                 110

Gln Ser Glu Asn Arg Thr Tyr Thr Ile Phe Gly Ile Gln Glu Gln Leu
                    115                 120                 125

Thr Val Ser Asn Thr Ser Gln Asp Gln Trp Lys Phe Ile Asp Val Val
                130                 135                 140

Lys Thr Thr Ala Asn Gly Ser Ile Gly Gln Tyr Gly Ser Leu Leu Ser
        145                 150                 155                 160

Ser Pro Lys Leu Tyr Ala Val Met Lys His Asn Glu Lys Leu Tyr Thr
                        165                 170                 175

Tyr Glu Gly Gln Thr Pro Asn Ala Arg Thr Gly His Tyr Ser Thr Thr
                    180                 185                 190

Asn Tyr Asp Ser Val Asn Met Thr Ala Phe Cys Asp Phe Tyr Ile Ile
                195                 200                 205

Pro Arg Ser Glu Glu Ser Lys Cys Thr Glu Tyr Ile Asn Asn Gly Leu
            210                 215                 220

Pro Pro Ile Gln Asn Thr Arg Asn Val Val Pro Leu Ser Leu Thr Ala
        225                 230                 235                 240

Arg Asp Val Ile His Tyr Arg Ala Gln Ala Asn Glu Asp Ile Val Ile
                        245                 250                 255

Ser Lys Thr Ser Leu Trp Lys Glu Met Gln Tyr Asn Arg Asp Ile Thr
                    260                 265                 270

Ile Arg Phe Lys Phe Ala Asn Thr Ile Ile Lys Ser Gly Gly Leu Gly
                275                 280                 285

Tyr Lys Trp Ser Glu Ile Ser Phe Lys Pro Ala Asn Tyr Gln Tyr Thr
            290                 295                 300

Tyr Thr Arg Asp Gly Glu Glu Val Thr Ala His Thr Thr Cys Ser Val
        305                 310                 315                 320

Asn Gly Val Asn Asp Phe Ser Phe Asn Gly Gly Ser Leu Pro Thr Asp
                        325                 330                 335

Phe Val Val Ser Lys Phe Glu Val Ile Lys Glu Asn Ser Tyr Val Tyr
                    340                 345                 350

Ile Asp Tyr Trp Asp Asp Ser Gln Ala Phe Arg Asn Val Met Tyr Val
                355                 360                 365

Arg Ser Leu Ala Ala Asn Leu Asn Ser Val Met Cys Thr Gly Gly Ser
        370                 375                 380

Tyr Asn Phe Ser Leu Pro Val Gly Gln Trp Pro Val Leu Thr Gly Gly
        385                 390                 395                 400

Ala Val Ser Leu His Ser Ala Gly Val Thr Leu Ser Thr Gln Phe Thr
                        405                 410                 415

Asp Phe Val Ser Leu Asn Ser Leu Arg Phe Arg Phe Arg Leu Ala Val
                    420                 425                 430

Glu Glu Pro His Phe Lys Leu Thr Arg Thr Arg Leu Asp Arg Leu Tyr
                435                 440                 445

Gly Leu Pro Ala Ala Asp Pro Asn Asn Gly Lys Glu Tyr Tyr Glu Ile
            450                 455                 460

Ala Gly Arg Phe Ser Leu Ile Ser Leu Val Pro Ser Asn Asp Asp Tyr
        465                 470                 475                 480

Gln Thr Pro Ile Ala Asn Ser Val Thr Val Arg Gln Asp Leu Glu Arg
                        485                 490                 495
```

```
Gln Leu Gly Glu Leu Arg Glu Phe Asn Ala Leu Ser Gln Glu Ile
            500                 505                 510

Ala Met Ser Gln Leu Ile Asp Leu Ala Leu Leu Pro Leu Asp Met Phe
        515                 520                 525

Ser Met Phe Ser Gly Ile Lys Ser Thr Ile Asp Ala Ala Lys Ser Met
        530                 535                 540

Ala Thr Asn Val Met Lys Lys Phe Lys Lys Ser Gly Leu Ala Asn Ser
545                 550                 555                 560

Val Ser Thr Leu Thr Asp Ser Leu Ser Asp Ala Ala Ser Ser Ile Ser
                565                 570                 575

Arg Gly Ser Ser Ile Arg Ser Ile Gly Ser Ser Ala Ser Ala Trp Thr
            580                 585                 590

Asp Val Ser Thr Gln Ile Thr Asp Ile Ser Ser Ser Val Ser Ser Val
        595                 600                 605

Ser Thr Gln Thr Ser Thr Ile Ser Arg Arg Leu Arg Leu Lys Glu Met
        610                 615                 620

Ala Thr Gln Thr Glu Gly Met Asn Phe Asp Asp Ile Ser Ala Ala Val
625                 630                 635                 640

Leu Lys Thr Lys Ile Asp Lys Ser Thr Gln Ile Ser Pro Asn Thr Ile
                645                 650                 655

Pro Asp Ile Val Thr Glu Ala Ser Glu Lys Phe Ile Pro Asn Arg Ala
            660                 665                 670

Tyr Arg Val Ile Asn Asn Asp Asp Val Phe Glu Ala Gly Ile Asp Gly
        675                 680                 685

Lys Phe Phe Ala Tyr Lys Val Asp Thr Phe Glu Glu Ile Pro Phe Asp
        690                 695                 700

Val Gln Lys Phe Ala Asp Leu Val Thr Asp Ser Pro Val Ile Ser Ala
705                 710                 715                 720

Ile Ile Asp Phe Lys Thr Leu Lys Asn Leu Asn Asp Asn Tyr Gly Ile
                725                 730                 735

Thr Lys Gln Gln Ala Phe Asn Leu Leu Arg Ser Asp Pro Arg Val Leu
            740                 745                 750

Arg Glu Phe Ile Asn Gln Asp Asn Pro Ile Ile Arg Asn Arg Ile Glu
        755                 760                 765

Gln Leu Ile Met Gln Cys Arg Leu
        770                 775

<210> SEQ ID NO 88
<211> LENGTH: 774
<212> TYPE: PRT
<213> ORGANISM: Rotovirus strain EDIM

<400> SEQUENCE: 88

Met Ala Ser Leu Ile Tyr Arg Gln Leu Leu Thr Asn Ser Phe Thr Val
1               5                   10                  15

Asp Ile Ser Asp Glu Ile Glu Thr Ile Gly Ala Glu Lys Thr Gln Asn
                20                  25                  30

Val Thr Val Asn Pro Gly Pro Phe Ala Gln Thr Gly Tyr Ala Pro Ala
            35                  40                  45

Asn Trp Gly Pro Gly Glu Thr Asn Asp Ser Thr Thr Val Glu Pro Val
        50                  55                  60

Leu Asp Gly Pro Tyr Gln Pro Ile Ala Phe Ser Pro Pro Glu Tyr
65                  70                  75                  80

Tyr Ile Leu Leu Ser Pro Thr Ala Pro Gly Val Ile Ala Glu Cys Thr
```

```
                    85                  90                  95
Asn Thr Val Asn Arg Trp Ile Ala Ile Ile Ala Ile Glu Pro Asn Val
                100                 105                 110
Ser Pro Thr Asn Arg Thr Tyr Thr Leu Phe Gly Ile Thr Glu Gln Leu
                115                 120                 125
Thr Val Glu Asn Ser Ser Val Asp Lys Trp Lys Phe Ile Asp Phe Met
                130                 135                 140
Lys Thr Pro Thr Thr Gly Ser Tyr Val Arg Tyr Asn Ile Leu Leu Ser
145                 150                 155                 160
Ser Thr Lys Leu Cys Ala Val Ala Lys His Thr Asp Asn Leu Tyr Ser
                165                 170                 175
Tyr Val Gly Glu Thr Pro Thr Ala Gly Gln Ala Tyr Tyr Ser Ser Phe
                180                 185                 190
Asn Ile Phe Asn Leu Thr Ala His Cys Asp Phe Tyr Ile Ile Pro Trp
                195                 200                 205
Ser Gln Gln Ser Leu Cys Thr Gln Tyr Val Asn Asn Gly Leu Pro Pro
                210                 215                 220
Ile Gln Asn Thr Arg Asn Val Val Pro Arg His Leu Ser Ala Arg Ser
225                 230                 235                 240
Ile Ile Thr Gln Arg Ala Gln Ala Asn Glu Asp Ile Val Val Ser Lys
                245                 250                 255
Thr Ser Leu Trp Lys Glu Met Gln Phe Asn Arg Asp Ile Thr Ile Arg
                260                 265                 270
Phe Lys Phe Ala Asn Ala Ile Ile Lys Ser Gly Gly Leu Gly Tyr Lys
                275                 280                 285
Trp Ser Glu Ile Ser Phe Lys Pro Ala Asn Tyr Gln Tyr Thr Tyr Thr
                290                 295                 300
Arg Asp Gly Glu Glu Val Thr Ala His Thr Thr Cys Ser Val Asn Gly
305                 310                 315                 320
Val Asn Asn Phe Asp Phe Phe Gly Gly Ser Leu Pro Thr Asp Phe Gly
                325                 330                 335
Ile Ser Arg Tyr Glu Val Ile Lys Glu Asn Ser Phe Val Tyr Ile Asp
                340                 345                 350
Tyr Trp Asp Asp Ser Gln Ala Phe Arg Asn Met Val Tyr Val Arg Ser
                355                 360                 365
Leu Ala Ala Asp Leu Asn Thr Val Glu Cys Thr Gly Gly Ala Tyr Ser
                370                 375                 380
Phe Ser Leu Pro Val Gly Gln Trp Pro Val Met Thr Gly Gly Ala Val
385                 390                 395                 400
Ser Leu Arg Ala Ala Gly Val Thr Leu Ser Thr Gln Phe Thr Asp Phe
                405                 410                 415
Val Ser Leu Asn Ser Leu Arg Phe Arg Phe Arg Leu Ser Val Glu Glu
                420                 425                 430
Pro Ser Phe Ser Ile Thr Arg Thr Arg Val Ser Gly Leu Tyr Gly Leu
                435                 440                 445
Pro Ala Ala Asp Pro Asn Asn Gly Arg Glu Tyr Tyr Glu Ile Ala Gly
                450                 455                 460
Arg Phe Ser Leu Ile Ser Leu Val Pro Ser Asn Asp Asn Tyr Gln Thr
465                 470                 475                 480
Pro Ile Met Asn Ser Val Thr Val Arg Gln Asp Leu Glu Arg Gln Leu
                485                 490                 495
Gly Glu Leu Arg Glu Glu Phe Asn Ala Leu Ser Gln Glu Ile Ala Leu
                500                 505                 510
```

```
Ser Gln Leu Val Asp Leu Ala Leu Leu Pro Leu Asp Met Phe Ser Met
    515                 520                 525

Phe Ser Gly Ile Lys Ala Thr Leu Asp Val Ala Lys Ser Met Ala Thr
    530                 535                 540

Asn Val Met Lys Lys Phe Lys Lys Ser Gly Leu Ala Thr Ser Ile Ser
545                 550                 555                 560

Ala Met Thr Glu Ser Leu Ser Asp Ala Ala Ser Ser Val Ser Arg Ser
                    565                 570                 575

Gly Ala Ile Arg Ser Val Ser Ser Thr Ser Ser Ala Trp Thr Asp Val
                580                 585                 590

Ser Ser Arg Val Ala Asn Val Glu Asn Ala Ala Ser Thr Val Ser Thr
        595                 600                 605

Gln Thr Ala Thr Ile Ser Arg Arg Leu Arg Leu Lys Glu Ile Thr Thr
            610                 615                 620

Gln Thr Glu Gly Met Asn Phe Asp Asp Ile Ser Ala Ala Val Leu Lys
625                 630                 635                 640

Thr Lys Leu Asp Lys Ser Val Arg Ile Ala Pro Asn Thr Leu Pro Asp
                    645                 650                 655

Ile Val Thr Glu Ala Ser Glu Lys Phe Ile Pro Asn Arg Ser Tyr Arg
                660                 665                 670

Val Ile Asn Asn Asn Glu Ala Phe Glu Thr Gly Thr Asp Gly Arg Phe
            675                 680                 685

Phe Ala Tyr Arg Val Asp Thr Leu Glu Glu Leu Pro Phe Asp Val Gln
            690                 695                 700

Lys Phe Ala Asp Leu Val Ala Glu Ser Pro Val Ile Ser Ala Ile Ile
705                 710                 715                 720

Asp Phe Lys Thr Leu Lys Asn Leu Asn Asp Asn Tyr Gly Ile Ser Lys
                    725                 730                 735

Glu Gln Ala Phe Ser Leu Leu Arg Ser Asp Pro Arg Val Leu Arg Glu
                740                 745                 750

Phe Ile Asn Gln Gly Asn Pro Ile Ile Arg Asn Arg Ile Glu Gln Leu
            755                 760                 765

Ile Met Gln Cys Arg Leu
    770

<210> SEQ ID NO 89
<211> LENGTH: 775
<212> TYPE: PRT
<213> ORGANISM: rotovirus genotype P[4]

<400> SEQUENCE: 89

Met Ala Ser Leu Ile Tyr Arg Gln Leu Leu Thr Asn Ser Tyr Ser Val
1               5                   10                  15

Asp Leu His Asp Glu Ile Glu Gln Ile Gly Ser Glu Lys Thr Gln Asn
                20                  25                  30

Val Thr Val Asn Pro Gly Pro Phe Ala Gln Thr Arg Tyr Ala Pro Val
            35                  40                  45

Asn Trp Gly His Gly Glu Ile Asn Asp Ser Thr Thr Val Glu Pro Val
        50                  55                  60

Leu Asp Gly Pro Tyr Gln Pro Thr Thr Phe Lys Pro Pro Asn Asp Tyr
65                  70                  75                  80

Trp Leu Leu Ile Ser Ser Asn Thr Asp Gly Val Val Tyr Glu Ser Thr
                    85                  90                  95

Asn Asn Ser Asp Phe Trp Thr Ala Val Ile Ala Val Glu Pro His Val
```

-continued

```
                100                 105                 110
Ser Gln Thr Asn Arg Gln Tyr Val Leu Phe Gly Glu Asn Lys Gln Phe
            115                 120                 125

Asn Ile Glu Asn Ser Ser Asp Lys Trp Lys Phe Leu Glu Met Phe Arg
            130                 135                 140

Gly Ser Gly Gln Ser Asp Phe Ser Asn Arg Arg Thr Leu Thr Ser Asn
145                 150                 155                 160

Asn Arg Leu Val Gly Met Leu Lys Tyr Gly Gly Arg Val Trp Thr Phe
                165                 170                 175

His Gly Glu Thr Pro Arg Ala Thr Thr Asp Ser Ser Asn Thr Ala Asp
                180                 185                 190

Leu Asn Asn Ile Ser Ile Ile His Ser Glu Phe Tyr Ile Ile Pro
            195                 200                 205

Arg Ser Gln Glu Ser Lys Cys Asn Glu Tyr Ile Asn Asn Gly Leu Pro
            210                 215                 220

Pro Ile Gln Asn Thr Arg Asn Val Val Pro Leu Ser Leu Ser Ser Arg
225                 230                 235                 240

Ser Ile Gln Tyr Arg Arg Ala Gln Val Asn Glu Asp Ile Thr Ile Ser
                245                 250                 255

Lys Thr Ser Leu Trp Lys Glu Met Gln Tyr Asn Arg Asp Ile Ile Ile
                260                 265                 270

Arg Phe Lys Phe Gly Asn Ser Val Ile Lys Leu Gly Gly Leu Gly Tyr
            275                 280                 285

Lys Trp Ser Glu Ile Ser Tyr Lys Ala Ala Asn Tyr Gln Tyr Ser Tyr
            290                 295                 300

Ser Arg Asp Gly Glu Gln Val Thr Ala His Thr Thr Cys Ser Val Asn
305                 310                 315                 320

Gly Val Asn Asn Phe Ser Tyr Asn Gly Gly Ser Leu Pro Thr Asp Phe
                325                 330                 335

Ser Ile Ser Arg Tyr Glu Val Ile Lys Glu Asn Ser Tyr Val Tyr Ile
                340                 345                 350

Asp Tyr Trp Asp Asp Ser Lys Ala Phe Arg Asn Met Val Tyr Val Arg
                355                 360                 365

Ser Leu Ala Ala Asn Leu Asn Ser Val Lys Cys Val Gly Gly Ser Tyr
            370                 375                 380

Asp Phe Arg Leu Pro Val Gly Glu Trp Pro Ile Met Asn Gly Gly Ala
385                 390                 395                 400

Val Ser Leu His Phe Ala Gly Val Thr Leu Ser Thr Gln Phe Thr Asp
                405                 410                 415

Phe Val Ser Leu Asn Ser Leu Arg Phe Arg Phe Ser Leu Thr Val Asp
            420                 425                 430

Glu Pro Ser Phe Ser Ile Ile Arg Thr Arg Thr Met Asn Leu Tyr Gly
            435                 440                 445

Leu Pro Ala Ala Asn Pro Asn Asn Gly Asn Glu Tyr Tyr Glu Val Ser
            450                 455                 460

Gly Arg Phe Ser Leu Ile Ser Leu Val Pro Thr Asn Asp Asp Tyr Gln
465                 470                 475                 480

Thr Pro Ile Met Asn Ser Val Thr Val Arg Gln Asp Leu Glu Arg Gln
                485                 490                 495

Leu Asn Asp Leu Arg Glu Glu Phe Asn Ser Leu Ser Gln Glu Ile Ala
            500                 505                 510

Met Ser Gln Leu Ile Asp Leu Ala Leu Leu Pro Leu Asp Met Phe Ser
            515                 520                 525
```

Met Phe Ser Gly Ile Lys Ser Thr Ile Asp Leu Thr Lys Ser Met Ala
530                 535                 540

Thr Ser Val Met Lys Lys Phe Arg Lys Ser Lys Leu Ala Thr Ser Ile
545                 550                 555                 560

Ser Glu Met Thr Asn Ser Leu Ser Asp Ala Ala Ser Ser Ala Ser Arg
            565                 570                 575

Ser Ala Ser Ile Arg Ser Asn Leu Ser Thr Ile Ser Asn Trp Ser Asp
            580                 585                 590

Ala Ser Lys Ser Val Leu Asn Val Thr Asp Ser Val Asn Asp Val Ser
            595                 600                 605

Thr Gln Thr Ser Thr Ile Ser Lys Lys Leu Arg Leu Arg Glu Met Ile
            610                 615                 620

Thr Gln Thr Glu Gly Ile Ser Phe Asp Asp Ile Ser Ala Ala Val Leu
625                 630                 635                 640

Lys Thr Lys Ile Asp Met Ser Thr Gln Ile Gly Lys Asn Thr Leu Pro
                645                 650                 655

Asp Ile Val Thr Glu Ala Ser Glu Lys Phe Ile Pro Lys Arg Ser Tyr
            660                 665                 670

Arg Val Leu Lys Asp Asp Glu Val Met Glu Val Asn Thr Glu Gly Lys
            675                 680                 685

Phe Phe Ala Tyr Lys Val Asp Thr Leu Asn Glu Ile Pro Phe Asp Ile
690                 695                 700

Asn Lys Phe Ala Glu Leu Val Thr Asp Ser Pro Val Ile Ser Ala Ile
705                 710                 715                 720

Ile Asp Phe Lys Thr Leu Lys Asn Leu Asn Asp Asn Tyr Gly Ile Thr
                725                 730                 735

Arg Ile Glu Ala Leu Asn Leu Ile Lys Ser Asn Pro Asn Val Leu Arg
            740                 745                 750

Asn Phe Ile Asn Gln Asn Asn Pro Ile Ile Arg Asn Arg Ile Glu Gln
            755                 760                 765

Leu Ile Leu Gln Cys Lys Leu
770                 775

<210> SEQ ID NO 90
<211> LENGTH: 775
<212> TYPE: PRT
<213> ORGANISM: rotovirus genotype P[6]

<400> SEQUENCE: 90

Met Ala Ser Leu Ile Tyr Arg Gln Leu Leu Thr Asn Ser Tyr Thr Val
1               5                   10                  15

Glu Leu Ser Asp Glu Ile Asn Thr Ile Gly Ser Glu Lys Ser Gln Asn
            20                  25                  30

Val Thr Ile Asn Pro Gly Pro Phe Ala Gln Thr Asn Tyr Ala Pro Val
            35                  40                  45

Thr Trp Ser His Gly Glu Val Asn Asp Ser Thr Thr Ile Glu Pro Val
        50                  55                  60

Leu Asp Gly Pro Tyr Gln Pro Thr Asn Phe Lys Pro Pro Asn Asp Tyr
65                  70                  75                  80

Trp Ile Leu Leu Asn Pro Thr Asn Gln Gln Val Val Leu Glu Gly Thr
                85                  90                  95

Asn Lys Thr Asp Ile Trp Val Ala Leu Leu Leu Val Glu Pro Asn Val
            100                 105                 110

Thr Asn Gln Ser Arg Gln Tyr Thr Leu Phe Gly Glu Thr Lys Gln Ile

-continued

```
            115                 120                 125
Thr Val Glu Asn Asn Thr Asn Lys Trp Lys Phe Phe Glu Met Phe Arg
130                 135                 140

Ser Asn Val Asn Ala Glu Phe Gln His Lys Arg Thr Leu Thr Ser Asp
145                 150                 155                 160

Thr Lys Leu Ala Gly Phe Met Lys Phe Tyr Asn Ser Val Trp Thr Phe
                165                 170                 175

His Gly Glu Thr Pro His Ala Thr Thr Asp Tyr Ser Ser Thr Ser Asn
            180                 185                 190

Leu Ser Glu Val Glu Thr Val Ile His Val Glu Phe Tyr Ile Ile Pro
            195                 200                 205

Arg Ser Gln Glu Ser Lys Cys Ser Glu Tyr Ile Asn Thr Gly Leu Pro
210                 215                 220

Pro Met Gln Asn Thr Arg Asn Ile Val Pro Val Ala Leu Ser Ser Arg
225                 230                 235                 240

Ser Val Thr Tyr Gln Arg Ala Gln Val Asn Glu Asp Ile Ile Ile Ser
                245                 250                 255

Lys Thr Ser Leu Trp Lys Glu Met Gln Tyr Asn Arg Asp Ile Ile Ile
            260                 265                 270

Arg Phe Lys Phe Asn Asn Ser Ile Val Lys Leu Gly Gly Leu Gly Tyr
            275                 280                 285

Lys Trp Ser Glu Ile Ser Phe Lys Ala Ala Asn Tyr Gln Tyr Ser Tyr
290                 295                 300

Leu Arg Asp Gly Glu Gln Val Thr Ala His Thr Thr Cys Ser Val Asn
305                 310                 315                 320

Gly Val Asn Asn Phe Ser Tyr Asn Gly Gly Ser Leu Pro Thr Asp Phe
                325                 330                 335

Ser Val Ser Arg Tyr Glu Val Ile Lys Glu Asn Ser Tyr Val Tyr Val
            340                 345                 350

Asp Tyr Trp Asp Asp Ser Gln Ala Phe Arg Asn Met Val Tyr Val Arg
            355                 360                 365

Ser Leu Ala Ala Asn Leu Asn Ser Val Lys Cys Ser Gly Gly Asn Tyr
370                 375                 380

Asn Phe Gln Ile Pro Val Gly Ala Trp Pro Val Met Ser Gly Gly Ala
385                 390                 395                 400

Val Ser Leu His Phe Ala Gly Val Thr Leu Ser Thr Gln Phe Thr Asp
                405                 410                 415

Phe Val Ser Leu Asn Ser Leu Arg Phe Arg Phe Ser Leu Thr Val Glu
            420                 425                 430

Glu Pro Pro Phe Ser Ile Leu Arg Thr Arg Val Ser Gly Leu Tyr Gly
            435                 440                 445

Leu Pro Ala Phe Asn Pro Asn Gly His Glu Tyr Tyr Glu Ile Ala
450                 455                 460

Gly Arg Phe Ser Leu Ile Ser Leu Val Pro Ser Asn Asp Asp Tyr Gln
465                 470                 475                 480

Thr Pro Ile Met Asn Ser Val Thr Val Arg Gln Asp Leu Glu Arg Gln
                485                 490                 495

Leu Gly Asp Leu Arg Glu Glu Phe Asn Ser Leu Ser Gln Glu Ile Ala
            500                 505                 510

Met Thr Gln Leu Ile Asp Leu Ala Leu Leu Pro Leu Asp Met Phe Ser
            515                 520                 525

Met Phe Ser Gly Ile Lys Ser Thr Ile Asp Val Ala Lys Ser Met Val
530                 535                 540
```

```
Thr Lys Val Met Lys Lys Phe Lys Lys Ser Gly Leu Ala Thr Ser Ile
545                 550                 555                 560

Ser Glu Leu Thr Gly Ser Leu Ser Asn Ala Ala Ser Ser Val Ser Arg
            565                 570                 575

Ser Ser Ser Ile Arg Ser Asn Ile Ser Ser Ile Ser Val Trp Thr Asp
        580                 585                 590

Val Ser Glu Gln Ile Ala Gly Ser Ser Asp Ser Val Arg Asn Ile Ser
    595                 600                 605

Thr Gln Thr Ser Ala Ile Ser Lys Arg Leu Arg Leu Arg Glu Ile Thr
610                 615                 620

Thr Gln Thr Glu Gly Met Asn Phe Asp Asp Ile Ser Ala Ala Val Leu
625                 630                 635                 640

Lys Thr Lys Ile Asp Arg Ser Thr His Ile Ser Pro Asp Thr Leu Pro
                645                 650                 655

Asp Ile Ile Thr Glu Ser Ser Glu Lys Phe Ile Pro Lys Arg Ala Tyr
                660                 665                 670

Arg Val Leu Lys Asp Asp Glu Val Met Glu Ala Asp Val Asp Gly Lys
            675                 680                 685

Phe Phe Ala Tyr Lys Val Gly Thr Phe Glu Val Pro Phe Asp Val
690                 695                 700

Asp Lys Phe Val Asp Leu Val Thr Asp Ser Pro Val Ile Ser Ala Ile
705                 710                 715                 720

Ile Asp Phe Lys Thr Leu Lys Asn Leu Asn Asp Asn Tyr Gly Ile Thr
                725                 730                 735

Arg Ser Gln Ala Leu Asp Leu Ile Arg Ser Asp Pro Arg Val Leu Arg
            740                 745                 750

Asp Phe Ile Asn Gln Asn Asn Pro Ile Ile Lys Asn Arg Ile Glu Gln
        755                 760                 765

Leu Ile Leu Gln Cys Arg Leu
    770                 775

<210> SEQ ID NO 91
<211> LENGTH: 775
<212> TYPE: PRT
<213> ORGANISM: rotovirus genotype P[8]

<400> SEQUENCE: 91

Met Ala Ser Leu Ile Tyr Arg Gln Leu Leu Thr Asn Ser Tyr Ser Val
1               5                   10                  15

Asp Leu His Asp Glu Ile Glu Gln Ile Gly Ser Glu Lys Thr Gln Asn
            20                  25                  30

Val Thr Ile Asn Pro Ser Pro Phe Ala Gln Thr Arg Tyr Ala Pro Val
        35                  40                  45

Asn Trp Gly His Gly Glu Ile Asn Asp Ser Thr Thr Val Glu Pro Met
50                  55                  60

Leu Asp Gly Pro Tyr Gln Pro Thr Thr Phe Thr Pro Pro Asn Asp Tyr
65                  70                  75                  80

Trp Ile Leu Ile Asn Ser Asn Thr Asn Gly Val Val Tyr Glu Ser Thr
                85                  90                  95

Asn Asn Ser Asp Phe Trp Thr Ala Val Ala Ile Glu Pro His Val
            100                 105                 110

Asn Pro Val Asp Arg Gln Tyr Thr Ile Phe Gly Glu Ser Lys Gln Phe
        115                 120                 125

Asn Val Ser Asn Asp Ser Asn Lys Trp Lys Phe Leu Glu Met Phe Arg
```

```
            130                 135                 140
Ser Ser Ser Gln Asn Glu Phe Tyr Asn Arg Arg Thr Leu Thr Ser Asp
145                 150                 155                 160

Thr Arg Phe Val Gly Ile Leu Lys Tyr Gly Arg Val Trp Thr Phe
                165                 170                 175

His Gly Glu Thr Pro Arg Ala Thr Thr Asp Ser Ser Thr Ala Asn
                180                 185                 190

Leu Asn Asn Ile Ser Ile Thr Ile His Ser Glu Phe Tyr Ile Ile Pro
                195                 200                 205

Arg Ser Gln Glu Ser Lys Cys Asn Glu Tyr Ile Asn Asn Gly Leu Pro
                210                 215                 220

Pro Ile Gln Asn Thr Arg Asn Val Val Pro Leu Pro Leu Ser Ser Arg
225                 230                 235                 240

Ser Ile Gln Tyr Lys Arg Ala Gln Val Asn Glu Asp Ile Ile Val Ser
                245                 250                 255

Lys Thr Ser Leu Trp Lys Glu Met Gln Tyr Asn Arg Asp Ile Ile Ile
                260                 265                 270

Arg Phe Lys Phe Gly Asn Ser Ile Val Lys Met Gly Gly Leu Gly Tyr
                275                 280                 285

Lys Trp Ser Glu Ile Ser Tyr Lys Ala Ala Asn Tyr Gln Tyr Asn Tyr
                290                 295                 300

Leu Arg Asp Gly Glu Gln Val Thr Ala His Thr Thr Cys Ser Val Asn
305                 310                 315                 320

Gly Val Asn Asn Phe Ser Tyr Asn Gly Gly Phe Leu Pro Thr Asp Phe
                325                 330                 335

Gly Ile Ser Arg Tyr Glu Val Ile Lys Glu Asn Ser Tyr Val Tyr Val
                340                 345                 350

Asp Tyr Trp Asp Ser Lys Ala Phe Arg Asn Met Val Tyr Val Arg
                355                 360                 365

Ser Leu Ala Ala Asn Leu Asn Ser Val Lys Cys Thr Gly Gly Ser Tyr
                370                 375                 380

Asn Phe Ser Ile Pro Val Gly Ala Trp Pro Val Met Asn Gly Gly Ala
385                 390                 395                 400

Val Ser Leu His Phe Ala Gly Val Thr Leu Ser Thr Gln Phe Thr Asp
                405                 410                 415

Phe Val Ser Leu Asn Ser Leu Arg Phe Arg Phe Ser Leu Thr Val Asp
                420                 425                 430

Glu Pro Pro Phe Ser Ile Leu Arg Thr Arg Thr Val Asn Leu Tyr Gly
                435                 440                 445

Leu Pro Ala Ala Asn Pro Asn Asn Gly Asn Glu Tyr Tyr Glu Ile Ser
450                 455                 460

Gly Arg Phe Ser Leu Ile Tyr Leu Val Pro Thr Asn Asp Asp Tyr Gln
465                 470                 475                 480

Thr Pro Ile Met Asn Ser Val Thr Val Arg Gln Asp Leu Glu Arg Gln
                485                 490                 495

Leu Thr Asp Leu Arg Glu Glu Phe Asn Ser Leu Ser Gln Glu Ile Ala
                500                 505                 510

Met Ala Gln Leu Ile Asp Leu Ala Leu Leu Pro Leu Asp Met Phe Ser
                515                 520                 525

Met Phe Ser Gly Ile Lys Ser Thr Ile Asp Leu Thr Lys Ser Met Ala
                530                 535                 540

Thr Ser Val Met Lys Lys Phe Arg Lys Ser Lys Leu Ala Thr Ser Ile
545                 550                 555                 560
```

```
Ser Glu Met Thr Asn Ser Leu Ser Asp Ala Ala Ser Ser Ala Ser Arg
            565                 570                 575

Asn Val Ser Ile Arg Ser Asn Leu Ser Ala Ile Ser Asn Trp Thr Asn
            580                 585                 590

Val Ser Asn Asp Val Ser Asn Val Thr Asn Ser Leu Asn Asp Ile Ser
        595                 600                 605

Thr Gln Thr Ser Thr Ile Ser Lys Lys Phe Arg Leu Lys Glu Met Ile
        610                 615                 620

Thr Gln Thr Glu Gly Met Ser Phe Asp Asp Ile Ser Ala Ala Val Leu
625                 630                 635                 640

Lys Thr Lys Ile Asp Met Ser Thr Gln Ile Gly Lys Asn Thr Leu Pro
                645                 650                 655

Asp Ile Val Thr Glu Ala Ser Glu Lys Phe Ile Pro Lys Arg Ser Tyr
                660                 665                 670

Arg Ile Leu Lys Asp Asp Glu Val Met Glu Ile Asn Thr Glu Gly Lys
            675                 680                 685

Phe Phe Ala Tyr Lys Ile Asn Thr Phe Asp Glu Val Pro Phe Asp Val
        690                 695                 700

Asn Lys Phe Ala Glu Leu Val Thr Asp Ser Pro Val Ile Ser Ala Ile
705                 710                 715                 720

Ile Asp Phe Lys Thr Leu Lys Asn Leu Asn Asp Asn Tyr Gly Ile Thr
                725                 730                 735

Arg Thr Glu Ala Leu Asn Leu Ile Lys Ser Asn Pro Asn Met Leu Arg
                740                 745                 750

Asn Phe Ile Asn Gln Asn Asn Pro Ile Ile Arg Asn Arg Ile Glu Gln
        755                 760                 765

Leu Ile Leu Gln Cys Lys Leu
770                 775
```

TRUNCATED ROTAVIRUS VP4 PROTEIN AND APPLICATION THEREOF

CROSS-REFERENCE TO RELATED APPLICATIONS

This application claims priority under 35 U.S.C. § 371 to Patent Cooperation Treaty application PCT/CN2016/082780, filed May 20, 2016, which claims the benefit of Chinese Patent Application No. 201510260020.7, filed May 21, 2015, the entire contents of which are incorporated herein by reference.

SEQUENCE LISTING

This application incorporates in its entirety the Sequence Listing entitled "IEC160054PUSPCT-SEQLIST_ST25.txt" (182,044 bytes), which was created on Nov. 16, 2017 and filed electronically herewith.

TECHNICAL FIELD

The invention relates to the fields of biochemistry, molecular biology, molecular virology and immunology. In particular, the invention relates to a truncated rotavirus VP4 protein, a sequence encoding the same, a method for preparing the same, and a pharmaceutical composition and a vaccine comprising the protein, wherein the protein, the pharmaceutical composition and the vaccine are useful for preventing, alleviating or treating rotavirus infection and a disease caused by rotavirus infection, such as rotavirus gastroenteritis and diarrhea. The invention further relates to use of the protein in the manufacture of a pharmaceutical composition or a vaccine for preventing, alleviating or treating rotavirus infection and a disease caused by rotavirus infection, such as rotavirus gastroenteritis and diarrhea.

BACKGROUND ART

Rotavirus (RV) belongs to the rotavirus genus belonging to the Reoviridae family, which is the main pathogen responsible for infant diarrhea and was found in duodenum from patients with gastroenteritis by Bishop in 1973 (Bishop, Davidson, Holmes, et al. Lancet, 2 (7841), 1281-1283, 1973). Studies showed that more than 95% of children were infected with rotavirus at least once before 5 years old. According to the WHO statistics, up to 600,000 people died of rotavirus infection annually, and cases of diarrhea reached up to 200 million; and in USA only, economic loss caused by rotavirus infection reached up to 1 billion dollars annually (Hsu, Staat, Roberts, et al. Pediatrics, 115 (1), 78-82, 2005; Tate, Burton, Boschi-Pinto, et al. The Lancet Infectious Diseases, 12 (2), 136-141, 2011), resulting in serious financial burden and social burden.

Rotavirus is a non-enveloped RNA virus, and its genome consists of 11 double-stranded RNA molecules which encode 6 structural proteins (VP1-VP4, VP6 and VP7) and 6 non-structural proteins (NSP1-NSP6) (Estes and Cohen. Microbiol Rev, 53 (4), 410-449, 1989). Rotavirus is icosahedral, and its capsid consists of three concentric layers, i.e. the core layer consisting of VP1, VP2 and VP3, the inner capsid consisting of VP6, and the outer capsid consisting of VP4 and VP7.

VP6 protein is a capsid protein comprised in the highest content in rotavirus. Depending on the antigenicity of VP6, rotavirus may be divided into 7 groups, i.e. rotavirus A-G, among which rotavirus A is the main pathogen responsible for diarrhea among infants and young children. VP4 and VP7 are the main neutralizing antigens, and, rotavirus A can be divided into P serotype and G serotype depending on their antigenicity. G serotype and P serotype are independent of each other but are also interacted with each other; the common combinations include G1P[8], G2P[4], G3P[8] and G4P[8]; in recent years, the prevalence of G9P[8] and G9P[6] is significantly increased (Li, Liu, Yu, et al. Vaccine, 27 F40-F45, 2009).

There are not specific drugs for rotavirus yet, and safe and effective vaccines are the important means for control of rotavirus infection. After years of research, the vaccine development has underwent three phases, i.e. monovalent attenuated vaccines, polyvalent gene recombinant vaccines, and genetically engineering vaccines. At present, there are five rotavirus vaccines appeared in the market one by one, including tetravalent human-ape gene recombinant vaccine from Wyeth, monovalent attenuated vaccine from Lanzhou Institute, pentavalent human-bovine gene recombinant vaccine from Merck, monovalent attenuated vaccine from GSK, and monovalent attenuated vaccine from Bharat Vaccines, India. However, these vaccines are attenuated live vaccines which have large potential safety hazard, and among them, the vaccines from Wyeth were recalled due to intestinal intussusception half a year after being in the market (Murphy, Gargiullo, Massoudi, et al. 344 (8), 564-572, 2001). Although the vaccines from MERCK and GSK were demonstrated to be safe and effective by a large number of clinical tests (Bernstein, Sack, Rothstein, et al. Lancet (British edition), 354 (9175), 287-290, 1999; Vesikari, Matson, Dennehy, et al. New England Journal of Medicine, 354 (1), 23-33, 2006; Linhares, Velázquez, Pérez-Schael, et al. Lancet, 371 (9619), 1181-1189, 2008; Vesikari, Itzler, Karvonen, et al. Vaccine, 28 (2), 345-351, 2009; Snelling, Andrews, Kirkwood, et al. Clinical Infectious Diseases, 52 (2), 191-200, 2011), in countries and regions with a high rotavirus mortality such as Asia and Africa, the protection efficiency was much lower than that in developed countries such as Europe and America (Armah, Sow, Breiman, et al. Lancet, 376 606-614, 2010; Zaman, Anh, Victor, et al. Lancet, 376 568-570, 2010; Madhi, Cunliffe, Steele, et al. N Engl J Med, 362 (4), 289-298, 2011). More and more evidence showed that upon vaccination with the two vaccines, excretion of virus occurred, which might cause horizontal transmission of virus (Anderson. Lancet Infect Dis, 8 (10), 642-9, 2008; Rivera, Pena, Stainier, et al. Vaccine, 29 (51), 9508-9513, 2011; Yen, Jakob, Esona, et al. Vaccine, 29 (24), 4151-5, 2011). It was also shown in some studies that serious gastroenteritis might be developed in immune-deficient children after vaccination with the vaccines (Steele, Cunliffe, Tumbo, et al. J Infect Dis, 200 Suppl 1 S57-62, 2009; Patel, Hertel, Estes, et al. N Engl J Med, 362 (4), 314-9, 2010). The vaccines from Lanzhou Institute have been commercially available for more than 10 years, and no serious problem is found yet; however, they can only prevent serious diarrhea, but cannot prevent rotavirus infection (Fu, Wang, Liang, et al. Vaccine, 25 (52), 8756-61, 2007). Therefore, although delightful results are obtained in the studies on attenuated vaccines against rotavirus, there are still some problems, and the safety and effectiveness need to be further improved. It is imperative to develop more safe and effective vaccines.

Non-replicating vaccines are the main direction for studies on rotavirus vaccines now, and genetically engineering vaccines attract much attention because of characteristics such as low cost, safety and effectiveness.

VP4 and VP7 protein, as neutralizing antigens of rotavirus, can stimulate generation of neutralizing antibodies in an organism, thereby inhibiting infection of rotavirus. Therefore, both VP4 and VP7 are the main candidate antigens for rotavirus subunit vaccines. VP7 protein, which is a glycosylated protein, comprises 4 intrachain disulfide bonds, and forms a $Ca^{2+}$-dependent trimer, but the level of neutralizing antibodies, generated by stimulation with a recombinantly expressed VP7 protein, is low. VP4 protein is not glycosylated, and a recombinantly expressed VP4 protein can stimulate generation of high immune response in an organism, and reduce the degree of diarrhea in suckling mice (Mackow, Vo, Broome, et al. J Virol, 64 (4), 1698-703, 1990). In another aspect, there are only two common P serotypes, but there are five G serotypes. Therefore, as compared to VP7 protein, VP4 protein is a candidate antigen more suitable for rotavirus genetic engineering vaccines.

VP4 protein consists of 776 amino acids, can be cleaved by trypsin to form two moieties, i.e., VP8* (aa1-231) and VP5* (aa248-776). VP4 protein consists of a head domain, a body and stalk domain and a foot domain, and as a spike protein of rotavirus, VP4 plays an important role in rotavirus infection. The head domain of a spike consists of two molecules of VP8 protein, and VP8 protein can bind to sialic acid receptor on the surface of a cell, and thereby mediate the adsorption of rotavirus. The body and stalk domain consists of three molecules of VP5 antigen domain, wherein two molecules of VP5 antigen domain form a dimer, and another VP5 antigen domain is present in a form of monomer. During the infection of rotavirus, the structure of VP4 is rearranged, to expose the membrane fusion site in VP5 and mediate the entry of rotavirus into a cell, during which, VP5 antigen domains change from a dimer to a trimer. The foot domain consists of three molecules of C-terminal domain of VP5 protein, and inserts into outer capsid and inner capsid by virtue of the domain. The first 25 Amino acids at N-terminal of VP8 protein form an α-helix, three α-helixes form a helical bundle that inserts into VP5 foot domain, and is linked to a VP8 head domain via a flexible jointing region, wherein the structure of the jointing region is not completely determined yet (Settembre, Chen, Dormitzer, et al. EMBO J, 30 (2), 408-16, 2011).

There are studies showing that neutralizing epitopes of VP4 protein are mainly present in VP8 head domain and VP5 antigen domain, neutralizing antibodies against VP8 can inhibit the absorption of rotavirus, and neutralizing antibodies against VP5 have cross-neutralizing activity, and can inhibit the entry of rotavirus into a cell (Dormitzer, Nason, Venkataram Prasad, et al. Nature, 430 (7003), 1053-1058, 2004; Abdelhakim, Salgado, Fu, et al. PLoS Pathog, 10 (9), e1004355, 2014). In addition, the results of scanning synthetic peptides show that there are also neutralizing epitopes in a-helical region at N-terminal and the jointing region of VP8 protein (Kovacs-Nolan, Yoo and Mine. Biochem J, 376 (Pt 1), 269-75, 2003).

There are a lot of research results showing that VP4 protein can stimulate protective immune response in an organism (Dunn, Fiore, Werner, et al. Arch Virol, 140 (11), 1969-78, 1995; Gil, De Souza, Asensi, et al. Viral Immunology, 13 (2), 187-200, 2000). However, expression of VP4 protein by eukaryotic system has the disadvantages of long cycle, high cost and low expression level; in addition, a full-length VP4 protein is mainly present in a form of inclusion body in prokaryotic system, is difficult to purify and cannot retain its natural conformation. Wen Xiaobo et al. solved the problem concerning the expression of VP8 protein in a form of inclusion body in prokaryotic system by means of expressing a truncated form thereof, and obtained the truncated VP8 protein (ΔVP8*, aa65-223) that could be effectively expressed in E. coli in a soluble form (Wen, Cao, Jones, et al. Vaccine, 30 (43), 6121-6, 2012); however, the immunogenicity of the truncated VP8 protein is significantly lower than the full-length VP8 protein. In order to solve the problem concerning the low immunogenicity of the truncated VP8 protein, after deep studies, the laboratory of the inventor obtained new truncated VP8 proteins with higher immunogenicity, which can stimulate generation of high-titer neutralizing antibodies in mice upon the immunization therewith in the presence of Freund's adjuvant, and can reduce the degree of diarrhea in suckling mice; and the truncated VP8 protein can be subjected to fusion expression with an intramolecular adjuvant, so as to produce a fusion protein with higher immunogenicity and immune-protection (CN201510165746.2). Although the new truncated VP8 proteins and the fusion protein thereof have achieved significantly advantageous technical effects, there are still shortcomings. For example, antibodies against VP8 protein are mainly serotype-specific antibodies, and therefore, the new truncated VP8 proteins as vaccines have a significantly lower neutralizing activity against virus strains of a different serotype than the neutralizing activity against virus strains of the same serotypes (Wen, Cao, Jones, et al. Vaccine, 30 (43), 6121-6, 2012). In addition, it is also found in the subsequent studies that the immune-protection of the new truncated VP8 proteins is not satisfactory enough in the presence of aluminum adjuvant, and needs to be further improved.

Therefore, there is still demand in the art to develop new vaccines against rotavirus, which can be produced more conveniently in a high expression level (e.g., by means of soluble expression and purification), can have stronger immunogenicity than the existing vaccines (e.g., the truncated VP8 protein mentioned above), can induce generation of high-titer neutralizing antibodies against rotavirus (particularly in the presence of aluminum adjuvant) in an organism, and therefore can be used in the large-scale industrial production of highly effective vaccines against rotavirus.

CONTENTS OF INVENTION

The inventors of the present application discovered surprisingly after extensive researches that VP4 protein having 1-64 amino acids (e.g., 5-64 amino acids) truncated at N-terminal, and having C-terminal ended at a position among amino acid positions 276-497, can be expressed in E. coli in a soluble form, and can be easily purified by chromatography; moreover, the high-purity truncated protein thus obtained (with a purity that can reach at least 50% or higher, e.g., 60%, 70%, 80%, 90%, 95%, 96%, 97%, 98%, 99%) has good homogeneity and immunogenicity, can induce generation of high-titer neutralizing antibodies against rotavirus in the presence of aluminum adjuvant in an organism, and therefore effectively solve the above-mentioned technical problem.

Therefore, in an aspect, the invention relates to a truncated rotavirus VP4 protein or a variant thereof having 1-64 amino acids (e.g., 5-64 amino acids) truncated at N-terminal and having C-terminal ended at a position among the amino acid positions 276-497.

In an aspect, the invention relates to a truncated rotavirus VP4 protein or a variant thereof, which as compared to a wild-type rotavirus VP4 protein, has 1-64 amino acids (e.g., 5-64 amino acids) truncated at N-terminal, and has C-terminal ended at the following position of the wild-type rotavirus VP4 protein: a position corresponding to any position among the amino acid positions 276-497 of SEQ ID NO: 40.

In some preferred embodiments, as compared to a wild-type rotavirus VP4 protein, the truncated rotavirus VP4 protein has 1-64 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63 or 64 amino acids (e.g., 1-5, 5-25, 5-21, 21-25, 21-64, or 25-64 amino acids, e.g., 1, 5, 21, 25, or 64 amino acids) truncated at N-terminal; and has C-terminal ended at the following position of a wild-type rotavirus VP4 protein: a position corresponding to any position among the amino acid positions 276-497 (e.g., amino acid positions 281-497, 291-497, 301-497, 311-497, 321-497, 331-497, 341-497, 351-497, 361-497, 371-497, 381-497, 391-497, 401-497, 411-497, 421-497, 431-497, 441-497, 451-497, 461-497, 471-497, 476-497, 482-497, 487-497, or 492-497) of SEQ ID NO: 40, for example, has C-terminal ended at the following position: a position corresponding to the amino acid position 276, 281, 291, 301, 311, 321, 331, 341, 351, 361, 371, 381, 391, 401, 411, 421, 431, 441, 451, 461, 471, 476, 482, 487, 492 or 497 of SEQ ID NO: 40 (e.g., a position corresponding to the amino acid position 331, 351, 381, 411, 441, 461, 471, 476, 482, 487, 492 or 497 of SEQ ID NO: 40).

In some preferred embodiments, as compared to a wild-type rotavirus VP4 protein, the truncated rotavirus VP4 protein has 1, 5, 21, 25, or 64 amino acids truncated at N-terminal, and has C-terminal ended at the following position of a wild-type rotavirus VP4 protein: a position corresponding to the amino acid position 276, 281, 291, 301, 311, 321, 331, 341, 351, 361, 371, 381, 391, 401, 411, 421, 431, 441, 451, 461, 471, 476, 482, 487, 492 or 497 of SEQ ID NO: 40 (e.g., a position corresponding to the amino acid position 331, 351, 381, 411, 441, 461, 471, 476, 482, 487, 492 or 497 of SEQ ID NO: 40).

In some preferred embodiments, as compared to a wild-type rotavirus VP4 protein, the truncated rotavirus VP4 protein has a characteristic selected from:

(1) having 25 amino acids truncated at N-terminal and having C-terminal ended at the following position: a position corresponding to the amino acid position 276, 281, 291, 301, 311, 321, 331, 341, 351, 361, 371, 381, 391, 401, 411, 421, 431, 441, 451, 461, 471, 476, 482, 487, 492 or 497 of SEQ ID NO: 40 (preferably, a position corresponding to the amino acid position 331, 351, 381, 411, 441, 461, 471, 476, 482, 487, 492 or 497 of SEQ ID NO: 40);

(2) having 1 amino acid truncated at N-terminal and having C-terminal ended at a position corresponding to the amino acid position 476 of SEQ ID NO: 40;

(3) having 5 amino acids truncated at N-terminal and having C-terminal ended at a position corresponding to the amino acid position 476 of SEQ ID NO: 40;

(4) having 21 amino acids truncated at N-terminal and having C-terminal ended at a position corresponding to the amino acid position 476 of SEQ ID NO: 40; and (5) having 64 amino acids truncated at N-terminal and having C-terminal ended at a position corresponding to the amino acid position 476 of SEQ ID NO: 40.

In some preferred embodiments, the wild-type rotavirus VP4 protein is a VP4 protein derived from rotavirus LLR strain, SA11 strain, or EDIM strain, or a VP4 protein derived from a rotavirus of P[4], P[6], or P[8] genotype.

In some preferred embodiments, the wild-type rotavirus VP4 protein has an amino acid sequence selected from: SEQ ID NO: 40 and 87-91.

In some preferred embodiments, the truncated rotavirus VP4 protein (also called the truncated protein for short) has an amino acid sequence selected from: SEQ ID NO: 2-5 and 10-39.

In another aspect, the invention relates to a polynucleotide encoding the truncated protein or variant thereof and a vector comprising the polynucleotide.

Vectors for inserting a polynucleotide of interest are well known in the art, including, but not limited to a cloning vector and an expression vector. In an embodiment, the vector is, for example, a plasmid, a cosmid, a phage, etc.

In another aspect, the invention further relates to a host cell comprising the polynucleotide or vector. Such a host cell includes, but is not limited to, a prokaryotic cell such as E. coli cell, and a eukaryotic cell such as yeast cell, insect cell, plant cell and animal cell (such as mammalian cell, e.g., mouse cell, human cell, etc.). The host cell according to the invention may be a cell line, such as 293T cell. However, it is particularly preferred that the host cell according to the invention is a prokaryotic cell such as an E. coli cell.

In another aspect, the invention further relates to a polymer comprising or consisting of the truncated rotavirus VP4 protein or variant thereof. In some preferred embodiments, the polymer is a trimer. In some preferred embodiments, the polymer is a polymer with a molecular weight of at least 600 kDa. In some preferred embodiments, the polymer comprises a truncated rotavirus VP4 protein, which, as compared to a wild-type rotavirus VP4 protein, has 25 amino acids truncated at N-terminal, and has C-terminal ended at a position of the wild-type rotavirus VP4 protein, which corresponds to the amino acid position 476 of SEQ ID NO: 40. In some preferred embodiments, the polymer comprises a truncated rotavirus VP4 protein, the amino acid sequence of which is set forth in SEQ ID NO: 30. In some preferred embodiments, the polymer is a trimer or a polymer with a molecular weight of at least 600kDa, comprising a truncated rotavirus VP4 protein set forth in SEQ ID NO: 30.

In another aspect, the invention further relates to a composition comprising the truncated protein or variant thereof, or the polynucleotide, or the vector, or the host cell, or the polymer. In some preferred embodiments, the composition comprises the truncated protein or variant thereof according to the invention. In some preferred embodiments, the composition comprises the polymer according to the invention.

In another aspect, the invention further relates to a pharmaceutical composition (e.g., a vaccine), comprising the truncated protein or variant thereof according to the invention or the polymer according to the invention, and optionally, a pharmaceutically acceptable carrier and/or excipient. The pharmaceutical composition (e.g., vaccine) according to the invention is useful for preventing or treating rotavirus infection or a disease caused by rotavirus infection, such as rotavirus gastroenteritis or diarrhea.

In some preferred embodiments, the truncated protein or variant thereof according to the invention or the polymer according to the invention is present in an amount effective for preventing or treating rotavirus infection or a disease caused by rotavirus infection. In some preferred embodiments, the pharmaceutical composition (e.g., the vaccine) according to the invention further comprises an additional active ingredient. Preferably, the additional active ingredient is capable of preventing or treating rotavirus infection or a disease caused by rotavirus infection. In some preferred embodiments, the pharmaceutical composition (e.g., vaccine) according to the invention further comprises an adjuvant, such as aluminum adjuvant.

In some preferred embodiments, the pharmaceutical composition further comprises a pharmaceutically acceptable carrier, excipient, stabilizer or an additional agent capable of providing advantageous properties for administration of the pharmaceutical composition (e.g., administration to a human subject). Suitable pharmaceutical carriers include, for example, sterile water, saline, glucose, condensation product of castor oil and ethylene oxide, liquid acid, lower alcohol (e.g., $C_{1-4}$ alcohol), oil (e.g., corn oil, peanut oil, sesame oil; optionally, further comprising an emulsifier such as fatty acid monoglyceride or diglyceride, or phospholipid such as lecithin), ethylene glycol, polyalkylene glycol, sodium alginate, polyvinyl pyrrolidone, and the like. Optionally, the carriers further include an adjuvant, a preservative, a stabilizer, a moistening agent, an emulsifier, a penetration enhancer, and the like. In some preferred embodiments, the pharmaceutical composition is sterile. In addition, the viscosity of the pharmaceutical composition can be controlled and maintained by selecting a suitable solvent or excipient. In some preferred embodiments, the pharmaceutical composition is formulated to have a pH of 4.5-9.0, 5.0-8.0, 6.5-7.5, or 6.5-7.0.

The pharmaceutical composition (e.g., vaccine) according to the invention may be administered by means well known in the art, for example, including, but not limited to oral administration or injection. In some preferred embodiments, the pharmaceutical composition (e.g., vaccine) according to the invention is administered in a form of a unit dose.

The amount of the pharmaceutical composition (e.g., vaccine) according to the invention necessary for preventing or treating a specific condition depends on the administration route, the severity of the condition to be treated, the gender, age, body weight and general healthy condition of a patient, and the like, and can be reasonably determined by a physician according to practical conditions.

In another aspect, the invention relates to a method for preparing the truncated rotavirus protein or variant thereof, comprising, under a condition that allows expression of the truncated protein or variant thereof, culturing the host cell according to the invention; and, recovering the expressed truncated protein or variant thereof.

In some preferred embodiments, the method comprises, using E. coli to express the truncated protein or variant thereof according to the invention, and then lysing the E. coli, and purifying the truncated protein or variant thereof from the lysate. In some preferred embodiments, the purification includes chromatography. In some preferred embodiments, the purification includes two-step chromatography. In some preferred embodiments, the two-step chromatography includes: anion-exchange chromatography (e.g., anion-exchange chromatography using Q-sepharose-HP); and subsequent hydrophobic affinity chromatography (e.g., hydrophobic affinity chromatography using Phenyl sepharose-HP).

In another aspect, the invention further relates to a method for preparing a vaccine, comprising mixing the truncated protein or variant thereof according to the invention or the polymer according to the invention with a pharmaceutically acceptable carrier and/or excipient, optionally, with an adjuvant such as aluminum adjuvant, and/or an additional active ingredient, such as an additional active ingredient capable of preventing or treating rotavirus infection or a disease caused by rotavirus infection. In some preferred embodiments, the method for preparing a vaccine comprising the following step: mixing the truncated protein or variant thereof according to the invention or the polymer according to the invention with an adjuvant (e.g., aluminum adjuvant).

As described above, the vaccine obtained is useful for preventing or treating rotavirus infection or a disease caused by rotavirus infection, such as rotavirus gastroenteritis and diarrhea.

In another aspect, the invention relates to a method for preventing or treating rotavirus infection or a disease caused by rotavirus infection in a subject, comprising administering to a subject a prophylactically or therapeutically effective amount of the truncated protein or variant thereof according to the invention or the polymer according to the invention or the pharmaceutical composition according to the invention. In some preferred embodiments, the disease caused by rotavirus infection includes, but is not limited to rotavirus gastroenteritis and diarrhea. In some preferred embodiments, the subject is a mammal, such as mouse and human.

In another aspect, the invention further relates to use of the truncated protein or variant thereof according to the invention or the polymer according to the invention in the manufacture of a pharmaceutical composition (e.g., vaccine) for preventing or treating rotavirus infection or a disease caused by rotavirus infection in a subject. In some preferred embodiments, the disease caused by rotavirus infection includes, but is not limited to rotavirus gastroenteritis and diarrhea. In some preferred embodiments, the subject is a mammal, such as mouse and human.

In another aspect, the invention further relates to the truncated protein or variant thereof or the polymer, for use in the prevention or treatment of rotavirus infection or a disease caused by rotavirus infection in a subject. In some preferred embodiments, the disease caused by rotavirus infection includes, but is not limited to rotavirus gastroenteritis and diarrhea. In some preferred embodiments, the subject is a mammal, such as mouse and human.

Definitions and Explanations of the Relevant Terms in the Invention

In the invention, unless otherwise specified, the scientific and technical terms used herein have the meanings as generally understood by a person skilled in the art. Moreover, the laboratory operations of cell culture, molecular genetics, nucleic acid chemistry and immunology used herein are routine operations widely used in the corresponding fields. In addition, in order to better understand the invention, the definitions and explanations of the relevant terms are provided as follows.

According to the invention, the expression "X amino acids truncated at N-terminal" refers to replacement of amino acid residues from positions 1 to X at N-terminal of a protein with a methionine residue encoded by the initiation codon. For example, a rotavirus VP4 protein having 25 amino acids truncated at N-terminal refers to a protein obtained by replacement of the amino acid residues from positions 1 to 25 of a wild-type rotavirus VP4 protein with a methionine residue encoded by the initiation codon.

According to the invention, the expression "C-terminal ended at amino acid position X" refers to deletion of all the amino acid residues following amino acid position X (i.e., started from amino acid position X+1). For example, C-terminal ended at amino acid position 441 of a wild-type rotavirus VP4 protein refers to deletion of all the amino acid residues following amino acid position 441 (i.e., started from amino acid position 442) of a wild-type rotavirus VP4 protein.

According to the invention, the term "variant" refers to such a protein that its amino acid sequence differs from the amino acid sequence of the truncated rotavirus VP4 protein according to the invention by one or more (e.g., 1-10 or 1-5 or 1-3) amino acids (e.g., conservative amino acid substitution) or has an identity of at least 60%, 80%, 85%, 90%, 95%, 96%, 97%, 98%, or 99% as compared to the amino acid sequence of the truncated rotavirus VP4 protein according to the invention, whilst retaining the necessary property of the truncated protein. The term "necessary property" used herein may be one or more of the following properties:

(i) capable of being expressed in a soluble form in *E. coli;*

(ii) capable of being purified easily by chromatography;

(iii) having good homogenicity and stability (not easy to be degraded) after purification;

(iv) capable of specifically binding to an anti-VP4 antibody that can inhibit the infection of a cell by a virus in vitro;

(v) capable of competing with rotavirus for binding to a cell receptor, and inhibiting the infection of a cell by the virus;

(vi) capable of inducing generation of high-titer neutralizing antibodies against rotavirus in an organism; and (vii) capable of protecting a subject (such as human and mouse) from rotavirus infection.

Preferably, the "variant" according to the invention retains all the above-mentioned properties of the truncated protein.

As used herein, the term "identity" refers to the match degree between two polypeptides or between two nucleic acids. When two sequences for comparison have the same base or amino acid monomer sub-unit at a certain site (e.g., each of two DNA molecules has an adenine at a certain site, or each of two polypeptides has a lysine at a certain site), the two molecules are identical at the site. The percent identity between two sequences is a function of the number of identical sites shared by the two sequences over the total number of sites for comparison×100. For example, if 6 of 10 sites of two sequences are matched, these two sequences have an identity of 60%. For example, DNA sequences: CTGACT and CAGGTT share an identity of 50% (3 of 6 sites are matched). Generally, the comparison of two sequences is conducted in a manner to produce maximum identity. Such alignment can be conducted by using a computer program such as Align program (DNAstar, Inc.) which is based on the method of Needleman, et al. (J. Mol. Biol. 48:443-453, 1970). The percent identity between two amino acid sequences can be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percentage of identity between two amino acid sequences can be determined by the algorithm of Needleman and Wunsch (J. Mol. Biol. 48:444-453 (1970)) which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

As used herein, the term "conservative substitution" refers to amino acid substitutions which would not disadvantageously affect or change the biological activity of a protein/polypeptide comprising the amino acid sequence. For example, a conservative substitution may be introduced by standard techniques known in the art such as site-directed mutagenesis and PCR-mediated mutagenesis. Conservative amino acid substitutions include substitutions wherein an amino acid residue is substituted with another amino acid residue having a similar side chain, for example, a residue physically or functionally similar (such as, having similar size, shape, charge, chemical property including the capability of forming covalent bond or hydrogen bond, etc.) to the corresponding amino acid residue. The families of amino acid residues having similar side chains have been defined in the art. These families include amino acids having alkaline side chains (for example, lysine, arginine and histidine), amino acids having acidic side chains (for example, aspartic acid and glutamic acid), amino acids having uncharged polar side chains (for example, glycine, asparagine, glutamine, serine, threonine, tyrosine, cysteine, tryptophan), amino acids having nonpolar side chains (for example, alanine, valine, leucine, isoleucine, proline, phenylalanine, methionine), amino acids having β-branched side chains (such as threonine, valine, isoleucine) and amino acids having aromatic side chains (for example, tyrosine, phenylalanine, tryptophan, histidine). Therefore, a corresponding amino acid residue is preferably substituted with another amino acid residue from the same side-chain family. Methods for identifying amino acid conservative substitutions are well known in the art (see, for example, Brummell et al., Biochem. 32: 1180-1187 (1993); Kobayashi et al., Protein Eng. 12(10): 879-884 (1999); and Burks et al., Proc. Natl. Acad. Sci. USA 94: 412-417 (1997), which are incorporated herein by reference).

According to the invention, the term "*E. coli* expression system" refers to an expression system consisting of *E. coli* (strains) and vectors, wherein the *E. coli* (strains) include, but are not limited to: GI698, ER2566, BL21 (DE3), B834 (DE3), BLR (DE3), and the like, which are available on the market.

According to the invention, the term "vector" refers to a nucleic acid carrier tool which can have a polynucleotide inserted therein. When a vector enables the expression of a protein encoded by a polynucleotide inserted therein, the vector is called an expression vector. The "vector" can have the carried genetic element expressed in a host cell by transformation, transduction, and transfection into the host cell. Vectors are well known for a person skilled in the art, including, but not limited to plasmids, phages, cosmids and the like.

According to the invention, the terms "VP4 protein", "VP4 full-length protein" and "rotavirus VP4 protein", which can be used interchangeably, refer to a structural protein, which, together with VP7, forms the outer capsid of RV virus particle. The amino acid sequence of VP4 protein is known by a person skilled in the art, and can be found in various public databases (e.g., GenBank database). For example, the exemplary amino acid sequences of VP4 protein are set forth in SEQ ID NOs: 40 and 87-91.

According to the invention, the term "truncated rotavirus VP4 protein" refers to the protein resulted from deletion of one or more amino acids at the N- and/or C-terminal of the wild-type rotavirus VP4 protein, wherein the amino acid sequence of the wild-type rotavirus VP4 protein can be easily found in public database (such as GenBank database), for example, under GenBank Accession Nos. AEV53329.1, BAA03850.1, AAB94758.2, AIS93087.1, ACJ06216.1 and AAA66953.1.

In the invention, the exemplary amino acid sequence of VP4 protein of wild-type rotavirus LLR is set forth in SEQ ID NO: 40. Therefore, when the sequence of VP4 protein is involved in the invention, it is described by the sequence set forth in SEQ ID NO: 40. For example, the expression "amino acid positions 276-497 of VP4 protein" refer to the amino acid positions 276-497 of SEQ ID NO: 40. However, a person skilled in the art understands that mutations or variations (including, but not limited to, substitution, deletion and/or addition) may occur naturally in or be introduced artificially into SEQ ID NO: 40 without affecting the biological properties of VP4 protein. For example, VP4 proteins from different virus strains of rotavirus may be naturally different in terms of amino acid sequence, but have substantively the same biological properties. Therefore, in the invention, the term "VP4 protein" intends to include all such polypeptides and variants, including the polypeptide set forth in SEQ ID NO: 40 and its natural or artificial variants, wherein the variants retain the biological properties of VP4 protein. In addition, when sequence fragments and amino acid positions of VP4 protein are described, they include not only the sequence fragments and amino acid positions of the polypeptide set forth in SEQ ID NO: 40, but also the corresponding sequence fragments and amino acid positions of the natural or artificial variants of the polypeptide. For example, the expression "amino acid positions 276-497 of VP4 protein" intends to include amino acid positions 276-497 of SEQ ID NO: 40, and the corresponding amino acid positions of the variants (natural or artificial variants) of the polypeptide set forth in SEQ ID NO: 40.

In the invention, the exemplary amino acid sequences of VP4 protein of wild-type rotavirus SA11, EDIM, P[4], P[6], and P[8] are set forth in SEQ ID NO: 87-91, respectively.

According to the invention, the expression "corresponding sequence fragments" or "corresponding fragments" refers to the fragments that are located in equal positions of sequences when the sequences are subjected to optimized alignment, namely, the sequences are aligned to obtain a highest percentage of identity. According to the invention, the expression "corresponding amino acid positions" refers to the amino acid positions/residues that are located in equal positions of sequences when the sequences are subjected to optimized alignment, namely, the sequences are aligned to obtain a highest percentage of identity.

In the invention, the term "a truncated gene fragment of rotavirus VP4 protein" refers to such a gene fragment that has the nucleotide(s) encoding one or more amino acids deleted at 5' or 3' terminal as compared to the wild-type truncated rotavirus VP4 gene, wherein the full-length sequence of the wild-type truncated rotavirus VP4 gene can be easily found in public database (e.g., GenBank database), for example, under the GenBank Accession Nos. JQ013506.1, D16346.1, AF039219.2, KJ940075.1, FJ183356.1 and L34161.1. For example, the nucleotide sequence of VP4 gene of wild-type rotavirus LLR is set forth in SEQ ID NO: 41.

According to the invention, the term "polymer" refers to a polymer consisting of polypeptide molecules (e.g., the truncated protein according to the invention) as monomers, which generally comprises at least 2 (e.g., 3, 4, 5 or more) polypeptide monomers (e.g., the truncated protein according to the invention). In such a polymer, monomer molecules are polymerized to form a multimer by intermolecular interaction (e.g., hydrogen bond, van der Waals force, hydrophobic interaction). In some embodiments of the invention, the polymer is a trimer comprising 3 monomers. In some embodiments of the invention, the polymer is a multimer that comprises multiple monomers and has a molecular weight of at least 600 kDa (such a multimer also calls polymer in the context).

According to the invention, the term "a pharmaceutically acceptable carrier and/or excipient" refers to a carrier and/or excipient that is pharmacologically and/or physiologically compatible to a subject and active ingredients, which is well known in the art (see, for example, Remington's Pharmaceutical Sciences. Edited by Gennaro AR, 19th ed. Pennsylvania: Mack Publishing Company, 1995), and includes, but is not limited to: pH regulators, surfactants, adjuvants, and ionic strength enhancers. For example, pH regulators include, but are not limited to, phosphate buffers; surfactants include, but are not limited to: cation surfactants, anion surfactants, or non-ionic surfactants such as Tween-80; adjuvants include, but are not limited to, aluminum hydroxide (e.g., aluminum hydroxide) and Freund's adjuvant (e.g., Freund's complete adjuvant); and ionic strength enhancers include, but are not limited to, NaCl.

According to the invention, the term "adjuvant" refers to a non-specific immunopotentiator, which can enhance immune response to an antigen or change the type of immune response in an organism when it is delivered together with the antigen to the organism or is delivered to the organism in advance. There are a variety of adjuvants, including, but not limited to, aluminum adjuvants (for example, aluminum hydroxide), Freund's adjuvants (for example, Freund's complete adjuvant and Freund's incomplete adjuvant), coryne bacterium parvum, lipopolysaccharide, cytokines, and the like. Freund's adjuvant is the most commonly used adjuvant in animal experiments now. Aluminum hydroxide adjuvant is more commonly used in clinical trials. In the invention, particularly preferably, the adjuvant is aluminum adjuvant.

According to the invention, the term "an effective amount" refers to an amount that is sufficient to achieve the expected effect. For example, an amount effective for preventing or treating a disease (such as rotavirus infection) refers to an amount effective for preventing, suppressing, or delaying the occurrence of a disease (such as rotavirus infection) or effective for alleviating, relieving or treating the severity degree of an existing disease (such as a disease caused by rotavirus infection). The determination of such an effective amount is within the ability of a person skilled in the art. For example, an amount effective for a therapeutic use depends on the severity degree of a disease to be treated, general state of the immune system in a patient, general conditions of a patient, such as age, body weight and gender, administration routes of drugs, additional therapies used simultaneously, and the like.

According to the invention, the term "chromatography" includes, but is not limited to: ion exchange chromatography (e.g. cation-exchange chromatography), hydrophobic interaction chromatography, absorbent chromatography (e.g. hydroxyapatite chromatography), gel filtrate chromatography (gel exclusion chromatography), and affinity chromatography.

According to the invention, the disrupting of a host cell may be carried out by various methods well known by a person skilled in the art, including, but not limited to: homogenizer disrupting, homogenate machine disrupting, ultrasonic treatment, grinding, high pressure extrusion, lysozyme treatment, and the like.

According to the invention, the term "immunogenicity" refers to ability of stimulating the formation of specific antibodies or sensitized lymphocytes in organisms. It not only refers to the property of an antigen to stimulate a specific immunocyte to activate, proliferate and differentiate the immunocyte so as to finally generate immunologic effector substances such as antibodies and sensitized lymphocytes, but also refers to the specific immune response that antibodies or sensitized T lymphocytes can be formed in the immune system of an organism, after stimulating the organism with an antigen.

According to the invention, the terms "polypeptide" and "protein" have the same meanings, which can be used interchangeably. Moreover, in the invention, amino acids are generally expressed as one-letter codes and three-letter codes. For example, alanine may be expressed as A or Ala.

As used herein, the term "subject" refers to animal, for example, vertebrate. Preferably, the subject is mammal, such as human, bovine, equine, feline, canine, rodent, or primate. The particularly preferred subject is human. As used herein, the term and the term "patient" may be used interchangeably.

Beneficial Technical Effects of the Invention

The truncated rotavirus VP4 protein and the preparation thereof as provided in the invention effectively solve the technical problem in the art.

Firstly, the truncated protein or variant thereof according to the invention can be expressed in a soluble form in E. coli, which achieves a high yield. This provides advantages for large-scale industrial production.

Secondly, the purification of the truncated protein or variant thereof according to the invention is relatively simple, and can be easily carried out. In particular, after soluble expression is carried out in E. coli, the E. coli can be lyzed, and the lysate is then treated by chromatography (e.g., by anion-exchange chromatography and hydrophobic affinity chromatography), thereby resulting in the truncated protein with a high purity (which may reach at least 50% or higher, e.g., 60%, 70%, 80%, 90%, 95%, 96%, 97%, 98%, 99%). This provides advantages for large-scale industrial production.

Thirdly, the truncated protein with a high purity as obtained in the invention has good homogenicity and stability. In particular, the purified truncated protein according to the invention can be present in a homogenous form, and is not easily degraded. This provides advantages for production in batches, avoids variation among different batches, and is good for accurate medication.

Fourthly, the truncated protein or variant thereof according to the invention can induce generation of high-titer neutralizing antibodies against rotavirus in the presence of aluminum adjuvant in an organism. Since aluminum adjuvant instead of Freund's adjuvant is generally used in clinic, the truncated protein or variant thereof according to the invention can be advantageously used in clinical conditions for protecting a subject from rotavirus infection.

In sum, the truncated protein or variant thereof according to the invention not only has the characteristics such as being easily expressed and purified, but also has good homogenicity and stability. More importantly, the truncated protein or variant thereof according to the invention has a strong immunogenicity, can induce high-titer neutralizing antibodies in the presence of aluminum adjuvant in an organism, and therefore provides a strong protection for a subject under clinical conditions. Hence, the truncated protein or variant thereof according to the invention can be used in the large-scale industrial production of highly effective vaccines against rotavirus, thereby providing an effective solution to solve the technical problem in the art.

The embodiments of the invention are illustrated in detail by reference to the following drawings and examples. However, it is understood by those skilled in the art that the following drawings and examples are used only for the purpose of illustrating the invention, rather than limiting the protection scope of the invention. According to the detailed description of the following drawings and preferred embodiments, various purposes and advantages of the invention are apparent for a person skilled in the art.

DESCRIPTION OF DRAWINGS

In FIG. 5A, lanes from left to right are: Protein Molecular Weight Marker (Marker), 1-476, 6-476, 22-476, 26-476, 65-476, 26-231, 26-271, 26-331 and 26-351. In FIG. 5B, lanes from left to right are: Protein Molecular Weight Marker (Marker), 26-381, 26-411, 26-441, 26-461, 26-471, 26-482, 26-487, 26-492 and 26-497. The results in FIGS. 5A and 5B show that after the purification steps, the truncated proteins had a concentration of above 0.2 mg/ml, and a purity of above 80%.

Figure 6:
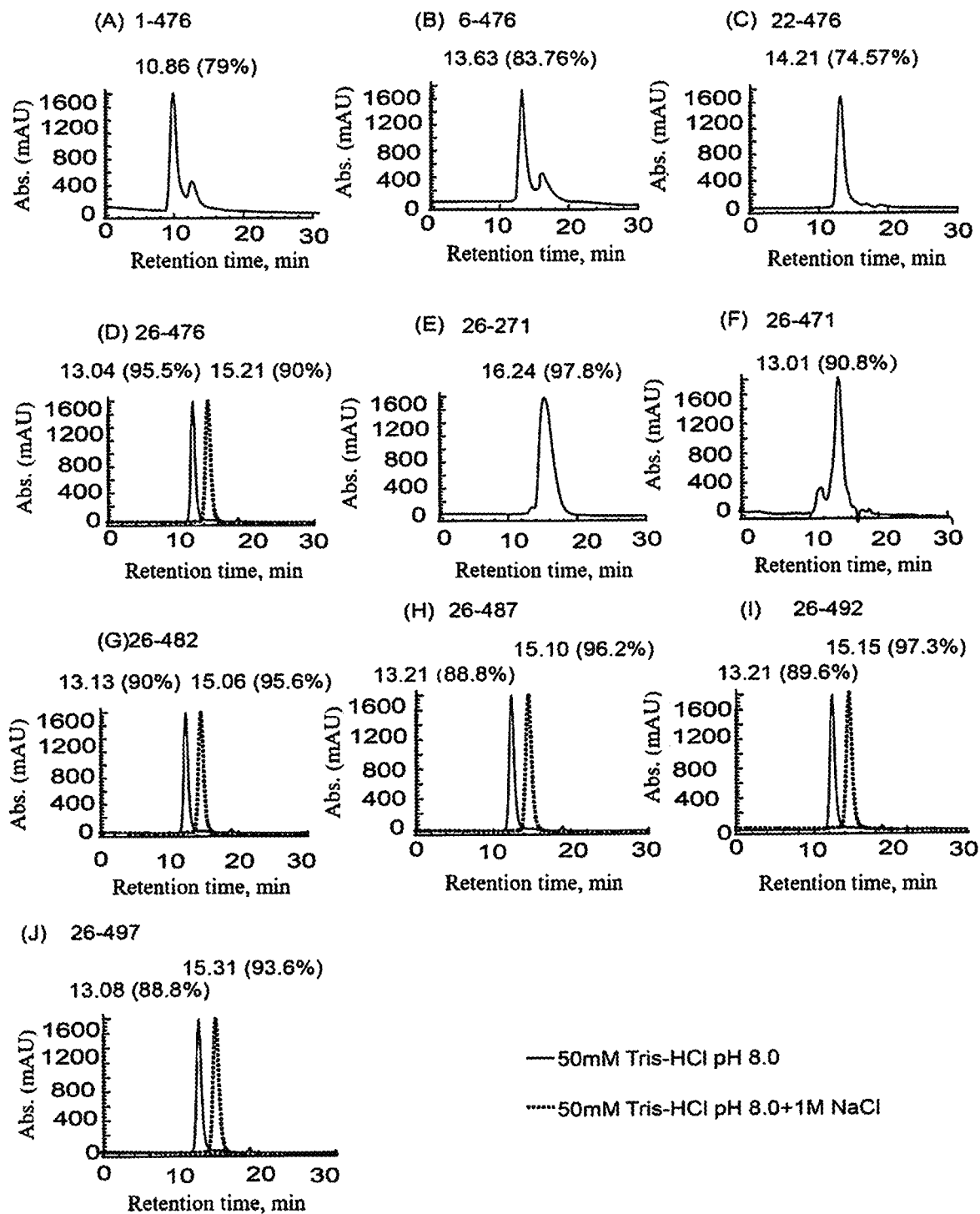
FIG. 6 shows the results of G3000$_{PWXL}$ Molecular sieve analysis with the truncated proteins 1-476, 6-476, 22-476, 26-476, 26-271, 26-471, 26-482, 26-487, 26-492, and 26-497. The axis of abscissas represents the retention time, and the axis of ordinates represents the absorbance value at 280 nm. The results show that in the presence of TB8.0, the truncated protein 1-476 was present in a form of polymer in the sample (the peak appeared at about 10-11 min); 26-271 was in a form of monomer (the peak appeared at about 16 min), at a content of above 90%; the other truncated proteins (6-476, 22-476, 26-476, 26-471, 26-482, 26-487, 26-492, 26-497) were in a form of trimer (the peak appeared at about 13-14 min), almost at a content of above 90%. In the presence of salts (TB8.0+1M NaCl), the truncated proteins 26-476, 26-482, 26-487, 26-492 and 26-497 were converted to monomers (the time the peak appeared changed from about 13-14 min to about 15-16 min), at a content of above 90%. This shows that in the presence of salts, the configurations of 26-476, 26-482, 26-487, 26-492 and 26-497 were affected by salt ions, resulting in depolymerization of trimers and the formation of monomers.
Figure 7:
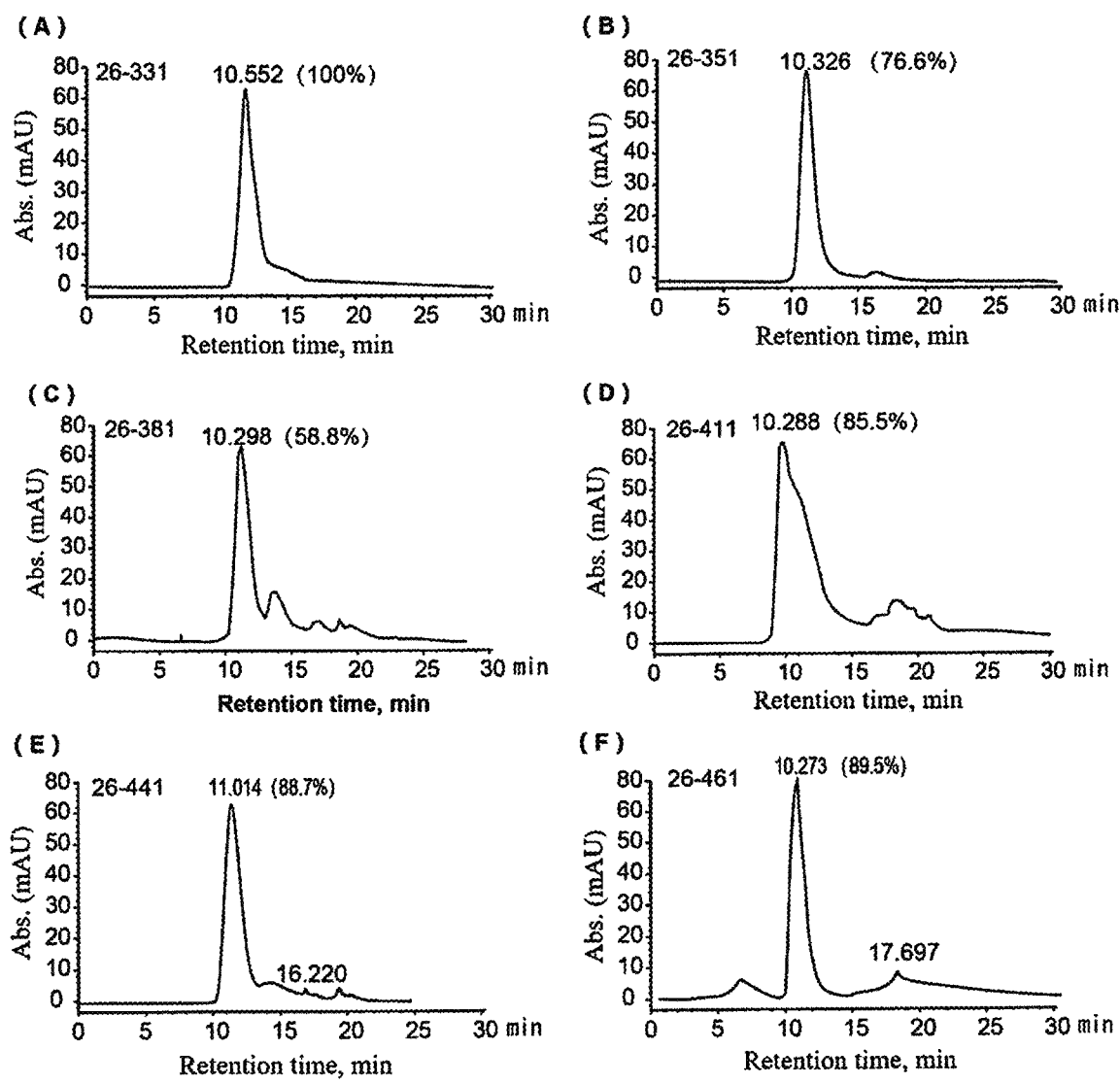
FIG. 7 shows the results of G5000$_{PWXL}$ Molecular sieve analysis with the truncated proteins 26-331, 26-351, 26-381, 26-411, 26-441 and 26-461. The axis of abscissas represents the retention time, and the axis of ordinates represents the absorbance value at 280 nm. The results show that in the presence of TB8.0, all these truncated proteins were present in a form of polymer in the sample (the peak appeared at about 10-11 min).

The results in FIG. 6 and FIG. 7 also show that the main absorption peaks of the truncated VP4 proteins obtained accounted for nearly above 80% or event above 90%, indicating that these truncated proteins had good homogenicity.

Figure 8A:
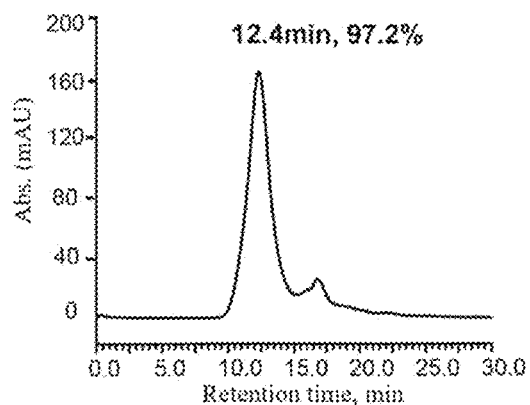

FIG. 8A shows the results of Molecular sieve analysis with the truncated protein 26-476 after standing in 50 mM Tris-HCl (pH8.0) at 37° C. for 12 h. The axis of abscissas represents the retention time, and the axis of ordinates represents the absorbance value at 280 nm. The results show that after standing in 50 mM Tris-HCl (pH8.0) at 37° C. for 12 h, the truncated protein 26-476 could form a homogeneous polymer (with a retention time of 12.4 min), and the polymer accounted for up to 97.2%.

Figure 8B:
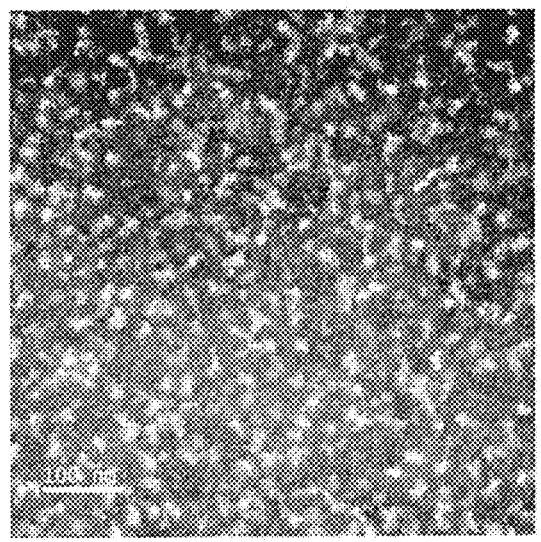

FIG. 8B shows the electron microscopic results of the truncated protein 26-476 after standing in 50 mM Tris-HCl (pH8.0) at 37° C. for 12 h. The results show that the truncated protein 26-476 could be assembled into a homogeneous polymer in vitro.

Figure 9:
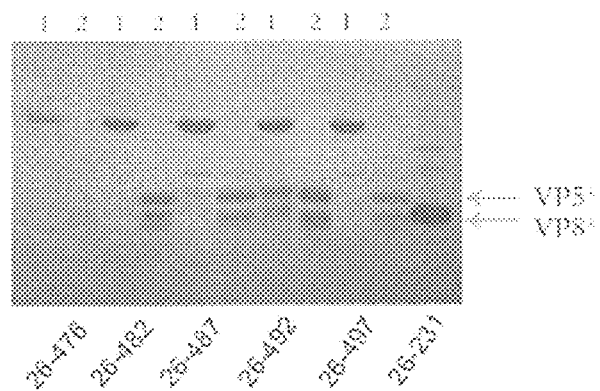

FIG. 9 shows the SDS-PAGE results of the truncated proteins 26-476, 26-482, 26-487, 26-492, and 26-497, either cleaved by an enzyme or not. On the lanes, the number "1" represents that the sample is not treated with trypsin; and the number "2" represents that the sample has been treated with 0.1 mg/ml trypsin. The results show that all these truncated proteins could be recognized and cleaved by trypsin, i.e., their enzyme cutting sites were exposed.

Figure 10:
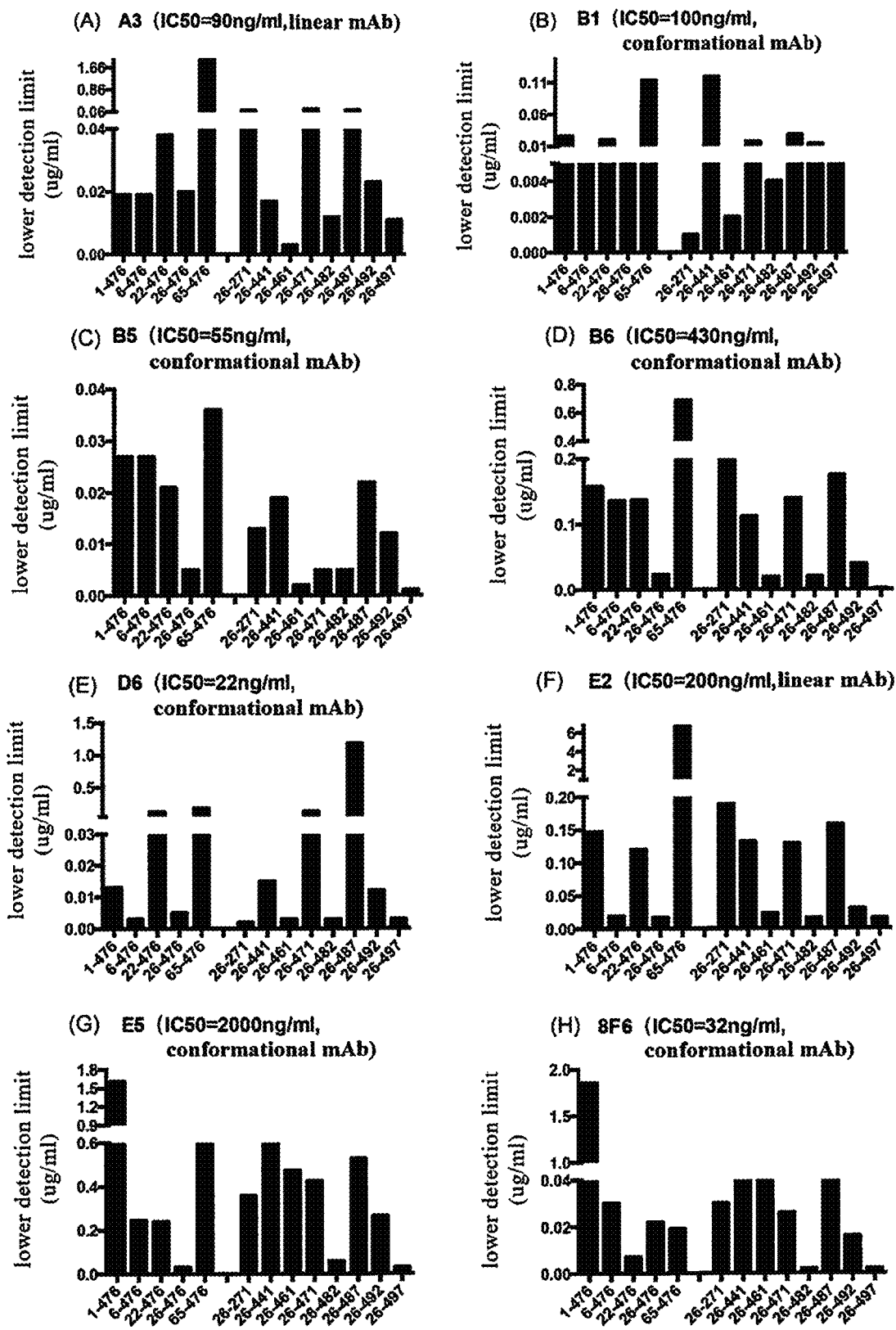
Figure 11A:
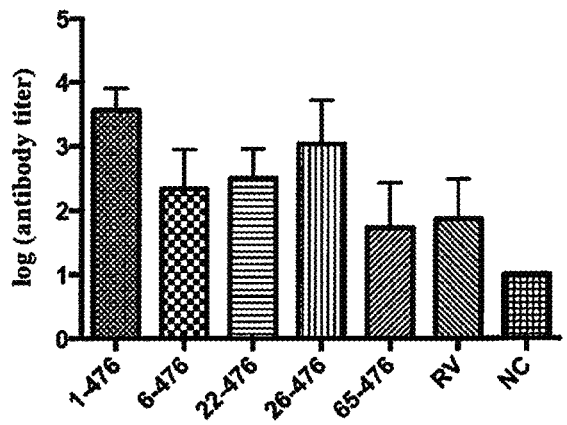
Figure 11B:
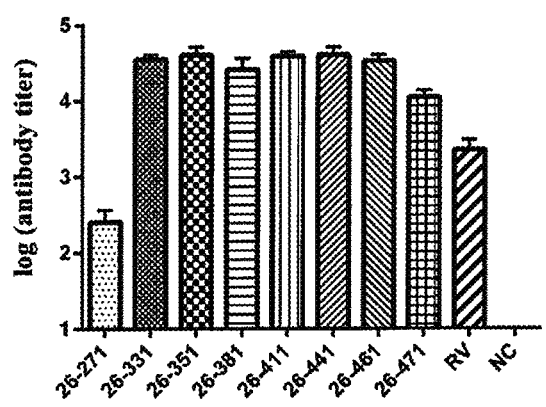
Figure 11C:
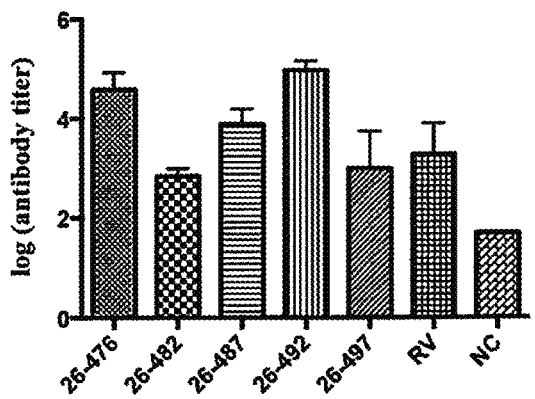
Figure 11D:
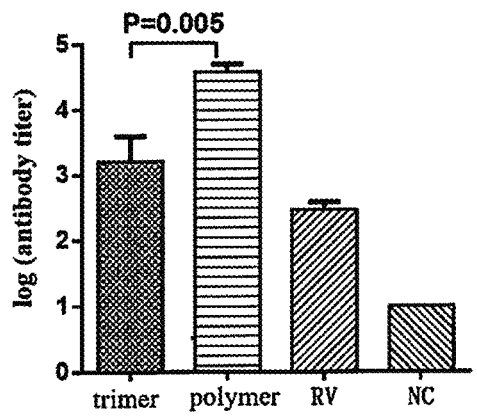
Figure 12A:
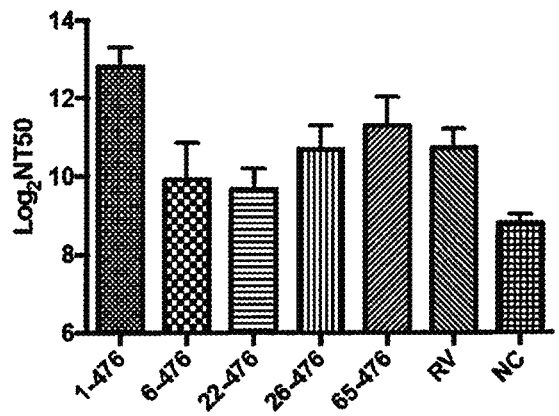
Figure 12B:
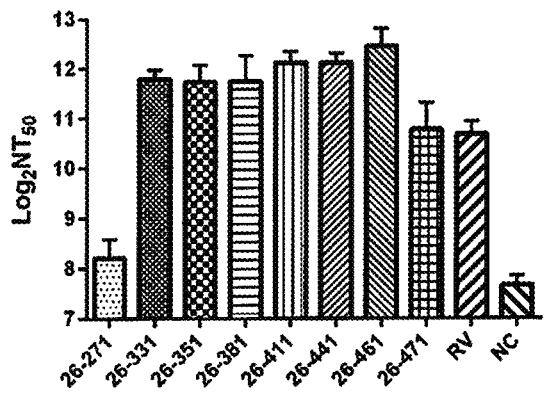
Figure 12C:
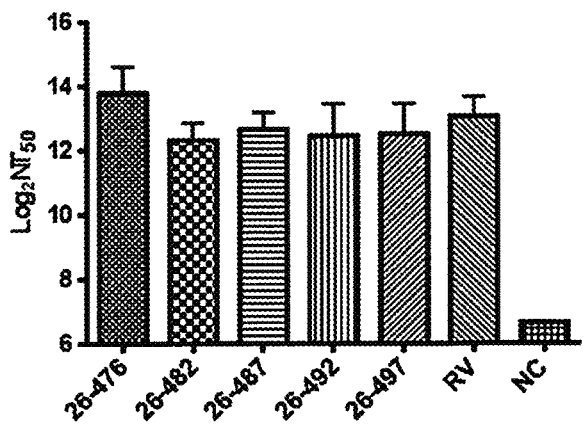
Figure 12D:
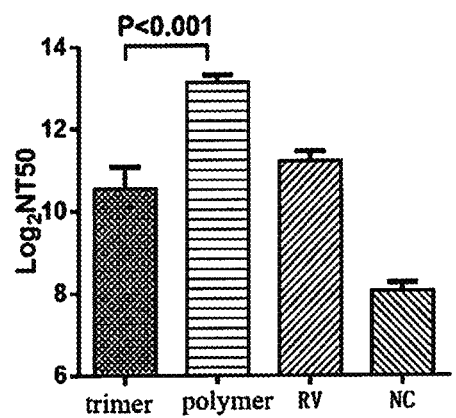
Figure 13A:
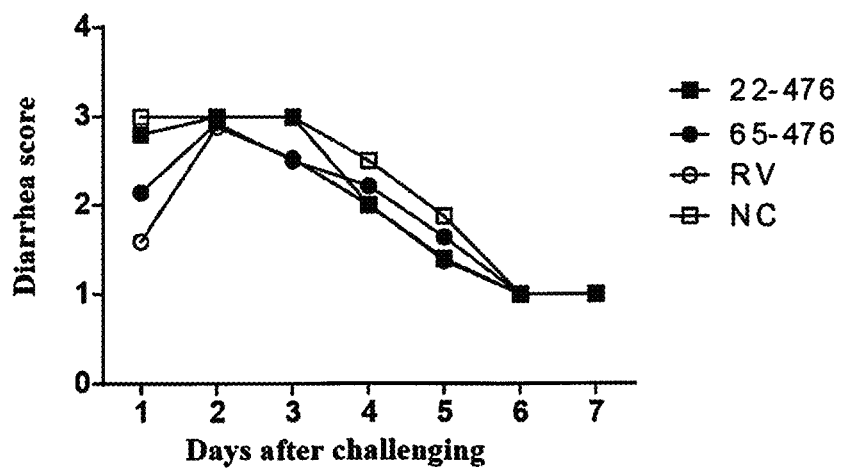
Figure 13B:
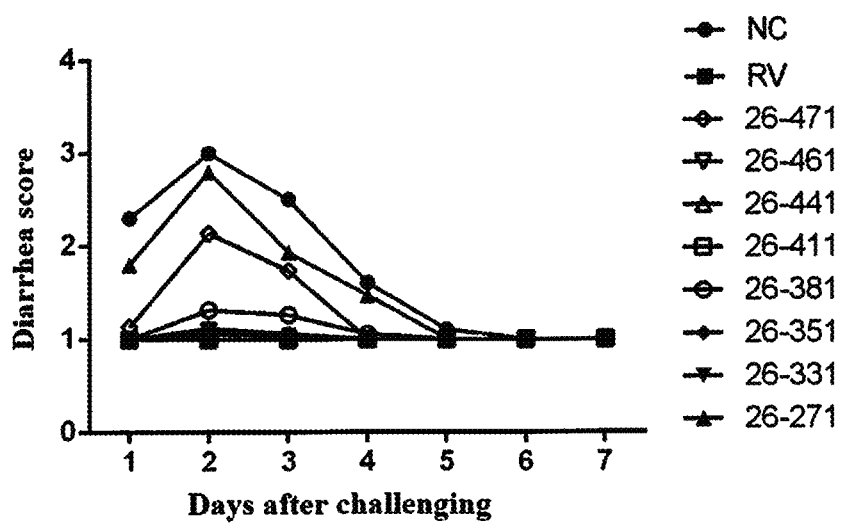
Figure 13C:
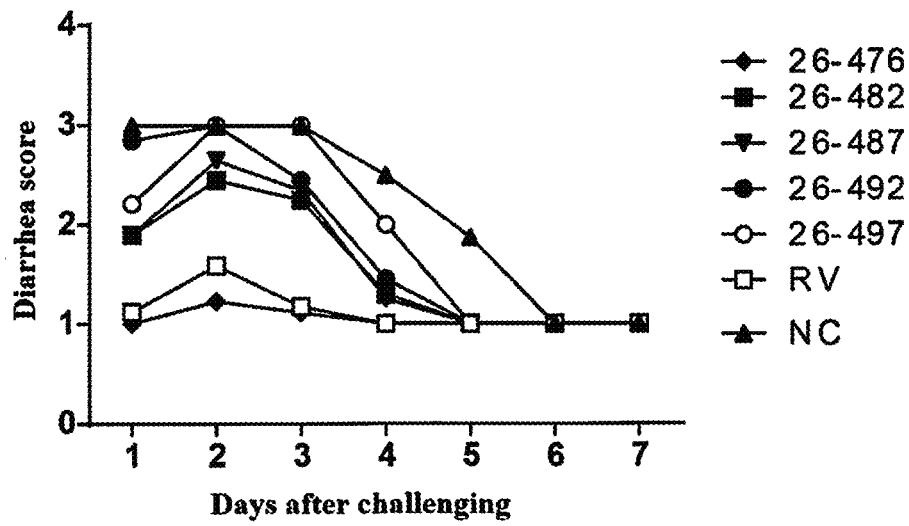
Figure 13D:
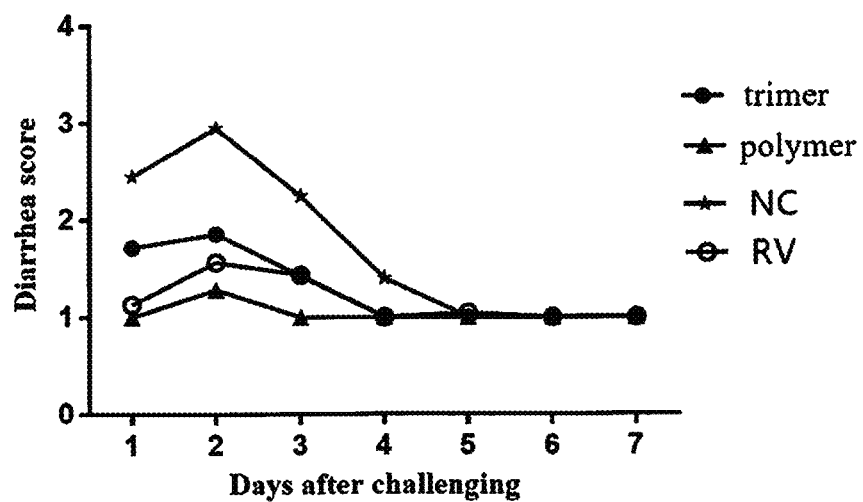

FIG. 10 shows that the results of indirect ELISA analysis with the truncated VP4 protein (1-476, 6-476, 22-476, 65-476, 26-271, 26-441, 26-461, 26-471, 26-476, 26-482, 26-487, 26-492, 26-497) and the neutralizing antibody A3 (FIG. 10A), B1 (FIG. 10B), B5 (FIG. 10C), B6 (FIG. 10D), D6 (FIG. 10E), E2 (FIG. 10F), E5 (FIG. 10G), 8F6 (FIG. 10H), wherein the abscissas represent the truncated proteins, and the ordinates represent the primary antibodies (A3, B1, B5, B6, D6, E2, E5, 8F6) having reactivity with the truncated proteins. The results show that all these truncated proteins had good antigenicity (i.e., antibody reactivity).

FIGS. 11A-11D show the results of indirect ELISA analysis with the truncated protein 26-476 and the immune sera obtained by immunizing Balb/c mice with the sample to be tested (1-476, 6-476, 22-476, 65-476, 26-271, 26-331, 26-351, 26-381, 26-411, 26-441, 26-461, 26-471, 26-476, 26-482, 26-487, 26-492, 26-497, trimer of 26-476, polymer of 26-476, inactivated virus), wherein the abscissa represents the protein sample for producing immune serum; the ordinate represents the greatest dilution (i.e., antibody titer) of the immune serum having reactivity with 26-476; RV: inactivated rotavirus; NC: negative control (PBS); trimer: trimer of 26-476; polymer: polymer of 26-476. FIGS. 11A, 11B, 11C and 11D show the results of different immunization batches. The results show that in the presence of aluminum adjuvant, at Day 42 after immunization, these proteins could induce generation of antibodies in mice (antibody titer of the immune serum (GMT) could reach $10^2$-$10^5$ or higher); and, except for 26-271, the antibody titers induced by the other protein samples were higher than the antibody titer induced by RV (1-476, 6-476, 22-476, 26-331, 26-351, 26-381, 26-411, 26-441, 26-461, 26-471, 26-476, 26-487, 26-492, trimer of 26-476 and polymer of 26-476), or were at least comparable to the antibody titer induced by RV (65-476, 26-482 and 26-497).

FIGS. 12A-12D show the analytic results of the neutralizing antibody titer of the immune sera induced in Balb/c mice with the protein samples (1-476, 6-476, 22-476, 65-476, 26-271, 26-331, 26-351, 26-381, 26-411, 26-441, 26-461, 26-471, 26-476, 26-482, 26-487, 26-492, 26-497, trimer of 26-476, polymer of 26-476, inactivated virus), wherein, the abscissa represents the protein sample for producing immune serum; the ordinate represents the greatest dilution (NT50, neutralizing antibody titer) of the immune serum achieving an infection inhibition rate of 50%; RV: inactivated rotavirus; NC: negative control (PBS); trimer: trimer of 26-476; polymer: polymer of 26-476. FIG. 12A, 12B, 12C and 12D show the results of different immunization batches. The results show that in the presence of aluminum adjuvant, at Day 42 after immunization (after three immunizations), all these protein samples could induce generation of neutralizing antibodies in mice, their neutralizing antibody titer ($NT_{50}$) could reach $2^8$-$2^{14}$ or higher; and, except for 26-271, the neutralizing antibody titer induced by the other protein samples was comparable to the neutralizing antibody titer induced by RV (6-476, 22-476, 26-476, 65-476, 26-471, 26-482, 26-487, 26-492, 26-497 and trimer of 26-476), or even higher than the neutralizing antibody titer induced by RV (1-476, 26-331, 26-351, 26-381, 26-411, 26-441, 26-461 and polymer of 26-476).

FIGS. 13A-13D show the diarrhea scores of suckling mice in different immunization groups (immunized with 22-476, 26-476, 65-476, 26-271, 26-331, 26-351, 26-381, 26-411, 26-441, 26-461, 26-471, 26-482, 26-487, 26-492, 26-497, trimer of 26-476, polymer of 26-476, inactivated rotavirus (RV, positive control) or PBS (NC, negative control)) 1-7 days after challenging with a virus, wherein the axis of ordinates represents the average diarrhea score; the axis of abscissas represents days after challenging mice with a virus; RV: inactivated rotavirus; NC: negative control (PBS); trimer: trimer of 26-476; polymer: polymer of 26-476.

FIGS. 14A-14D show the average duration of diarrhea after challenging with a virus and the average diarrhea scores 48 h after challenging with a virus in suckling mice in different immunization groups (immunized with 22-476, 26-476, 65-476, 26-271, 26-331, 26-351, 26-381, 26-411, 26-441, 26-461, 26-471, 26-482, 26-487, 26-492, 26-497, trimer of 26-476, polymer of 26-476, inactivated rotavirus (RV, positive control) or PBS (NC, negative control)), wherein, the average duration (days) for diarrhea is represented by bar diagram, and the average diarrhea score is represented by curve graph, the left axis of ordinates represents the average duration (days) for diarrhea; the right axis of ordinates represents the diarrhea score; the axis of abscissas represents the corresponding immunization groups of the protein samples; RV: inactivated rotavirus; NC: negative control (PBS); trimer: trimer of 26-476; polymer: polymer of 26-476.

The results in FIGS. 13-14 show that in terms of the average diarrhea score and the average duration (days) for diarrhea, the corresponding immunization groups of the protein samples were superior to the NC group. This indicates that the protein samples had significant protective effect, and could help the mice to combat rotavirus infection and diarrhea caused by rotavirus infection. In addition, the results in FIGS. 13-14 also show that the protective effects of 26-331, 26-351, 26-381, 26-411, 26-441, 26-461, 26-476, trimer of 26-476, and polymer of 26-476 were comparable to that of RV, or even better than that of RV. According to the experimental results of Example 1, in the presence of aluminum adjuvant, the protective effects of these protein samples were superior to that of VP8-5 in animal. In addition, the experimental results in FIG. 13D and FIG. 14D also show that the protective effect of the polymer of the truncated protein 26-476 was significantly superior to that of trimer of 26-476 in animal, and could be used to prepare vaccines having a higher efficacy.

FIG. 15 shows the SDS-PAGE results of the 26-476 protein from different virus strains, wherein, the lanes from left to right are: the truncated protein 26-476 from rotavirus LLR; the truncated protein 26-476-SA11 from rotavirus SA11; the truncated protein 26-476-EDIM from rotavirus EDIM; the truncated protein 26-476-P[8] from rotavirus P[8]; the truncated protein 26-476-P[6] from rotavirus P[6]; the truncated protein 26-476-P[4] from rotavirus P[4]; and, Protein Molecular Weight Marker (Marker). The results show that the method according to the invention was applicable to different strains of rotavirus; the truncated VP4 protein (26-476) from different virus strains could be effectively expressed in *E. coli,* and had a purity of above 80% after purification by chromatography.

Figure 16:
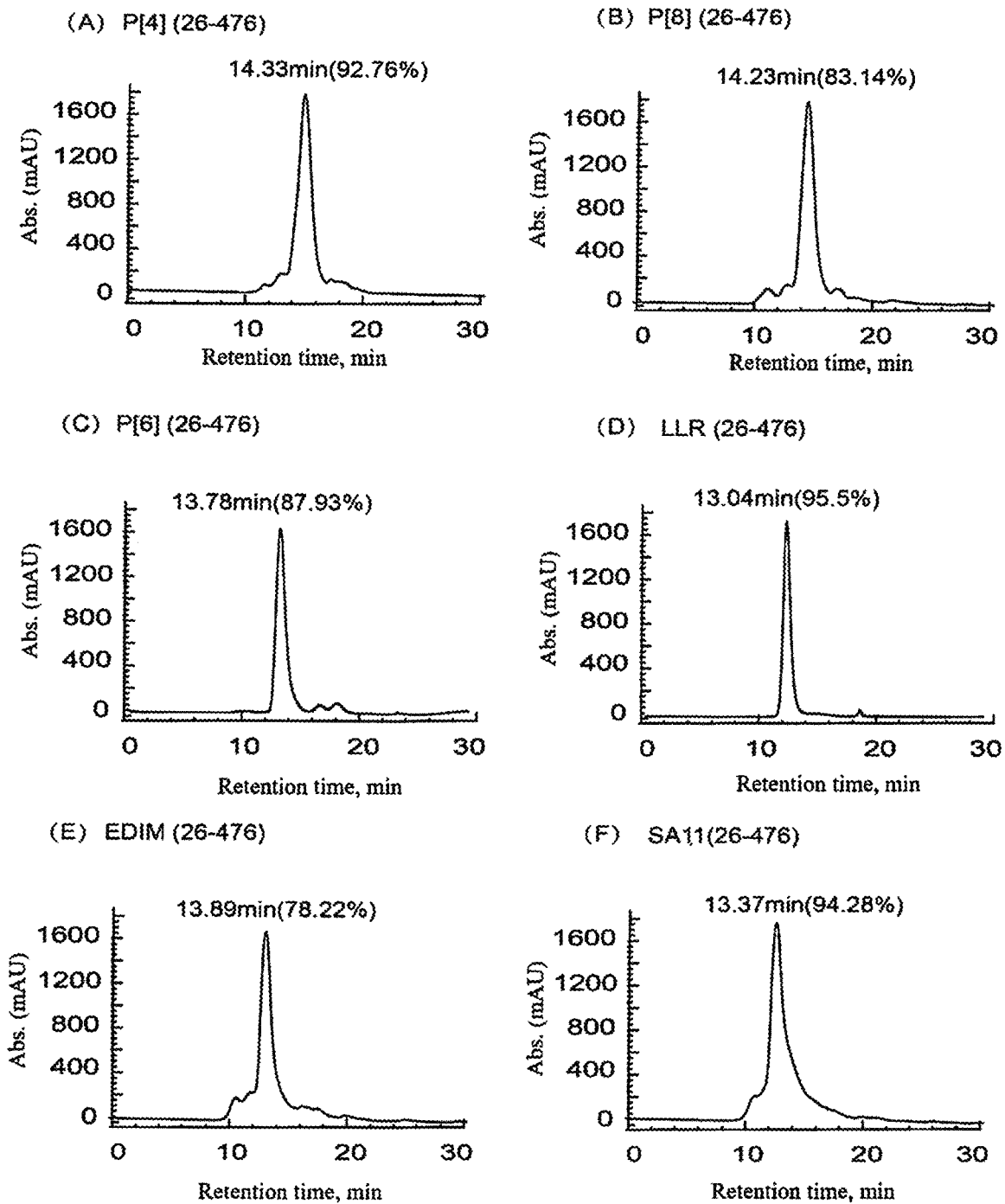

FIG. 16 shows the results of Molecular sieve analysis with the truncated VP4 protein 26-476 derived from different virus strains. The axis of abscissas represents the retention time, and the axis of ordinates represents the absorbance value at 280 nm. The results show that in the presence of TB8.0, the 26-476 protein derived from different virus strains was mainly present in a form of trimer (the peak appeared at about 13-14 min), at a content of above 80%. This indicates that in the presence of TB8.0, the 26-476 protein derived from different virus strains had good homogenicity.

Figure 17:
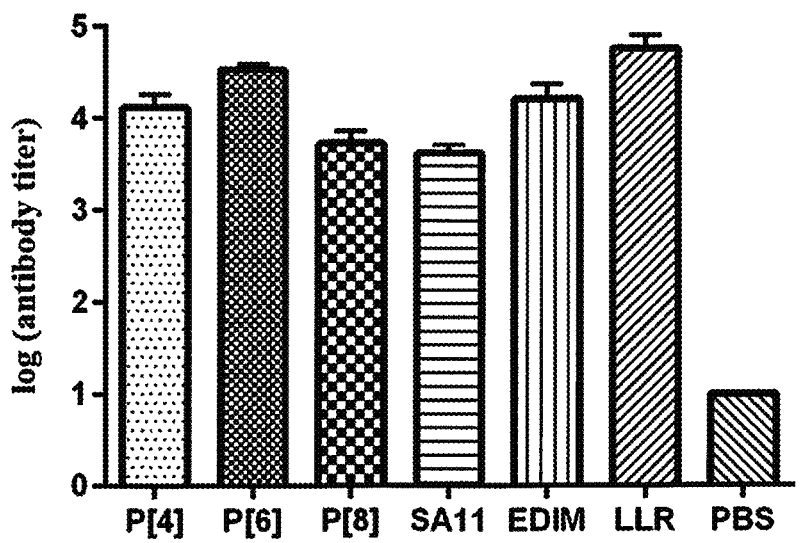

FIG. 17 shows the results of indirect ELISA analysis with the immune sera obtained by immunizing Balb/c mice with the truncated proteins (26-476-P[4], 26-476-P[6], 26-476-P[8], 26-476-EDIM, 26-476-SA11, and 26-476 derived from LLR) and the corresponding truncated protein, wherein the abscissa represents the virus strain from which the truncated protein for producing immune serum was derived, and the ordinate represents the greatest dilution (i.e., antibody titer) of the immune serum having reactivity with the corresponding truncated protein; P[4]: 26-476-P[4]; P[6]: 26-476-P[6]; P[8]: 26-476-P[8]; SA11: 26-476-SA11; EDIM: 26-476-EDIM; LLR: 26-476 prepared in Example 4. The results show that in the presence of aluminum adjuvant, at Day 42 after immunization, all these 26-476 proteins derived from different virus strains could induce generation of antibodies in mice, and the antibody titers (GMT) in the immune sera induced thereby were substantively comparable (the antibody titer could reach $10^4$-$10^5$ or higher, much higher than that of the negative control group). These results show that in the presence of aluminum adjuvant, the 26-476 proteins derived from different virus strains had good immunogenicity, could effectively induce the generation of antibodies in animal; and, the 26-476 proteins derived from different virus strains were substantively comparable in terms of immunogenicity, and were superior to VP8-5.

Figure 18:
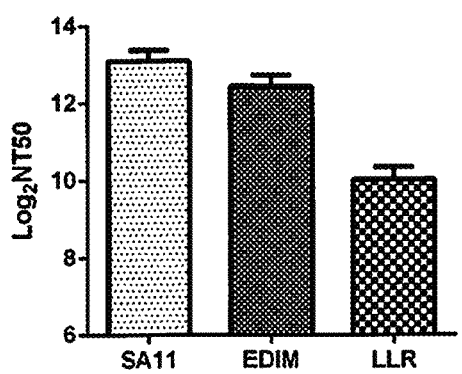

FIG. 18 shows the analytic results of the neutralizing antibody titer of the immune sera induced in Balb/c mice with the 26-476 proteins derived from different virus strains (26-476-SA11, 26-476-EDIM, 26-476 derived from LLR), wherein, the abscissa represents the virus strain from which the protein sample for producing immune serum was derived; the ordinate represents the greatest dilution ($NT_{50}$, neutralizing antibody titer) achieving an infection inhibition rate of 50%; SA11: 26-476-SA11; EDIM: 26-476-EDIM; LLR: 26-476 prepared in Example 4. The results show that in the presence of aluminum adjuvant, at Day 42 after immunization (after three immunizations), the 26-476 proteins derived from SA11, EDIM and LLR virus strains could induce generation of high-titer neutralizing antibodies in mice, and their neutralizing antibody titer ($NT_{50}$) could reach $2^{10}$-$2^{14}$ or higher; and, the neutralizing antibody titers induced by 26-476-SA11 and 26-476-EDIM were even higher than that induced by 26-476 derived from LLR.

Figure 19A:
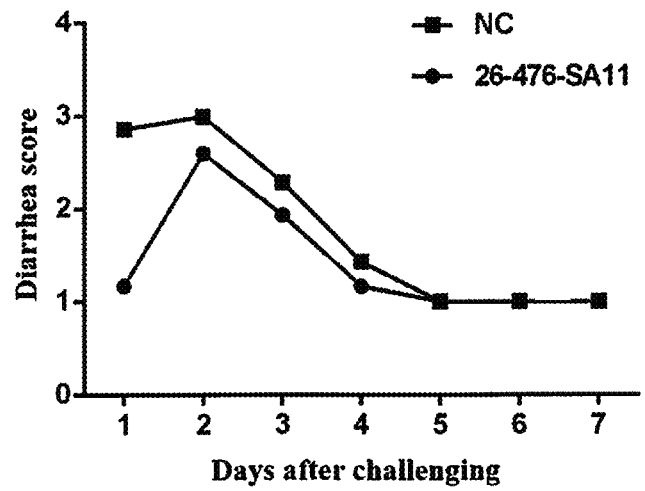
Figure 19B:
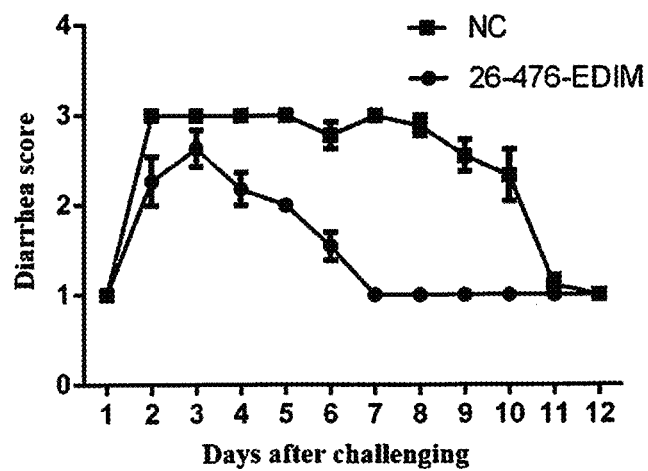

FIG. 19A shows the diarrhea scores of suckling mice in different immunization groups (immunized with 26-476-SA11 or PBS (NC, negative control)) 1-7 days after challenging with SA11 virus; FIG. 19B shows the diarrhea scores of suckling mice in different immunization groups (immunized with 26-476-EDIM or PBS (NC, negative control)) 1-12 days after challenging with EDIM virus; wherein, the abscissa represents days after challenging with a virus, and the ordinate represents the average diarrhea score. The results show that similar to the 26-476 protein derived from LLR, both of the 26-476 proteins derived from SA11 and EDIM had significant protective effect, and could help the mice to combat rotavirus infection and diarrhea caused by rotavirus infection.

Figure 19C:
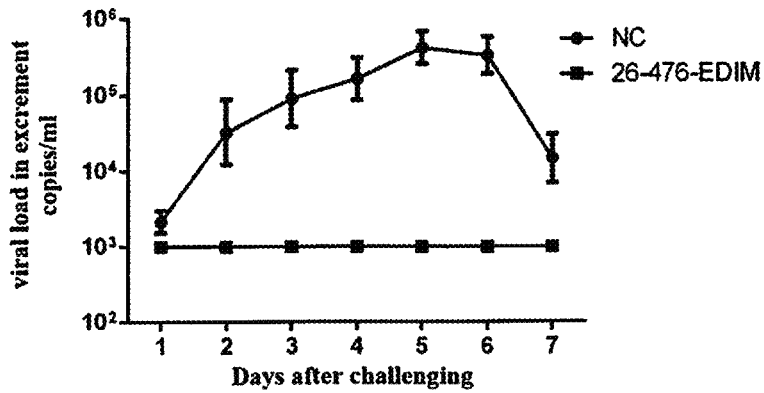

FIG. 19C shows the viral load of the stool suspension sample of the mice immunized with 26-476-EDIM or PBS (NC, negative control) 1-7 days after challenging with EDIM, wherein the abscissa represents days after challenging with a virus, and the ordinate represents the copy number of the EDIM genome contained in 1 ml stool suspension sample. The results show that after challenging with a virus, significant excretion of virus was detected in the stool of the mice immunized with PBS, and in the stool of the mice immunized with 26-476-EDIM, no excretion of virus was detected.

The results in FIG. 19A-19C show that 26-476-EDIM could not only enable the mice to combat rotavirus infection and diarrhea caused by rotavirus infection, but also inhibit the excretion of virus in the stool of the mice (i.e., excretion of virus).

SEQUENCE INFORMATION

Information on the sequences involved in the invention is provided in the following Table 1.

TABLE 1

Sequence description

| SEQ ID NO: | Description |
|---|---|
| 1 | LLR VP8 protein having 25 amino acids truncated at N-terminal, VP8-5 |
| 2 | LLR VP4 protein having C-terminal ended at amino acid position 476, 1-476 |
| 3 | LLR VP4 protein having 5 amino acids truncated at N-terminal and having C-terminal ended at 476, 6-476 |
| 4 | LLR VP4 protein having 21 amino acids truncated at N-terminal and having C-terminal ended at amino acid position 476, 22-476 |
| 5 | LLR VP4 protein having 64 amino acids truncated at N-terminal and having C-terminal ended at amino acid position 476, 65-476 |
| 6 | LLR VP4 protein having 25 amino acids truncated at N-terminal and having C-terminal ended at amino acid position 247, 26-247 |
| 7 | LLR VP4 protein having 25 amino acids truncated at N-terminal and having C-terminal ended at amino acid position 251, 26-251 |
| 8 | LLR VP4 protein having 25 amino acids truncated at N-terminal and having C-terminal ended at amino acid position 261, 26-261 |
| 9 | LLR VP4 protein having 25 amino acids truncated at N-terminal and having C-terminal ended at amino acid position 271, 26-271 |
| 10 | LLR VP4 protein having 25 amino acids truncated at N-terminal and having C-terminal ended at amino acid position 281, 26-281 |
| 11 | LLR VP4 protein having 25 amino acids truncated at N-terminal and having C-terminal ended at amino acid position 291, 26-291 |
| 12 | LLR VP4 protein having 25 amino acids truncated at N-terminal and having C-terminal ended at amino acid position 301, 26-301 |
| 13 | LLR VP4 protein having 25 amino acids truncated at N-terminal and having C-terminal ended at amino acid position 311, 26-311 |
| 14 | LLR VP4 protein having 25 amino acids truncated at N-terminal and having C-terminal ended at amino acid position 321, 26-321 |
| 15 | LLR VP4 protein having 25 amino acids truncated at N-terminal and having C-terminal ended at amino acid position 331, 26-331 |
| 16 | LLR VP4 protein having 25 amino acids truncated at N-terminal and having C-terminal ended at amino acid position 341, 26-341 |
| 17 | LLR VP4 protein having 25 amino acids truncated at N-terminal and having C-terminal ended at amino acid position 351, 26-351 |
| 18 | LLR VP4 protein having 25 amino acids truncated at N-terminal and having C-terminal ended at amino acid position 361, 26-361 |
| 19 | LLR VP4 protein having 25 amino acids truncated at N-terminal and having C-terminal ended at amino acid position 371, 26-371 |
| 20 | LLR VP4 protein having 25 amino acids truncated at N-terminal and having C-terminal ended at amino acid position 381, 26-381 |
| 21 | LLR VP4 protein having 25 amino acids truncated at N-terminal and having C-terminal ended at amino acid position 391, 26-391 |
| 22 | LLR VP4 protein having 25 amino acids truncated at N-terminal and having C-terminal ended at amino acid position 401, 26-401 |
| 23 | LLR VP4 protein having 25 amino acids truncated at N-terminal and having C-terminal ended at amino acid position 411, 26-411 |
| 24 | LLR VP4 protein having 25 amino acids truncated at N-terminal and having C-terminal ended at amino acid position 421, 26-421 |
| 25 | LLR VP4 protein having 25 amino acids truncated at N-terminal and having C-terminal ended at amino acid position 431, 26-431 |
| 26 | LLR VP4 protein having 25 amino acids truncated at N-terminal and having C-terminal ended at amino acid position 441, 26-441 |
| 27 | LLR VP4 protein having 25 amino acids truncated at N-terminal and having C-terminal ended at amino acid position 451, 26-451 |
| 28 | LLR VP4 protein having 25 amino acids truncated at N-terminal and having C-terminal ended at amino acid position 461, 26-461 |
| 29 | LLR VP4 protein having 25 amino acids truncated at N-terminal and having C-terminal ended at amino acid position 471, 26-471 |
| 30 | LLR VP4 protein having 25 amino acids truncated at N-terminal and having C-terminal ended at amino acid position 476, 26-476 |
| 31 | LLR VP4 protein having 25 amino acids truncated at N-terminal and having C-terminal ended at amino acid position 482, 26-482 |
| 32 | LLR VP4 protein having 25 amino acids truncated at N-terminal and having C-terminal ended at amino acid position 487, 26-487 |
| 33 | LLR VP4 protein having 25 amino acids truncated at N-terminal and having C-terminal ended at amino acid position 492, 26-492 |
| 34 | LLR VP4 protein having 25 amino acids truncated at N-terminal and having C-terminal ended at amino acid position 497, 26-497 |
| 35 | P[4] VP4 protein having 25 amino acids truncated at N-terminal and having C-terminal ended at amino acid position 476, 26-476-P[4] |
| 36 | P[6] VP4 protein having 25 amino acids truncated at N-terminal and having C-terminal ended at amino acid position 476, 26-476-P[6] |

TABLE 1-continued

Sequence description

| SEQ ID NO: | Description |
|---|---|
| 37 | P[8] VP4 protein having 25 amino acids truncated at N-terminal and having C-terminal ended at amino acid position 476, 26-476-P[8] |
| 38 | EDIM VP4 protein having 25 amino acids truncated at N-terminal and having C-terminal ended at amino acid position 476, 26-476-EDIM |
| 39 | SA11 VP4 protein having 25 amino acids truncated at N-terminal and having C-terminal ended at amino acid position 476, 26-476-SA11 |
| 40 | the amino acid sequence of wild-type LLR VP4 |
| 41 | the nucleotide sequence of wild-type LLR VP4 |
| 42-86 | primers |
| 87 | the amino acid sequence of wild-type SA11 VP4 |
| 88 | the amino acid sequence of wild-type EDIM VP4 |
| 89 | the amino acid sequence of wild-type P[4] VP4 |
| 90 | the amino acid sequence of wild-type P[6] VP4 |
| 91 | the amino acid sequence of wild-type P[8] VP4 |

```
Sequence 1 (SEQ ID NO: 1):
MGSEKTQRTTVNPGPFAQTGYAPVNWGPGETSDSTTVEPVLNGPYQPTTFNPPVEYWMLLAPTS

EGVVVEGTNGTDRWLATILIEPNVPETTRNYTLFGETASISVANPSQSKWRFVDVAKTTANGTYS

QYGPLLSDTKLYGVMKYNGKLYTYNGETPNATTNYYSTTNYDSVNMTSYCDFYIIPRAQESKCT

EYVNNGLPPIQNTR

Sequence 2 (SEQ ID NO: 2):
MASLIYRQLLTNSYTVNLSDEIQLIGSEKTQRTTVNPGPFAQTGYAPVNWGPGETSDSTTVEPVLN

GPYQPTTFNPPVEYWMLLAPTSEGVVVEGTNGTDRWLATILIEPNVPETTRNYTLFGETASISVAN

PSQSKWRFVDVAKTTANGTYSQYGPLLSDTICLYGVMKYNGKLYTYNGETPNATTNYYSTTNYD

SVNMTSYCDFYIIPRAQESKCTEYVNNGLPPIQNTRNVVPLALSSRSIVARRAAVNEDIVISKTSL

WKEMQYNRDIIIRFKFANSIIKSGGLGYKWSEISFKPANYQYTYIRDGEEVTAHTTCSVNGVNDFN

YNGGSLPTDFVISRYEVIKENSYVYIDYWDDSQAFRNMVYVRSLAADLNEVTCAGGTYNFQLPV

GQWPVMSGGSVSLRSAGVTLSTQFTDFVSLNSLRFRFSLAVEEPPFSISRTRISGLYGLPAANPNN

GRDFYEIAGRFSLILLVPS

Sequence 3 (SEQ ID NO: 3):
MYRQLLTNSYTVNLSDEIQLIGSEKTQRTTVNPGPFAQTGYAPVNWGPGETSDSTTVEPVLNGPY

QPTTFNPPVEYWMLLAPTSEGVVVEGTNGTDRWLATILIEPNVPETTRNYTLFGETASISVANPSQ

SKWRFVDVAKTTANGTYSQYGPLLSDTICLYGVMKYNGKLYTYNGETPNATTNYYSTTNYDSV

NMTSYCDFYIIPRAQESKCTEYVNNGLPPIQNTRNVVPLALSSRSIVARRAAVNEDIVISKTSLWK

EMQYNRDIIIRFKFANSIIKSGGLGYKWSEISFKPANYQYTYIRDGEEVTAHTTCSVNGVNDFNYN

GGSLPTDFVISRYEVIKENSYVYIDYWDDSQAFRNMVYVRSLAADLNEVTCAGGTYNFQLPVGQ

WPVMSGGSVSLRSAGVTLSTQFTDFVSLNSLRFRFSLAVEEPPFSISRTRISGLYGLPAANPNNGR

DFYEIAGRFSLILLVPS

Sequence 4 (SEQ ID NO: 4):
MIQLIGSEKTQRTTVNPGPFAQTGYAPVNWGPGETSDSTTVEPVLNGPYQPTTFNPPVEYWMLLA

PTSEGVVVEGTNGTDRWLATILIEPNVPETTRNYTLFGETASISVANPSQSKWRFVDVAKTTANG

TYSQYGPLLSDTKLYGVMKYNGKLYTYNGETPNATTNYYSTTNYDSVNMTSYCDFYIIPRAQES

KCTEYVNNGLPPIQNTRNVVPLALSSRSIVARRAAVNEDIVISKTSLWKEMQYNRDIIIRFKFANSI

IKSGGLGYKWSEISFKPANYQYTYIRDGEEVTAHTTCSVNGVNDFNYNGGSLPTDFVISRYEVIICE

NSYVYIDYWDDSQAFRNMVYVRSLAADLNEVTCAGGTYNFQLPVGQWPVMSGGSVSLRSAGV

TLSTQFTDFVSLNSLRFRFSLAVEEPPFSISRTRISGLYGLPAANPNNGRDFYEIAGRFSLILLVPS
```

Sequence 5 (SEQ ID NO: 5):
MLNGPYQPTTENPPVEYWMLLAPTSEGVVVEGTNGTDRWLATILIEPNVPETTRNYTLFGETASI

SVANPSQSKWRFVDVAKTTANGTYSQYGPLLSDTKLYGVMKYNGKLYTYNGETPNATTNYYST

TNYDSVNMTSYCDFYIIPRAQESKCTEYVNNGLPPIQNTRNVVPLALSSRSIVARRAAVNEDIVIS

KTSLWKEMQYNRDIIIRFKFANSIIKSGGLGYKWSEISFKPANYQYTYIRDGEEVTAHTTCSVNGV

NDFNYNGGSLPTDFVISRYEVIKENSYVYIDYWDDSQAFRNMVYVRSLAADLNEVTCAGGTYNF

QLPVGQWPVMSGGSVSLRSAGVTLSTQFTDFVSLNSLRFRFSLAVEEPPFSISRTRISGLYGLPAA

NPNNGRDFYEIAGRFSLILLVPS

Sequence 6 (SEQ ID NO: 6):
MGSEKTQRTTVNPGPFAQTGYAPVNWGPGETSDSTTVEPVLNGPYQPTTFNPPVEYWMLLAPTS

EGVVVEGTNGTDRWLATILIEPNVPETTRNYTLFGETASISVANPSQSKWRFVDVAKTTANGTYS

QYGPLLSDTICLYGVMKYNGKLYTYNGETPNATTNYYSTTNYDSVNMTSYCDFYIIPRAQESKCT

EYVNNGLPPIQNTRNVVPLALSSRSIVARR

Sequence 7 (SEQ ID NO: 7):
MGSEKTQRTTVNPGPFAQTGYAPVNWGPGETSDSTTVEPVLNGPYQPTTFNPPVEYWMLLAPTS

EGVVVEGTNGTDRWLATILIEPNVPETTRNYTLFGETASISVANPSQSKWRFVDVAKTTANGTYS

QYGPLLSDTKLYGVMKYNGICLYTYNGETPNATTNYYSTTNYDSVNMTSYCDFYIIPRAQESKCT

EYVNNGLPPIQNTRNVVPLALSSRSIVARRAAVN

Sequence 8 (SEQ ID NO: 8):
MGSEKTQRTTVNPGPFAQTGYAPVNWGPGETSDSTTVEPVLNGPYQPTTFNPPVEYWMLLAPTS

EGVVVEGTNGTDRWLATILIEPNVPETTRNYTLFGETASISVANPSQSKWRFVDVAKTTANGTYS

QYGPLLSDTKLYGVMKYNGKLYTYNGETPNATTNYYSTTNYDSVNMTSYCDFYIIPRAQESKCT

EYVNNGLPPIQNTRNVVPLALSSRSIVARRAAVNEDIVISKTSL

Sequence 9 (SEQ ID NO: 9):
MGSEKTQRTTVNPGPFAQTGYAPVNWGPGETSDSTTVEPVLNGPYQPTTFNPPVEYWMLLAPTS

EGVVVEGTNGTDRWLATILIEPNVPETTRNYTLFGETASISVANPSQSKWRFVDVAKTTANGTYS

QYGPLLSDTKLYGVMKYNGICLYTYNGETPNATTNYYSTTNYDSVNMTSYCDFYIIPRAQESKCT

EYVNNGLPPIQNTRNVVPLALSSRSIVARRAAVNEDIVISKTSLWICEMQYNRDI

Sequence 10 (SEQ ID NO: 10):
MGSEKTQRTTVNPGPFAQTGYAPVNWGPGETSDSTTVEPVLNGPYQPTTFNPPVEYWMLLAPTS

EGVVVEGTNGTDRWLATILIEPNVPETTRNYTLFGETASISVANPSQSKWRFVDVAKTTANGTYS

QYGPLLSDTKLYGVMKYNGKLYTYNGETPNATTNYYSTTNYDSVNMTSYCDFYIIPRAQESKCT

EYVNNGLPPIQNTRNVVPLALSSRSIVARRAAVNEDIVISKTSLWKEMQYNRDIIIRFKFANSI

Sequence 11 (SEQ ID NO: 11):
MGSEKTQRTTVNPGPFAQTGYAPVNWGPGETSDSTTVEPVLNGPYQPTTFNPPVEYWMLLAPTS

EGVVVEGTNGTDRWLATILIEPNVPETTRNYTLFGETASISVANPSQSKWRFVDVAKTTANGTYS

QYGPLLSDTKLYGVMKYNGICLYTYNGETPNATTNYYSTTNYDSVNMTSYCDFYIIPRAQESKCT

EYVNNGLPPIQNTRNVVPLALSSRSIVARRAAVNEDIVISKTSLWKEMQYNRDIIIRFKFANSIIKS

GGLGYKW

Sequence 12 (SEQ ID NO: 12):
MGSEKTQRTTVNPGPFAQTGYAPVNWGPGETSDSTTVEPVLNGPYQPTTFNPPVEYWMLLAPTS

EGVVVEGTNGTDRWLATILIEPNVPETTRNYTLFGETASISVANPSQSKWRFVDVAKTTANGTYS

QYGPLLSDTKLYGVMKYNGKLYTYNGETPNATTNYYSTTNYDSVNMTSYCDFYIIPRAQESKCT

EYVNNGLPPIQNTRNVVPLALSSRSIVARRAAVNEDIVISKTSLWKEMQYNRDIIIRFKFANSIIKS

GGLGYKWSEISFKPANY

Sequence 13 (SEQ ID NO: 13):
MGSEKTQRTTVNPGPFAQTGYAPVNWGPGETSDSTTVEPVLNGPYQPTTFNPPVEYWMLLAPTS

EGVVVEGTNGTDRWLATILIEPNVPETTRNYTLFGETASISVANPSQSKWRFVDVAKTTANGTYS

QYGPLLSDTKLYGVMKYNGKLYTYNGETPNATTNYYSTTNYDSVNMTSYCDFYIIPRAQESKCT

EYVNNGLPPIQNTRNVVPLALSSRSIVARRAAVNEDIVISKTSLWICEMQYNRDIIIRFKFANSIIKS

GGLGYKWSEISFKPANYQYTYIRDGEE

Sequence 14 (SEQ ID NO: 14):
MGSEKTQRTTVNPGPFAQTGYAPVNWGPGETSDSTTVEPVLNGPYQPTTFNPPVEYWMLLAPTS

EGVVVEGTNGTDRWLATILIEPNVPETTRNYTLFGETASISVANPSQSKWRFVDVAKTTANGTYS

QYGPLLSDTKLYGVMKYNGICLYTYNGETPNATTNYYSTTNYDSVNMTSYCDFYIIPRAQESKCT

EYVNNGLPPIQNTRNVVPLALSSRSIVARRAAVNEDIVISKTSLWICEMQYNRDIIIRFKFANSIIKS

GGLGYKWSEISFKPANYQYTYIRDGEEVTAHTTCSVN

Sequence 15 (SEQ ID NO: 15):
MGSEKTQRTTVNPGPFAQTGYAPVNWGPGETSDSTTVEPVLNGPYQPTTFNPPVEYWMLLAPTS

EGVVVEGTNGTDRWLATILIEPNVPETTRNYTLFGETASISVANPSQSKWRFVDVAKTTANGTYS

QYGPLLSDTKLYGVMKYNGKLYTYNGETPNATTNYYSTTNYDSVNMTSYCDFYIIPRAQESKCT

EYVNNGLPPIQNTRNVVPLALSSRSIVARRAAVNEDIVISKTSLWKEMQYNRDIIIRFKFANSIIKS

GGLGYKWSEISFKPANYQYTYIRDGEEVTAHTTCSVNGVNDFNYNGG

Sequence 16 (SEQ ID NO: 16):
MGSEKTQRTTVNPGPFAQTGYAPVNWGPGETSDSTTVEPVLNGPYQPTTFNPPVEYWMLLAPTS

EGVVVEGTNGTDRWLATILIEPNVPETTRNYTLFGETASISVANPSQSKWRFVDVAKTTANGTYS

QYGPLLSDTKLYGVMKYNGKLYTYNGETPNATTNYYSTTNYDSVNMTSYCDFYIIPRAQESKCT

EYVNNGLPPIQNTRNVVPLALSSRSIVARRAAVNEDIVISKTSLWKEMQYNRDIIIRFKFANSIIKS

GGLGYKWSEISFKPANYQYTYIRDGEEVTAHTTCSVNGVNDFNYNGGSLPTDFVISR

Sequence 17 (SEQ ID NO: 17):
MGSEKTQRTTVNPGPFAQTGYAPVNWGPGETSDSTTVEPVLNGPYQPTTFNPPVEYWMLLAPTS

EGVVVEGTNGTDRWLATILIEPNVPETTRNYTLFGETASISVANPSQSKWRFVDVAKTTANGTYS

QYGPLLSDTKLYGVMKYNGKLYTYNGETPNATTNYYSTTNYDSVNMTSYCDFYIIPRAQESKCT

EYVNNGLPPIQNTRNVVPLALSSRSIVARRAAVNEDIVISKTSLWKEMQYNRDIIIRFKFANSIIKS

GGLGYKWSEISFKPANYQYTYIRDGEEVTAHTTCSVNGVNDFNYNGGSLPTDFVISRYEVIKENS

YV

Sequence 18 (SEQ ID NO: 18):
MGSEKTQRTTVNPGPFAQTGYAPVNWGPGETSDSTTVEPVLNGPYQPTTFNPPVEYWMLLAPTS

EGVVVEGTNGTDRWLATILIEPNVPETTRNYTLFGETASISVANPSQSKWRFVDVAKTTANGTYS

QYGPLLSDTKLYGVMKYNGKLYTYNGETPNATTNYYSTTNYDSVNMTSYCDFYIIPRAQESKCT

EYVNNGLPPIQNTRNVVPLALSSRSIVARRAAVNEDIVISKTSLWKEMQYNRDIIIRFKFANSIIKS

GGLGYKWSEISFKPANYQYTYIRDGEEVTAHTTCSVNGVNDFNYNGGSLPTDFVISRYEVIKENS

YVYIDYWDDSQA

Sequence 19 (SEQ ID NO: 19):
MGSEKTQRTTVNPGPFAQTGYAPVNWGPGETSDSTTVEPVLNGPYQPTTFNPPVEYWMLLAPTS

EGVVVEGTNGTDRWLATILIEPNVPETTRNYTLFGETASISVANPSQSKWRFVDVAKTTANGTYS

QYGPLLSDTKLYGVMKYNGKLYTYNGETPNATTNYYSTTNYDSVNMTSYCDFYIIPRAQESKCT

-continued

EYVNNGLPPIQNTRNVVPLALSSRSIVARRAAVNEDIVISKTSLWICEMQYNRDIIIRFKFANSIIKS

GGLGYKWSEISFKPANYQYTYIRDGEEVTAHTTCSVNGVNDFNYNGGSLPTDFVISRYEVIKENS

YVYIDYWDDSQAFRNMVYVRSL

Sequence 20 (SEQ ID NO: 20):
MGSEKTQRTTVNPGPFAQTGYAPVNWGPGETSDSTTVEPVLNGPYQPTTFNPPVEYWMLLAPTS

EGVVVEGTNGTDRWLATILIEPNVPETTRNYTLFGETASISVANPSQSKWRFVDVAKTTANGTYS

QYGPLLSDTKLYGVMKYNGKLYTYNGETPNATTNYYSTTNYDSVNMTSYCDFYIIPRAQESKCT

EYVNNGLPPIQNTRNVVPLALSSRSIVARRAAVNEDIVISKTSLWKEMQYNRDIIIRFKFANSIIKS

GGLGYKWSEISFKPANYQYTYIRDGEEVTAHTTCSVNGVNDFNYNGGSLPTDFVISRYEVIICENS

YVYIDYWDDSQAFRNMVYVRSLAADLNEVTCA

Sequence 21 (SEQ ID NO: 21):
MGSEKTQRTTVNPGPFAQTGYAPVNWGPGETSDSTTVEPVLNGPYQPTTFNPPVEYWMLLAPTS

EGVVVEGTNGTDRWLATILIEPNVPETTRNYTLFGETASISVANPSQSKWRFVDVAKTTANGTYS

QYGPLLSDTKLYGVMKYNGICLYTYNGETPNATTNYYSTTNYDSVNMTSYCDFYIIPRAQESKCT

EYVNNGLPPIQNTRNVVPLALSSRSIVARRAAVNEDIVISKTSLWICEMQYNRDIIIRFKFANSIIKS

GGLGYKWSEISFKPANYQYTYIRDGEEVTAHTTCSVNGVNDFNYNGGSLPTDFVISRYEVIKENS

YVYIDYWDDSQAFRNMVYVRSLAADLNEVTCAGGTYNFQLPV

Sequence 22 (SEQ ID NO: 22):
MGSEKTQRTTVNPGPFAQTGYAPVNWGPGETSDSTTVEPVLNGPYQPTTFNPPVEYWMLLAPTS

EGVVVEGTNGTDRWLATILIEPNVPETTRNYTLFGETASISVANPSQSKWRFVDVAKTTANGTYS

QYGPLLSDTKLYGVMKYNGKLYTYNGETPNATTNYYSTTNYDSVNMTSYCDFYIIPRAQESKCT

EYVNNGLPPIQNTRNVVPLALSSRSIVARRAAVNEDIVISKTSLWKEMQYNRDIIIRFKFANSIIKS

GGLGYKWSEISFKPANYQYTYIRDGEEVTAHTTCSVNGVNDFNYNGGSLPTDFVISRYEVIKENS

YVYIDYWDDSQAFRNMVYVRSLAADLNEVTCAGGTYNFQLPVGQWPVMSGGS

Sequence 23 (SEQ ID NO: 23):
MGSEKTQRTTVNPGPFAQTGYAPVNWGPGETSDSTTVEPVLNGPYQPTTFNPPVEYWMLLAPTS

EGVVVEGTNGTDRWLATILIEPNVPETTRNYTLFGETASISVANPSQSKWRFVDVAKTTANGTYS

QYGPLLSDTICLYGVMKYNGKLYTYNGETPNATTNYYSTTNYDSVNMTSYCDFYIIPRAQESKCT

EYVNNGLPPIQNTRNVVPLALSSRSIVARRAAVNEDIVISKTSLWICEMQYNRDIIIRFKFANSIIKS

GGLGYKWSEISFKPANYQYTYIRDGEEVTAHTTCSVNGVNDFNYNGGSLPTDFVISRYEVIICENS

YVYIDYWDDSQAFRNMVYVRSLAADLNEVTCAGGTYNFQLPVGQWPVMSGGSVSLRSAGVTL

Sequence 24 (SEQ ID NO: 24):
MGSEKTQRTTVNPGPFAQTGYAPVNWGPGETSDSTTVEPVLNGPYQPTTFNPPVEYWMLLAPTS

EGVVVEGTNGTDRWLATILIEPNVPETTRNYTLFGETASISVANPSQSKWRFVDVAKTTANGTYS

QYGPLLSDTKLYGVMKYNGKLYTYNGETPNATTNYYSTTNYDSVNMTSYCDFYIIPRAQESKCT

EYVNNGLPPIQNTRNVVPLALSSRSIVARRAAVNEDIVISKTSLWICEMQYNRDIIIRFKFANSIIKS

GGLGYKWSEISFKPANYQYTYIRDGEEVTAHTTCSVNGVNDFNYNGGSLPTDFVISRYEVIICENS

YVYIDYWDDSQAFRNMVYVRSLAADLNEVTCAGGTYNFQLPVGQWPVMSGGSVSLRSAGVTL

STQFTDFVSL

Sequence 25 (SEQ ID NO: 25):
MGSEKTQRTTVNPGPFAQTGYAPVNWGPGETSDSTTVEPVLNGPYQPTTFNPPVEYWMLLAPTS

EGVVVEGTNGTDRWLATILIEPNVPETTRNYTLFGETASISVANPSQSKWRFVDVAKTTANGTYS

QYGPLLSDTKLYGVMKYNGKLYTYNGETPNATTNYYSTTNYDSVNMTSYCDFYIIPRAQESKCT

-continued

EYVNNGLPPIQNTRNVVPLALSSRSIVARRAAVNEDIVISKTSLWKEMQYNRDIIIRFKFANSIIKS

GGLGYKWSEISFKPANYQYTYIRDGEEVTAHTTCSVNGVNDFNYNGGSLPTDFVISRYEVIKENS

YVYIDYWDDSQAFRNMVYVRSLAADLNEVTCAGGTYNFQLPVGQWPVMSGGSVSLRSAGVTL

STQFTDFVSLNSLRFRFSLA

Sequence 26 (SEQ ID NO: 26):
MGSEKTQRTTVNPGPFAQTGYAPVNWGPGETSDSTTVEPVLNGPYQPTTFNPPVEYWMLLAPTS

EGVVVEGTNGTDRWLATILIEPNVPETTRNYTLFGETASISVANPSQSKWRFVDVAKTTANGTYS

QYGPLLSDTICLYGVMKYNGICLYTYNGETPNATTNYYSTTNYDSVNMTSYCDFYIIPRAQESKCT

EYVNNGLPPIQNTRNVVPLALSSRSIVARRAAVNEDIVISKTSLWKEMQYNRDIIIRFKFANSIIKS

GGLGYKWSEISFKPANYQYTYIRDGEEVTAHTTCSVNGVNDFNYNGGSLPTDFVISRYEVIKENS

YVYIDYWDDSQAFRNMVYVRSLAADLNEVTCAGGTYNFQLPVGQWPVMSGGSVSLRSAGVTL

STQFTDFVSLNSLRFRFSLAVEEPPFSISR

Sequence 27 (SEQ ID NO: 27):
MGSEKTQRTTVNPGPFAQTGYAPVNWGPGETSDSTTVEPVLNGPYQPTTFNPPVEYWMLLAPTS

EGVVVEGTNGTDRWLATILIEPNVPETTRNYTLFGETASISVANPSQSKWRFVDVAKTTANGTYS

QYGPLLSDTKLYGVMKYNGKLYTYNGETPNATTNYYSTTNYDSVNMTSYCDFYIIPRAQESKCT

EYVNNGLPPIQNTRNVVPLALSSRSIVARRAAVNEDIVISKTSLWKEMQYNRDIIIRFKFANSIIKS

GGLGYKWSEISFKPANYQYTYIRDGEEVTAHTTCSVNGVNDFNYNGGSLPTDFVISRYEVIICENS

YVYIDYWDDSQAFRNMVYVRSLAADLNEVTCAGGTYNFQLPVGQWPVMSGGSVSLRSAGVTL

STQFTDFVSLNSLRFRFSLAVEEPPFSISRTRISGLYGLP

Sequence 28 (SEQ ID NO: 28):
MGSEKTQRTTVNPGPFAQTGYAPVNWGPGETSDSTTVEPVLNGPYQPTTFNPPVEYWMLLAPTS

EGVVVEGTNGTDRWLATILIEPNVPETTRNYTLFGETASISVANPSQSKWRFVDVAKTTANGTYS

QYGPLLSDTKLYGVMKYNGKLYTYNGETPNATTNYYSTTNYDSVNMTSYCDFYIIPRAQESKCT

EYVNNGLPPIQNTRNVVPLALSSRSIVARRAAVNEDIVISKTSLWKEMQYNRDIIIRFKFANSIIKS

GGLGYKWSEISFKPANYQYTYIRDGEEVTAHTTCSVNGVNDFNYNGGSLPTDFVISRYEVIKENS

YVYIDYWDDSQAFRNMVYVRSLAADLNEVTCAGGTYNFQLPVGQWPVMSGGSVSLRSAGVTL

STQFTDFVSLNSLRFRFSLAVEEPPFSISRTRISGLYGLPAANPNNGRDF

Sequence 29 (SEQ ID NO: 29):
MGSEKTQRTTVNPGPFAQTGYAPVNWGPGETSDSTTVEPVLNGPYQPTTFNPPVEYWMLLAPTS

EGVVVEGTNGTDRWLATILIEPNVPETTRNYTLFGETASISVANPSQSKWRFVDVAKTTANGTYS

QYGPLLSDTICLYGVMKYNGKLYTYNGETPNATTNYYSTTNYDSVNMTSYCDFYIIPRAQESKCT

EYVNNGLPPIQNTRNVVPLALSSRSIVARRAAVNEDIVISKTSLWKEMQYNRDIIIRFKFANSIIKS

GGLGYKWSEISFKPANYQYTYIRDGEEVTAHTTCSVNGVNDFNYNGGSLPTDFVISRYEVIKENS

YVYIDYWDDSQAFRNMVYVRSLAADLNEVTCAGGTYNFQLPVGQWPVMSGGSVSLRSAGVTL

STQFTDFVSLNSLRFRFSLAVEEPPFSISRTRISGLYGLPAANPNNGRDFYEIAGRFSLI

Sequence 30 (SEQ ID NO: 30):
MGSEKTQRTTVNPGPFAQTGYAPVNWGPGETSDSTTVEPVLNGPYQPTTFNPPVEYWMLLAPTS

EGVVVEGTNGTDRWLATILIEPNVPETTRNYTLFGETASISVANPSQSKWRFVDVAKTTANGTYS

QYGPLLSDTKLYGVMKYNGKLYTYNGETPNATTNYYSTTNYDSVNMTSYCDFYIIPRAQESKCT

EYVNNGLPPIQNTRNVVPLALSSRSIVARRAAVNEDIVISKTSLWKEMQYNRDIIIRFKFANSIIKS

GGLGYKWSEISFKPANYQYTYIRDGEEVTAHTTCSVNGVNDFNYNGGSLPTDFVISRYEVIKENS

YVYIDYWDDSQAFRNMVYVRSLAADLNEVTCAGGTYNFQLPVGQWPVMSGGSVSLRSAGVTL

STQFTDFVSLNSLRFRFSLAVEEPPFSISRTRISGLYGLPAANPNNGRDFYEIAGRFSLILLVPS

Sequence 31 (SEQ ID NO: 31):
MGSEKTQRTTVNPGPFAQTGYAPVNWGPGETSDSTTVEPVLNGPYQPTTFNPPVEYWMLLAPTS

EGVVVEGTNGTDRWLATILIEPNVPETTRNYTLFGETASISVANPSQSKWRFVDVAKTTANGTYS

QYGPLLSDTKLYGVMKYNGKLYTYNGETPNATTNYYSTTNYDSVNMTSYCDFYIIPRAQESKCT

EYVNNGLPPIQNTRNVVPLALSSRSIVARRAAVNEDIVISKTSLWICEMQYNRDIIIRFKFANSIIKS

GGLGYKWSEISFICPANYQYTYIRDGEEVTAHTTCSVNGVNDFNYNGGSLPTDFVISRYEVIKENS

YVYIDYWDDSQAFRNMVYVRSLAADLNEVTCAGGTYNFQLPVGQWPVMSGGSVSLRSAGVTL

STQFTDFVSLNSLRFRFSLAVEEPPFSISRTRISGLYGLPAANPNNGRDFYEIAGRFSLILLVPSNDD

YQT

Sequence 32 (SEQ ID NO: 32):
MGSEKTQRTTVNPGPFAQTGYAPVNWGPGETSDSTTVEPVLNGPYQPTTFNPPVEYWMLLAPTS

EGVVVEGTNGTDRWLATILIEPNVPETTRNYTLFGETASISVANPSQSKWRFVDVAKTTANGTYS

QYGPLLSDTKLYGVMKYNGICLYTYNGETPNATTNYYSTTNYDSVNMTSYCDFYIIPRAQESKCT

EYVNNGLPPIQNTRNVVPLALSSRSIVARRAAVNEDIVISKTSLWKEMQYNRDIIIRFKFANSIIKS

GGLGYKWSEISFKPANYQYTYIRDGEEVTAHTTCSVNGVNDFNYNGGSLPTDFVISRYEVIKENS

YVYIDYWDDSQAFRNMVYVRSLAADLNEVTCAGGTYNFQLPVGQWPVMSGGSVSLRSAGVTL

STQFTDFVSLNSLRFRFSLAVEEPPFSISRTRISGLYGLPAANPNNGRDFYEIAGRFSLILLVPSNDD

YQTPIMNS

Sequence 33 (SEQ ID NO: 33):
MGSEKTQRTTVNPGPFAQTGYAPVNWGPGETSDSTTVEPVLNGPYQPTTFNPPVEYWMLLAPTS

EGVVVEGTNGTDRWLATILIEPNVPETTRNYTLFGETASISVANPSQSKWRFVDVAKTTANGTYS

QYGPLLSDTKLYGVMKYNGKLYTYNGETPNATTNYYSTTNYDSVNMTSYCDFYIIPRAQESKCT

EYVNNGLPPIQNTRNVVPLALSSRSIVARRAAVNEDIVISKTSLWICEMQYNRDIIIRFKFANSIIKS

GGLGYKWSEISFKPANYQYTYIRDGEEVTAHTTCSVNGVNDFNYNGGSLPTDFVISRYEVIICENS

YVYIDYWDDSQAFRNMVYVRSLAADLNEVTCAGGTYNFQLPVGQWPVMSGGSVSLRSAGVTL

STQFTDFVSLNSLRFRFSLAVEEPPFSISRTRISGLYGLPAANPNNGRDFYEIAGRFSLILLVPSNDD

YQTPIMNSVTVRQ

Sequence 34 (SEQ ID NO: 34):
MGSEKTQRTTVNPGPFAQTGYAPVNWGPGETSDSTTVEPVLNGPYQPTTFNPPVEYWMLLAPTS

EGVVVEGTNGTDRWLATILIEPNVPETTRNYTLFGETASISVANPSQSKWRFVDVAKTTANGTYS

QYGPLLSDTKLYGVMKYNGKLYTYNGETPNATTNYYSTTNYDSVNMTSYCDFYIIPRAQESKCT

EYVNNGLPPIQNTRNVVPLALSSRSIVARRAAVNEDIVISKTSLWKEMQYNRDIIIRFICFANSIIKS

GGLGYKWSEISFICPANYQYTYIRDGEEVTAHTTCSVNGVNDFNYNGGSLPTDFVISRYEVIKENS

YVYIDYWDDSQAFRNMVYVRSLAADLNEVTCAGGTYNFQLPVGQWPVMSGGSVSLRSAGVTL

STQFTDFVSLNSLRFRFSLAVEEPPFSISRTRISGLYGLPAANPNNGRDFYEIAGRFSLILLVPSNDD

YQTPIMNSVTVRQDLERQ

Sequence 35 (SEQ ID NO: 35):
MGSEKTQNVTVNPGPFAQTRYAPVNWGHGEINDSTTVEPVLDGPYQPTTFKPPNDYWLLISSNT

DGVVYESTNNSDFWTAVIAVEPHVSQTNRQYVLFGENKQFNIENSSDKWICFLEMFRGSGQSDFS

NRRTLTSNNRLVGMLKYGGRVWTFHGETPRATTDSSNTADLNNISIIIHSEFYIIPRSQESKCNEYI

NNGLPPIQNTRNVVPLSLSSRSIQYRRAQVNEDITISKTSLWKEMQYNRDIIIRFKFGNSVIICLGGL

-continued

GYKWSEISYKAANYQYSYSRDGEQVTAHTTCSVNGVNNFSYNGGSLPTDFSISRYEVIICENSYVY

IDYWDDSICAFRNMVYVRSLAANLNSVKCVGGSYDFRLPVGEWPIMNGGAVSLHFAGVTLSTQF

TDFVSLNSLRFRFSLTVDEPSFSIIRTRTMNLYGLPAANPNNGNEYYEVSGRFSLISLVPTN

Sequence 36 (SEQ ID NO: 36)
MGSEKSQNVTINPGPFAQTNYAPVTWSHGEVNDSTTIEPVLDGPYQPTNFICPPNDYWILLNPTNQ

QVVLEGTNKTDIWVALLLVEPNVTNQSRQYTLFGETKQITVENNTNKWKFFEMFRSNVSAEFQH

KRTLTSDTKLAGFMKFYNSVWTFHGETPHATTDYSSTSNLSEVETVIHVEFYIIPRSQESKCSEY1N

TGLPPMQNTRNIVPVALSSRSVTYQRAQVNEDIIISKTSLWKEMQYNRDIIIRFKFNNSIVKLGGLG

YKWSEISFKAANYQYSYLRDGEQVTAHTTCSVNGVNNFSYNGGSLPTDFSVSRYEVIKENSYVY

VDYWDDSQAFRNMVYVRSLAANLNSVKCSGGNYNFQIPVGAWPVMSGGAVSLHFAGVTLSTQ

FTDFVSLNSLRFRFSLTVEEPPFSILRTRVSGLYGLPAFNPNNGHEYYEIAGRFSLISLVPSN

Sequence 37 (SEQ ID NO: 37):
MGSEKTQNVTINPSPFAQTRYAPVNWGHGEINDSTTVEPMLDGPYQPTTFTPPNDYWILINSNTN

GVVYESTNNSDFWTAVVAIEPHVNPVDRQYTIFGESKQFNVSNDSNKWKFLEMFRSSSQNEFYN

RRTLTSDTRFVGILKYGGRVWTFHGETPRATTDSSSTANLNNISITIHSEFYIIPRSQESKCNEYINN

GLPPIQNTRNVVPLPLSSRSIQYKRAQVNEDIIVSKTSLWKEMQYNRDIIIRFKFGNSIVICMGGLGY

KWSEISYKAANYQYNYLRDGEQVTAHTTCSVNGVNNFSYNGGFLPTDFGISRYEVIKENSYVYV

DYWDDSICAFRNMVYVRSLAANLNSVKCTGGSYNFSIPVGAWPVMNGGAVSLHFAGVTLSTQFT

DFVSLNSLRFRFSLTVDEPPFSILRTRTVNLYGLPAANPNNGNEYYEISGRFSLIYLVPTN

Sequence 38 (SEQ ID NO: 38):
MGAEKTQNVTVNPGPFAQTGYAPANWGPGETNDSTTVEPVLDGPYQPIAFSPPPEYYILLSPTAP

GVIAECTNTVNRWIAIIAIEPNVSPTNRTYTLFGITEQLTVENSSVDKWICFIDFMKTPTTGSYVRYN

ILLSSTKLCAVAKHTDNLYSYVGETPTAGQAYYSSFNIFNLTAHCDFYIIPWSQQSLCTQYVNNGL

PPIQNTRNVVPRHLSARSIITQRAQANEDIVVSKTSLWKEMQFNRDITIRFKFANAIIKSGGLGYK

WSEISFKPANYQYTYTRDGEEVTAHTTCSVNGVNNFDFFGGSLPTDFGISRYEVIKENSFVYIDY

WDDSQAFRNMVYVRSLAADLNTVECTGGAYSFSLPVGQWPVMTGGAVSLRAAGVTLSTQFTDF

VSLNSLRFRFRLSVEEPSFSITRTRVSGLYGLPAADPNNGREYYEIAGRFSLISLVPSND

Sequence 39 (SEQ ID NO: 39):
MGSTKSQNVTINPGPFAQTGYAPVNWGPGEINDSTTVEPLLDGPYQPTTFNPPVDYWMLLAPTTP

GVIVEGTNNTDRWLATILIEPNVQSENRTYTIFGIQEQLTVSNTSQDQWKFIDVVKTTANGSIGQY

GSLLSSPKLYAVMICHNEKLYTYEGQTPNARTGHYSTTNYDSVNMTAFCDFYIIPRSEESKCTEYI

NNGLPPIQNTRNVVPLSLTARDVIHYRAQANEDIVISKTSLWKEMQYNRDITIRFKFANTIIKSGGL

GYKWSEISFKPANYQYTYTRDGEEVTAHTTCSVNGVNDFSFNGGSLPTDFVVSKFEVIKENSYVY

IDYWDDSQAFRNVVYVRSLAANLNSVMCTGGSYNFSLPVGQWPVLTGGAVSLHSAGVTLSTQF

TDFVSLNSLRFRFRLAVEEPHFKLTRTRLDRLYGLPAADPNNGKEYYEIAGRFSLISLVPS

Sequence 40 (SEQ ID NO: 40):
MASLIYRQLLTNSYTVNLSDEIQLIGSEKTQRTTVNPGPFAQTGYAPVNWGPGETSDSTTVEPVLN

GPYQPTTFNPPVEYWMLLAPTSEGVVVEGINGTDRWLATILIEPNVPETTRNYTLFGETASISVAN

PSQSKWRFVDVAKTTANGTYSQYGPLLSDTKLYGVMKYNGKLYTYNGETPNATTNYYSTTNYD

SVNMTSYCDFYIIPRAQESKCTEYVNNGLPPIQNTRNVVPLALSSRSIVARRAAVNEDIVISKTSL

WKEMQYNRDIIIRFKFANSIIKSGGLGYKWSEISFKPANYQYTYIRDGEEVTAHTTCSVNGVNDFN

YNGGSLPTDFVISRYEVIKENSYVYIDYWDDSQAFRNMVYVRSLAADLNEVTCAGGTYNFQLPV

GQWPVMSGGSVSLRSAGVTLSTQFTDFVSLNSLRFRFSLAVEEPPFSISRTRISGLYGLPAANPNN

GRDFYEIAGRFSLILLVPSNDDYQTPIMNSVTVRQDLERQLGELREEFNALSQEIAMSQLIDLALLP
LDMFSMFSGIKTTIDAAKSMATNVMKKFKSSGLATSVSTLTDSLSDAASAVSRNSSIRSIGSTASA
WTDISSQIVDTQASVNTLATQTSTISKRLRLICEIATQTEGMNFDDISAAVLKTKIDKSSQIGPSTLP
DIVTEASEKFIPNRTYRVIDDDTVFEAGTDGRFYAYRVETFEEVPFDVQKFADLVTDSPVISAIIDF
KTLKNLNDNYGITRSQALNLIRSDPRVLREFINQDNPIIRNRIEQLILQCRL

Sequence 41 (SEQ ID NO: 41):
ATGGCTTCGCTCATTTACAGACAATTACTTACGAATTCATATACAGTGAATCTTTCAGATGAA
ATACAGTTAATTGGATCAGAAAAAACGCAGAGAACTACAGTAAATCCAGGTCCATTTGCACA
AACTGGTTATGCACCAGTGAATTGGGGGCCTGGGGAAACGAGTGATTCCACTACTGTTGAGC
CAGTGTTGAATGGACCATATCAGCCGACGACTTTCAATCCACCAGTAGAATATTGGATGCTT
CTAGCACCAACATCAGAAGGGGTAGTTGTTGAAGGTACTAATGGTACGGATAGATGGCTAGC
TACAATACTTATAGAACCAAATGTGCCTGAGACGACTAGAAATTACACATTATTTGGGGAAA
CAGCGAGTATATCAGTAGCAAACCCATCACAAAGTAAATGGCGTTTTGTTGACGTAGCTAAG
ACCACTGCAAATGGAACATATTCACAATATGGACCATTACTATCAGATACAAAACTGTATGG
AGTAATGAAATACAACGGGAAGTTGTATACGTATAATGGTGAAACTCCGAATGCTACAACAA
ATTATTATTCAACTACAAATTATGACTCAGTGAATATGACATCTTATTGCGATTTTTACATTAT
ACCAAGAGCACAAGAATCAAAGTGCACAGAATACGTAAATAATGGATTACCACCAATACAA
AACACCAGAAATGTCGTACCATTAGCTTTATCTTCACGATCAATAGTTGCTAGAAGAGCTGC
AGTGAACGAAGACATAGTTATATCGAAAACGTCATTGTGGAAAGAAATGCAATATAATCGA
GATATCATAATAAGATTTAAGTTTGCAAACTCAATTATTAAATCAGGTGGACTAGGGTATAA
ATGGTCAGAGATTTCATTCAAACCAGCAAACTATCAATATACATATATACGTGATGGAGAGG
AAGTAACTGCACATACAACATGTTCAGTGAATGGAGTGAACGACTTCAACTATAACGGAGGA
TCATTACCAACTGACTTTGTAATATCACGTTATGAAGTTATAAAAGAGAACTCTTATGTATAT
ATAGATTATTGGGATGATTCACAAGCATTCAGAAACATGGTATATGTGAGATCATTAGCTGC
GGACTTAAATGAAGTGACATGTGCAGGGGGTACTTATAATTTCCAACTACCAGTTGGACAAT
GGCCTGTGATGAGTGGTGGCTCAGTATCATTGCGTTCAGCTGGAGTAACGTTATCAACTCAAT
TTACAGACTTTGTGTCATTAAATTCGTTAAGATTTAGGTTCAGTTTAGCAGTAGAAGAACCGC
CATTCTCTATTTCAAGGACACGGATATCAGGGTTATATGGGTTACCGGCAGCCAATCCAAAT
AATGGAAGAGACTTCTATGAAATTGCGGGTAGATTTTCATTAATTTTATTAGTACCATCAAAT
GATGATTATCAAACTCCTATAATGAACTCAGTGACGGTGAGACAGGACTTAGAGAGGCAGTT
AGGAGAATTGAGAGAAGAATTTAACGCATTATCACAAGAGATAGCTATGTCACAATTGATAG
ATCTAGCTTTACTACCATTGGACATGTTCTCAATGTTTTCAGGAATTAAAACAACGATAGATG
CAGCTAAATCAATGGCCACTAATGTAATGAAGAAGTTTAAAAGCTCAGGCTTGGCCACGTCT
GTATCCACGTTGACAGACTCATTATCTGACGCCGCATCAGCGGTATCAAGGAACAGCTCAAT
AAGATCAATTGGATCAACAGCATCAGCTTGGACAGACATTTCTTCACAAATAGTGGATACGC
AAGCATCAGTCAATACGTTGCAACTCAAACGTCAACTATCAGCAAGAGATTAAGGTTAAAA
GAAATTGCGACTCAAACAGAGGGAATGAATTTCGACGACATATCAGCAGCTGTGTTAAAAAC
TAAAATTGACAAATCATCACAAATAGGACCAAGTACTTTACCAGATATTGTTACTGAAGCGT
CGGAGAAGTTTATACCAAATAGAACGTATAGAGTAATTGACGATGATACTGTGTTTGAAGCA
GGAACAGATGGGAGATTTTACGCATATAGAGTCGAGACGTTTGAGGAAGTTCCATTTGATGT
GCAAAAATTCGCAGATTTAGTAACTGACTCTCCAGTAATCTCGGCCATTATAGACTTTAAAAC -continued

GCTTAAAAACTTGAATGATAACTATGGAATTACTCGTTCGCAAGCATTAAATCTAATTAGATC

AGATCCAAGGGTTCTGCGAGAATTTATCAATCAAGATAATCCAATAATAAGAAACAGGATAG

AGCAGTTAATTCTGCAATGTAGATTGTAA

Sequence 42 (SEQ ID NO: 42):
GGATCCCATATGATGGCTTCGCTCATTTAC

Sequence 43 (SEQ ID NO: 43):
GGATCCCATATGTACAGACAATTACTTACGAATTC

Sequence 44 (SEQ ID NO: 44):
GGATCCCATATGATACAGTTAATTGGATCAGAAAA

Sequence 45 (SEQ ID NO: 45):
GGATCCCATATGGGATCAGAAAAAACGCAG

Sequence 46 (SEQ ID NO: 46):
GGATCCCATATGTTGAATGGACCA

Sequence 47 (SEQ ID NO: 47):
AAGCTTAGGTGTTTTGTATTGGTGG

Sequence 48 (SEQ ID NO: 48):
AAGCTTATCTTCTAGCAACTATTGATCGT

Sequence 49 (SEQ ID NO: 49):
AAGCTTAGTTCACTGCAGCTCTTCTAGC

Sequence 50 (SEQ ID NO: 50):
AAGCTTACAATGACGTTTTCGATATAACTA

Sequence 51 (SEQ ID NO: 51):
AAGCTTAGATATCTCGATTATATTGCATTTC

Sequence 52 (SEQ ID NO: 52):
AAGCTTAAATTGAGTTTGCAAACTTAAAT

Sequence 53 (SEQ ID NO: 53):
AAGCTTACCATTTATACCCTAGTCCACC

Sequence 54 (SEQ ID NO: 54):
AAGCTTAATAGTTTGCTGGTTTGAATGA

Sequence 55 (SEQ ID NO: 55):
AAGCTTATTCCTCTCCATCACGTATATATG

Sequence 56 (SEQ ID NO: 56):
AAGCTTAATTCACTGAACATGTTGTATGTG

Sequence 57 (SEQ ID NO: 57):
AAGCTTATCCTCCGTTATAGTTGAAGTC

Sequence 58 (SEQ ID NO: 58):
AAGCTTAACGTGATATTACAAAGTCAGTTG

Sequence 59 (SEQ ID NO: 59):
AAGCTTATACATAAGAGTTCTCTTTTATAACTTC

Sequence 60 (SEQ ID NO: 60):
AAGCTTATGCTTGTGAATCATCCCAA

Sequence 61 (SEQ ID NO: 61):
AAGCTTATAATGATCTCACATATACCATGTTT

Sequence 62 (SEQ ID NO: 62):
AAGCTTATGCACATGTCACTTCATTTAAG

Sequence 63 (SEQ ID NO: 63):
AAGCTTAAACTGGTAGTTGGAAATTATAAGTA

Sequence 64 (SEQ ID NO: 64):
AAGCTTATGAGCCACCACTCATCACA

Sequence 65 (SEQ ID NO: 65):
AAGCTTATAACGTTACTCCAGCTGAAC

Sequence 66 (SEQ ID NO: 66):
AAGCTTATAATGACACAAAGTCTGTAAATTG

-continued

Sequence 67 (SEQ ID NO: 67):
AAGCTTATGCTAAACTGAACCTAAATCTTA

Sequence 68 (SEQ ID NO: 68):
AAGCTTACCTTGAAATAGAGAATGGCG

Sequence 69 (SEQ ID NO: 69):
AAGCTTACGGTAACCCATATAACCCT

Sequence 70 (SEQ ID NO: 70):
AAGCTTAGAAGTCTCTTCCATTATTTGGA

Sequence 71 (SEQ ID NO: 71):
AAGCTTAAATTAATGAAAATCTACCCGC

Sequence 72 (SEQ ID NO: 72):
AGATCTAAGCTTATGATGGTACTAATAAAATTAATGAAAATC

Sequence 73 (SEQ ID NO: 73):
AGATCTAAGCTTAAGTTTGATAATCATCATTTGATGGTACTA

Sequence 74 (SEQ ID NO: 74):
AGATCTAAGCTTATGAGTTCATTATAGGAGTTTGATAATCAT

Sequence 75 (SEQ ID NO: 75):
AGATCTAAGCTTATGTCTCACCGTCACTGAGTTCA

Sequence 76 (SEQ ID NO: 76):
AGATCTAAGCTTACTGCCTCTCTAAGTCCTGTCTCA

Sequence 77 (SEQ ID NO: 77):
GGATCCCATATGGGATCGGAGAAAACTCAA

Sequence 78 (SEQ ID NO: 78):
AAGCTTAATTAGTTGGAACTAAAGAAATAAGT

Sequence 79 (SEQ ID NO: 79)
GGATCCCATATGGGATCAGAGAAAAGTCAAAT

Sequence 80 (SEQ ID NO: 80)
AAGCTTAATTAGACGGTACTAATGAAA

Sequence 81 (SEQ ID NO: 81):
GGATCCCATATGGGATCAGAAAAAACTCAAAATG

Sequence 82 (SEQ ID NO: 82):
AAGCTTAGTTGGTTGGAACTAAAGAAA

Sequence 83 (SEQ ID NO: 83):
GGATCCCATATGGGAGCAGAGAAGACACA

Sequence 84 (SEQ ID NO: 84):
AAGCTTAATCGTTGGACGGCAC

Sequence 85 (SEQ ID NO: 85):
GGATCCCATATGGGATCAACTAAATCACAAAATG

Sequence 86 (SEQ ID NO: 86):
AAGCTTATGATGGCACTAATGATATAAGT

Sequence 87 (SEQ ID NO: 87):
MASLIYRQLLTNSYTVDLSDEIQEIGSTKSQNVTINPGPFAQTGYAPVNWGPGEINDSTTVEPLLD

GPYQPMTFNPPVDYWMLLAPTTPGVIVEGTNNTDRWLATILIEPNVQSENRTYTIFGIQEQLTVSN

TSQDQWKFIDVVKTTANGSIGQYGSLLSSPKLYAVMKHNEKLYTYEGQTPNARTGHYSTTNYDS

VNMTAFCDFYIIPRSEESKCTEYINNGLPPIQNTRNVVPLSLTARDVIHYRAQANEDIVISKTSLWK

EMQYNRDITIRFKFANTIIKSGGLGYKWSEISFKPANYQYTYTRDGEEVTAHTTCSVNGVNDFSF

NGGSLPTDFVVSKFEVIKENSYVYIDYWDDSQAFRNVMYVRSLAANLNSVMCTGGSYNFSLPVG

QWPVLTGGAVSLHSAGVTLSTQFTDFVSLNSLRFRFRLAVEEPHFKLTRTRLDRLYGLPAADPNN

GICEYYEIAGRFSLISLVPSNDDYQTPIANSVTVRQDLERQLGELREEFNALSQEIAMSQLIDLALLP

LDMFSMFSGIKSTIDAAKSMATNVMKKFKKSGLANSVSTLTDSLSDAASSISRGSSIRSIGSSASA

WTDVSTQITDISSSVSSVSTQTSTISRRLRLKEMATQTEGMNFDDISAAVLKTKIDKSTQISPNTIPD

```
IVTEASEKFIPNRAYRVINNDDVFEAGIDGKFFAYKVDTFEEIPFDVQKFADLVTDSPVISAIIDFKT

LICNLNDNYGITKQQAFNURSDPRVLREFINQDNPIIRNRIEQLIMQCRL

Sequence 88 (SEQ ID NO: 88):
MASLIYRQLLTNSFTVDISDEIETIGAEKTQNVTVNPGPFAQTGYAPANWGPGETNDSTTVEPVLD

GPYQPIAFSPPPEYYILLSPTAPGVIAECTNTVNRWIAIIAIEPNVSPTNRTYTLFGITEQLTVENSSV

DKWKFIDFMKTPTTGSYVRYNILLSSTKLCAVAKHTDNLYSYVGETPTAGQAYYSSFNIFNLTAH

CDFYIIPWSQQSLCTQYVNNGLPPIQNTRNVVPRHLSARSIITQRAQANEDIVVSKTSLWICEMQFN

RDITIRFKFANAIIKSGGLGYKWSEISFKPANYQYTYTRDGEEVTAHTTCSVNGVNNFDFFGGSLP

TDFGISRYEVIKENSFVYIDYWDDSQAFRNMVYVRSLAADLNTVECTGGAYSFSLPVGQWPVMT

GGAVSLRAAGVTLSTQFTDFVSLNSLRFRFRLSVEEPSFSITRTRVSGLYGLPAADPNNGREYYEI

AGRFSLISLVPSNDNYQTPIMNSVTVRQDLERQLGELREEFNALSQEIALSQLVDLALLPLDMFSM

FSGIKATLDVAKSMATNVMKKFKKSGLATSISAMTESLSDAASSVSRSGAIRSVSSTSSAWTDVSS

RVANVENAASTVSTQTATISRRLRLKEITTQTEGMNFDDISAAVLKTKLDKSVRIAPNTLPDIVTE

ASEKFIPNRSYRVINNNEAFETGTDGRFFAYRVDTLEELPFDVQKFADLVAESPVISAIIDFKTLICN

LNDNYGISICEQAFSLLRSDPRVLREFINQGNPIIRNRIEQLIMQCRL

Sequence 89 (SEQ ID NO: 89):
MASLIYRQLLTNSYSVDLHDEIEQIGSEKTQNVTVNPGPFAQTRYAPVNWGHGEINDSTTVEPVL

DGPYQPTTFKPPNDYWLLISSNTDGVVYESTNNSDFWTAVIAVEPHVSQTNRQYVLFGENKQFNI

ENSSDKWKFLEMFRGSGQSDFSNRRTLTSNNRLVGMLKYGGRVWTFHGETPRATTDSSNTADL

NNISIIIHSEFYIIPRSQESKCNEYINNGLPPIQNTRNVVPLSLSSRSIQYRRAQVNEDI-
TISKTSLWICE

MQYNRDIIIRFKFGNSVIKLGGLGYKWSEISYKAANYQYSYSRDGEQVTAHTTCSVNGVNNFSY

NGGSLPTDFSISRYEVIICENSYVYIDYWDDSKAFRNMVYVRSLAANLNSVKCVGGSYDFRLPVG

EWPIMNGGAVSLHFAGVTLSTQFTDFVSLNSLRFRFSLTVDEPSFSIIRTRTMNLYGLPAANPNNG

NEYYEVSGRFSLISLVPTNDDYQTPIMNSVTVRQDLERQLNDLREEFNSLSQEIAMSQLIDLALLP

LDMFSMFSGIKSTIDLTKSMATSVMKKFRKSICLATSISEMINSLSDAASSASRSASIRSNLSTISNW

SDASKSVLNVTDSVNDVSTQTSTISICKLRLREMITQTEGISFDDISAAVLKTKIDMSTQIGKNTLPD

IVTEASEKFIPICRSYRVLKDDEVMEVNTEGKFFAYKVDTLNEIPFDINKFAELVTDSPVISAIIDFKT

LKNLNDNYGITRIEALNLIKSNPNVLRNFINQNNPIIRNRIEQULQCKL

Sequence 90 (SEQ ID NO: 90):
MASLIYRQLLTNSYTVELSDEINTIGSEKSQNVTINPGPFAQTNYAPVTWSHGEVNDSTTIEPVLD

GPYQPTNFKPPNDYWILLNPTNQQVVLEGTNKTDIWVALLLVEPNVTNQSRQYTLFGETKQITVE

NNTNKWKFFEMFRSNVNAEFQHKRTLTSDTKLAGFMKFYNSVWTFHGETPHATTDYSSTSNLSE

VETVIHVEFYIIPRSQESKCSEYINTGLPPMQNTRNIVPVALSSRSVTYQRAQVNEDIIISKTSLWKE

MQYNRDIIIRFICFNNSIVICLGGLGYKWSEISFKAANYQYSYLRDGEQVTAHTTCSVNGVNNFSYN

GGSLPTDFSVSRYEVIICENSYVYVDYWDDSQAFRNMVYVRSLAANLNSVKCSGGNYNFQIPVG

AWPVMSGGAVSLHFAGVTLSTQFTDFVSLNSLRFRFSLTVEEPPFSILRTRVSGLYGLPAFNPNNG

HEYYEIAGRFSLISLVPSNDDYQTPIMNSVTVRQDLERQLGDLREEFNSLSQEIAMTQLIDLALLPL

DMFSMFSGIKSTIDVAKSMVTKVMKICFKKSGLATSISELTGSLSNAASSVSRSSSIRSNISSISVWT

DVSEQIAGSSDSVRNISTQTSAISKRLRLREITTQTEGMNFDDISAAVLKTKIDRSTHISPDTLPDIIT

ESSEKFIPKRAYRVLICDDEVMEADVDGKFFAYKVGTFEEVPFDVDKFVDLVTDSPVISAIIDFKTL

KNLNDNYGITRSQALDLIRSDPRVLRDFINQNNPIIKNRIEQLILQCRL
```

-continued

Sequence 91 (SEQ ID NO: 91):
MASLIYRQLLTNSYSVDLHDEIEQIGSEKTQNVTINPSPFAQTRYAPVNWGHGEINDSTTVEPMLD

GPYQPTTFTPPNDYWILINSNTNGVVYESTNNSDFWTAVVAIEPHVNPVDRQYTIFGESKQFNVS

NDSNKWKFLEMFRSSSQNEFYNRRTLTSDTRFVGILKYGGRVWTFHGETPRATTDSSSTANLNNI

SITIHSEFYIIPRSQESKCNEYINNGLPPIQNTRNVVPLPLSSRSIQYKRAQVNEDIIVSKTSLWICEM

QYNRDIIIRFKFGNSIVICIVIGGLGYKWSEISYKAANYQYNYLRDGEQVTAHTTCSVNGVNNFSYN

GGFLPTDFGISRYEVIKENSYVYVDYWDDSICAFRNMVYVRSLAANLNSVKCTGGSYNFSIPVGA

WPVMNGGAVSLHFAGVTLSTQFTDFVSLNSLRFRFSLTVDEPPFSILRTRTVNLYGLPAANPNNG

NEYYEISGRFSLIYLVPTNDDYQTPIMNSVTVRQDLERQLTDLREEFNSLSQEIAMAQLIDLALLPL

DMFSMFSGIKSTIDLTKSMATSVMKKFRKSICLATSISEMTNSLSDAASSASRNVSIRSNLSAISNW

TNVSNDVSNVTNSLNDISTQTSTISICKFRLKEMITQTEGMSFDDISAAVLKTKIDMSTQIGKNTLP

DIVTEASEKFIPKRSYRILICDDEVMEINTEGKFFAYKINTFDEVPFDVNKFAELVTDSPVISAIIDFK

TLKNLNDNYGITRTEALNLIKSNPNMLRNFINQNNPIIRNRIEQLILQCKL

Specific Modes for Carrying Out the Invention

The embodiments of the invention are illustrated by reference to the following examples. A person skilled in the art would understand that the following examples are only for the purpose of illustrating the invention, rather than being regarded as limiting the protection scope of the invention.

Unless indicated otherwise, the molecular biological experimental methods and immunological assays used in the invention are carried out substantially in accordance with the methods as described in Sambrook J et al., Molecular Cloning: A Laboratory Manual (Second Edition), Cold Spring Harbor Laboratory Press, 1989, and F. M. Ausubel et al., Short Protocols in Molecular Biology, 3rd Edition, John Wiley & Sons, Inc., 1995, or in accordance with the instructions of products. The reagents or apparatuses, the manufacturers of which are not indicated, are the conventional products that are commercially available. Those skilled in the art understand that the examples are used for illustrating the present invention, but not intended to limit the protection scope of the present invention. Without departing from the spirit and essence of the invention, modifications or replacements made to the methods, steps or conditions of the invention all fall into the scope of the invention.

Sources of the biological materials and reagents used in Examples:

Rotavirus LLR strain was given as a gift by Beijing Wantai Biological Pharmacy Enterprise CO., LTD; rotavirus SA11 strain was purchased from Chinese Veterinary Culture Collection Center; rotavirus Wa and DS-1 strains were purchased from ATCC; rotavirus EDIM strain was given as a gift by Institute of Pathogenic Biology; prokaryotic expression vector PTO-T7 was constructed by the laboratory; *Escherichia coli* (*E.coli*) ER2566 and BL21 (DE3) were purchased from New England Biolabs; the primers used were synthesized by Sangon Biotech (Shanghai) Co., Ltd.

EXAMPLE 1

Study on Immunogenicity and Immune-Protection of the Truncated VP8 Protein (VP8-5)

Figure 1A:
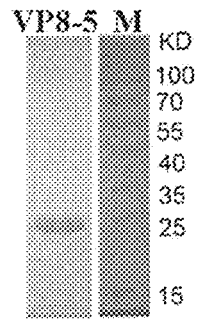
FIG. 1A shows the SDS-PAGE results of the purified VP8-5 protein. The results show that the purified VP8-5 protein obtained had a purity of above 90%.

In accordance with the method as described in the Chinese patent application CN 201510165746.2, the truncated rotavirus VP8 protein, VP8-5 (the amino acid sequence of which was set forth in SEQ ID NO: 1), was expressed and purified. In brief, the genomic RNA of rotavirus was extracted from the culture of rotavirus LLR strain, and cDNA encoding the VP4 protein was obtained by reverse transcription. Then, the cDNA obtained was used as a template, and the gene fragment encoding VP8-5 was obtained by PCR amplification. The gene fragment obtained was then used to construct an expression vector for VP8-5, and the expression vector was transformed into *E. coli*. The *E. coli* containing the VP8-5 expression vector was cultured at 37° C. until $OD_{600}$ was about 0.6, and the temperature was then reduced to 25° C. IPTG was added at a final concentration of 0.8 mM, and the *E. coli* was further cultured for 6 h. After the culture, the bacteria were collected by centrifugation and disrupted ultrasonically, and the soluble fraction was collected. Then, the VP8-5 protein was collected from the soluble fraction by anion-exchange chromatography, wherein the instrument system used was AKTA Explorer 100 Preparative Chromatography System produced by GE Healthcare Company; the chromatographic medium used was Q-sepharose-HP (GE Healthcare Company); the buffer used was 50 mM Tris-HCl pH 8.0 and 50 mM Tris-HCl pH 8.0, 2M NaCl; the elution program was as followed: the impure protein was eluted with 1000 mM NaCl, the protein of interest was eluted with 50 mM NaCl, and the product eluted with 50 mM NaCl was collected. The eluted product obtained was identified by 13.5% SDS-PAGE, and the result was shown in FIG. 1. The results in FIG. 1 showed that the purified VP8-5 protein obtained had a purity of above 90%.

It has been demonstrated by using a mouse model in the Chinese Patent Application CN 201510165746.2 that in the presence of Freund's adjuvant, the purified VP8-5 protein had good immunogenicity and immune-protection (see, Example 5-8 and FIGS. 4-9 of the application). In order to further investigate the immune-protective effect of the VP8-5 protein in the presence of aluminum adjuvant, the mouse model was used to evaluate the immunogenicity and immune-protection of the purified VP8-5protein+aluminum adjuvant.

The embodiment was as followed: 5-6-week old female Balb/c mice were randomly divided into 3 groups, 7 mice per group, wherein two groups were used as control groups, and one group was used as experimental group. The purified VP8-5 protein, an equal dose of the inactivated virus LLR strain and PBS were separately mixed with aluminum phosphate adjuvant at a ratio of 1:1 (v/v), and then the mice were immunized by muscular injection, at an immunization dose of 10 μg/mouse, wherein, the mice in the experimental group were immunized with VP8-5, the mice in the positive control group were immunized with the inactivated virus LLR, and the mice in the negative control group were immunized with PBS. The mice in each group were immunized for three times, at an interval of two weeks for each immunization. At Day 0, 14, 28 and 42 of the immunization procedure, blood was collected from the eyeballs of the mice, respectively, and was determined for antibody titer and neutralizing antibody titer.

Determination of Antibody Titer

The immune serum was subjected to serial dilution, and the diluted immune serum and the VP8-5 coated on the plate were subjected to indirect ELISA analysis (wherein the secondary antibody used was a goat anti-mouse antibody (Wanyumeilan)), to determine the greatest dilution of the immune serum having reactivity with VP8-5. The greater the greatest dilution of the immune serum was, the higher the titer of anti-VP8-5 antibody in the immune serum was, and the higher the immunogenicity of the protein for producing the immune serum was.

Figure 1B:
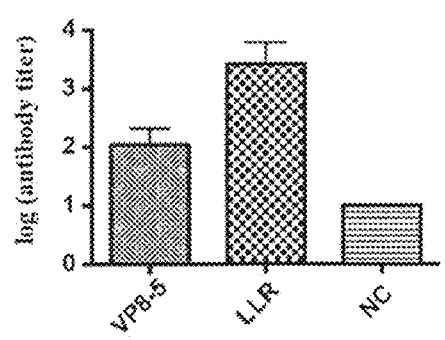
FIG. 1B shows the results of indirect ELISA analysis with the VP8-5 protein and the immune serum obtained by immunization of Balb/c mice with the VP8-5 protein, wherein, the abscissa represents the experimental group (VP8-5), the positive control group (LLR) and the negative control group (NC), and the ordinate represents the greatest dilution (i.e., antibody titer) of the immune serum having reactivity with the VP8-5 protein. The results show that in the presence of aluminum adjuvant, at Day 42 after immunization, VP8-5 could induce generation of antibodies in mice, but its efficiency was lower than the efficiency of the inactivated virus LLR. This result shows that in the presence of aluminum adjuvant, VP8-5 protein had immunogenicity and could induce the generation of antibodies in mice, but its ability of inducing generation of antibodies in animal was lower than that of the inactivated virus LLR.

The indirect ELISA results were shown in FIG. 1B, wherein, the ordinate represents the greatest dilution (i.e., antibody titer) of the immune serum having reactivity with VP8-5. The results showed that in the presence of aluminum adjuvant, at Day 42 after immunization, VP8-5 could induce generation of antibodies in mice, but its efficiency was lower than the efficiency of the inactivated virus LLR. These results showed that in the presence of aluminum adjuvant, the VP8-5 protein had immunogenicity and could induce generation of antibodies in mice, but its ability of inducing generation of antibodies in animal was lower than that of the inactivated virus LLR.

Determination of Neutralizing Antibody Titer

The MA104 cells were spread onto a 96-well cell culture plate ($1.9*10^4$ cells/well). 20 h later, neutralizing antibody titer of the immune serum was determined by ELISPOT (Li, Lin, Yu, et al. J Virol Methods, 209 7-14, 2014). The particular method was as followed: an immune serum sample to be tested (containing a neutralizing antibody to be tested) was subjected to double dilution continuously by using DMEM containing trypsin; 100 μL of each diluted sample was then mixed with a rotavirus solution diluted in DMEM (TCID50=$1.5*10^5$); after incubation at 37° C. for 1 h, the mixture was added to a 96-well cell culture plate pre-spread with MA104 cells, and cultured at 37° C. for 14 h; and then, the viral infection inhibition rate of the immune serum sample was calculated as followed.

The infectious inhibition rate=(the number of virus spots in a well without serum−the number of virus spots in a well with serum)/the number of virus spots in a well without serum*100%.

The neutralizing antibody titer in immune serum is defined as: the greatest dilution of the immune serum achieving 50% infection inhibition rate. If a 50-fold diluted immune serum sample can still achieve an infection inhibition rate of above 50%, the sample is regarded as having neutralizing ability.

Figure 1C:
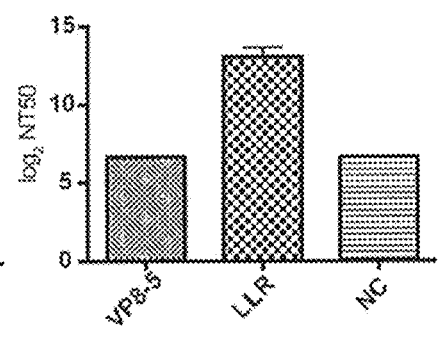
FIG. 1C shows the analytic results of the neutralizing antibody titer of the immune serum induced with VP8-5 in Balb/c mice, wherein, the abscissa represents the experimental group (VP8-5), the positive control group (LLR) and the negative control group (NC), and the ordinate represents the log value of the greatest dilution of the immune serum achieving an infection inhibition rate of 50% ($\log_2$NT50, neutralizing antibody titer). The results show that in the presence of aluminum adjuvant, VP8-5 could induce the generation of neutralizing antibodies in mice at Day 42 after immunization (after three immunizations), but the neutralizing antibody titer (NT50) of the immune serum was lower than that of the inactivated virus LLR. After the immunization procedure was finished, the neutralizing antibody titer (NT50) of the immune serum induced with VP8-5 protein merely reached about 64. This result shows that in the presence of aluminum adjuvant, VP8-5 could induce the generation of neutralizing antibodies in an organism, however, the neutralizing antibody titer (NT50) of the immune serum induced therewith was lower than that of the inactivated virus LLR.

The analytic results of the neutralizing antibody titer of immune sera were shown in FIG. 1C, wherein, the ordinate represents the greatest dilution (NT50, neutralizing antibody titer) of immune serum achieving an infection inhibition rate of 50%. The results showed that in the presence of aluminum adjuvant, VP8-5 could induced generation of neutralizing antibodies in mice at Day 42 after immunization (after three immunizations), but the neutralizing antibody titer (NT50) of the immune serum was lower than that of the inactivated virus LLR. After the immunization procedure was finished, the neutralizing antibody titer (NT50) of the immune serum induced with VP8-5 protein merely reached about 64. These results showed that in the presence of aluminum adjuvant, VP8-5 could induce generation of neutralizing antibodies in an organism, however, the neutralizing antibody titer (NT50) of the immune serum induced therewith was lower than that of the inactivated virus LLR.

Analysis on the Protective Effect in Animal

Figures 2A, 2B, 2C:
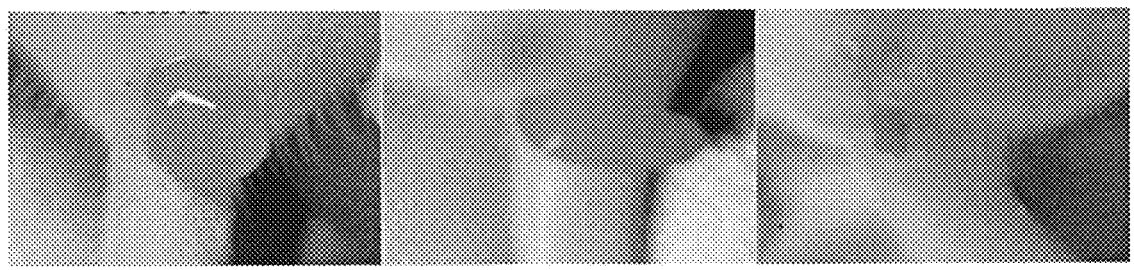
FIGS. 2A-2C show the scoring criteria of diarrhea in protective experiments. Depending on the degree of diarrhea in suckling mice, the scores are divided into three grades: normal stool is scored as 1 point (FIG. 2C), soft stool is scored as 2 point (FIG. 2B), and unshaped watery stool is scored as 3 point (FIG. 2A).

After the immunization procedure was finished (42 days after immunization), the mice in each group were mated at a ratio of two female mice to one male mouse. About 20 days after mating, the female mice gave birth to suckling mice, and the suckling mice were raised for 7 days. The 7-day old suckling mice were intragastrically challenged with LLR virus strain, at a dose of $5*10^6$ TCID50/mouse. After the challenge, the diarrhea condition of the suckling mice was observed and recorded every day for 7 days, and scored depending on the shape and state of the excrement. The scoring criteria were as shown in FIG. 2. Depending on the degree of diarrhea in suckling mice, the scores are divided into three grades: normal stool is scored as 1 point (FIG. 2C), soft stool is scored as 2 points (FIG. 2B), and unshaped watery stool is scored as 3 points (FIG. 2A).

Figure 3:
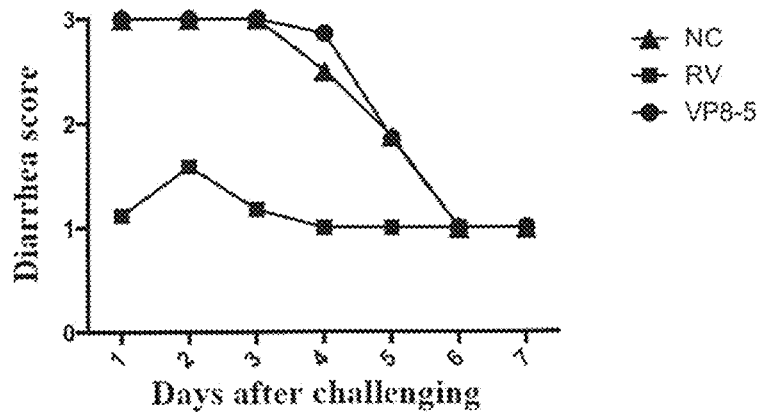
FIG. 3 shows the diarrhea scores of the suckling mice in different immunization groups after challenge with a virus, wherein, the axis of ordinates represents the diarrhea score; the axis of abscissas represents days after challenging mice with a virus. The results show that the diarrhea scores of the suckling mice in the experimental group (VP8-5) were not significantly different from that of the negative control group (NC). This show that in the presence of aluminum adjuvant, VP8-5 had a low ability of protecting an organism from rotavirus infection (lower than that of the inactivated virus), and could not sufficiently alleviate the diarrhea caused by rotavirus infection.
Figure 4A:
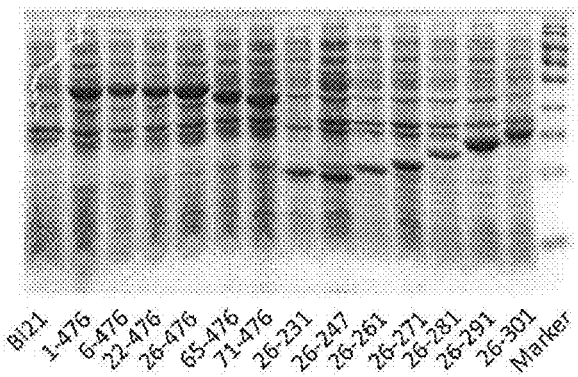
FIGS. 4A-4D show the SDS-PAGE results of the truncated proteins expressed in E. coli. The results show that except for 26-311, 26-331 and 26-381 with a relatively low expression level, the other truncated proteins could be expressed in a high level in E. coli.
Figure 4B:
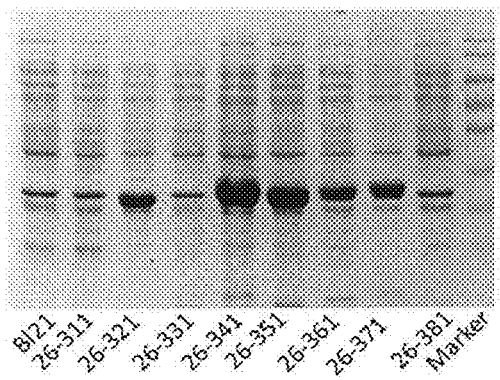
Figure 4C:
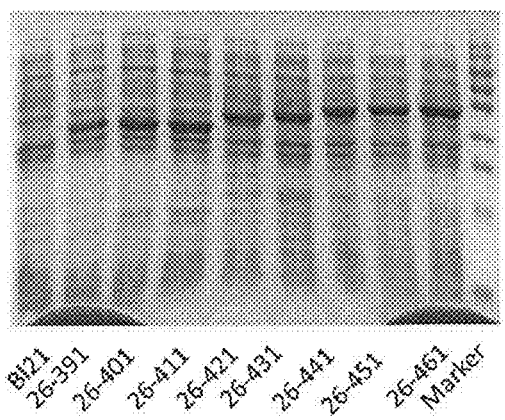
Figure 4D:
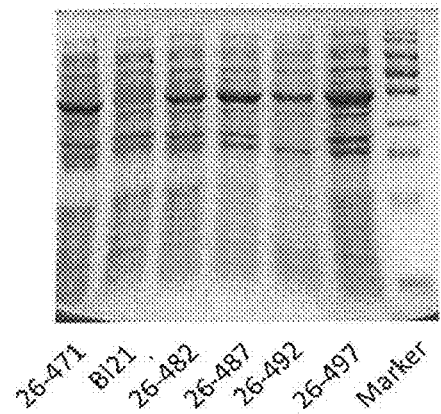

FIG. 3 showed the diarrhea scores of the suckling mice in different immunization groups after challenging with a virus, wherein, the axis of ordinates represents the diarrhea score; the axis of abscissas represents days after challenging with a virus in mice. The results showed that the diarrhea scores of the suckling mice in the experimental group (VP8-5) were not significantly different from that of the negative control group (NC). This showed that in the presence of aluminum adjuvant, VP8-5 had a low ability of protecting an organism from rotavirus infection (lower than that of the inactivated virus), and could not sufficiently alleviate diarrhea caused by rotavirus infection.

EXAMPLE 2

Construction of Expression Vectors Encoding the Truncated VP4 Protein

Rotavirus LLR and SA11 strains were cultured with a fetal rhesus monkey kidney cell line (MA-104). The culture medium used was DMEM, supplemented with 2 μg/ml trypsin, 0.5 mg/ml ampicillin and 0.4 mg/ml streptomycin, 3.7 mg/ml sodium bicarbonate, and 0.34 mg/ml L-glutamine.

In accordance with the instructions of the manufacturer, the Virus DNA/RNA Kit produced by Beijing GenMag Biotechnology Co., Ltd. was used to extract the genomic RNA of rotavirus, and cDNA encoding the VP4 protein of LLR strain was obtained by reverse transcription. The obtained cDNA was used as a template, and the gene fragment encoding the truncated VP4 protein of the rotavirus LLR strain was obtained by PCR amplification.

The PCR primers used are as follows:

upstream primers:

(SEQ ID NO: 42)
5'-GGATCCCATATGATGGCTTCGCTCATTTAC-3'

-continued (SEQ ID NO: 43)
5'-GGATCCCATATGTACAGACAATTACTTACGAATTC-3'

(SEQ ID NO: 44)
5'-GGATCCCATATGATACAGTTAATTGGATCAGAAAA-3'

(SEQ ID NO: 45)
5'-GGATCCCATATGGGATCAGAAAAAACGCAG-3'

(SEQ ID NO: 46)
5'-GGATCCCATATGTTGAATGGACCA-3' downstream primers:

(SEQ ID NO: 47)
5'-AAGCTTAGGTGTTTTGTATTGGTGG-3'

(SEQ ID NO: 48)
5'-AAGCTTATCTTCTAGCAACTATTGATCGT-3'

(SEQ ID NO: 49)
5'-AAGCTTAGTTCACTGCAGCTCTTCTAGC-3'

(SEQ ID NO: 50)
5'-AAGCTTACAATGACGTTTTCGATATAACTA-3'

(SEQ ID NO: 51)
5'-AAGCTTAGATATCTCGATTATATTGCATTTC-3'

(SEQ ID NO: 52)
5'-AAGCTTAAATTGAGTTTGCAAACTTAAAT-3'

(SEQ ID NO: 53)
5'-AAGCTTACCATTTATACCCTAGTCCACC-3'

(SEQ ID NO: 54)
5'-AAGCTTAATAGTTTGCTGGTTTGAATGA-3'

(SEQ ID NO: 55)
5'-AAGCTTATTCCTCTCCATCACGTATATATG-3'

(SEQ ID NO: 56)
5'-AAGCTTAATTCACTGAACATGTTGTATGTG-3'

(SEQ ID NO: 57)
5'-AAGCTTATCCTCCGTTATAGTTGAAGTC-3'

(SEQ ID NO: 58)
5'-AAGCTTAACGTGATATTACAAAGTCAGTTG-3'

(SEQ ID NO: 59)
5'-AAGCTTATACATAAGAGTTCTCTTTTATAACTTC-3'

(SEQ ID NO: 60)
5'-AAGCTTATGCTTGTGAATCATCCCAA-3'

(SEQ ID NO: 61)
5'-AAGCTTATAATGATCTCACATATACCATGTTT-3'

(SEQ ID NO: 62)
5'-AAGCTTATGCACATGTCACTTCATTTAAG-3'

(SEQ ID NO: 63)
5'-AAGCTTAAACTGGTAGTTGGAAATTATAAGTA-3'

(SEQ ID NO: 64)
5'-AAGCTTATGAGCCACCACTCATCACA-3'

(SEQ ID NO: 65)
5'-AAGCTTATAACGTTACTCCAGCTGAAC-3'

(SEQ ID NO: 66)
5'-AAGCTTATAATGACACAAAGTCTGTAAATTG-3'

(SEQ ID NO: 67)
5'-AAGCiTGCTAAACTGAACCTAAATCTTA-3'

(SEQ ID NO: 68)
5'-AAGCTTACCTTGAAATAGAGAATGGCG-3'

(SEQ ID NO: 69)
5'-AAGCTTACGGTAACCCATATAACCCT-3'

(SEQ ID NO: 70)
5'-AAGCTTAGAAGTCTCTTCCATTATTTGGA-3'

(SEQ ID NO: 71)
5'-AAGCTTAAATTAATGAAAATCTACCCGC-3'

(SEQ ID NO: 72)
5'-AGATCTAAGCTTATGATGGTACTAATAAAATTAATGAAAATC-3'

(SEQ ID NO: 73)
5'-AGATCTAAGCTTAAGTTTGATAATCATCATTTGATGGTACTA-3'

(SEQ ID NO: 74)
5'-AGATCTAAGCTTATGAGTTCATTATAGGAGTTTGATAATCAT-3'

(SEQ ID NO: 75)
5'-AGATCTAAGCTTATGTCTCACCGTCACTGAGTTCA-3'

(SEQ ID NO: 76)
5'-AGATCTAAGCTTACTGCCTCTCTAAGTCCTGTCTCA-3' wherein the underlined sequences indicate the enzymatic restriction sites, and the italic letters indicate the introduced terminator codons.

By using the above-mentioned primers, the gene encoding the truncated VP4 protein was amplified by PCR, and the PCR system used are as follows:

| Sample | Volume |
| --- | --- |
| 10 x buffer | 5 μL |
| F (upstream primer) | 0.5 μL |
| R (downstream primer) | 0.5 μL |
| rTaq enzyme | 0.5 μL |
| dNTP mix | 0.5 μL |
| cDNA (reverse transcription product) | 5 μL |
| DEPC water | 38 μL |

The primer pairs for amplification of the gene encoding the truncated VP4 protein were shown in Table 2:

TABLE 2

Primers for amplification of the genes encoding the truncated VP4 proteins

| Protein name | Upstream primer | Downstream primer |
| --- | --- | --- |
| 1-476 | SEQ ID NO: 42 | SEQ ID NO: 72 |
| 6-476 | SEQ ID NO: 43 | SEQ ID NO: 72 |
| 22-476 | SEQ ID NO: 44 | SEQ ID NO: 72 |
| 26-476 | SEQ ID NO: 45 | SEQ ID NO: 72 |
| 65-476 | SEQ ID NO: 46 | SEQ ID NO: 72 |
| 26-247 | SEQ ID NO: 45 | SEQ ID NO: 48 |
| 26-251 | SEQ ID NO: 45 | SEQ ID NO: 49 |
| 26-261 | SEQ ID NO: 45 | SEQ ID NO: 50 |
| 26-271 | SEQ ID NO: 45 | SEQ ID NO: 51 |
| 26-281 | SEQ ID NO: 45 | SEQ ID NO: 52 |
| 26-291 | SEQ ID NO: 45 | SEQ ID NO: 53 |
| 26-301 | SEQ ID NO: 45 | SEQ ID NO: 54 |
| 26-311 | SEQ ID NO: 45 | SEQ ID NO: 55 |
| 26-321 | SEQ ID NO: 45 | SEQ ID NO: 56 |
| 26-331 | SEQ ID NO: 45 | SEQ ID NO: 57 |
| 26-341 | SEQ ID1 NO: 45 | SEQ ID NO: 58 |
| 26-351 | SEQ ID NO: 45 | SEQ ID NO: 59 |
| 26-361 | SEQ ID NO: 45 | SEQ ID NO: 60 |
| 26-371 | SEQ ID NO: 45 | SEQ ID NO: 61 |
| 26-381 | SEQ ID NO: 45 | SEQ ID NO: 62 |
| 26-391 | SEQ ID NO: 45 | SEQ ID NO: 63 |
| 26-401 | SEQ ID NO: 45 | SEQ ID NO: 64 |
| 26-411 | SEQ ID NO: 45 | SEQ ID NO: 65 |
| 26-421 | SEQ ID NO: 45 | SEQ ID NO: 66 |
| 26-431 | SEQ ID NO: 45 | SEQ ID NO: 67 |
| 26-441 | SEQ ID NO: 45 | SEQ ID NO: 68 |

TABLE 2-continued

Primers for amplification of the genes encoding the truncated VP4 proteins

| Protein name | Upstream primer | Downstream primer |
|---|---|---|
| 26-451 | SEQ ID NO: 45 | SEQ ID NO: 69 |
| 26-461 | SEQ ID NO: 45 | SEQ ID NO: 70 |
| 26-471 | SEQ ID NO: 45 | SEQ ID NO: 71 |
| 26-476 | SEQ ID NO: 45 | SEQ ID NO: 72 |
| 26-482 | SEQ ID NO: 45 | SEQ ID NO: 73 |
| 26-487 | SEQ ID NO: 45 | SEQ ID NO: 74 |
| 26-492 | SEQ ID NO: 45 | SEQ ID NO: 75 |
| 26-497 | SEQ ID NO: 45 | SEQ ID NO: 76 |

PCR conditions were as followed: pre-denaturation at 95° C. for 5 min, 35 cycles of (95° C., 40 s; 55° C., 80 s; 72° C., 1 min), and final extension at 72° C. for 10 min. The amplification product obtained was subjected to 1.5% agarose gel electrophoresis.

The PCR amplification product was ligated into the pMD18-T vector, and was transformed into *E. coli* DH5α. The positive bacterial colony was then screened, and the plasmid was extracted, and identified by cleavage with Nde I/Hind III enzymes, and the positive clonal plasmids, into which the gene fragments of interest were inserted, were obtained. The positive clonal plasmids obtained were sequenced. The sequencing results showed that the nucleotide sequences of the fragments of interest which were inserted into the positive clonal plasmids were identical to the sequences expected, and the amino acid sequences encoded thereby were set forth in SEQ ID NOs: 2-34.

The positive clonal plasmids were cleaved by Nde I/Hind III enzymes, respectively, to obtain the gene fragments encoding the truncated VP4 proteins, which were ligated to the non-fusion expression vector pTO-T7 cleaved with Nde I/Hind III enzymes (Luo Wenxin et al., Chinese Journal of Biotechnology, 2000, 16: 53-57), and the vector was transformed into *E. coli* DH5α. The positive bacterial colony was screened, the plasmid was extracted, and the positive expression vector, into which the gene fragment of interest was inserted, was identified by cleavage with Nde I/Hind III enzymes.

1 μL positive expression vector was used to transform 40 μL competent *E. coli* B121 (DE3) (purchased from NEB Company). The transformed *E. coli* was coated onto solid LB culture medium (the components of the LB culture medium: 10 g/L peptone, 5 g/L yeast powder, and 10 g/L NaCl, the same below) containing kanamycin (final concentration of 25 mg/mL, the same below), and was subjected to static culture at 37° C. for 10-12 h until the single colonies were clear and discernible. Single colonies were picked and placed in 4 mL liquid LB culture medium (containing kanamycin), and then cultured at 37° C., under shaking at 200 r/min for 10 h. After culture, to 1 mL bacterial solution, glycerol was added at a final concentration of 10%, and the resultant mixture was stored at −70° C.

EXAMPLE 3

Expression of the Truncated VP4 Proteins

The *E. coli* solution carrying positive expression vector prepared in Example 2, was taken from a refrigerator at −70° C., seeded into 50 ml liquid LB culture medium containing kanamycin, and cultured at 180 rpm, 37° C. for about 4 h; and was then transferred to 10 bottles of 500 ml kanamycin-containing LB culture medium (500 ul bacterial solution for each bottle). When the absorbance value of the culture reached 0.5 at a wavelength of 600 nm, IPTG was added to a final concentration of 1 mM, and further cultured at 180 rpm, 25° C. for 6 h.

1 ml said bacterial solution was centrifuged, and the bacterial precipitate was collected. To the bacterial precipitate, 100 μL deionized water was added, and the bacteria were re-suspended. 20 μL 6*loading buffer was then added, and the resultant mixture was mixed homogeneously and incubated in a boiling water bath for 10 min, to lyse the cells. 10 μL sample was subjected to 12% SDS-PAGE analysis. SDS-PAGE results were shown in FIG. 4A-4D. The results showed that except for 26-311, 26-331 and 26-381 with a relatively low expression level, the other truncated proteins could be expressed in a high level in *E. coli*.

EXAMPLE 4

Purification and Characterization of the Truncated VP4 Proteins

The *E. coli* solution obtained in Example 3 was centrifuged, and the bacterial precipitate was collected. At a ratio of 15 ml/g wet bacteria, 50 mM TB8.0 was used to re-suspend the bacteria expressing the truncated VP4 proteins. The *E. coli* cells were then disrupted ultrasonically, and the condition for ultrasonic disruption was as followed: ultra-sonication for 2 s and pause for 4 s, with an ultrasonication period of 4 min for the disruption of one gram of bacteria. After the ultrasonic disruption, the mixture was centrifuged at 25000 g, and the supernatant was collected (i.e., the soluble fraction of the *E. coli* lysate containing the recombinantly expressed truncated VP4 protein).

The truncated VP4 protein in the soluble fraction of the *E. coli* lysate could be purified by two-step chromatography. For 26-331, 26-351, 26-381, 26-411, 26-441 and 26-461, prior to the two-step chromatography, the soluble fraction of the *E. coli* lysate was treated with 40% ammonium sulfate, and then centrifuged to collect the protein precipitate; the obtained protein precipitate was then dissolved in 50 mM Tris-HCl pH 8.0, and applied to the two-step chromatography. The method of two-step chromatography was as followed.

Firstly, the primary purification was carried out by Q-HP anion-exchange chromatography, to obtain the truncated VP4 protein with a purity of about 60%, wherein the purification conditions were as followed:

Instrument system: AKTA Explorer 100 Preparative Liquid Chromatography System produced by GE Healthcare Company (the original Amershan Pharmacia Company).

Chromatographic medium: Q-sepharose-HP (GE Healthcare Company).

Column volume: 5.5 cm*20 cm.

Buffer: A pump: 50 mM Tris-HCl pH 8.0;

B pump: 50 mM Tris-HCl pH 8.0, 2M NaCl

Flow rate: 6 mL/min.

Wavelength of the detector: 280 nm.

The sample was the supernatant containing the recombinantly expressed truncated VP4 protein, as prepared above (i.e., the soluble fraction of the *E. coli* lysate or the protein sample dissolved in 50 mM Tris-HCl pH 8.0).

The elution program was as followed: the protein of interest was eluted with 50 mM NaCl, and the impure protein was eluted with 1 M NaCl. The fraction eluted with 50 mM NaCl was collected, and 30 mL primarily purified sample containing the recombinantly expressed truncated protein was obtained (Note: during the primary purification, the truncated proteins 1-476, 26-331, 26-351, 26-381, 26-411, 26-441 and 26-461 were not bound to the chromatographic column, and were contained in the flow-through fraction. Therefore, the flow-through fractions containing the truncated proteins were collected and used as the primarily purified samples).

The sample primarily purified by anion-exchange chromatography was dialyzed to TB8.0 buffer containing 2 M NaCl, and then was subjected to secondary purification by Phenyl sepharose-HP hydrophobic affinity chromatography.

Chromatographic medium: Phenyl sepharose-HP (GE Healthcare Company).
Column volume: 5.5 cm*20 cm.
Buffer: A pump: 50 mM Tris-HCl pH 8.0, 2M NaCl;
B pump: 50 mM Tris-HCl pH 8.0
Flow rate: 6 mL/min.
Wavelength of the detector: 280 nm.

The sample was the product purified by Q-HP chromatographic column and dialyzed to 2M NaCl solution.

Elution program was as followed: the impure protein was eluted with 1.5 M NaCl, the protein of interest was eluted with 1 M NaCl, and the impure protein was eluted with 50 mM NaCl. The fraction eluted with 1 M NaCl was collected, and 30 mL the purified, recombinantly expressed truncated VP4 protein was obtained (Note: during the secondary purification, the truncated proteins 1-476, 26-331, 26-351, 26-381, 26-411, 26-441, 26-461 and 26-471 were eluted with 50 mM TB8.0, and the fractions eluted with 50 mM TB8.0 were collected).

To the sample (150 μL) purified by the above-mentioned method, 30 μL 6× Loading Buffer was added, and the mixture was mixed homogeneously and incubated in a 100° C. water bath for 10 min; and the mixture (10 μl) was then subjected to electrophoresis in 13.5% SDS-polyacrylamide gel at a voltage of 120V for 120 min; and the electrophoresis strips were then shown by coomassie brilliant blue staining. The electrophoresis results were shown in FIG. 5.

Figure 5A:
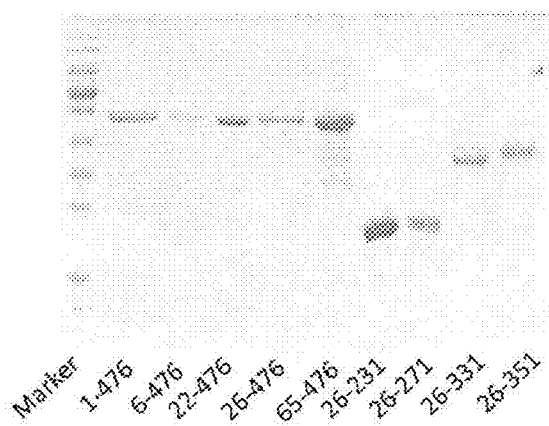
FIGS. 5A-5B show the SDS-PAGE results of the purified truncated VP4 proteins.
Figure 5B:
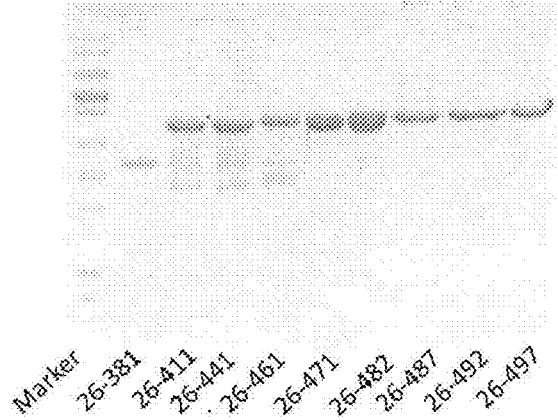

FIG. 5A-5B show the SDS-PAGE results of the purified truncated VP4 proteins. In FIG. 5A, the lanes from left to right are: Protein Molecular Weight Marker (Marker), 1-476, 6-476, 22-476, 26-476, 65-476, 26-231, 26-271, 26-331 and 26-351. In FIG. 5B, the lanes from left to right are: Protein Molecular Weight Marker (Marker), 26-381, 26-411, 26-441, 26-461, 26-471, 26-482, 26-487, 26-492 and 26-497. The results in FIGS. 5A and 5B showed that after the purification steps, the truncated proteins 1-476, 6-476, 22-476, 26-476, 65-476, 26-231, 26-271, 26-331, 26-351, 26-381, 26-411, 26-441, 26-461, 26-471, 26-482, 26-487, 26-492 and 26-497 all had a concentration of above 0.2mg/ml, and a purity of above 80%.

In addition, HPLC was also used to analyze the homogenicity of the purified samples under different buffering conditions. The apparatus used was Agilent 1200 High Performance Liquid Chromatography Apparatus, wherein the chromatographic column was G3000$_{PWXL}$ or G5000$_{PWXL}$, the column volume was 7.8*300 mm, the flow rate was 0.5 ml/min, and the detection wavelength was 280 nm; wherein, the homogenicity of 26-331, 26-351, 26-381, 26-411, 26-441 and 26-461 was determined by using G5000$_{PWXL}$; and the other proteins were detected by using G3000$_{PWXL}$. The SEC-HPLC analytic results were shown in FIG. 6 and FIG. 7.

The results showed: in the presence of TB8.0, the truncated proteins 1-476, 26-331, 26-351, 26-381, 26-411, 26-441 and 26-461 had a retention time of about 11 min, and a molecular weight of above 600 kDa; this indicates that these truncated proteins were mainly present in a form of polymer. The truncated protein 26-271 had a retention time of about 16 min; this indicates that the protein was mainly present in a form of monomer. The other proteins (6-476, 22-476, 26-476, 26-471, 26-482, 26-487, 26-492, 26-497) had a retention time of about 13-14 min, which was comparable to the retention time of IgG (150 kDa); this indicated that these proteins were mainly present in a form of trimer.

In addition, in the presence of TB8.0+1 M NaCl, the truncated VP4 proteins 26-476, 26-482, 26-487, 26-492 and 26-497 had a retention time of about 15 min, which was comparable to that of VP8 dimer (40 kDa); this indicated that these truncated proteins were mainly present in a form of monomer in the presence of TB8.0+1 M NaCl. This further indicated that in the presence of salts, the configurations of 26-476, 26-482, 26-487, 26-492 and 26-497 were affected by salt ions, resulting in depolymerization of trimer and the formation of monomers.

In addition, the results in FIG. 6 and FIG. 7 also showed that the main absorption peaks of the truncated VP4 proteins obtained accounted for nearly above 80% or even above 90%. This indicated that these truncated proteins had good homogenicity, were suitable for industrial production in batches, and were good for accurate medication.

The experimental results in FIG. 6 and FIG. 7 are also summarized in the following Table 3.

TABLE 3

| Truncated protein | Retention time (min) | Percentage of main peak area (%) | Existing form |
|---|---|---|---|
| 1-476 | 10.86 | 79 | polymer |
| 6-476 | 13.63 | 83.76 | trimer |
| 22-476 | 14.21 | 74.57 | trimer |
| 26-476 | 13.04 | 95.5 | trimer |
|  | 15.21 (1M NaCl) | 90 | monomer |
| 26-271 | 16.24 | 97.8 | monomer |
| 26-471 | 13.01 | 90.8 | trimer |
| 26-482 | 13.13 | 90 | trimer |
|  | 15.06 (1M NaCl) | 95.6 | monomer |
| 26-487 | 13.21 | 88.8 | trimer |
|  | 15.10 (1M NaCl) | 96.2 | monomer |
| 26-492 | 13.21 | 89.6 | trimer |
|  | 15.15 (1M NaCl) | 97.3 | monomer |
| 26-497 | 13.08 | 88.8 | trimer |
|  | 15.31 (1M NaCl) | 93.6 | monomer |
| 26-331 | 10.552 | 100 | polymer |
| 26-351 | 10.326 | 76.6 | polymer |
| 26-381 | 10.298 | 58.8 | polymer |
| 26-411 | 10.288 | 85.5 | polymer |
| 26-441 | 11.014 | 88.7 | polymer |
| 26-461 | 10.273 | 89.5 | polymer |

EXAMPLE 5

In Vitro Assembly and Characterization of the Truncated VP4 Protein

The in vitro assembly of the truncated protein 26-476 was performed by the following method. At room temperature, the truncated protein 26-476 was dialyzed from TB8.0 buffer to the dialysis buffer specified in Table 4, the dialysis buffer was changed once every 6 h. After dialysis, the solution was centrifuged at 12000 rpm for 10 min, and the supernatant was collected. Later, the supernatant was on standing at the temperature specified in Table 4 for a period of from 30 min to 24 h. After standing, the supernatant was quickly placed in an ice bath, and was centrifuged at 12000 rpm/min for 10 min. The supernatant (containing the in vitro assembled 26-476) was collected after the second centrifugation, for further analysis.

HPLC was employed to analyze the homogenicity of the polymer formed by in vitro assembly of the truncated protein 26-476 in the obtained supernatant. The apparatus used in HPLC analysis was 1200 High-Performance Liquid Chromatography Apparatus produced by Agilent or E2695 High-Performance Liquid Chromatography Apparatus produced by Waters, wherein the chromatographic column was $G5000_{PWXL}$, the column volume was 7.8*300 mm, the flow rate was 0.5 ml/min, and the detection wavelength was 280 nm. SEC-HPLC analytic results were shown in Table 4 and FIG. 8A.

TABLE 4

Conditions and results of in vitro assembly of the truncated protein

| Buffer system | NaCl concentration (M) | Temperature (° C.) | Standing time | Percentage of polymer |
|---|---|---|---|---|
| 20 mM phosphate buffer pH 7.4 | 0 | 37 | 12 h | 93.6% |
| 50 mM Tris-HCl pH 8.0 | 0 | 4 | 12 h | 0% |
| | 0 | 25 | 12 h | 0% |
| | 0 | 37 | 0.5 h | 90.5% |
| | 0 | 37 | 1 h | 91.5% |
| | 0 | 37 | 2 h | 95.4% |
| | 0 | 37 | 6 h | 96.8% |
| | 0 | 37 | 12 h | 97.2% |
| | 0 | 37 | 24 h | 98.1% |
| | 0 | 45 | 12 h | 100% |
| | 0 | 50 | 12 h | 100% |
| | 0.15 | 37 | 12 h | 26.6% |
| | 0.5 | 37 | 12 h | 18.4% |
| | 1 | 37 | 12 h | 5.3% |
| 50 mM carbonate buffer pH 9.6 | 0 | 37 | 12 h | 98.7% |

FIG. 8A showed the results of Molecular sieve analysis with the truncated protein 26-476 after standing in 50 mM Tris-HCl (pH8.0) at 37° C. for 12 h. The results showed that after standing in 50 mM Tris-HCl (pH8.0) at 37° C. for 12 h, the truncated protein 26-476 could form a homogeneous polymer (with a retention time of 12.4 min), and the polymer accounted for up to 97.2%.

It can be seen from the results in Table 4 and FIG. 8A that after standing at a temperature of 37° C.-50° C. at a pH in a range of 7.4-9.6, the truncated protein 26-476 could be assembled to form a homogeneous polymer, and the percentage of the polymer may be more than 90%. In addition, the results in Table 4 also showed that the presence of salt ions (e.g., NaCl) may inhibit the truncated protein 26-476 to form a polymer. The higher the concentration of salt ions (e.g., NaCl) was, the lower the percentage of the formed polymer was.

In addition, electron microscope was also used to observe the polymer formed by in vitro assembly of the truncated protein 26-476, and the apparatus used was G2 Spirit electron microscope produced by FEI Company. In brief, the sample was fixed onto a copper grid and negatively stained with 2% phosphotungstic acid (pH 7.4) for 30 min, and then was observed by the electron microscope. The results were shown in FIG. 8B, wherein a large number of asymmetric particles with a radius of about 10 nm were observed. The results showed that the truncated protein 26-476 could be assembled in vitro into a homogeneous polymer.

EXAMPLE 6

Identification of the Truncated VP4 Protein by Enzymatic Cleavage

The purified truncated VP4 protein obtained in Example 4 was cleaved by trypsin at 37° C. for 1 h. To the enzymatically cleaved component (100 ul), 20 μL 6× Loading Buffer was added, and the resultant mixture was mixed homogeneously and incubated in a 100° C. water bath for 10 min. The mixture (10 μl) was then subjected to electrophoresis in 13.5% SDS-polyacrylamide gel at a voltage of 120V for 120 min; and the electrophoresis strips were then shown by coomassie blue staining. The electrophoresis results were shown in FIG. 9.

FIG. 9 showed the SDS-PAGE results of the truncated protein 26-476, 26-482, 26-487, 26-492, 26-497 cleaved by enzyme or not. On the lanes, the number "1" represents that the sample is not treated with trypsin; and the number "2" represents that the sample has been treated with 0.1 mg/ml trypsin. The sample used in the rightmost lane was VP8-5, as a control. The results in FIG. 9 showed that all these truncated proteins could be recognized and cleaved by trypsin, i.e., their enzymatic recognition sites were exposed.

EXAMPLE 7

Analysis of Antigenicity of the Truncated VP4 Proteins

The purified truncated VP4 protein obtained in Example 4 was coated onto a plate, to obtain a coated plate. The neutralizing antibodies A3, B1, B5, B6, D6, E2, E5, and 8F6 (prepared by hybridoma technology in the laboratory, at a concentration of 1 mg/ml) were subjected to gradient dilution, and then detected by indirect ELISA method as described in Example 1.

The detection results were shown in FIG. 10, wherein the abscissa represents the truncated proteins, and the ordinate represents the least antibody concentration capable of reacting with the truncated proteins ($OD_{450/620}$ of greater than 0.2). The results showed that the truncated VP4 proteins had good antigenicity (i.e., antibody reactivity).

EXAMPLE 8

Analysis of the Immunogenicity of the Truncated VP4 Proteins

The purified truncated protein 26-476 obtained in Example 4 was coated on a plate, to obtain the coated plate. In accordance with the method as described in Example 1, in the presence of aluminum adjuvant, Balb/c mice were immunized with the sample to be tested (the truncated VP4 protein, and the trimer of 26-476 obtained in Example 4, the polymer of 26-476 obtained in Example 5, the inactivated virus (RV, as a positive control) and PBS (NC, negative control)), respectively, and the sera of mice were collected. Later, in accordance with the method as described in Example 1, the antibody titer in the mouse serum was determined by indirect ELISA using the 26-476-coated plate.

Indirect ELISA results were shown in FIGS. 11A-11D, wherein, the abscissa represents the protein sample for preparing immune serum, and the ordinate represents the greatest dilution (i.e., antibody titer) of the immune serum having reactivity with 26-476; and, FIGS. 11A, 11B, 11C and 11D showed the results of different immunization batches. The results showed that in the presence of aluminum adjuvant, at Day 42 after immunization, these proteins could induce generation of antibodies (antibody titer of the immune serum (GMT) could reach $10^2$-$10^5$ or higher) in mice; and, except for 26-271, the antibody titers induced by the other protein samples were higher than the antibody titer induced by RV (1-476, 6-476, 22-476, 26-331, 26-351, 26-381, 26-411, 26-441, 26-461, 26-471, 26-476, 26-487, 26-492, trimer of 26-476 and polymer of 26-476), or were at least comparable to the antibody titer induced by RV (65-476, 26-482 and 26-497).

It can be seen by combining the experimental results in Example 1 that in the presence of aluminum adjuvant, all the protein samples (except for 26-271) had good immunogenicity, and could stimulate generation of high-titer antibodies in mice; their immunogenicity was significantly higher than that of VP8-5, and the antibody titer in the immune serum was significantly higher than that in the serum of the mice immunized with VP8-5. In addition, the experimental results in FIG. 11D also show that the immunogenicity of the polymer of the truncated protein 26-476 was significantly higher than that of the trimer of 26-476 (p=0.005).

EXAMPLE 9

Analysis of the Immune Neutralizing Activity of the Truncated VP4 Protein

By the method as described in Example 1, the Balb/c mice in the experimental group (7 mice per group) were immunized with the sample to be tested (the truncated VP4 proteins and the trimer of 26-476 obtained in Example 4, the polymer of 26-476 obtained in Example 5, the inactivated virus (RV, as a positive control) and PBS (NC, negative control)), respectively, and the immune sera were collected.

Later, in accordance with the detection method as described in Example 1, the immune serum samples collected were evaluated for neutralizing antibody titer. The analytic results of the neutralizing antibody titer of the immune sera were shown in FIGS. 12A-12D, wherein, the abscissa represents the virus strain from which the protein sample for preparing immune serum was derived; the ordinate represents the greatest dilution ($NT_{50}$, neutralizing antibody titer) of the immune serum achieving an infection inhibition rate of 50%. FIG. 12A, 12B, 12C and 12D showed the results of different immunization batches. The results showed that in the presence of aluminum adjuvant, at Day 42 after immunization (after three immunizations), all these protein samples could induce generation of neutralizing antibodies in mice, and their neutralizing antibody titer ($NT_{50}$) could reach $2^8$-$2^{14}$ or higher; and, except for 26-271, the neutralizing antibody titer induced by the other protein samples was comparable to the neutralizing antibody titer induced by RV (6-476, 22-476, 26-476, 65-476, 26-471, 26-482, 26-487, 26-492, 26-497 and trimer of 26-476), or even higher than the neutralizing antibody titer induced by RV (1-476, 26-331, 26-351, 26-381, 26-411, 26-441, 26-461 and polymer of 26-476).

It can be seen by combining the experimental results in Example 1 that in the presence of aluminum adjuvant, all the protein samples (except for 26-271) had a strong ability of inducing generation of neutralizing antibodies in an organism, and could induce the immune serum having a high neutralizing antibody titer in animal, and the immune serum could effectively inhibit rotavirus infection. The protein samples (except for 26-271) was superior to VP8-5 in terms of the ability of inducing generation of neutralizing antibodies in an organism, and therefore had a stronger ability of combating/preventing RV infection. In addition, the experimental results in FIG. 12D also showed that the polymer of the truncated protein 26-476 was significantly superior to the trimer of 26-476 in terms of the ability of inducing generation of neutralizing antibodies in an organism (p<0.001), and had a significantly stronger ability of combating/preventing RV infection.

EXAMPLE 10

Evaluation of the Protective Effect of the Truncated VP4 Protein in Animal

By using the method as described in Example 1, Balb/c mice (7 mice per group) were immunized with the samples to be tested (the truncated VP4 proteins and the trimer of 26-476 obtained in Example 4, the polymer of 26-476 obtained in Example 5, the inactivated virus (RV, as a positive control) and PBS (NC, negative control)), respectively, and the sera were collected.

In accordance with the method as described in Example 1, the protein sample was evaluated for its protective effect in animal. Except for the groups immunized with 1-476 and 6-476 (the mating of the animals in the two groups was not successful), the experimental results of the other immunization groups were shown in FIGS. 13-14.

FIGS. 13A-13D showed the diarrhea scores of suckling mice in different immunization groups (immunized with 22-476, 26-476, 65-476, 26-271, 26-331, 26-351, 26-381, 26-411, 26-441, 26-461, 26-471, 26-482, 26-487, 26-492, 26-497, trimer of 26-476, polymer of 26-476, inactivated rotavirus (RV, positive control) or PBS (NC, negative control)) 1-7 days after challenging with a virus, wherein the axis of ordinates represents the average diarrhea score; the axis of abscissas represents days after challenging with a virus in mice; RV: inactivated rotavirus; NC: negative control (PBS); trimer: trimer of 26-476; polymer: polymer of 26-476. FIGS. 14A-14D showed the average duration of diarrhea after challenge with a virus and the average diarrhea scores 48 h after challenge with a virus in the suckling mice in different immunization groups (immunized with 22-476, 26-476, 65-476, 26-271, 26-331, 26-351, 26-381, 26-411, 26-441, 26-461, 26-471, 26-482, 26-487, 26-492, 26-497, trimer of 26-476, polymer of 26-476, inactivated rotavirus (RV, positive control) or PBS (NC, negative control)), wherein, the average duration (days) for diarrhea is represented by bar diagram; the average diarrhea score is represented by curve graph; the left axis of ordinates represents the average duration (days) for diarrhea; the right axis of ordinates represents the diarrhea score; the axis of abscissas represents the corresponding immunization groups with the protein samples.

The results showed that in terms of the average diarrhea score and the average duration (days) for diarrhea, the corresponding immunization groups with the protein samples were superior to the NC group. This indicated that the protein samples had significant protective effect, and could help the mice to combat rotavirus infection and diarrhea caused by rotavirus infection. In addition, the results further showed that the protective effects of 26-331, 26-351, 26-381, 26-411, 26-441, 26-461, 26-476, trimer of 26-476, and polymer of 26-476 were comparable to that of RV, or even better than that of RV. According to the experimental results of Example 1, in the presence of aluminum adjuvant, the protective effects of these protein samples were superior to that of VP8-5 in animal. In addition, the experimental results in FIG. 13D and FIG. 14D also showed that the protective effect of the truncated protein polymer of 26-476 was significantly superior to that of trimer of 26-476 in animal, and could be used to prepare vaccines having a higher efficacy.

EXAMPLE 11

Evaluation of Expression, Purification and Immune-Protection of the Truncated VP4 Proteins from Different Virus Strains Based on the VP4 gene sequence of EDIM virus strain (Accession Number: AF039219.2) as provided in Gene bank, the gene fragment encoding 26-476 from rotavirus EDIM strain was synthesized by Sangon Biotech (Shanghai) Co., Ltd. In addition, based on the VP4 gene sequence of rotavirus P[6] (Accession Number: FJ183356.1) as provided in Gene bank, the gene fragment encoding 26-476 from rotavirus P[6] was synthesized by Sangon Biotech (Shanghai) Co., Ltd. Later, the synthesized gene fragments were used as templates, and the gene fragments encoding the truncated protein 26-476 from rotavirus P[6] and EDIM were obtained by PCR amplification.

In addition, as described in Example 2, Rotavirus SA11 strain was cultured with a fetal rhesus monkey kidney cell line (MA-104), to obtain the virus culture of rotavirus SA11. Rotavirus P[4] and P[8] were derived from the diarrhea specimens collected by Children's Hospital of Chongqing Medical University, under a specimen number of 20131281 (P[4]) and a specimen number of 20131028 (P[8]).

According to the instructions of the manufacturer, the Virus DNA/RNA Kit produced by Beijing GenMag Biotechnology Co., Ltd. was used to extract the genomic RNAs of rotavirus SA11, P[4], and P[8] from virus culture or virus specimen, and the cDNAs encoding the VP4 proteins from different virus strains were obtained by reverse transcription. The cDNAs obtained were used as templates, and the gene fragments encoding the truncated protein 26-476 from rotavirus strains SA11, P[4] and P[8] were obtained by PCR amplification.

In accordance with the method as described in Example 2, clonal plasmids and expression vectors were constructed, wherein the PCR primers used were as followed:

```
upstream primer:
                                   (SEQ ID NO: 77)
5'-GGATCCCATATGGGATCGGAGAAAACTCAA-3'

(SEQ ID NO: 79)
5'-GGATCCCATATGGGATCAGAGAAAAGTCAAAT-3'

(SEQ ID NO: 81)
5'-GGATCCCATATGGGATCAGAAAAAACTCAAAATG-3'

(SEQ ID NO: 83)
5'-GGATCCCATATGGGAGCAGAGAAGACACA-3'

(SEQ ID NO: 85)
5'-GGATCCCATATGGGATCAACTAAATCACAAAATG-3' downstream primer:
                                   (SEQ ID NO: 78)
5'-AAGCTTAATTAGTTGGAACTAAAGAAATAAGT-3'

(SEQ ID NO: 80)
5'-AAGCTTAATTAGACGGTACTAATGAAA-3'

(SEQ ID NO: 82)
5'-AAGCTTAGTTGGTTGGAACTAAAGAAA-3'

(SEQ ID NO: 84)
5'-AAGCTTAATCGTTGGACGGCAC-3'

(SEQ ID NO: 86)
5'-AAGCTTATGATGGCACTAATGATATAAGT-3'
``` wherein the underlined sequences indicate the enzymatic recognition sites, and the italic letters indicate the introduced terminator codons.

The primer pairs for amplification of gene fragments are shown in Table 5:

TABLE 5

Primer pairs for amplification of gene fragments encoding 26-476 from different virus strains

| Protein | Upstream primer | Downstream primer |
| --- | --- | --- |
| 26-476-P[4] | SEQ ID NO: 77 | SEQ ID NO: 78 |
| 26-476-P[6] | SEQ ID NO: 79 | SEQ ID NO: 80 |
| 26-476-P[8] | SEQ ID NO: 81 | SEQ ID NO: 82 |
| 26-476-EDIM | SEQ ID NO: 83 | SEQ ID NO: 84 |
| 26-476-SA11 | SEQ ID NO: 85 | SEQ ID NO: 86 |

The amino acid sequences of the truncated proteins 26-476-P[4], 26-476-P[6], 26-476-P[8], 26-476-EDIM, and 26-476-SA11 are set forth in SEQ ID NOs: 35-39, respectively.

In accordance with the methods described in Examples 3-4, the truncated protein 26-476 from different virus strains (i.e., 26-476-P[4], 26-476-P[6], 26-476-P[8], 26-476-EDIM, 26-476-SA11) was expressed in E. coli, and purified by two-step chromatography; and the purified protein was identified by SDS-PAGE.

The SDS-PAGE results were shown in FIG. 15, wherein, the lanes from left to right are: the truncated protein 26-476 from rotavirus LLR; the truncated protein 26-476-SA11 from rotavirus SA11; the truncated protein 26-476-EDIM from rotavirus EDIM; the truncated protein 26-476-P[8] from rotavirus P[8]; the truncated protein 26-476-P[6] from rotavirus P[6]; the truncated protein 26-476-P[4] from rotavirus P[4]; and, Protein Molecular Weight Marker (Marker).

The results showed that the method according to the invention was applicable to different virus strains. The truncated VP4 protein (26-476) from different virus strains could be effectively expressed in E. coli, and had a purity of above 80% after purification by chromatography.

In addition, in accordance with the method described in Example 4, HPLC was used to analyze the homogenicity of the purified truncated protein 26-476 in the presence of 50 mM TB8.0. The SEC-HPLC analytic results were shown in FIG. 16.

The results showed that in the presence of TB8.0, the truncated VP4 proteins 26-476 from different virus strains had a retention time of about 13-14 min, which was comparable to the retention time of IgG (150 kDa); this indicated that these proteins were mainly present in a form of trimer. In addition, the results in FIG. 16 also showed that the main absorption peaks of the truncated proteins 26-476 obtained accounted for nearly above 80%, indicating that these truncated proteins had good homogenicity, were suitable for industrial production in batches, and were good for accurate medication.

Furthermore, the truncated protein 26-476 from different rotavirus strains was coated onto a plate, to obtain the coated plate. In accordance with the method as described in Example 1, Balb/c mice were immunized with the purified truncated protein 26-476 obtained above (i.e., 26-476-P[4], 26-476-P[6], 26-476-P[8], 26-476-EDIM, 26-476-SA11, 26-476 from LLR and PBS (negative control)), and the sera of mice were collected. Later, in accordance with the method as described in Example 1, the antibody titers in the sera of mice was determined by indirect ELISA using the coated plate.

The indirect ELISA results were shown in FIG. 17, wherein, the abscissa represents the virus strain from which the truncated protein for preparing immune serum was derived, and the ordinate represents the greatest dilution (i.e., antibody titer) of the immune serum having reactivity with the corresponding truncated protein; P[4]: 26-476-P[4]; P[6]: 26-476-P[6]; P[8]: 26-476-P[8]; SA11: 26-476-SA11; EDIM: 26-476-EDIM; LLR: 26-476 prepared in Example 4.

The results showed that in the presence of aluminum adjuvant, at Day 42 after immunization, all these 26-476 proteins derived from different virus strains could induce generation of antibodies in mice, and the antibody titers (GMT) in the immune sera induced thereby were comparable (the antibody titer could reach $10^4$-$10^5$ or higher, much higher than that of the negative control group). These results indicated that in the presence of aluminum adjuvant, the 26-476 proteins derived from different virus strains had good immunogenicity, and could effectively induce generation of antibodies in animal; and, the 26-476 proteins derived from different virus strains were substantively comparable in terms of immunogenicity, and were superior to VP8-5.

Furthermore, by using the method as described in Example 1, Balb/c mice (7 mice per group) in the experimental group were immunized with the 26-476 protein from different virus strains (26-476-SA11; 26-476-EDIM; 26-476 from LLR), and the immune sera were collected. Later, in accordance with the method described in Example 1, each immune serum sample collected was evaluated for the neutralizing antibody titer. The analytic results of the neutralizing antibody titer of the immune sera were shown in FIG. 18, wherein, the abscissa represents the virus strain from which the protein sample for preparing immune serum was derived; and the ordinate represents the greatest dilution ($NT_{50}$, neutralizing antibody titer) of the immune serum achieving an infection inhibition rate of 50%; SA11: 26-476-SA11; EDIM: 26-476-EDIM; LLR: 26-476 prepared in Example 4.

The results showed that in the presence of aluminum adjuvant, at Day 42 after immunization (after three immunizations), all the 26-476 proteins derived from SA11, EDIM and LLR virus strains could induce generation of high-titer neutralizing antibodies in mice, and their neutralizing antibody titer ($NT_{50}$) could reach $2^{10}$-$2^{14}$ or higher; and, the neutralizing antibody titers induced by 26-476-SA11 and 26-476-EDIM were even higher than that induced by 26-476 derived from LLR. Therefore, the immune neutralizing activity of the 26-476 protein from SA11 virus strain and EDIM virus strain was even superior to that of 26-476 protein from LLR.

In addition, it can also be demonstrated by similar methods that the 26-476 protein from rotavirus P[4], P[6] and P[8] had good immune neutralizing activity, and could induce generation of high-titer neutralizing antibodies in mice.

These results showed that in the presence of aluminum adjuvant, the 26-476 protein from different virus strains had a strong ability of inducing generation of neutralizing antibodies in an organism, and could induce the immune serum having a high neutralizing antibody titer in animal.

Furthermore, by using the method as described in Example 1, Balb/c mice (7 mice per group) were immunized with the 26-476 protein from different virus strains (26-476-SA11, 26-476-EDIMand PBS (NC, negative control)), and the sera were collected. Later, in accordance with the method as described in Example 1, the protein sample was evaluated for its protective effect in animal. The experimental results were shown in FIGS. 19A-19B.

FIG. 19A showed the diarrhea scores of suckling mice in different immunization groups (immunized with 26-476-SA11 or PBS (NC, negative control)) 1-7 days after challenging with SA11 virus; FIG. 19B shows the diarrhea scores of suckling mice in different immunization groups (immunized with 26-476-EDIM or PBS (NC, negative control)) 1-12 days after challenging with EDIM virus; wherein, the abscissa represents days after challenging with a virus, and the ordinate represents the average diarrhea score. The results showed that similar to the 26-476 protein derived from LLR, both of the 26-476 proteins derived from SA11 and EDIM had significant protective effect, and could help the mice to combat rotavirus infection and diarrhea caused by rotavirus infection.

In addition, in accordance with the method as described in Example 1, adult mice were immunized with 26-476-EDIM or PBS (NC, negative control) (immunization for three times in total). After the immunization procedure was finished, the mice were challenged with 500 μL EDIM virus ($2*10^7$ copies/ml). 1-7 days after the challenge, the stool specimens from the mice were collected every day, and were re-suspended in PBS to obtain 1% stool suspension. Later, by Fluorescence Quantitative PCR assay, the virus in each stool suspension sample was determined quantitatively. The experimental results were shown in FIG. 19C.

FIG. 19C showed the viral load of the stool suspension sample of the mice immunized with 26-476-EDIM or PBS 1-7 days after challenging with a virus, wherein the abscissa represents days after challenge with a virus, and the ordinate represents the copy number of the EDIM genome contained in 1 ml stool suspension sample. Since Fluorescence Quantitative PCR Assay Kit has a lower detection limit of $10^4$ copies/ml, the negative detection result is defined as $10^3$ copies/ml. The results showed that after challenge with a virus, significant excretion of virus was detected in the stool of the mice immunized with PBS, while in the stool of the mice immunized with 26-476-EDIM, no excretion of virus was detected. The results in FIGS. 19A-19C showed that 26-476-EDIM could not only enable the mice to combat rotavirus infection and diarrhea caused by rotavirus infection, but also inhibit the excretion of virus in the stool of the mice (i.e., excretion of virus).

Although the embodiments of the invention have been described in detail, a person skilled in the art would understand that according to all the disclosed teachings, details can be amended and modified, and all these modifications fall into the protection scope of the invention. The scope of the invention is defined by the claims and any equivalent thereof.

The invention claimed is:

1. A truncated rotavirus VP4 protein, wherein as compared to a wild-type rotavirus VP4 protein, the truncated rotavirus VP4 protein has the segment of the first X amino acids at the N-terminal of the wild-type rotavirus VP4 protein as a whole and replaced with one methionine residue, and has its C-terminal ending at the following position of the wild-type rotavirus VP4 protein: a position corresponding to any position among the amino acid positions 331-497 of SEQ ID NO: 40, wherein X is an integer that is greater than or equal to 5 but less than or equal to 64.

2. A polymer comprising or consisting of the truncated rotavirus VP4 protein according to claim 1.

3. A composition comprising the truncated rotavirus VP4 protein according to claim 1, or a polymer comprising or consisting of the truncated rotavirus VP4 protein.

4. A pharmaceutical composition, comprising (1) the truncated rotavirus VP4 protein according to claim 1 or a polymer comprising or consisting of the truncated rotavirus VP4 protein and (2) optionally, a pharmaceutically acceptable carrier and/or excipient.

5. A method for preparing a pharmaceutical composition, comprising mixing the truncated rotavirus VP4 protein according to claim 1 or a polymer comprising or consisting of the truncated rotavirus VP4 protein with a pharmaceutically acceptable carrier and/or excipient, and optionally, with an adjuvant and/or an additional active ingredient.

6. A method for inhibiting rotavirus infection, comprising administering to a subject an effective amount of the truncated rotavirus VP4 protein according to claim 1, or a polymer comprising or consisting of the truncated rotavirus VP4 protein, or a pharmaceutical composition comprising the truncated rotavirus VP4 protein or the polymer.

7. The truncated rotavirus VP4 protein according to claim 1, wherein as compared to the wild-type rotavirus VP4 protein, the truncated rotavirus VP4 protein has the first X amino acids at the N-terminal mutated as methionine; and has C-terminal ending at the following position of the wild-type rotavirus VP4 protein: a position corresponding to any position among the amino acid positions 331-497, 341-497, 351-497, 361-497, 371-497, 381-497, 391-497, 401-497, 411-497, 421-497, 431-497, 441-497, 451-497, 461-497, 471-497, 476-497, 482-497, 487-497, or 492-497 of SEQ ID NO: 40, wherein X is an integer that is greater than or equal to 5 but less than or equal to 64.

8. The truncated rotavirus VP4 protein according to claim 1, wherein as compared to the wild-type rotavirus VP4 protein, the truncated rotavirus VP4 protein has the first 5, 21, 25 or 64 amino acids at the N-terminal mutated as methionine, and has C-terminal ending at the following position of the wild-type rotavirus VP4 protein: a position corresponding to the amino acid position 331, 341, 351, 361, 371, 381, 391, 401, 411, 421, 431, 441, 451, 461, 471, 476, 482, 487, 492 or 497 of SEQ ID NO: 40.

9. The truncated rotavirus VP4 protein according to claim 1, wherein as compared to the wild-type rotavirus VP4 protein, the truncated rotavirus VP4 protein has the first 25 amino acids at N-terminal mutated as methionine and has C-terminal ending at the following position: a position corresponding to the amino acid position 331, 351, 381, 411, 441, 461, 471, 476, 482, 487, 492 or 497 of SEQ ID NO: 40; or, the truncated rotavirus VP4 protein has the first 5, 21, 25 or 64 amino acids at N-terminal mutated as methionine and has C-terminal ending at the following position: a position corresponding to the amino acid position 476 of SEQ ID NO: 40.

10. The truncated rotavirus VP4 protein according to claim 1, wherein the wild-type rotavirus VP4 protein is a VP4 protein derived from rotavirus LLR strain, SA11 strain, or EDIM strain, or a VP4 protein derived from a rotavirus of P[4], P[6], or P[8] genotype.

11. The truncated rotavirus VP4 protein according to claim 1, wherein the wild-type rotavirus VP4 protein has an amino acid sequence selected from: SEQ ID NO: 40 and 87-91.

12. The truncated rotavirus VP4 protein according to claim 1, wherein the truncated rotavirus VP4 protein has an amino acid sequence selected from: SEQ ID NO: 3-5 and 15-39.

13. The pharmaceutical composition according to claim 4, wherein the pharmaceutical composition is characterized by one or more of the following items:

(1) the pharmaceutical composition further comprises an adjuvant;

(2) the truncated protein or the polymer is present in an amount effective for inhibiting rotavirus infection;

(3) the pharmaceutical composition further comprises an additional active ingredient.

14. The pharmaceutical composition according to claim 13, wherein the adjuvant is aluminum adjuvant.

15. The method according to claim 6, wherein the subject is a mammal.

16. The method according to claim 6, wherein the subject is mouse or human.

* * * * *